US008796623B2

(12) United States Patent
Nakatsugawa et al.

(10) Patent No.: US 8,796,623 B2
(45) Date of Patent: Aug. 5, 2014

(54) RADIATION IMAGING DEVICE, RADIATION IMAGING SYSTEM, AND METHOD FOR AFFIXING RADIATION CONVERSION PANEL IN RADIATION IMAGING DEVICE

(71) Applicant: FUJIFILM Corporation, Tokyo (JP)

(72) Inventors: Haruyasu Nakatsugawa, Kanagawa-ken (JP); Naoyuki Nishino, Kanagawa-ken (JP); Yasunori Ohta, Kanagawa-ken (JP); Naoto Iwakiri, Kanagawa-ken (JP)

(73) Assignee: FUJIFILM Corporation, Tokyo (JP)

( * ) Notice: Subject to any disclaimer, the term of this patent is extended or adjusted under 35 U.S.C. 154(b) by 0 days.

(21) Appl. No.: 13/661,419

(22) Filed: Oct. 26, 2012

(65) Prior Publication Data

US 2013/0043400 A1  Feb. 21, 2013

Related U.S. Application Data

(63) Continuation of application No. PCT/JP2011/060101, filed on Apr. 26, 2011.

(30) Foreign Application Priority Data

| Apr. 30, 2010 | (JP) | 2010-105855 |
| Apr. 30, 2010 | (JP) | 2010-105858 |
| Apr. 30, 2010 | (JP) | 2010-105862 |
| May 25, 2010 | (JP) | 2010-119553 |

(51) Int. Cl.
*G01J 1/00* (2006.01)
*G01T 1/24* (2006.01)
*G01T 1/29* (2006.01)

(52) U.S. Cl.
USPC ............. 250/336.1; 250/370.08; 250/370.1

(58) Field of Classification Search
CPC .................. A61B 6/102; A61B 6/4283
USPC .......... 250/366, 370.01, 370.08, 370.1, 336.1
See application file for complete search history.

(56) References Cited

U.S. PATENT DOCUMENTS

| 7,513,094 B2 * | 4/2009 | Denney et al. ............. 54/8 |
| 2002/0014594 A1 | 2/2002 | Endo |

(Continued)

FOREIGN PATENT DOCUMENTS

| JP | 09-054162 A | 2/1997 |
| JP | 09-257944 A | 10/1997 |

(Continued)

OTHER PUBLICATIONS

Rejection of the Application issued by the Japanese Patent Office on Jul. 16, 2013 in Japanese Patent Application No. 2010-105858, which corresponds to the present application.

(Continued)

*Primary Examiner* — David Porta
*Assistant Examiner* — Carolyn Igyarto
(74) *Attorney, Agent, or Firm* — Jean C. Edwards; Edwards Neils PLLC

(57) ABSTRACT

Disclosed is a radiation imaging device configuring a radiation imaging system. Specifically disclosed is a radiation imaging device wherein external force action mechanisms are capable of applying external force to the peripheral sections of a radiation conversion panel, or applying the external force while being laminated on the radiation conversion panel, or pressing the radiation conversion panel against the inner wall of a panel containing unit, which contains the radiation conversion panel, at least in imaging when radiation is applied.

7 Claims, 92 Drawing Sheets

(56) References Cited

U.S. PATENT DOCUMENTS

| | | |
|---|---|---|
| 2004/0178350 A1* | 9/2004 | Nagano et al. .......... 250/370.11 |
| 2004/0188626 A1 | 9/2004 | Yamamoto |
| 2007/0075253 A1 | 4/2007 | Misawa et al. |
| 2010/0243908 A1 | 9/2010 | Shoji et al. |

FOREIGN PATENT DOCUMENTS

| | | |
|---|---|---|
| JP | 2706725 B2 | 1/1998 |
| JP | 2000066318 A | 3/2000 |
| JP | 2002-014168 A | 1/2002 |
| JP | 2002-311526 A | 10/2002 |
| JP | 2003-156564 A | 5/2003 |
| JP | 2003-262678 A | 9/2003 |
| JP | 2004294114 A | 10/2004 |
| JP | 2005-326403 A | 11/2005 |
| JP | 2006-311575 A | 11/2006 |
| JP | 2007-101256 A | 4/2007 |
| JP | 2008102382 A | 5/2008 |
| WO | 2009/031574 A1 | 3/2009 |

OTHER PUBLICATIONS

Rejection of the Application issued by JPO on Aug. 20, 2013, in connection with corresponding Japanese Patent Application No. 2010-105855.

Rejection of the Application issued by JPO on Aug. 20, 2013, in connection with corresponding Japanese Patent Application No. 2010-119553.

Rejection of the Application issued by JPO on Oct. 1, 2013, in connection with corresponding Japanese Patent Application No. 2010-105862.

* cited by examiner

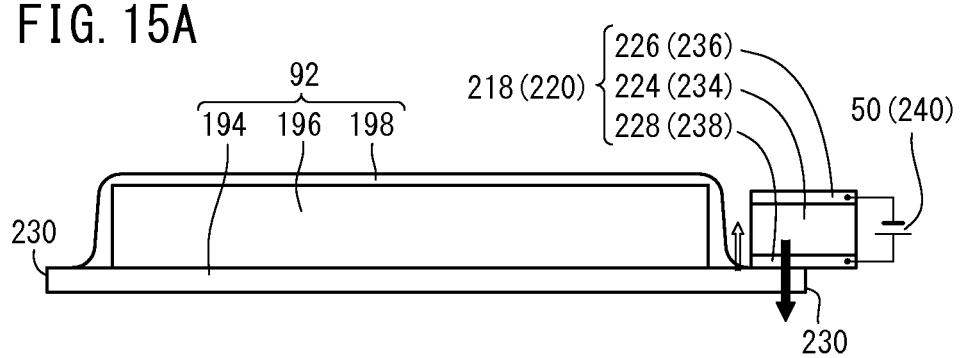
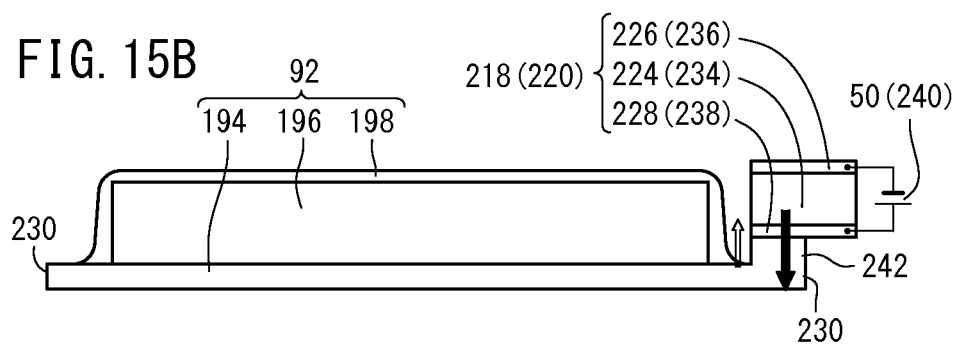

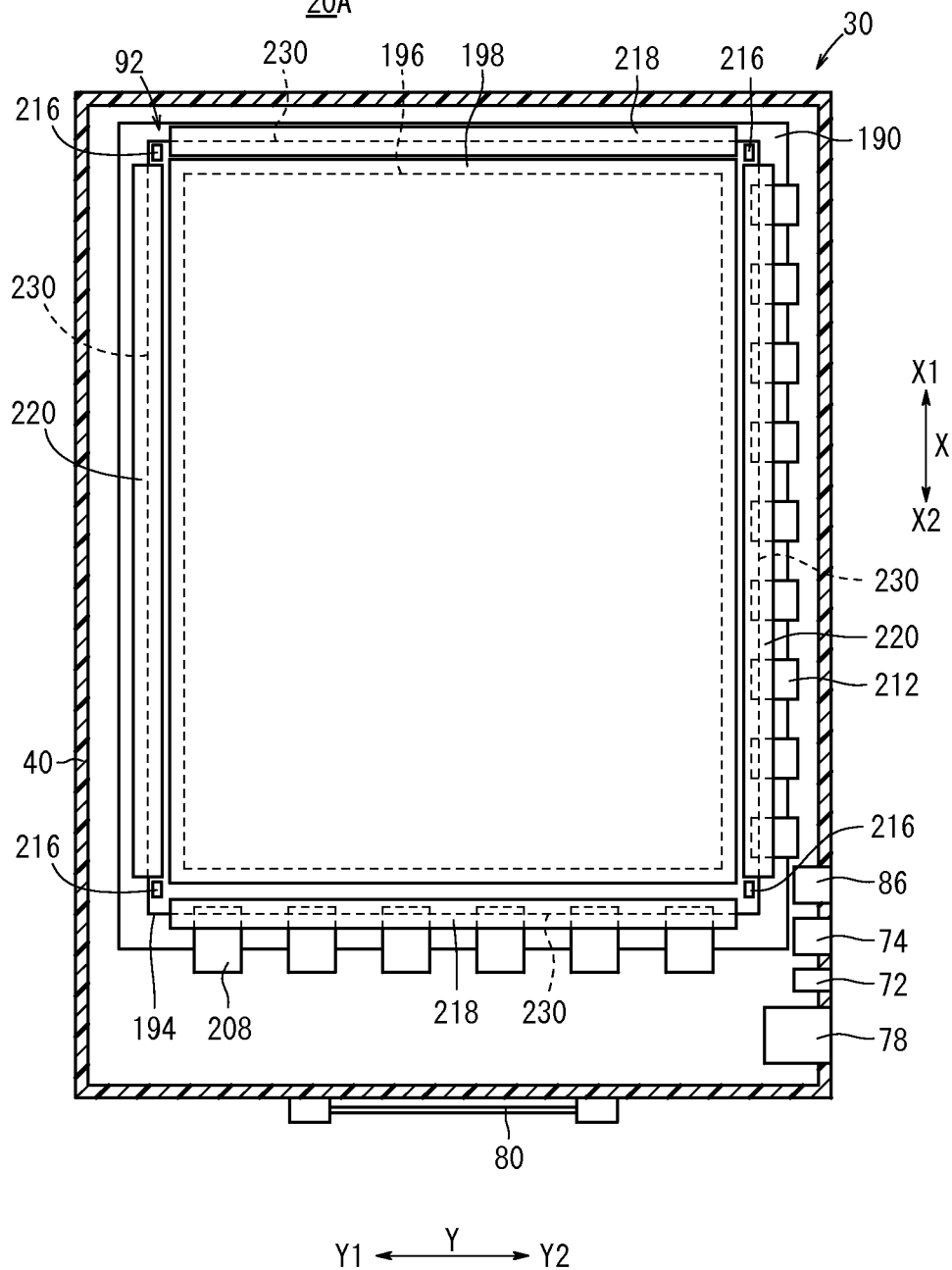

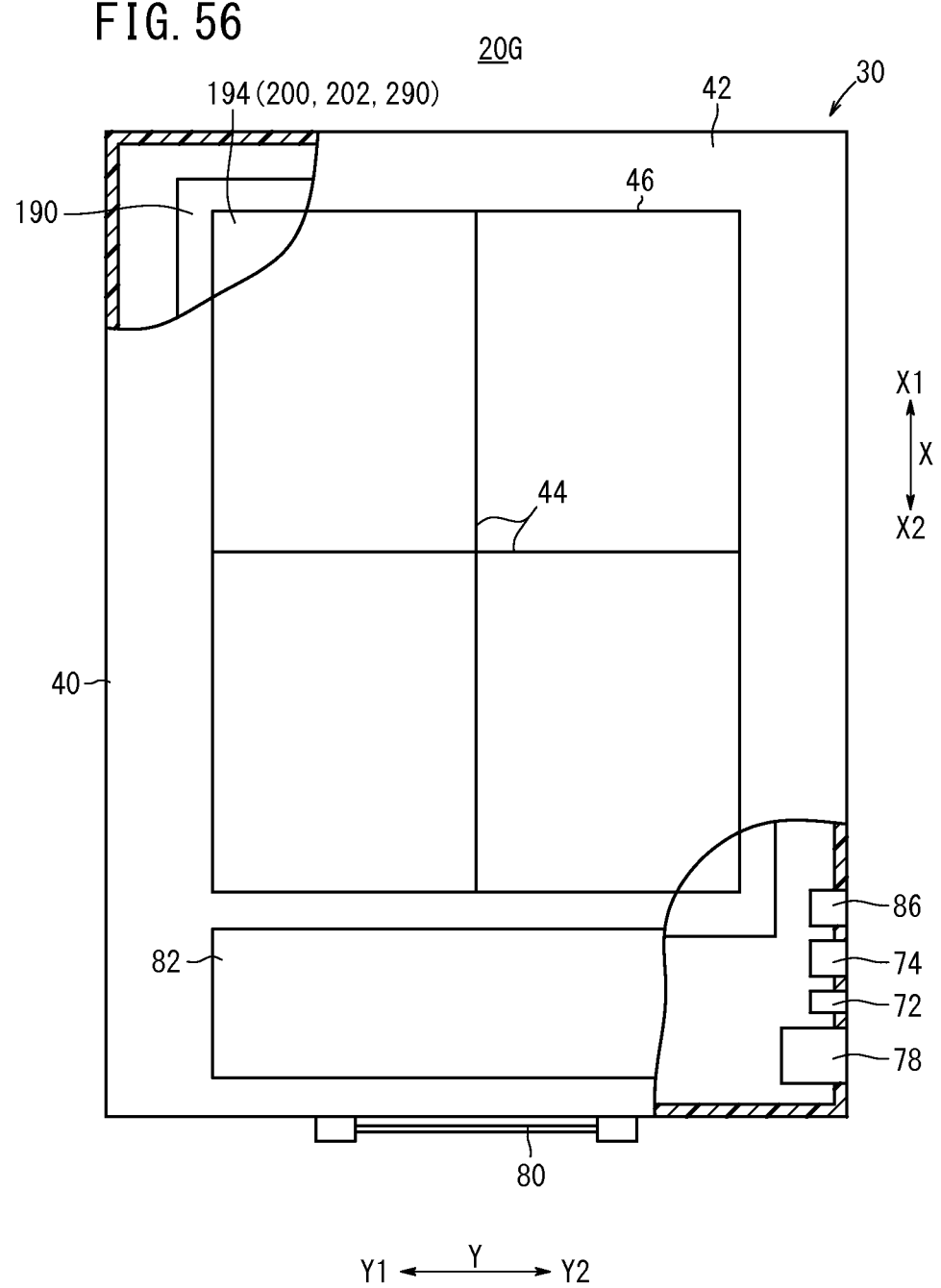

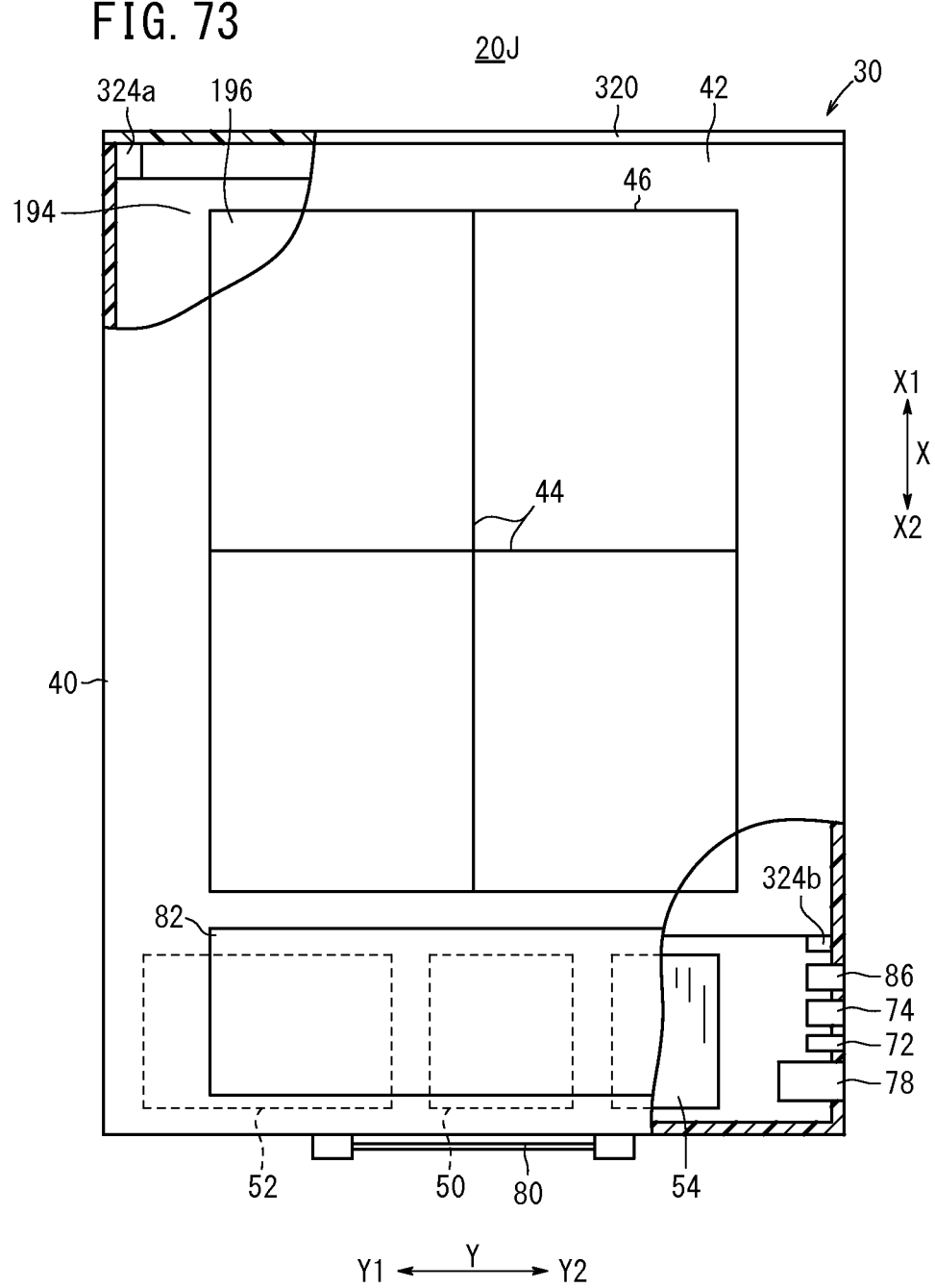

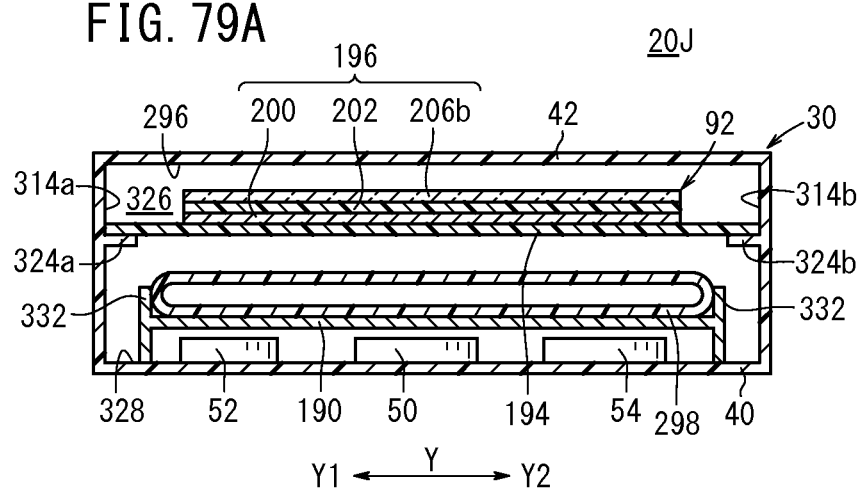
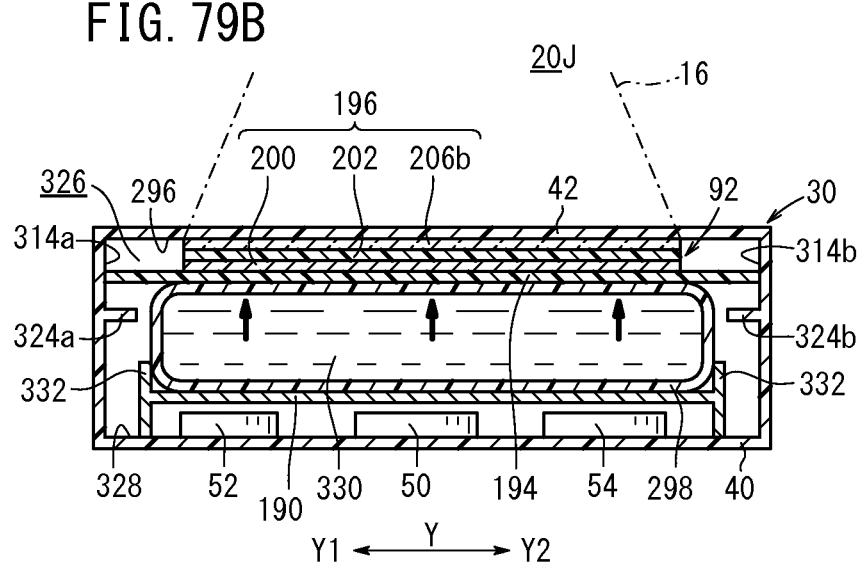

PRESSED

SPACED
(RELEASED)

PRESSED

SPACED
(RELEASED)

RADIATION IMAGING DEVICE, RADIATION IMAGING SYSTEM, AND METHOD FOR AFFIXING RADIATION CONVERSION PANEL IN RADIATION IMAGING DEVICE

CROSS-REFERENCE TO RELATED APPLICATIONS AND PRIORITY CLAIMS

This application is a Continuation of International Application No. PCT/JP2011/060101 filed on Apr. 26, 2011, which was published under PCT Article 21(2) in Japanese, which is based upon and claims the benefit of priority from Japanese Patent Applications No. 2010-105855 filed on Apr. 30, 2010, No. 2010-105858 filed on Apr. 30, 2010, No. 2010-105862 filed on Apr. 30, 2010, and No. 2010-119553 filed on May 25, 2010, the contents all of which are incorporated herein by reference.

TECHNICAL FIELD

The present invention relates to a radiographic image capturing apparatus (radiation imaging device) having a radiation conversion panel for converting radiation into a radiographic image, a radiographic image capturing system (radiation imaging system) having a radiographic image capturing apparatus and a control device for controlling the radiographic image capturing apparatus, and a method of securing (affixing) a radiation conversion panel in a radiographic image capturing apparatus.

BACKGROUND ART

In the medical field, there have widely been used radiographic image capturing apparatus that apply radiation to a subject and guide radiation that has passed through the subject to a radiation conversion panel, which captures a radiographic image from such radiation. Known forms of radiation conversion panels include a conventional radiation film for recording a radiographic image by way of exposure, and a stimulable phosphor panel for storing radiation energy representing a radiographic image in a phosphor, and reproducing the radiographic image as stimulated light by applying stimulating light to the phosphor. The radiation film with the recorded radiographic image is supplied to a developing device to develop the radiographic image. Alternatively, the stimulable phosphor panel is supplied to a reading device to read the radiographic image as a visible image.

In an operating room or the like, it is necessary to read a recorded radiographic image immediately from a radiation conversion panel after the radiographic image has been captured for the purpose of quickly and appropriately treating a patient. As a radiation conversion panel that meets such requirements, there have been developed a radiation conversion panel of a direct conversion type having a solid-state detector for converting radiation directly into an electric signal, and a radiation conversion panel of an indirect conversion type having a scintillator for temporarily converting radiation into fluorescence and a solid-state detector for converting the fluorescence into an electric signal.

A radiation conversion panel of the direct conversion type or the indirect conversion type, a controller for controlling the radiation conversion panel to read a radiographic image therefrom as an electric signal, a communication unit for sending signals including the electric signal to an external circuit, and a power supply are encased in a panel housing unit, thereby making up a radiographic image capturing apparatus, which also is referred to as an electronic cassette. The electronic cassette is thicker and heavier than a radiographic image capturing apparatus that incorporates a stimulable phosphor panel therein.

In order to make the electronic cassette as light and thin as a radiographic image capturing apparatus that incorporates a stimulable phosphor panel therein, it is desirable to reduce the thickness of the panel housing unit as much as possible, and also to construct the radiation conversion panel from lighter components. For example, if a radiation conversion panel of the indirect conversion type comprises a stacked assembly made up of a board, a signal output layer disposed on the board for outputting a radiographic image as an electric signal, a photoelectric transducer layer for converting fluorescence into the electric signal, and a scintillator, then the board may be non-vitrified, i.e., the board may be made of plastic rather than glass, and the signal output layer may be constructed from TFTs (Thin Film Transistors) made of an amorphous oxide semiconductor.

However, since plastic has a greater coefficient of thermal expansion than glass, plastic tends to be deformed under environmental conditions, e.g., temperature, humidity, etc., of the radiation conversion panel.

Japanese Patent No. 2706725 discloses that a thermal strain corrector, which has the same coefficient of thermal expansion as a photoelectric transducer layer, is bonded to a surface of a board disposed oppositely to the photoelectric transducer layer, thereby minimizing deformation (warpage) of the board.

According to the technology disclosed in Japanese Patent No. 2706725, since the thermal strain corrector and the board, which have widely different coefficients of thermal expansion, are bonded to each other, the interface therebetween is stressed due to repeated temperature changes, which tends to cause the assembly to crack or peel. More specifically, since the thermal strain corrector simply is bonded in a planar form to the radiation conversion panel, in a case where the radiation conversion panel is deformed due to temperature changes, the radiation conversion panel is likely to crack or peel. It is difficult to prevent the radiation conversion panel from being deformed due to temperature changes.

Since plastic has a greater coefficient of thermal expansion than glass and tends to be deformed under environmental conditions, e.g., temperature, humidity, etc., of the radiation conversion panel, plastic fails to provide sufficient adhesion between the photoelectric transducer layer and the scintillator of the radiation conversion panel.

Japanese Laid-Open Patent Publication No. 09-054162 discloses that adhesion between a scintillator and a photoelectric transducer layer is achieved by performing adhesive bonding therebetween. Japanese Laid-Open Patent Publication No. 09-257944 reveals that increased adhesion is achieved by depressurizing the cassette.

However, adhesive bonding is problematic in that due to the different coefficients of thermal expansion of various components used in the radiation conversion panel, the bonded surfaces (interfaces) are stressed due to repeated temperature changes, which also tends to bring about cracking or peeling in the radiation conversion panel. Depressurization of the cassette requires an evacuating system including a vacuum pump and other parts, resulting in increased system size and cost.

In an electronic cassette, radiation is applied through a subject to the panel housing unit in order to capture a radiographic image of the subject. If in the electronic cassette, the radiation conversion panel is held closely against an inner wall surface of the panel housing unit without any gap therebetween, then the radiation conversion panel can be brought in close proximity to the subject, thereby reducing image blurs of the radiographic image, and the electronic cassette can be manufactured with a low profile. From the standpoint of reworking (recycling) and maintenance of the radiation conversion panel, the radiation conversion panel should preferably be pressed against and secured to the inner wall surface, rather than being bonded thereto. The panel housing unit should preferably be of an integrally molded seamless structure for preventing ambient light from entering into the panel housing unit, so as to provide a desired light blocking capability.

Japanese Laid-Open Patent Publication No. 2002-311526 discloses that a unit including a radiation conversion panel is movable into and out of a casing along rails that are formed on an inner wall of the casing.

If the panel housing unit is made of CFRP (Carbon-Fiber-Reinforced Plastics) or the like to provide better load resistance and reduced weight, then if the radiation conversion panel is taken into and out of the panel housing unit while the radiation conversion panel is held in contact with the inner wall surface of the panel housing unit, some of the carbon fibers that constitute the CFRP may become broken and frayed, which tends to degrade the quality of the captured radiographic image. Furthermore, if the radiation conversion panel is taken into and out of the panel housing unit while the radiation conversion panel is held in contact with the inner wall surface of the panel housing unit, the surface of the radiation conversion panel, e.g., the surface of the scintillator, is likely to become damaged. In the case where the surface of the radiation conversion panel is damaged, the quality of the captured radiographic image is degraded, and control lines for supplying control signals to read the radiographic image, as well as signal lines for outputting signals representative of the radiographic image to an external circuit, are likely to be cut off.

SUMMARY OF INVENTION

Objects of the Invention

It is a first object of the present invention to keep a radiation conversion panel flat, i.e., to maintain planarity of a radiation conversion panel, while taking into account environmental conditions, e.g., temperature, humidity, etc., of the radiation conversion panel.

A second object of the present invention is to increase adhesion in a radiation conversion panel with a simple structure.

A third object of the present invention is to move a radiation conversion panel into and out of a panel housing unit without coming into contact with an inner wall surface of the panel housing unit, and to increase adhesion between the inner wall surface and the radiation conversion panel with a simple structure.

DESCRIPTION OF THE INVENTION

In order to achieve the first through third objects, a radiographic image capturing apparatus according to the present invention comprises:

a radiation conversion panel for converting radiation into a radiographic image, and an external force applying mechanism for applying an external force to the radiation conversion panel, wherein the external force applying mechanism applies an external force to a peripheral edge of the radiation conversion panel, applies an external force to the radiation conversion panel while being stacked on the radiation conversion panel, or presses the radiation conversion panel against an inner wall surface of a panel housing unit that houses the radiation conversion panel at least during capturing of a radiographic image by applying radiation to the radiation conversion panel.

In order to achieve the first through third objects, a radiographic image capturing system according to the present invention comprises:

a radiographic image capturing apparatus having a radiation conversion panel for converting radiation into a radiographic image, and an external force applying mechanism for applying an external force to the radiation conversion panel; and a control device for controlling the radiographic image capturing apparatus, wherein the external force applying mechanism applies an external force to a peripheral edge of the radiation conversion panel, applies an external force to the radiation conversion panel while being stacked on the radiation conversion panel, or presses the radiation conversion panel against an inner wall surface of a panel housing unit that houses the radiation conversion panel at least during capturing of a radiographic image by applying radiation to the radiation conversion panel.

In order to achieve the first and second objects, there is provided in accordance with the present invention a method of securing a radiation conversion panel in a radiographic image capturing apparatus, comprising:

housing, in a panel housing unit, a radiation conversion panel for converting radiation into a radiographic image; and pressing the radiation conversion panel against an inner wall surface of the panel housing unit with an external force applying mechanism at least during capturing of a radiographic image by applying radiation to the radiation conversion panel.

With the above arrangements, the present invention offers the following advantages.

The peripheral edge of the radiation conversion panel tends to be deformed, i.e., warped, depending on environmental conditions such as temperature and humidity in a panel housing unit that houses the radiation conversion panel therein. According to the present invention, the external force applying mechanism applies an external force to the peripheral edge in order to prevent the peripheral edge from being deformed, i.e., warped, thereby keeping the radiation conversion panel flat. According to the present invention, therefore, it is possible to keep the radiation conversion panel flat, i.e., to maintain planarity of the radiation conversion panel, in view of environmental conditions such as the temperature and humidity in the panel housing unit.

According to the present invention, since the radiation conversion panel is not bonded to other members, but rather, an external force is applied to the peripheral edge of the radiation conversion panel in order to keep the radiation conversion panel flat, the radiation conversion panel is prevented from being deformed and hence from cracking or peeling.

According to the present invention, furthermore, if the radiation conversion panel and the external force applying mechanism are stacked together in an integral combination, then if the radiation conversion panel is deformed, i.e., if the radiation conversion panel is caused to expand or shrink thermally, depending on the environmental conditions, the radiation conversion panel and the external force applying mechanism are deformed integrally together. According to the present invention, while the radiation conversion panel and the external force applying mechanism are allowed to become deformed, the external force applying mechanism applies an external force to the radiation conversion panel depending on the environmental conditions, thereby keeping the radiation conversion panel flat, i.e., maintaining planarity of the radiation conversion panel. As a consequence, the present invention is more effective in avoiding cracking and peeling of the radiation conversion panel caused by deformation of the radiation conversion panel than if other members were simply bonded to the radiation conversion panel similar to the technology disclosed in Japanese Patent No. 2706725.

According to the present invention, furthermore, the external force applying mechanism is used to press the radiation conversion panel against the inner wall surface of the panel housing unit, thereby holding components in the radiation conversion panel closely together in a natural configuration, and also easily and securely positioning the radiation conversion panel. According to the present invention, therefore, the components in the radiation conversion panel are held closely together by a simple structure. Since the radiation conversion panel is securely positioned by pressing the components thereof, the components do not need to be bonded by an adhesive. Accordingly, the radiation conversion panel is prevented from cracking or peeling, and the radiation conversion panel can easily be replaced for providing increased maintainability.

According to the present invention, moreover, at least during capturing of radiographic images by applying radiation, the external force applying mechanism is capable of pressing the radiation conversion panel against the inner wall surface of the panel housing unit. In a case where a radiographic image is not captured and the radiation conversion panel is taken into and out of the panel housing unit, the radiation conversion panel can be taken into and out of the panel housing unit without contact with the inner wall surface. Therefore, in a case where the panel housing unit is made of CFRP or the like, it is possible to prevent carbon fibers of the CFRP from becoming broken and frayed thereby to degrade the quality of the captured radiographic image due to such frayed portions. In addition, it is possible to prevent the radiation conversion panel from becoming damaged by contact with the inner wall surface thereby to degrade the quality of the captured radiographic image, and to prevent control lines and signal lines from being broken by contact of the radiation conversion panel with the inner wall surface.

During capturing of a radiographic image, the external force applying mechanism holds the inner wall surface and the radiation conversion panel closely together in a natural configuration, and the radiation conversion panel is easily and securely positioned with respect to the inner wall surface. As a result, since the inner wall surface and the radiation conversion panel are held very closely together by a simple structure, the load resistance and the shock resistance of the radiographic image capturing apparatus are increased, and the radiation conversion panel is effectively prevented from wobbling. Inasmuch as the radiation conversion panel is easily brought close to the inner wall surface, it is possible to minimize blurring of the radiographic image as well as to reduce the thickness of the radiographic image capturing apparatus.

Since the radiation conversion panel does not need to be bonded to the inner wall surface and can easily be taken into and out of the panel housing unit, reworkability and maintainability of the radiation conversion panel are increased.

Specific structural details and associated advantages of the present invention will be described successively below.

The radiographic image capturing apparatus further comprises an environmental condition detector for detecting an environmental condition in the panel housing unit, and an external force controller for controlling the external force applying mechanism to apply the external force to the peripheral edge or the radiation conversion panel based on the environmental condition detected by the environmental condition detector.

In a case where the peripheral edge of the radiation conversion panel or the radiation conversion panel itself tends to become deformed under an environmental condition in the panel housing unit, an appropriate external force based on the environmental condition is applied to the peripheral edge or to the radiation conversion panel in order to effectively prevent the peripheral edge or the radiation conversion panel from becoming deformed.

The environmental condition detector comprises at least one of a temperature detector for detecting the temperature of the radiation conversion panel and a humidity detector for detecting the humidity in the panel housing unit, and the external force controller controls the external force applying mechanism to apply the external force, which depends on at least one of a temperature change of the radiation conversion panel and a humidity change in the panel housing unit, to the peripheral edge or to the radiation conversion panel based on at least one of the temperature detected by the temperature detector and the humidity detected by the humidity detector.

The peripheral edge of the radiation conversion panel is deformed depending on at least one of a temperature change and a humidity change. Consequently, at least one of the temperature and the humidity is detected, and an appropriate external force depending on at least one of the temperature change and the humidity change, i.e., depending on a deformation of the peripheral edge due to at least one of the temperature change and the humidity change, is applied to the peripheral edge based on the detected temperature or humidity, for thereby effectively preventing the peripheral edge from becoming deformed. In other words, if a deformation, e.g., warpage or elongation, of the peripheral edge, which would be caused by at least one of the temperature change and the humidity change, is grasped in advance, then an external force for eliminating the deformation may be applied continuously to the peripheral edge to thereby keep the radiation conversion panel flat.

The entire radiation conversion panel also is deformed depending on at least one of a temperature change and a humidity change. Consequently, an appropriate external force depending on at least one of the temperature change and the humidity change, i.e., depending on a deformation of the radiation conversion panel due to at least one of the temperature change and the humidity change, is applied to the radiation conversion panel based on the temperature or humidity, for thereby effectively maintaining planarity of the radiation conversion panel. In other words, if a deformation, e.g., warpage or elongation, of the radiation conversion panel, which would be caused by at least one of the temperature change and the humidity change, is grasped in advance, then an external force depending on the deformation may be continuously applied to the radiation conversion panel to thereby keep the radiation conversion panel flat.

The radiation conversion panel has a board and a radiation conversion layer mounted on the board for converting radiation into an electric signal representative of the radiographic image. Further, the external force applying mechanism is disposed on the peripheral edge of the board, or on at least one of a bottom surface of the board and an upper surface of the radiation conversion layer.

As at least one of the temperature and the humidity of the radiation conversion panel changes, the peripheral edge of the board becomes warped in the thicknesswise direction of the board. Therefore, the external force applying mechanism applies an external force to the peripheral edge in order to prevent the peripheral edge from becoming warped, thereby keeping the radiation conversion panel including the board thereof flat as a whole. Application of the external force to the peripheral edge with the external force applying mechanism, which is disposed on at least one of the bottom surface of the board and the upper surface of the radiation conversion layer, is effective to keep the radiation conversion panel flat in its entirety.

The board comprises a substantially rectangular flexible board, which is deformable depending on at least one of the temperature change and the humidity change, and the board has four sides, at least one of which has an external connector for inputting a signal to or outputting a signal from the radiation conversion layer, and the external force applying mechanism applies the external force to at least the side of the board that has the external connector.

If the board is made of plastic, then if the board tends to become warped in the thicknesswise direction thereof depending on at least one of the temperature change and the humidity change, the external force is applied to the side of the board that has the external connector, thereby keeping the board flat and preventing the external connector from peeling off from the board.

The board is flexible and deformable depending on at least one of the temperature change and the humidity change, and the external force applying mechanism has a planar shape along the board or the radiation conversion layer. Further, the external force applying mechanism is shrinkable along the thicknesswise direction of the board or the radiation conversion layer, and is expandable along the planar direction of the board or the radiation conversion layer, or is expandable along the thicknesswise direction and is shrinkable along the planar direction, depending on at least one of the temperature change and the humidity change.

By deforming the external force applying mechanism depending on at least one of the temperature change and the humidity change, i.e., by shrinking or expanding the external force applying mechanism in the thicknesswise direction, or expanding or shrinking the external force applying mechanism in the planar direction, the external force applying mechanism easily applies the external force to the radiation conversion panel. Therefore, planarity of the entire radiation conversion panel can be maintained by applying the external force to either the board or the radiation conversion layer, or to both the board and the radiation conversion layer. For example, if the board is made of plastic, then if the board tends to become warped in the thicknesswise direction depending on at least one of the temperature change and the humidity change, the external force is applied to the plastic board, thereby maintaining planarity of the radiation conversion panel including the plastic board.

It is desirable that the panel housing unit houses therein the radiation conversion panel and the external force applying mechanism, and that the panel housing unit is permeable to radiation. The external force applying mechanism has one end fixed to an inner wall surface of the panel housing unit, and the external force applying mechanism has another end held in contact with or fixed to the peripheral edge of the radiation conversion panel.

The external force can thus be applied reliably to the radiation conversion panel, which is housed in the panel housing unit.

The radiographic image capturing apparatus may further comprise a controller for controlling the radiation conversion panel and the external force applying mechanism. The panel housing unit may house therein the radiation conversion panel and the external force applying mechanism, and is permeable to radiation. The controller may be housed in the panel housing unit or housed in a control unit that is joined to the panel housing unit.

The external force applying mechanism is bonded by a dismantlable adhesive to the peripheral edge of the radiation conversion panel, the radiation conversion panel, or the panel housing unit.

Consequently, the external force applying mechanism can easily be replaced if functions thereof are lowered due to being irradiated with radiation.

The external force applying mechanism may comprise an actuator made of a polymeric material, an actuator made of a shape memory alloy, or an actuator made of a piezoelectric material.

The radiation conversion panel may include a scintillator for converting radiation into fluorescence, and a photoelectric transducer layer for converting the fluorescence into a radiographic image. The scintillator and the photoelectric transducer layer may be stacked along a direction in which radiation is applied, and the external force applying mechanism may comprise a pressing mechanism for pressing a side of the radiation conversion panel close to the scintillator, or for pressing a side of the radiation conversion panel close to the photoelectric transducer layer, against the inner wall surface.

Thus, the scintillator and the photoelectric transducer layer can be held very closely together, and the scintillator or the photoelectric transducer layer and the inner wall can be held very closely together as well.

The panel housing unit includes a substantially rectangular casing which houses therein the radiation conversion panel and the external force applying mechanism, and which is permeable to radiation. The pressing mechanism presses the side of the radiation conversion panel close to the scintillator, or presses the side of the radiation conversion panel close to the photoelectric transducer layer, against an inner wall surface of the substantially rectangular casing beneath an image capturing surface thereof, which is irradiated with radiation.

Inasmuch as the side of the radiation conversion panel, which is close to the scintillator or the photoelectric transducer layer, is pressed against the inner wall surface beneath the image capturing surface, the distance between the subject and the scintillator or the photoelectric transducer layer is reduced.

The pressing mechanism should desirably be arranged in the following manner.

(1) The pressing mechanism comprises a scintillator housing bag capable of being filled with the scintillator in the form of a liquid. The scintillator housing bag is filled with the scintillator to press the side of the radiation conversion panel close to the photoelectric transducer layer against the inner wall surface beneath the image capturing surface.

Therefore, the scintillator, which is in the form of a liquid, and the photoelectric transducer layer can be held closely together by the scintillator housing bag, and can reliably be brought toward the inner wall surface beneath the image capturing surface. Since the scintillator housing bag also functions as a shock dampening member for the panel housing unit, load resistance and shock resistance of the panel housing unit can be increased.

(2) The pressing mechanism comprises a pressing material housing bag, which is capable of being filled with a fluid or a foamed material, and the pressing material housing bag is filled with the fluid or the foamed material to press the radiation conversion panel against the inner wall surface beneath the image capturing surface.

In this case as well, the scintillator and the photoelectric transducer layer can be held closely together by the scintillator housing bag, and can reliably be brought toward the inner wall surface beneath the image capturing surface. Since the pressing material housing bag also functions as a shock dampening member for the panel housing unit, load resistance and shock resistance of the panel housing unit are increased.

(3) The casing houses therein a base table, and the pressing mechanism mechanically moves the base table toward the image capturing surface to press the radiation conversion panel against the inner wall surface beneath the image capturing surface.

Accordingly, the side of the radiation conversion panel close to the scintillator or the side of the radiation conversion panel close to the photoelectric transducer layer is reliably and easily held closely against the inner wall surface beneath the image capturing surface.

The radiation conversion panel may comprise an integral assembly of the scintillator and the photoelectric transducer layer, which are stacked along the direction in which radiation is applied, and the pressing mechanism may move the radiation conversion panel along the direction in which radiation is applied so as to press the radiation conversion panel against the inner wall surface beneath the image capturing surface, or to space the radiation conversion panel from the inner wall surface beneath the image capturing surface.

Therefore, if the inner wall surface becomes damaged, the casing can easily be replaced.

The radiation conversion panel may comprise a separable assembly made up of the scintillator and the photoelectric transducer layer, which are stacked along the direction in which radiation is applied. One of the scintillator and the photoelectric transducer layer may be fixed to the inner wall surface beneath the image capturing surface, and the pressing mechanism may move the other of the scintillator and the photoelectric transducer layer along the direction in which radiation is applied, so as to press the other of the scintillator and the photoelectric transducer layer against, or to space the other of the scintillator and the photoelectric transducer layer from, the one of the scintillator and the photoelectric transducer layer, which is fixed to the inner wall surface beneath the image capturing surface.

If either one of the scintillator and the photoelectric transducer layer needs to be replaced, the scintillator or the photoelectric transducer layer can easily be replaced.

The radiographic image capturing apparatus may further comprise an acceleration detector for detecting an acceleration of the radiographic image capturing apparatus. The pressing mechanism releases the radiation conversion panel from being pressed against the inner wall surface based on the acceleration detected by the acceleration detector.

If the acceleration detector detects an acceleration at which the radiographic image capturing apparatus falls, or an acceleration caused by a shock from an external source, then the radiation conversion panel is released from being pressed against the inner wall surface. The radiation conversion panel, i.e., the scintillator and the photoelectric transducer layer, is prevented from becoming damaged due to falling of the radiation conversion panel, or due to shocks applied to the radiation conversion panel. In a case where the radiation conversion panel, the scintillator, the photoelectric transducer layer, and the casing need to be replaced, such components can easily be replaced by releasing the radiation conversion panel from being pressed against the inner wall surface.

The external force applying mechanism changes into a state capable of releasing the radiation conversion panel from being pressed against the inner wall surface, at least at times that the radiation conversion panel is taken into and out of the panel housing unit. Therefore, if the radiation conversion panel is taken into and out of the panel housing unit, the radiation conversion panel can easily be taken into and out of the panel housing unit while reliably avoiding contact with the inner wall surface.

Structural details and associated advantages according to the present invention have been described above. More specific structural details and advantages thereof according to the present invention (structural details and advantages according to first through fourth inventions) will be described in detail below.

Description of the First Invention

The first invention relates to a radiographic image capturing apparatus and a radiographic image capturing system, which include the radiation conversion panel described above, as well as the aforementioned external force applying mechanism, which applies an external force to the peripheral edge of the radiation conversion panel.

According to the first invention, external connectors are mounted on each of adjacent two of the four sides of the board. One of the external connectors supplies a control signal for reading the electric signal to the radiation conversion layer, whereas the other external connector outputs an electric signal that is read from the radiation conversion layer in response to the control signal supplied thereto.

The external force may be applied to each of the two sides. Thus, since the external connectors are reliably prevented from becoming peeled off from the board, the control signal can be supplied, and electric signals can be output regardless of at least one of the temperature change and the humidity change.

The external force may also be applied to the external connectors as well as the sides on which the external connectors are mounted, for thereby preventing the sides from becoming warped, and for reliably preventing the external connectors from becoming peeled off from the sides.

In a case where the external connectors are joined to the sides by thermocompression, for example, the external connectors may possibly become peeled off from the sides if external forces are applied to the external connectors. In this case, the external force may be applied from the external force applying mechanism to the sides on which the external connectors are mounted, but not to the external connectors themselves.

Protruding bosses may be disposed on the sides on which the external connectors are mounted, but not on the external connectors. External force may be applied through the bosses from the external force applying mechanism to the sides on which the external connectors are mounted. In this manner, the external connectors are effectively prevented from peeling off from the sides.

The external force applying mechanism may apply an external force to sides on which the external connectors are mounted, and to sides that confront the sides on which the external connectors are mounted. Alternatively, the external force applying mechanism may apply the external force to the four sides of the board. By thus applying the external force to plural sides of the board, the peripheral edge of the board is reliably prevented from becoming warped, thereby keeping the radiation conversion panel including the board flat in its entirety.

If the panel housing unit comprises a substantially rectangular casing, then the external force applying mechanism may apply an external force to the radiation conversion panel by way of either one of the arrangements (1) and (2) below.

(1) The external force applying mechanism has one end fixed to an upper surface of the casing, and another end of the external force applying mechanism is held in contact with the peripheral edge of the radiation conversion panel. The external force applying mechanism applies the external force in a direction from the upper surface toward the peripheral edge. In this case, the external force applying mechanism applies the external force to the peripheral edge in a downward direction.

(2) The external force applying mechanism has one end fixed to a side surface of the casing, and another end of the external force applying mechanism is fixed to the peripheral edge of the radiation conversion panel. The external force applying mechanism applies the external force in a direction from the peripheral edge toward the side surface. In this case, the external force applying mechanism applies the external force to the peripheral edge in a horizontal direction.

Either arrangement (1) or arrangement (2) makes it possible to apply an external force to the peripheral edge to reliably keep the radiation conversion panel flat.

The polymeric material constituting the actuator may be a polymeric gel, a polymeric electrolytic gel, a non-ionic polymeric gel, or an electrically conductive polymer. The piezoelectric material constituting the actuator may be crystal, Rochelle salt, barium titanate, or lead zirconate titanate.

Description of the Second Invention

The second invention relates to a radiographic image capturing apparatus and a radiographic image capturing system, which include the radiation conversion panel described above, and the external force applying mechanism described above, which is stacked on the radiation conversion panel and applies an external force to the radiation conversion panel.

According to the second invention, in order to apply an external force from the external force applying mechanism to the radiation conversion panel, the external force applying mechanism is deformed depending on at least one of the temperature change and the humidity change. The following arrangement may be employed.

A first planar external force applying mechanism is disposed on a bottom surface of the board, and a second planar external force applying mechanism is disposed on an upper surface of the radiation conversion layer. The upper and side surfaces of the radiation conversion layer, which is disposed on the board, are covered with a protective film. The second external force applying mechanism may be disposed on the protective film in close proximity to the upper surface of the radiation conversion layer.

With the radiation conversion panel sandwiched between the first external force applying mechanism and the second external force applying mechanism, the external force applying mechanisms apply respective external forces to the radiation conversion panel to thereby reliably maintain planarity of the radiation conversion panel. If the board, the protective film, and the radiation conversion layer are thermally expanded by different degrees, then the external force applied to the board by the first external force applying mechanism and the external force applied to the protective film by the second external force applying mechanism may be adjusted to different magnitudes and different directions, depending on the different degrees to which the board, the protective film, and the radiation conversion layer are thermally expanded.

The external force applying mechanism may also include a third planar external force applying mechanism and a fourth planar external force applying mechanism that are stacked on a bottom surface of the board. The third external force applying mechanism shrinks and expands in directions along the planar direction, whereas the fourth external force applying mechanism shrinks and expands in directions that differ from the directions in which the third external force applying mechanism shrinks and expands along the planar direction. If the board thermally expands to a degree greater than other portions of the radiation conversion panel, e.g., if the board is made of plastic, then the third external force applying mechanism and the fourth external force applying mechanism are caused to shrink and expand depending on the amount and direction of deformation of the board, thereby keeping the board flat efficiently.

The external force applying mechanism may further include a fifth external force applying mechanism, which is disposed on a bottom surface of the board in alignment with the radiation conversion layer as viewed in plan, and at least one sixth external force applying mechanism, which is disposed in a location out of alignment with the radiation conversion layer. Since the radiation conversion layer is stacked on the board, the board is deformed to a greater degree at the peripheral edges thereof than on the portion of the board where the radiation conversion layer is disposed. The fifth external force applying mechanism and the sixth external force applying mechanism apply respective external forces to the board of different magnitudes and in different directions depending on the deformation of the board, to thereby keep the board flat efficiently.

If the controller is housed in the panel housing unit, then the controller, the external force applying mechanism, and the radiation conversion panel may be stacked successively in the panel housing unit.

The external force applying mechanism may be disposed in the panel housing unit, or may be constructed as a bottom surface of the panel housing unit, or as respective bottom surfaces of the panel housing unit and the control unit.

If the external force applying mechanism is constructed as a bottom surface of the panel housing unit, or as respective bottom surfaces of the panel housing unit and the control unit, then a plurality of external force applying mechanisms may be arranged in a direction from the panel housing unit toward the control unit.

If, before radiation is applied to the subject, the panel housing unit is inserted between a subject and an image capturing base on which the subject is placed, the external force applying mechanism on a distal end of the panel housing unit stops applying the external force, whereas the other external force applying mechanisms start to apply the external forces, or alternatively, the external force applying mechanisms apply the external forces in order to curve the panel housing unit. After the panel housing unit has been inserted between the subject and the image capturing base, the external force applying mechanisms all apply external forces in order to keep the panel housing unit flat, or to keep the panel housing unit and the control unit flat.

Since the panel housing unit can be inserted smoothly between the subject and the image capturing base, a preparatory process for capturing radiographic images can be carried out efficiently.

Description of the Third Invention

The third invention is concerned with a radiographic image capturing apparatus and a radiographic image capturing system, which include the aforementioned radiation conversion panel and the above-described external force applying mechanism, which applies an external force to the inner wall surface of the panel housing unit. The third invention also concerns a method of securing the radiation conversion panel in the radiographic image capturing apparatus.

According to the third invention, the casing may house therein a base table on which the radiation conversion panel is disposed. A portion of the base table, which faces toward the inner wall surface beneath the image capturing surface, may be constructed as a pressing material housing bag. The radiation conversion panel may be disposed beneath the image capturing surface between the pressing material housing bag and the inner wall surface. Since the base table is constructed as the pressing material housing bag, the scintillator and the photoelectric transducer layer can be held closely together, and load and shock resistance of the panel housing unit can efficiently be increased without the need for increasing the number of parts.

In order for the pressing mechanism to mechanically move the base table toward the image capturing surface, cams, a link mechanism, or springs may be disposed as a pressing mechanism between the base table and the bottom surface of the casing. In this manner, the scintillator and the photoelectric transducer layer can be held closely together by a simple structure.

If each of the scintillator housing bag and the pressing material housing bag are in the form of a resin bag, then the housing bags expand upon being filled with the liquid scintillator, the fluid, or the foamed material, thereby reliably and securely positioning the radiation conversion panel. Upon removal of the liquid scintillator, the fluid, or the foamed material from the bag, the thickness of the bag along the direction in which the bag presses the radiation conversion panel is reduced, thereby releasing the radiation conversion panel from the positioned state. If the bag is filled to securely position the radiation conversion panel only at times that radiographic images are captured, then the radiation conversion panel including the scintillator, which may be expected to deteriorate due to aging by way of exposure to radiation, can easily be replaced, thereby increasing maintainability.

The controller that controls the radiation conversion panel may be disposed between the base table and the bottom surface of the casing, and the base table may be made of a material for blocking radiation, or a radiation blocking member may be disposed on a portion of the base table that faces toward the controller. Thus, the controller can be protected against deterioration caused by radiation.

The scintillator and the photoelectric transducer layer may have opposite sides thereof held in contact with side wall surfaces of the casing. In the case that the scintillator and the photoelectric transducer layer are pressed against the inner wall surface beneath the image capturing surface, the scintillator and the photoelectric transducer layer are held very closely together.

Description of the Fourth Invention

The fourth invention is concerned with a radiographic image capturing apparatus and a radiographic image capturing system, which include the radiation conversion panel as described above. Further, the fourth invention relates to an external force applying mechanism, which as described above, presses the radiation conversion panel against the inner wall surface of the panel housing unit at least during times that radiation is applied to capture a radiographic image. The fourth invention also concerns a method of securing the radiation conversion panel in the radiographic image capturing apparatus.

According to the fourth invention, the arrangement of the third invention is applied in order to press the radiation conversion panel against the inner wall surface at least during times that a radiographic image is captured. Therefore, the advantages of the third invention can easily be attained. Further, according to the fourth invention, in the casing, the base table may be disposed on the bottom surface of the casing, and the pressing material housing bag and the radiation conversion panel may be stacked successively on the base table.

Main Advantages Accruing from the First through Fourth Inventions

According to the first invention, as described above, the external force applying mechanism applies an external force to the peripheral edge of the radiation conversion panel in order to prevent the peripheral edge from becoming deformed, i.e., warped, depending on at least one of a temperature change and a humidity change, i.e., a change in environmental conditions, thereby keeping the radiation conversion panel flat. According to the first invention, therefore, the radiation conversion panel is kept flat, i.e., planarity of the radiation conversion panel is maintained, in view of changes in environmental conditions.

According to the first invention, since the radiation conversion panel is not bonded to other members, but rather an external force is applied to the peripheral edge of the radiation conversion panel in order to keep the radiation conversion panel flat, the radiation conversion panel is prevented from becoming deformed and hence from cracking or peeling.

According to the second invention, the radiation conversion panel and the external force applying mechanism are stacked together in integral combination. If the radiation conversion panel becomes deformed due to a change in environmental conditions, the radiation conversion panel and the external force applying mechanism are deformed integrally together. According to the second invention, while the radiation conversion panel and the external force applying mechanism are allowed to deform, the external force applying mechanism applies an external force depending on the environmental conditions in order to change the radiation conversion panel, thereby keeping the radiation conversion panel flat, i.e., to maintain planarity of the radiation conversion panel. As a consequence, the second invention is more effective in preventing cracking and peeling of the radiation conversion panel due to deformation thereof than if other members were simply bonded to the radiation conversion panel according to the technology disclosed in Japanese Patent No. 2706725.

According to the third invention, the external force applying mechanism is used to press the radiation conversion panel against the inner wall surface of the panel housing unit, thereby holding components in the radiation conversion panel closely together in a natural configuration, and also easily and securely positioning the radiation conversion panel. According to the third invention, therefore, the components in the radiation conversion panel can be held closely together by a simple structure. Since the radiation conversion panel is securely positioned by pressing the components thereof, the components do not need to be bonded by an adhesive. Thus, the radiation conversion panel is prevented from cracking or peeling, and can easily be replaced for enabling increased maintainability.

According to the fourth invention, at least during capturing of a radiographic image by applying radiation, the external force applying mechanism is capable of pressing the radiation conversion panel against the inner wall surface of the panel housing unit. In a case where a radiographic image is not being captured and the radiation conversion panel is taken into and out of the panel housing unit, the radiation conversion panel can be taken into and out of the panel housing unit without contact with the inner wall surface. Therefore, in a case where the panel housing unit is made of CFRP or the like, it is possible to prevent carbon fibers of the CFRP from becoming broken and frayed thereby to degrade the quality of the captured radiographic image due to such frayed portions. Further, it is possible to prevent the radiation conversion panel from becoming damaged by contact with the inner wall surface thereby to degrade the quality of the captured radiographic images. In addition, control lines and signal lines can be prevented from breaking by contact of the radiation conversion panel with the inner wall surface.

During capturing of a radiographic image, the external force applying mechanism holds the inner wall surface and the radiation conversion panel closely together in a natural configuration, and the radiation conversion panel is easily and securely positioned with respect to the inner wall surface. As a result, since the inner wall surface and the radiation conversion panel are held very closely together by a simple structure, the load resistance and the shock resistance of the radiographic image capturing apparatus are increased, and the radiation conversion panel is effectively prevented from wobbling. Inasmuch as the radiation conversion panel is easily brought in close proximity to the inner wall surface, it is possible to minimize blurring of the radiographic image and to reduce the thickness of the radiographic image capturing apparatus.

Since the radiation conversion panel does not need to be bonded to the inner wall surface and can easily be taken into and out of the panel housing unit, reworkability and maintainability of the radiation conversion panel are increased.

BRIEF DESCRIPTION OF DRAWINGS

FIGS. 15A and 15B are views schematically showing the manner in which the external force applying unit of the cassette shown in FIG. 14 applies an external force to a peripheral portion of a board;

FIG. 16 is a plan view showing an internal arrangement of a cassette according to a third modification;

FIG. 56 is a plan view, partially cut away, of a cassette according to a seventh embodiment of the present invention;

FIG. 73 is a plan view, partially cut away, of the cassette shown in FIG. 70;

FIGS. 79A and 79B are cross-sectional views of a cassette according to a seventeenth modification;

DESCRIPTION OF EMBODIMENTS

Radiographic image capturing apparatus and radiographic image capturing systems according to preferred embodiments of the present invention, in relation to a method of securing a radiation conversion panel in a radiographic image capturing apparatus, will be described in detail below with reference to FIGS. 1 through 92B.

1. Description of First Embodiment:

A radiographic image capturing system 10A according to a first embodiment of the present invention will be described below with reference to FIGS. 1 through 20.

<Arrangement of the First Embodiment>

Figure 1:
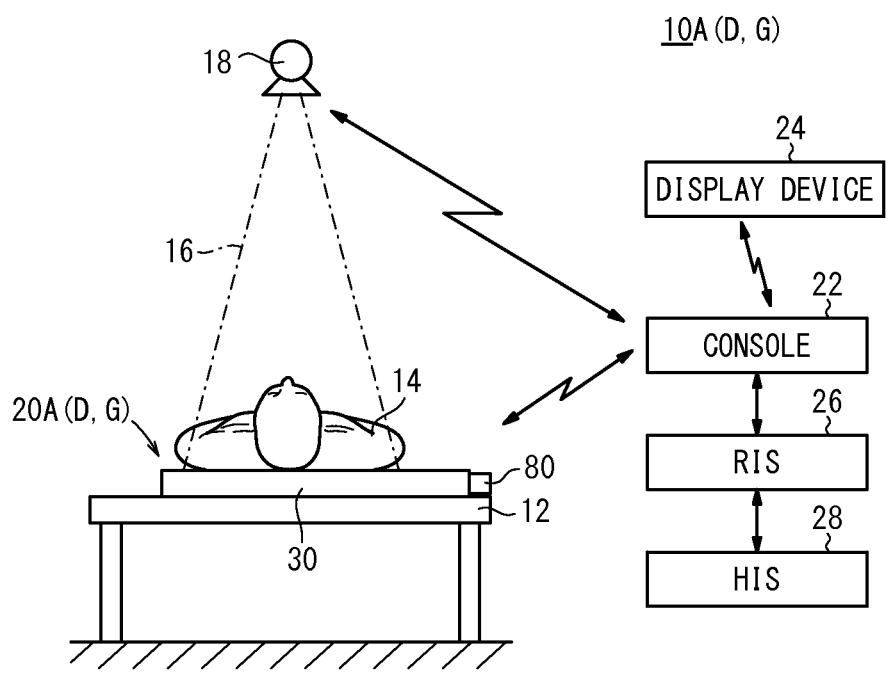
FIG. 1 is a schematic view of a radiographic image capturing system incorporating a cassette according to a first embodiment of the present invention.
Figure 2:
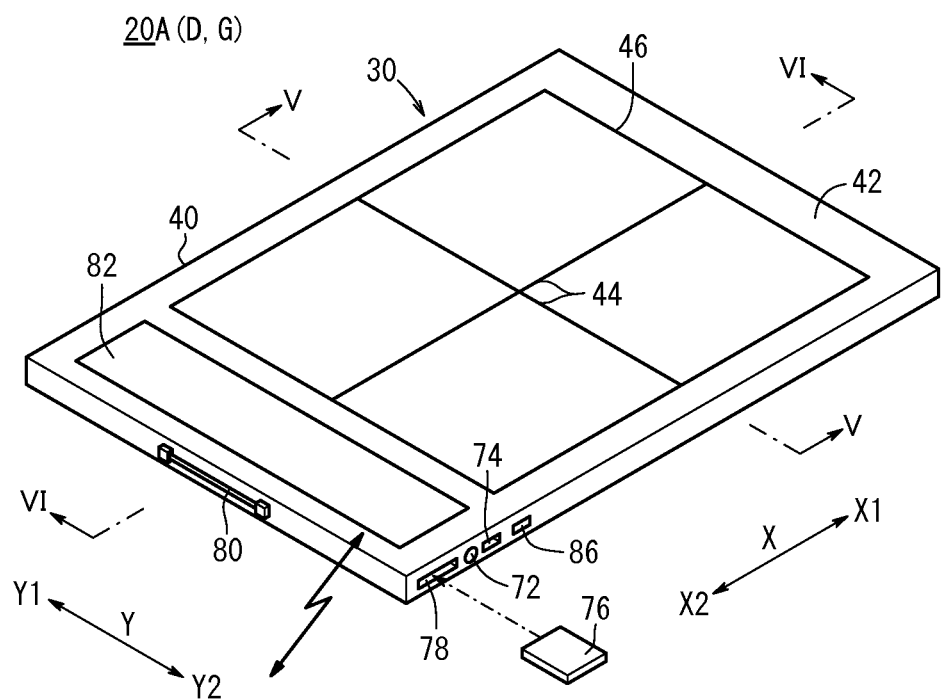
FIG. 2 is a perspective view of the cassette shown in FIG. 1.

As shown in FIG. 1, the radiographic image capturing system 10A has a radiation source 18 for applying radiation 16 having a dose according to image capturing conditions to a subject 14, such as a patient or the like lying on an image capturing base 12 such as a bed or the like, an electronic cassette (radiographic image capturing apparatus) 20A for detecting radiation 16 that has passed through the subject 14 and converting the detected radiation 16 into a radiographic image, a console (control device) 22 for controlling the radiation source 18 and the electronic cassette 20A, and a display device 24 for displaying the radiographic image.

The console 22, the radiation source 18, the electronic cassette 20A, and the display device 24 send signals to and receive signals from each other via UWB (Ultra Wide Band) communications, a wireless LAN (Local Area Network) communications according to standards such as IEEE 802.11.a/g/n, or millimeter-wave communications. Alternatively, signals may be sent and received between the components via wired communications using cables.

The console 22 is connected to a radiology information system (RIS) 26, which generally manages radiographic images and other information that are handled in the radiological department of a hospital. The RIS 26 is connected to a hospital information system (HIS) 28, not shown, which generally manages medical information in the hospital.

The electronic cassette 20A is a portable electronic cassette including a panel housing unit 30 disposed between the image capturing base 12 and the subject 14.

As shown in FIGS. 2 through 6, the panel housing unit 30 has a substantially rectangular casing 40 made of a material permeable to radiation 16. The casing 40 has an upper surface on which a subject 14 lies, and which serves as an image capturing surface (irradiated surface) 42 that is irradiated with radiation 16. The casing 40 has guide lines 44 disposed centrally on the image capturing surface 42, which serve as a reference for an image capturing position for the subject 14. The guide lines 44 provide an outer frame, which defines an image capturing field 46 indicative of an area that can be irradiated with radiation 16. The guide lines 44 include two crisscross guide lines crossing each other at a central position, which serves as a central position of the image capturing field 46.

The image capturing surface 42 includes a display unit 82 for displaying various items of information disposed outside the image capturing field 46 at an end in the direction of the arrow X2. The casing 40 has a handle 80 mounted on a side surface facing in the direction of the arrow X2. The handle 80 is gripped by a doctor or radiological technician. The casing 40 also has, on a side surface facing in the direction of the arrow Y2, an AC adapter input terminal 72 for charging a power supply 52 from an external power supply 52, a USB (Universal Serial Bus) terminal 74 as an interface means for sending information to and receiving information from an external device, a card slot 78 for receiving a memory card 76 such as a PC card or the like, and a power supply switch 86 for the electronic cassette 20A.

As shown in FIGS. 3 through 6, the casing 40 has a bottom wall on which there are disposed a cassette controller 50 for controlling the electronic cassette 20A as a whole, a power supply 52 such as a battery or the like for supplying electric power to various components in the electronic cassette 20A, and a communication unit 54 for sending signals to and receiving signals from the console 22 through a wireless communication link. The casing 40 houses therein a base table 190 covering the cassette controller 50, the power supply 52, and the communication unit 54. The base table 190 has a ceiling on which there is mounted a shield plate 192 such as a lead plate or the like for blocking radiation 16. The shield plate 192 faces toward the cassette controller 50, the power supply 52, and the communication unit 54.

A radiation conversion panel 92 for detecting radiation 16 that has passed through the subject 14 is placed on the base table 190 and disposed between the image capturing surface 42 and the base table 190 in the casing 40.

The radiation conversion panel 92 may comprise an indirect conversion type of radiation conversion panel including a scintillator for converting radiation 16 having passed through the subject 14 into fluorescence such as visible light, ultraviolet radiation, or the like, and solid-state detectors (hereinafter also referred to as pixels) for converting the fluorescence into an electric signal. Alternatively, the radiation conversion panel 92 may comprise a direct conversion type of radiation conversion panel comprising solid-state detectors made of amorphous selenium (a-Se) or the like for converting the dose of radiation 16 directly into an electric signal. The solid-state detectors used in the indirect conversion type radiation conversion panel 92 may be solid-state detectors made of an amorphous oxide semiconductor such as IGZO(InGaZnOx), for example, having an ultraviolet sensitivity range for converting ultraviolet fluorescence (ultraviolet radiation) emitted from the scintillator into an electric signal, or solid-state detectors made of an organic photoconductor (OPC) material for converting visible fluorescence (visible light) emitted from the scintillator into an electric signal. Details of the scintillator and the solid-state detectors will be described later.

According to the first embodiment, the radiation conversion panel 92 comprises an indirect conversion type of radiation conversion panel.

Figure 5:
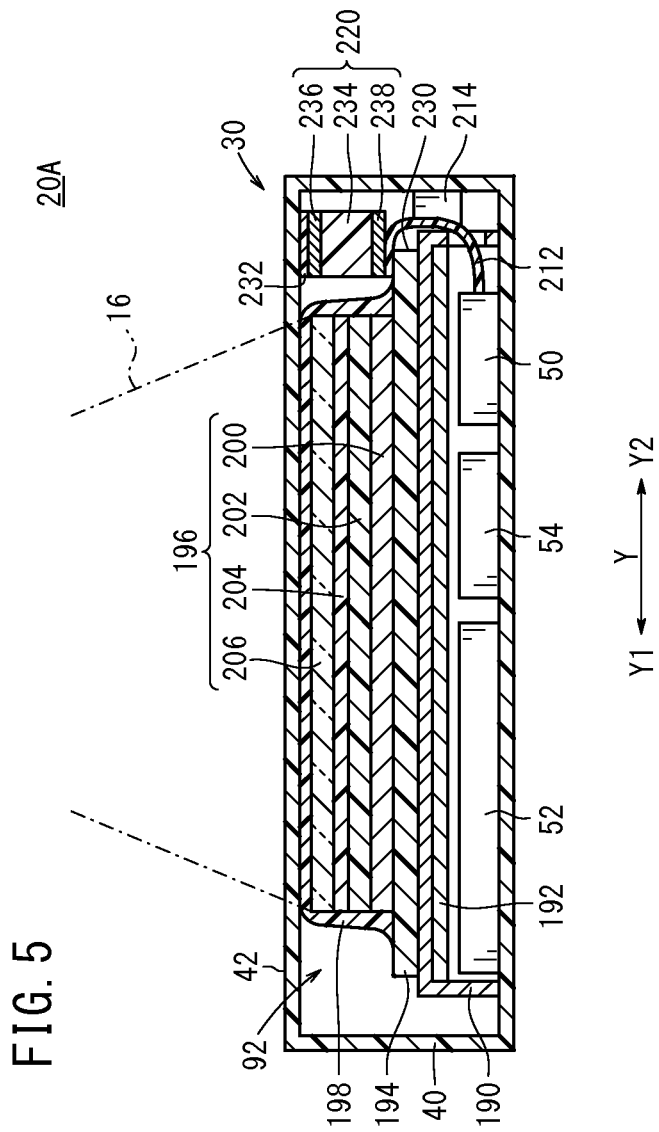
FIG. 5 is a cross-sectional view taken along line V-V of FIG. 2.
Figure 6:
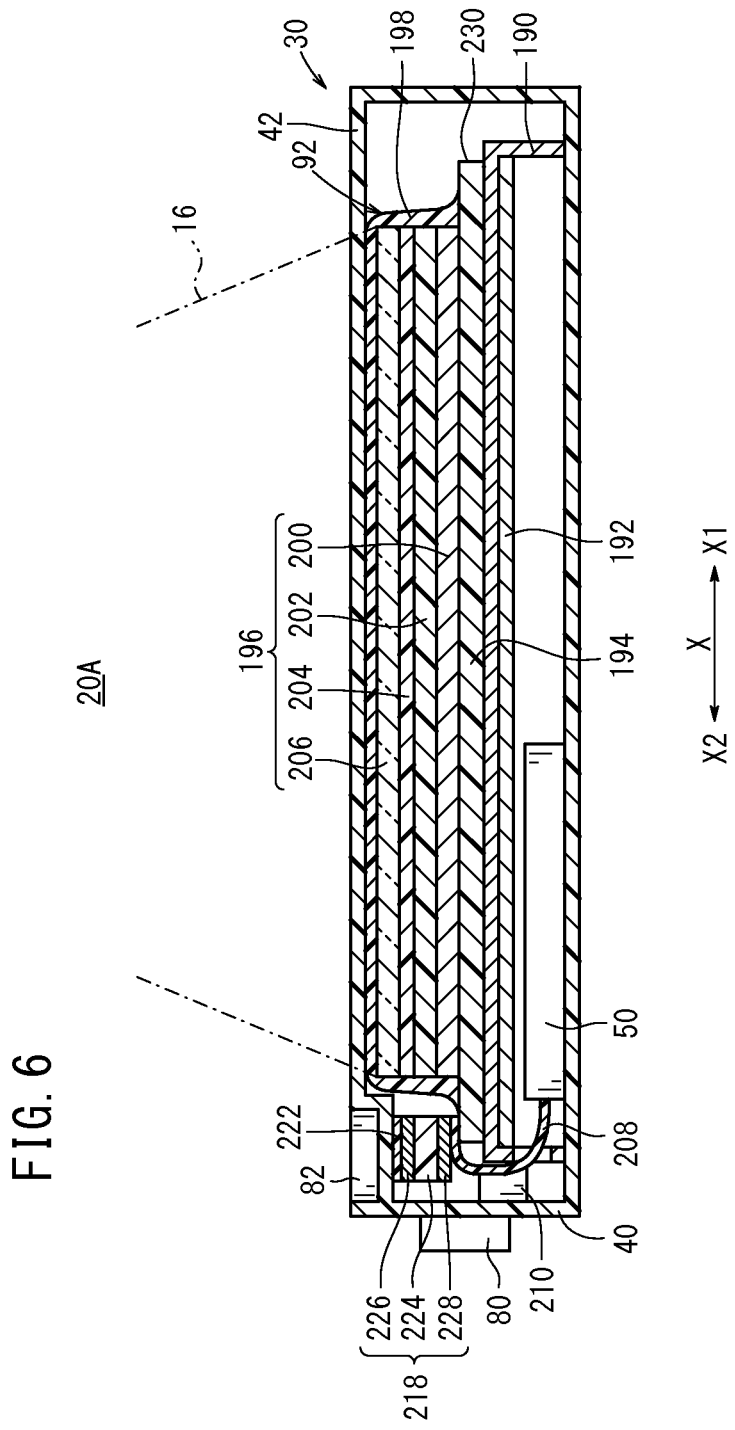
FIG. 6 is a cross-sectional view taken along line VI-VI of FIG. 2.

As shown in FIGS. 5 and 6, the radiation conversion panel 92 comprises a board 194 mounted on the base table 190, a radiation conversion layer 196 mounted on the board 194 for converting radiation 16 into an electric signal representative of a radiographic image, and a protective film 198 covering the side and upper surfaces of the radiation conversion layer 196 for protecting the radiation conversion layer 196 from humidity or the like.

The board 194 comprises a substantially rectangular flexible board, which is made of plastic for reducing the overall weight of the electronic cassette 20A.

The radiation conversion layer 196, which has substantially the same area as the image capturing field 46 as viewed in plan, includes a signal output layer 200 disposed on the board 194, a photoelectric transducer layer 202 deposited on the signal output layer 200, and a scintillator 206 bonded to the photoelectric transducer layer 202 through an adhesive layer 204.

The scintillator 206 is made of columnar crystals of CsI or the like, which are arranged perpendicularly to the board 194. The scintillator 206 converts radiation 16 into fluorescence. More specifically, the scintillator 206, which is made of CsI, converts radiation 16 into visible light. The adhesive layer 204 is made of a material permeable to such fluorescence. The adhesive layer 204, which bonds the photoelectric transducer layer 202 close to the board 194 and the scintillator 206 to each other, prevents dust from entering between the photoelectric transducer layer 202 and the scintillator 206, and also prevents the photoelectric transducer layer 202 and the scintillator 206 from becoming positionally displaced.

The photoelectric transducer layer 202, which includes pixels made of an amorphous oxide semiconductor, e.g., IGZO or OPC, converts the fluorescence into electric signals. The signal output layer 200 comprises an array of TFTs (Thin Film Transistors) fabricated from an amorphous oxide semiconductor, e.g., IGZO, according to a room-temperature process on the board 194. The signal output layer 200 reads the electric signals from the photoelectric transducer layer 202 and outputs the read electric signals.

A plurality of flexible boards (external connectors) 208 arranged at spaced intervals along the direction of the arrow Y are connected at respective ends by thermocompression bonding or the like to a side surface, i.e., a peripheral edge 230, of the board 194, which faces in the direction of the arrow X2. The other ends of the flexible boards 208 are connected to the cassette controller 50. Drive circuits 210 are combined respectively with the flexible boards 208. A plurality of flexible boards (external connectors) 212 arranged at spaced intervals along the direction of the arrow X are connected at respective ends by thermocompression bonding or the like to a side surface, i.e., a peripheral edge 230, of the board 194, which faces in the direction of the arrow Y2. Other ends of the flexible boards 212 are connected to the cassette controller 50. Reading circuits 214 are combined respectively with the flexible boards 212.

The cassette controller 50 sends signals to and receives signals from the drive circuits 210, the reading circuits 214, and the radiation conversion layer 196 through the flexible boards 208, 212. The power supply 52 supplies electric power to the cassette controller 50 and the communication unit 54 in the casing 40, and also supplies electric power to the drive circuits 210, the reading circuits 214, and the radiation conversion layer 196 through the flexible boards 208, 212. Regardless of whether or not the power supply switch 86 has been turned on by the doctor or radiological technician, the power supply 52 supplies electric power to the cassette controller 50 and to temperature sensors (temperature detectors, environmental condition detectors) 216 disposed in the respective four corners of the board 194.

In FIGS. 5 and 6, the size of some of the components in the casing 40 is shown as exaggerated, and the structure of the radiation conversion panel 92 is shown schematically for illustrative purposes.

As described above, the board 194 is made of flexible plastic and is mounted on the base table 190. The signal output layer 200 of the radiation conversion layer 196 is made of an amorphous oxide semiconductor, and the photoelectric transducer layer 202 is made of an amorphous oxide semiconductor or OPC. Therefore, the coefficient of thermal expansion of the board 194, which is on the order of $10^{-5}/°$ C., is much greater than the coefficients of thermal expansion of the signal output layer 200 and the photoelectric transducer layer 202, which are on the order of $10^{-6}/°$ C.

At times that the electronic cassette 20A is in use, the photoelectric transducer layer 202 converts fluorescence (light in the ultraviolet or visible range), which is converted from radiation 16 by the scintillator 206, into an electric signal, and the signal output layer 200 outputs the electric signal to the cassette controller 50 through the flexible boards 212 and the reading circuits 214. Therefore, while in operation, the photoelectric transducer layer 202 and the signal output layer 200 generate heat. Hence, the temperature of the overall radiation conversion panel 92 including the radiation conversion layer 196 rises to a temperature higher than normal temperature.

Figure 7A:
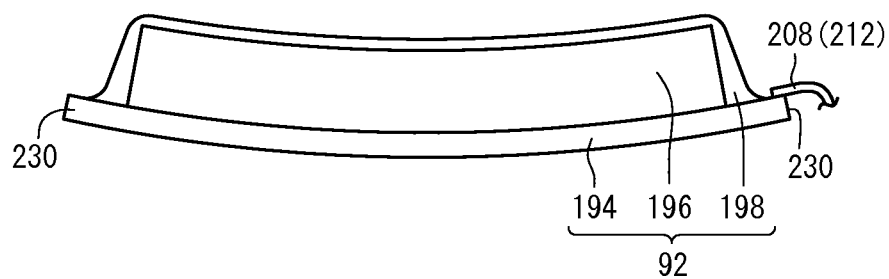
FIG. 7A is a view schematically showing the shape of a radiation conversion panel during a rise in temperature thereof.

If the temperature of the overall radiation conversion panel 92 increases, as shown in FIG. 7A, the peripheral edges 230 of the board 194 are deformed upwardly, i.e., become warped, due to the difference in the coefficients of thermal expansion referred to above. More specifically, since the coefficients of thermal expansion of the signal output layer 200 and the photoelectric transducer layer 202 are smaller than the coefficient of thermal expansion of the board 194, a central region of the board 194 does not expand easily since it is held down by the radiation conversion layer 196, which includes the signal output layer 200 and the photoelectric transducer layer 202, whereas the peripheral edges 230 of the board 194 expand easily since the radiation conversion layer 196 is not present on the peripheral edges 230. As a result, the radiation conversion panel 92 becomes deformed as a whole into a downwardly convex shape, or an upwardly concave shape, owing to the increased temperature of the radiation conversion panel 92.

Figure 7B:
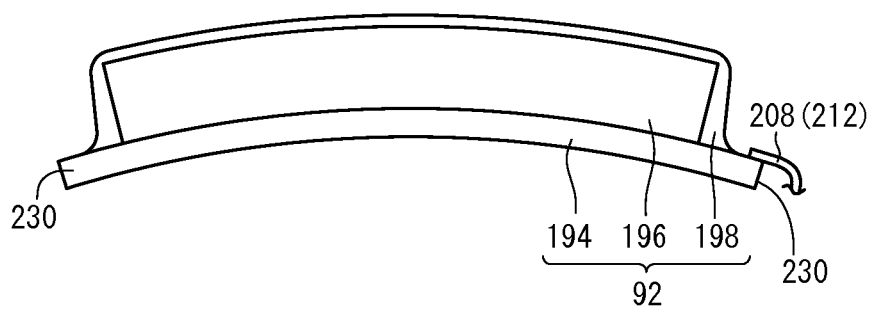
FIG. 7B is a view schematically showing the shape of the radiation conversion panel during a temperature drop thereof.

During winter or at night in the hospital, or in a case where the electronic cassette 20A is not in use outside of the hospital, the peripheral edges 230 of the board 194 are deformed downwardly, i.e., become warped, as the overall temperature of the radiation conversion panel 92 drops below normal temperature, as shown in FIG. 7B. More specifically, the central region of the board 194 does not shrink easily since the central region is held down by the radiation conversion layer 196, whereas the peripheral edges 230 of the board 194 shrink easily since the radiation conversion layer 196 is not present on the peripheral edges 230. As a result, the radiation conversion panel 92 is deformed as a whole into an upwardly convex shape, or a downwardly concave shape, owing to the reduced temperature of the radiation conversion panel 92.

Unless some measures are taken to prevent deformation of the radiation conversion panel 92 owing to the temperature change, the radiation conversion layer 196 tends to crack or peel on account of the deformation, or the ability of the protective film 198 to protect the radiation conversion layer 196 from humidity tends to be lowered. Warpage of the peripheral edges 230 owing to the temperature change is liable to cause the flexible boards 208, 212, which are joined to the peripheral edges 230 by thermocompression bonding, to peel or to suffer from a connection failure.

According to the first embodiment, as shown in FIGS. 3 through 6, 8A, and 8B, the temperature sensors 216 disposed in the respective four corners of the board 194 detect the temperature of the board 194, i.e., the temperature of the radiation conversion panel 92. According to the first embodiment, furthermore, the electronic cassette 20A includes external force applying units (external force applying mechanisms) 218, 220 for applying an external force that depends on the temperature change of the radiation conversion panel 92 based on the detected temperature, i.e., an external force which is capable of reducing the amount of deformation, i.e., the amount of warpage or expansion, of the peripheral edges 230 of the board 194 owing to the temperature change. From among the four sides (peripheral edges 230) of the board 194, the external force is applied to a peripheral edge 230 (side) in the direction of the arrow X2 to which the flexible boards 208 are connected, and to a peripheral edge 230 (side) in the direction of the arrow Y2 to which the flexible boards 212 are connected.

Figure 3:
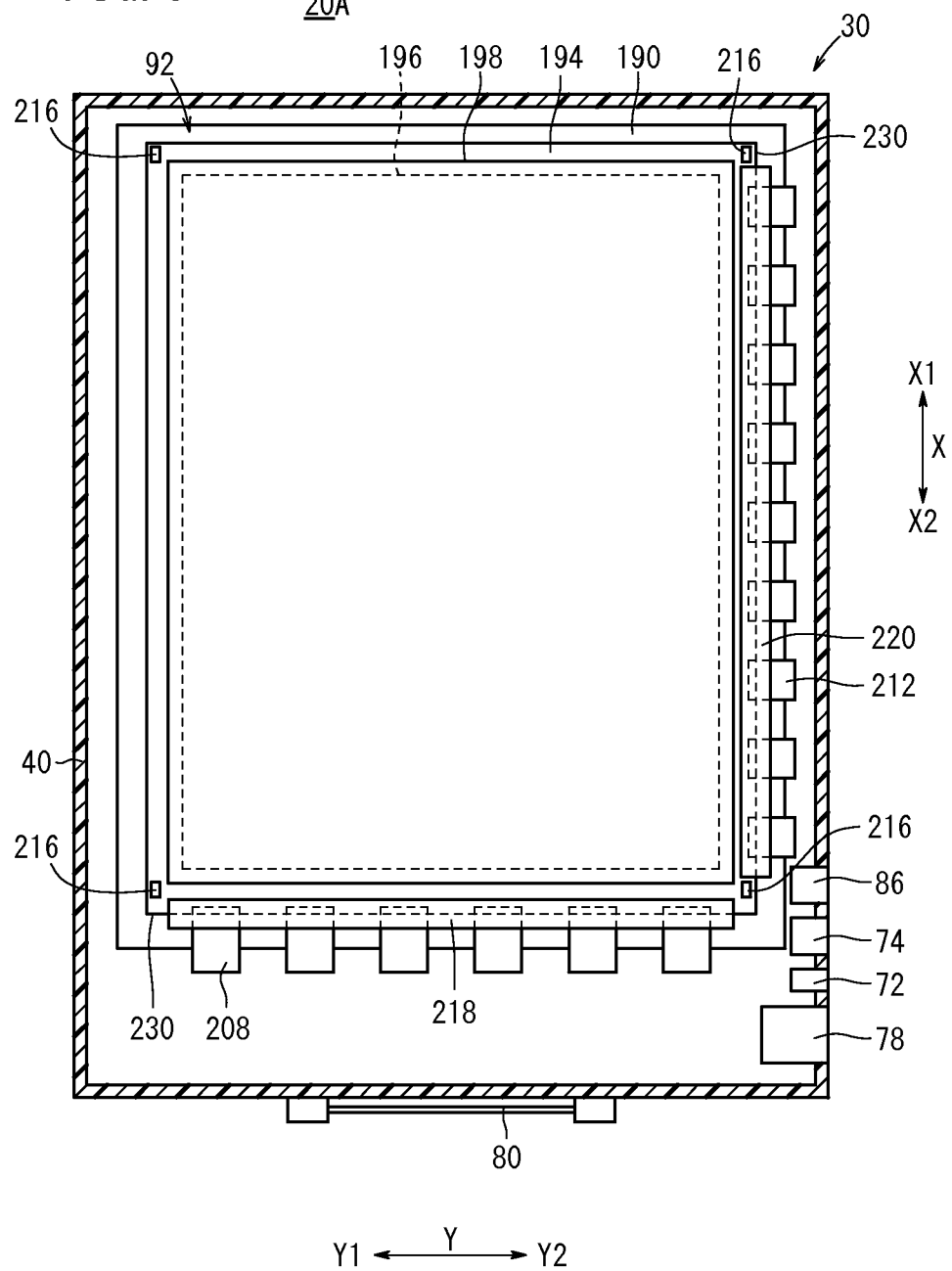
FIG. 3 is a plan view of the cassette shown in FIG. 1, with an upper wall thereof cut away.
Figure 4:
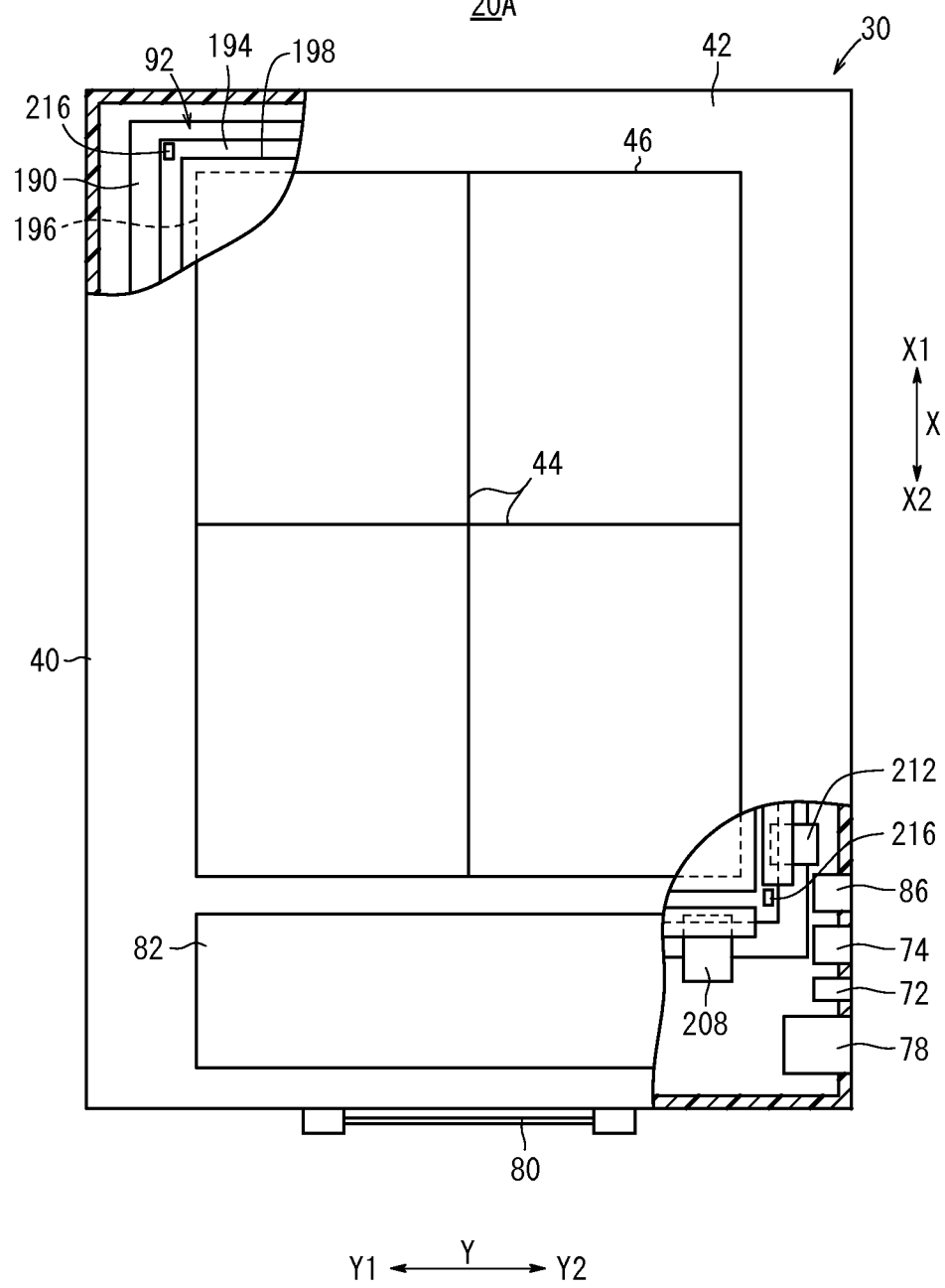
FIG. 4 is a plan view, partially cut away, of the cassette shown in FIG. 1.
Figure 8A:
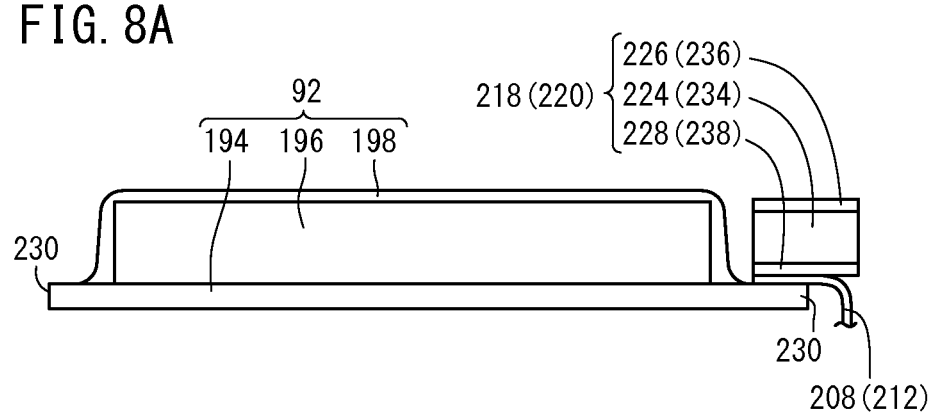
FIG. 8A is a view schematically showing the position of an external force applying unit with respect to the radiation conversion panel.
Figure 8B:
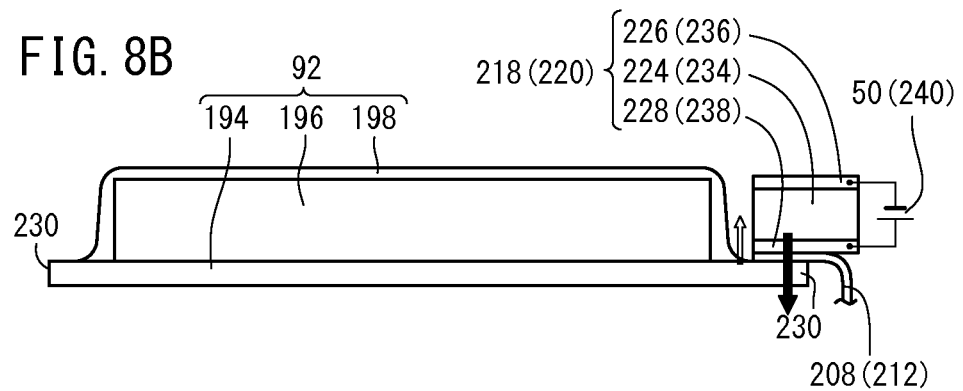
FIG. 8B is a view schematically showing the manner in which the external force applying unit applies an external force to a peripheral portion of a board.

As shown in FIGS. 3, 4, and 6, the external force applying unit 218 has one end bonded to an upper surface (inner wall) of the casing 40 by a dismantlable adhesive 222, and another end held in contact with the peripheral edge 230 in the direction of the arrow X2 of the board 194 including ends of the flexible boards 208. As shown in FIGS. 6, 8A, and 8B, the external force applying unit 218 is of a structure having an actuator element 224, which is deformable by application of a voltage thereto, sandwiched between two electrodes 226, 228. The external force applying unit 218 serves as an actuator for applying an external force downwardly to the peripheral edge 230 in the direction of the arrow X2 and to the ends of the flexible boards 208 by applying a control voltage to the electrodes 226, 228 through the cassette controller 50. The magnitude and polarity of the control voltage depend on the temperature change of the radiation conversion panel 92. The control voltage is applied to the actuator element 224, thereby deforming the actuator element 224, i.e., causing the actuator element 224 to expand or shrink vertically in FIGS. 6, 8A, and 8B.

The external force applying unit 220 is of essentially the same structure as the external force applying unit 218. As shown in FIGS. 3 through 5, the external force applying unit 220 has one end bonded to an upper surface (inner wall) of the casing 40 by a dismantlable adhesive 232, and another end held in contact with the peripheral edge 230 in the direction of the arrow Y2 of the board 194 including ends of the flexible boards 212. As shown in FIGS. 5, 8A, and 8B, the external force applying unit 220 is of a structure having an actuator element 234, which is deformable by application of a voltage thereto, sandwiched between two electrodes 236, 238. The external force applying unit 220 serves as an actuator for applying an external force downwardly to the peripheral edge 230 in the direction of the arrow Y2 and to the ends of the flexible boards 212 by applying a control voltage to the electrodes 236, 238 through the cassette controller 50. The magnitude and polarity of the control voltage depend on the temperature change of the radiation conversion panel 92. The control voltage is applied to the actuator element 234, thereby deforming the actuator element 234, i.e., causing the actuator element 234 to expand or shrink vertically in FIGS. 5, 8A, and 8B.

According to the first embodiment, therefore, the external force applying units 218, 220, which serve as actuators, continuously apply an external force, indicated by the solid arrow in FIG. 8B, based on the temperature change of the radiation conversion panel 92, to the flexible boards 208, 212 and to the peripheral edges 230, whereby warpage of the peripheral edges 230, as indicated by the outline arrow in FIG. 8B, is minimized depending on the temperature change of the radiation conversion panel 92, thereby keeping the radiation conversion panel 92 including the board 194 flat as a whole.

The amorphous oxide semiconductor, which the signal output layer 200 and the photoelectric transducer layer 202 may be made of, and the OPC, which the photoelectric transducer layer 202 may be made of, are suitable for use as materials of the signal output layer 200 and the photoelectric transducer layer 202 because they have a tensile strength greater than that of amorphous silicon (a-Si).

FIG. 8B shows the manner in which a downward external force is applied to the peripheral edges 230 and to the flexible boards 208, 212 in order to minimize the tendency of the radiation conversion panel 92 to deform as shown in FIG. 7A. If the radiation conversion panel 92 deforms as shown in FIG. 7B, then the polarity of the control voltages applied to the electrodes 226, 228, 236, 238 may be changed, so as to apply an upward external force to the peripheral edges 230 and to the flexible boards 208, 212.

If the board 194 is at normal temperature, the overall radiation conversion panel 92 including the board 194 is likely to be kept flat and is not likely to become deformed. At this time, control voltages need not be applied to the electrodes 226, 228, 236, 238.

The material of the dismantlable adhesives 222, 232 and the material of the electrodes 226, 228, 236, 238 of the external force applying units 218, 220 and the actuator elements 224, 234 will be described below.

The dismantlable adhesives 222, 232 comprise an adhesive, such as a thermoplastic adhesive, an electrically heatable plastic adhesive, an ultraviolet plastic adhesive, a water absorbing plastic adhesive, or the like, which can be peeled off by the adhesive being heated, electrically heated, irradiated with ultraviolet radiation, or if the adhesive absorbs water after the adhesive has bonded the external force applying units 218, 220 to the casing 40. Since the external force applying units 218, 220 are made to expand or shrink if control voltages are applied thereto, the dismantlable adhesives 222, 232 should preferably be an epoxy-resin or silicone-resin adhesive, which is elastic.

The actuator elements 224, 234 are made of a polymeric material, a shape-memory alloy, or a piezoelectric material. The polymeric material may be a polymeric gel, a polymeric electrolytic gel, a non-ionic polymeric gel, or an electrically conductive polymer. If the actuator elements 224, 234 are made of a rubber-like polymeric film, i.e., an elastomer, then since the actuator elements 224, 234 expand and shrink vertically upon application of voltages thereto, the external force applying units 218, 220 function as shock dampening members for dampening external shocks.

The piezoelectric material may be crystal, Rochelle salt, barium titanate, or lead zirconate titanate.

No matter what material the actuator elements 224, 234 is made of, the actuator elements 224, 234 expand or shrink vertically, as shown in FIGS. 5, 6, 8A, and 8B, upon application of control voltages to the electrodes 226, 228, 236, 238, thereby applying downward external forces to the flexible boards 208, 212 and to the peripheral edges 230.

The external force applying units 218, 220, the actuator elements 224, 234, which are made of a polymeric material or a shape memory alloy, function as an actuator, which is referred to as an artificial muscle. If the actuator elements 224, 234 are made of a shape memory alloy, then the actuator elements 224, 234 are required to remember the shapes thereof at two temperatures. In this case, the temperature of the board 194 does not need to be monitored by the temperature sensors 216.

The electrodes 226, 228, 236, 238 may be made of an electrically conductive material, e.g., a metal or an electrically conductive resin such as an electrically conductive polymer or the like.

A circuit arrangement, including blocks, of the electronic cassette 20A, which incorporates therein an indirect conversion type radiation conversion panel 92, for example, will be described in detail below with reference to FIG. 9.

Figure 9:
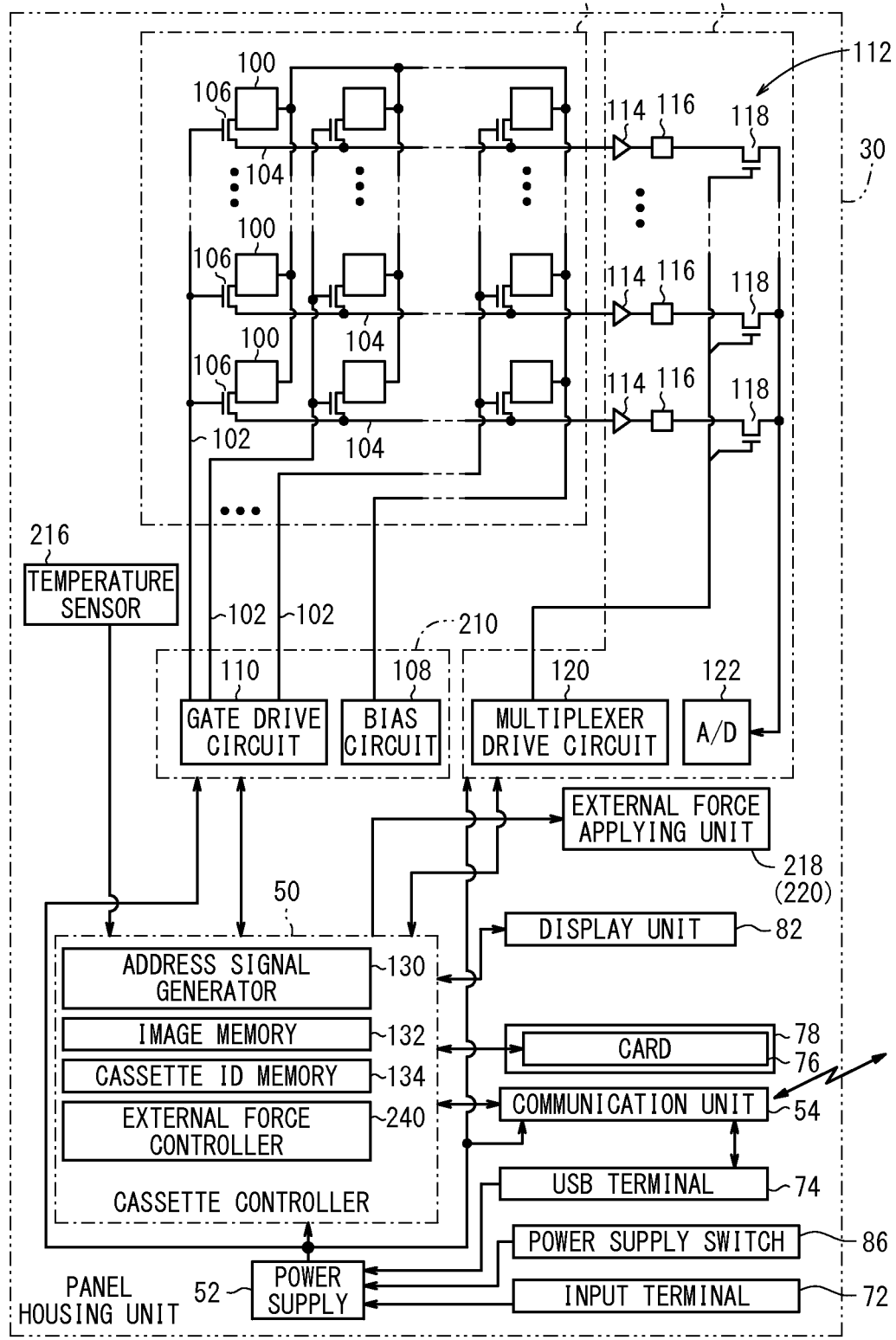
FIG. 9 is a block diagram of the cassette shown in FIG. 1.
Figure 10:
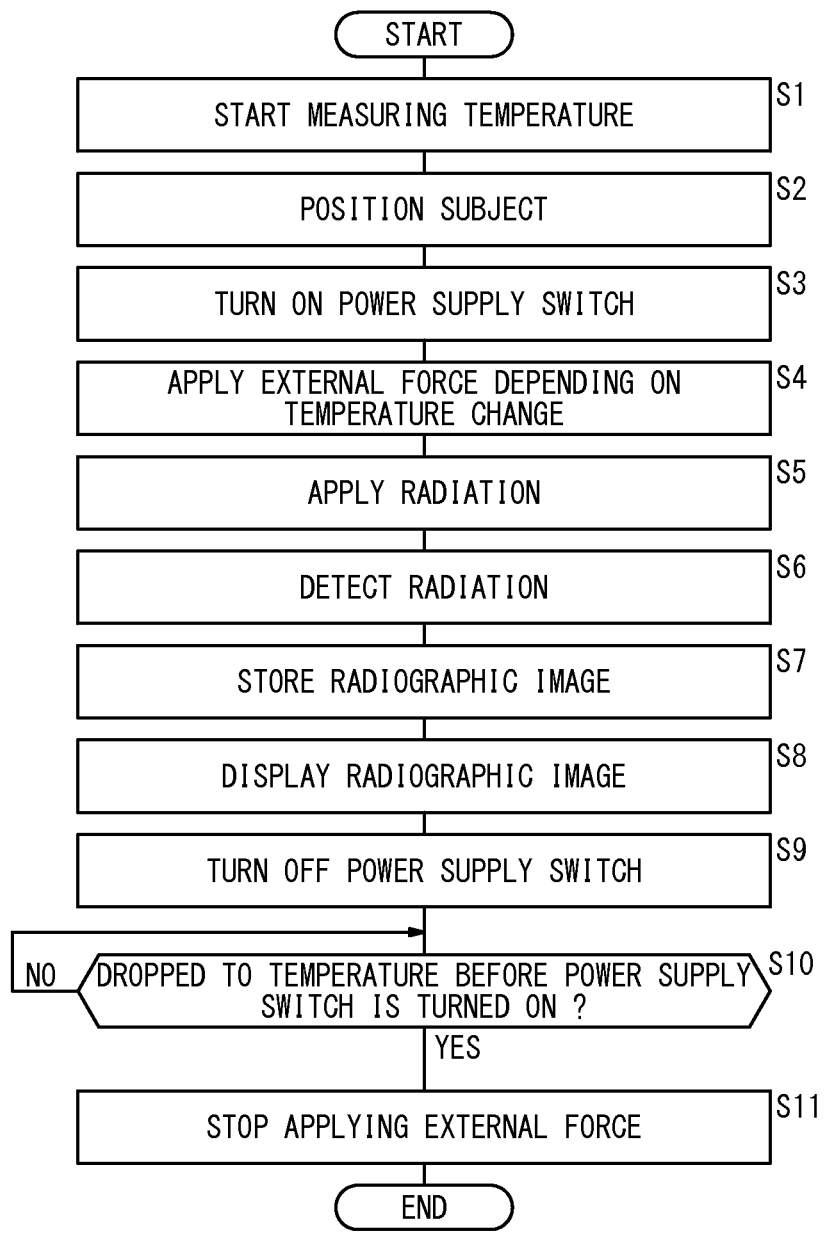
FIG. 10 is a flowchart of a sequence for capturing a radiographic image of a subject with the radiographic image capturing system shown in FIG. 1.

As shown in FIG. 9, the radiation conversion panel 92 includes a matrix of pixels 100, which make up the photoelectric transducer layer 202 (see FIGS. 5 and 67), disposed in rows and columns on the signal output layer 200. To the pixels 100, there are connected a plurality of gate lines 102 for supplying control signals from a gate drive circuit 110 of a drive circuit 210 to the pixels 100, and a plurality of signal lines 104 for reading electric signals output from the pixels 100 and outputting the electric signals to a reading circuit 214. The photoelectric transducer layer 202 made up of the pixels 100 is disposed on an array of TFTs 106, which make up the signal output layer 200. The gate lines 102 serve as part of the flexible boards 208, and the signal lines 104 serve as part of the flexible boards 212.

The pixels 100, which are supplied with a bias voltage from a bias circuit 108 of the drive circuit 210, store electric charges that are generated by converting fluorescence into analog electric signals. By turning on the TFTs 106 in successive columns, the stored electric charges can be read as image signals from the pixels 100.

The gate lines 102 that extend parallel to the columns, and the signal lines 104 that extend parallel to the rows are connected to the TFTs 106, which are connected to the respective pixels 100. The gate lines 102 are connected to the gate drive circuit 110, and the signal lines 104 are connected to a multiplexer 112 of the reading circuit 214. The gate lines 102 are supplied with control signals for turning on and off the TFTs 106 arranged along the columns from the gate drive circuit 110. The gate drive circuit 110 is supplied with address signals from the cassette controller 50 through the flexible board 208.

Electric charges, which are stored in the pixels 100, flow into the signal lines 104 through the TFTs 106 arranged along the rows. The electric charges are then amplified by amplifiers 114 of the reading circuit 214. The amplifiers 114 are connected to the multiplexer 112 through sample and hold circuits 116. The multiplexer 112 includes a plurality of FET (Field Effect Transistor) switches 118 for switching between the signal lines 104, and a multiplexer drive circuit 120 for outputting selection signals for turning on one of the FET switches 118 at a time. The multiplexer drive circuit 120 is supplied with address signals from the cassette controller 50 through the flexible boards 212 (see FIG. 5). The FET switches 118 are connected to an A/D converter 122. The A/D converter 122 converts analog electric signals from the pixels 100 into digital signals representative of radiographic information, and the digital signals are supplied through the flexible boards 208 (see FIG. 6) to the cassette controller 50.

The TFTs 106, which function as switching elements, may be combined with any of various other image capturing devices such as a CMOS (Complementary Metal-Oxide Semiconductor) image sensor or a CCD (Charge-Coupled Device) image sensor in which electric charges are shifted and transferred by shift pulses that correspond to gate signals used in the TFTs 106.

The cassette controller 50 has an address signal generator 130, an image memory 132, a cassette ID memory 134, and an external force controller 240.

The address signal generator 130 supplies address signals to the gate drive circuit 110 and the multiplexer drive circuit 120. The image memory 132 stores radiographic images that have been detected by the radiation conversion panel 92. The cassette ID memory 134 stores cassette ID information that identifies the electronic cassette 20A.

The external force controller 240 supplies the external force applying units 218, 220 with control voltages, the magnitude and polarity of which depend on the temperature change of the radiation conversion panel 92, based on the temperature of the board 194 that is detected by the temperature sensor 216. If the external force controller 240 changes the polarity and magnitude of the control voltages depending on the temperature change of the board 194, the magnitude and direction of the external forces, which are applied from the external force applying units 218, 220 to the peripheral edges 230 of the board 194 and the flexible boards 208, 212, can be changed, i.e., adjusted.

<Operations of the First Embodiment>

The radiographic image capturing system 10A, which incorporates the electronic cassette 20A according to the first embodiment, is basically constructed as described above. Operations of the radiographic image capturing system 10A will be described below with reference to the flowchart shown in FIG. 10, and also to FIGS. 1 through 9, if necessary.

Before the power supply switch 86 is turned on, the electronic cassette 20A is kept at normal temperature. If the power supply switch 86 is turned on, the temperature of the electronic cassette 20A starts to rise. If the power supply switch 86 is turned off, the temperature of the electronic cassette 20A drops back to normal temperature. Operations of the radiographic image capturing system 10A during such a temperature change sequence will be described below.

In step S1, before the power supply switch 86 is turned on, the power supply 52 supplies electric power only to the cassette controller 50 and the temperature sensors 216 in the casing 40 of the electronic cassette 20A. In other words, the electronic cassette 20A is in a sleep mode.

The temperature sensors 216 detect the temperature of the board 194 and output the detected temperature to the cassette controller 50. Based on the temperature detected by the temperature sensors 216, the external force controller 240 of the cassette controller 50 judges whether or not the external force applying units 218, 220 should be operated. As described above, since the power supply switch 86 is not turned on, the board 194 is kept at normal temperature, and the radiation conversion panel 92 including the board 194 is held flat. Since the board 194 is kept at normal temperature and does not undergo a temperature change, the external force controller 240 judges that there is no need to supply control voltages to the external force applying units 218, 220, and hence control voltages are not supplied to the electrodes 226, 228, 236, 238. In step S1, therefore, the external force applying units 218, 220 do not apply external forces to the flexible boards 208, 212 and the peripheral edges 230.

In step S2, the doctor or radiological technician grips the handle 80 and carries the electronic cassette 20A from a prescribed storage location to the image capturing base 12. Thereafter, the doctor or radiological technician adjusts the imaging distance between the radiation source 18 and the radiation conversion panel 92 to a given SID (source-to-image distance), and places the subject 14 on the image capturing surface 42. The doctor or radiological technician positions the subject 14 in order to bring an area to be imaged of the subject 14 within the image capturing field 46, and also to keep the central position of the area to be imaged in substantial alignment with the central position of the image capturing field 46. The doctor or radiological technician also operates the console 22 to register image capturing conditions, e.g., a tube voltage and a tube current for the radiation source 18, and an exposure time for the radiation 16, as well as subject information about the subject 14 as the object to be imaged. If the area to be imaged and the imaging method have been given in advance, then the doctor or radiological technician also registers such image capturing conditions.

In step S3, the doctor or radiological technician turns on the power supply switch 86. In response to turning-on the power supply switch 86, the power supply 52 starts supplying electric power to the various components in the casing 40. The communication unit 54 is made capable of sending signals to and receiving signals from the console 22 through a wireless communication link. The communication unit 54 receives the image capturing conditions registered in the console 22 through the wireless communication link, and outputs the received image capturing conditions to the cassette controller 50. The display unit 82 is able to display various pieces of information. The drive circuits 210 are activated by electric power supplied from the power supply 52. The bias circuit 108 supplies a bias voltage to the pixels 100, thereby making the pixels 100 capable of storing electric charges. The reading circuits 214 also are activated by electric power supplied from the power supply 52, and are placed in a state capable of reading electric charges from the pixels 100. Therefore, by turning on the power supply switch 86, the electronic cassette 20A changes from the sleep mode into an active mode.

If the electronic cassette 20A enters the active mode, whereupon the signal output layer 200 and the photoelectric transducer layer 202 of the radiation conversion panel 92 become operational, the signal output layer 200 and the photoelectric transducer layer 202 generate heat, so as to increase the temperature of the radiation conversion panel 92 including the board 194. Such a temperature change tends to deform the radiation conversion panel 92, as shown in FIG. 7A.

In step S4, the temperature sensors 216 sequentially monitor or detect the temperature of the board 194, and output the monitored temperature to the cassette controller 50. Based on the temperature information sequentially input from the temperature sensors 216, the external force controller 240 judges whether or not the radiation conversion panel 92 is undergoing a temperature change, i.e., a temperature rise. If the external force controller 240 decides that the radiation conversion panel 92 is undergoing a temperature rise, then the external force controller 240 generates control voltages in magnitudes and directions required for the external force applying units 218, 220 to apply appropriate external forces depending on the temperature rise to the flexible boards 208, 212 and to the peripheral edges 230 of the board 194. The generated control voltages are applied to the electrodes 226, 228, 236, 238.

Depending on the polarity and magnitude of the control voltages applied to the electrodes 226, 228, 236, 238, the actuator elements 224, 234 expand or contract vertically. The external force applying unit 218 applies a downward external force to the flexible board 208 and to the peripheral edge 230 facing in the direction of the arrow X2, and the external force applying unit 220 applies a downward external force to the flexible board 212 and to the peripheral edge 230 facing in the direction of the arrow Y2. Consequently, even if the radiation conversion panel 92 including the board 194 tends to deform due to a rise in temperature, external forces depending on the temperature rise are applied to the flexible boards 208, 212 and to the peripheral edges 230 in order to prevent the radiation conversion panel 92 from becoming deformed. As a result, the radiation conversion panel 92 including the board 194 remains in a flat condition.

As described above, since the temperature sensors 216 sequentially monitor and output the temperature of the board 194 to the cassette controller 50, even after step S4, the external force controller 240 sequentially judges whether or not external forces depending on a temperature rise should be applied based on the temperature of the board 194, and the external force controller 240 sequentially generates and outputs control voltages in magnitudes and directions required to apply external forces to the external force applying units 218, 220. By sequentially detecting the temperature of the board 194, the electronic cassette 20A can continuously apply external forces to prevent deformation of the radiation conversion panel 92 due to a temperature rise thereof. As a consequence, the electronic cassette 20A can maintain the radiation conversion panel 92 in a flat state as a whole.

In step S5, after steps S1 through S4, which serve as a preparatory process, the doctor or radiological technician turns on an exposure switch, not shown, provided on the console 22 or the radiation source 18. If the exposure switch is provided on the console 22, then after the exposure switch is turned on, the console 22 sends the image capturing conditions to the radiation source 18 through a wireless communication link. If the exposure switch is provided on the radiation source 18, then after the exposure switch is turned on, the radiation source 18 sends a request for image capturing conditions to the console 22 through the wireless communication link, and in response to the request, the console 22 sends the image capturing conditions to the radiation source 18 through the wireless communication link.

Upon reception of the image capturing conditions, the radiation source 18 applies radiation 16 having a dose according to the image capturing conditions to the subject 14 for a given exposure time. Radiation 16 passes through the subject 14 to the radiation conversion panel 92 in the panel housing unit 30.

In step S6, if an indirect conversion type of radiation conversion panel 92 is used, then the scintillator 206 of the radiation conversion panel 92 radiates fluorescence, e.g., visible light, having an intensity depending on the intensity of the radiation 16, and the pixels 100 of the photoelectric transducer layer 202 convert the fluorescence into electric signals and store the signals as electric charges. Then, electric charge information, which is representative of a radiographic image of the subject 14 and is held by the pixels 100, is read from the pixels 100 by address signals, which are supplied from the address signal generator 130 of the cassette controller 50 to the gate drive circuit 110 and the multiplexer drive circuit 120.

The gate drive circuit 110 supplies control signals to the gates of the TFTs 106 connected to gate lines 102 that correspond to the address signals supplied from the address signal generator 130. The multiplexer drive circuit 120 outputs selection signals to successively select, i.e., turn on and off, the FET switches 118 according to the address signals supplied from the address signal generator 130, thereby successively reading via the signal lines 104 the radiographic image represented by the electric charge information, which is held by the pixels 100 connected to the gate lines 102 selected by the gate drive circuit 110.

The radiographic image read from the pixels 100 connected to the selected gate lines 102 is amplified by the amplifiers 114, sampled by the sample and hold circuits 116, and supplied through the FET switches 118 to the A/D converter 122, which converts the radiographic image into a digital signal. The digital signal, which is converted from the radiographic image, is temporarily stored in the image memory 132 of the cassette controller 50 in step S7.

Similarly, the gate drive circuit 110 successively selects the gate lines 102 for outputting control signals according to the address signals supplied from the address signal generator 130, reads the radiographic image represented by the electric charge information held by the pixels 100 connected to the gate lines 102, and sends the radiographic image through the FET switches 118 and the A/D converter 122 to the image memory 132 of the cassette controller 50, where the radiographic image is stored in step S7.

The radiographic image, which is stored in the image memory 132, is sent, together with the cassette ID information stored in the cassette ID memory 134, from the communication unit 54 to the console 22 through a wireless communication link. The console 22 performs a given image processing technique on the received radiographic image, and sends the processed radiographic image to the display device 24 through a wireless communication link. In step S8, the display device 24 displays the received radiographic image.

In step S8, the display unit 82 of the electronic cassette 20A may also display raw data or decimated data of the radiographic image.

The doctor or radiological technician visually checks the radiographic image displayed on the display device 24 or the display unit 82, and confirms that the displayed radiographic image is a proper radiographic image of the subject 14. Thereafter, in step S9, the doctor or radiological technician releases the subject 14 from the image capturing base 12, thereby completing the image capturing process on the subject 14, and presses the power supply switch 86 to de-energize the electronic cassette 20A. The power supply 52 stops supplying electric power to the components in the casing 40, except for the cassette controller 50 and the temperature sensors 216. As a result, the electronic cassette 20A changes from an active mode into a sleep mode. Then, the doctor or radiological technician grips the handle 80 and carries the electronic cassette 20A to a prescribed storage location.

In the sleep mode, the temperature sensors 216 detect the temperature of the board 194, and output the detected temperature to the cassette controller 50. In step S10, the external force controller 240 judges whether or not the temperature detected by the temperature sensors 216 has dropped to the temperature before the power supply switch 86 was turned on, i.e., to normal temperature. If the temperature detected by the temperature sensors 216 has not dropped to normal temperature, then the external force controller 240 decides that the radiation conversion panel 92 may possibly become deformed depending on a temperature change, i.e., a temperature drop (step S10: NO), and continues to supply control voltages to the external force applying units 218, 220. Conversely, if the temperature detected by the temperature sensors 216 has dropped to normal temperature, then the external force controller 240 decides that the radiation conversion panel 92 is not likely to become deformed, but will remain flat (step S10: YES). The external force controller 240 stops supplying control voltages to the external force applying units 218, 220, which in turn stop applying external forces to the flexible boards 208, 212 and to the peripheral edges 230 in step S11.

<Advantages of the First Embodiment>

With the electronic cassette 20A and the radiographic image capturing system 10A according to the first embodiment, as described above, the external force applying units 218, 220 apply external forces to the peripheral edges 230 of the board 194 in order to prevent the peripheral edges 230 from becoming deformed, i.e., warped, depending on a temperature change of the radiation conversion panel 92, thereby keeping the radiation conversion panel 92 flat. According to the first embodiment, therefore, the radiation conversion panel 92 can be kept flat, i.e., planarity of the radiation conversion panel 92 can be maintained, while taking into account temperature changes of the radiation conversion panel 92.

According to the first embodiment, since the radiation conversion panel 92 is not bonded to other members, but rather, external forces are applied to the peripheral edges 230 of the board 194 in order to keep the radiation conversion panel 92 flat, the radiation conversion panel 92 is prevented from becoming deformed, and hence the radiation conversion panel 92 is prevented from cracking or peeling.

The peripheral edges 230 of the board 194 are deformed depending on the temperature change. Consequently, the temperature of the board 194 is detected by the temperature sensors 216, and appropriate external forces depending on the temperature change, i.e., depending on deformation of the peripheral edges 230 due to the temperature change, are applied to the peripheral edges 230 based on the detected temperature, thereby effectively preventing the peripheral edges 230 from becoming deformed. In other words, if a deformation, e.g., warpage or elongation of the peripheral edges 230, which could be caused by the temperature change, is grasped in advance, then external forces for eliminating such a deformation may be continuously applied to the peripheral edges 230, thereby keeping the radiation conversion panel 92 including the board 194 flat as a whole.

As the temperature of the radiation conversion panel 92 changes, the peripheral edges 230 of the board 194, which is made of plastic, tends to become warped in the thicknesswise direction of the board 194. Therefore, the external force applying units 218, 220 apply external forces to the peripheral edges 230 in order to prevent the peripheral edges 230 from becoming warped, thereby keeping the radiation conversion panel 92 including the board 194 flat as a whole. Application of external forces to the peripheral edges 230 with the flexible boards 208, 212 mounted thereon is effective to keep the board 194 flat, and also to prevent the flexible boards 208, 212 from peeling off from the board 194. As a result, address signals can be supplied and electric signals can be output regardless of the temperature change.

Inasmuch as the external force applying units 218, 220 have ends fixed to the upper surface of the casing 40, and other ends held in contact with the peripheral edges 230 of the board 194 and the flexible boards 208, 212, downward forces can reliably be applied to the peripheral edges 230 and to the flexible boards 208, 212.

According to the first embodiment, as described above, since the radiation conversion panel 92 is kept flat by external forces applied thereto depending on the temperature change, columnar crystals of CsI, which the scintillator 206 is made of, are kept perpendicular to the board 194. As a consequence, crosstalk, which otherwise could be caused between adjacent columnar crystals due to warpage of the radiation conversion panel 92, can be minimized, thereby allowing the electronic cassette 20A to acquire sharp radiographic images easily that are free of image blurs.

The external force applying units 218, 220 are bonded to the casing 40 by the dismantlable adhesives 222, 232. Consequently, the external force applying units 218, 220 can easily be replaced at the time functions thereof are lowered due to being irradiated with radiation 16.

According to the first embodiment, if the actuator elements 224, 234 are made of a polymeric material, particularly, a rubber-like polymeric film, i.e., an elastomer, then since the actuator elements 224, 234 serve as a shock absorbing member for absorbing shocks, i.e., loads, vibrations, etc., from external sources, the actuator elements 224, 234 are effectively capable of protecting the components in the casing 40 from such shocks.

It has been described above that external forces depending on a temperature change are applied to the peripheral edges 230 and the flexible boards 208, 212 based on the temperature of the board 194, which is detected by the temperature sensor 216. However, the first embodiment is not limited to this description. If the tendency of a temperature rise of the board 194 over an elapsed period of time after the power supply switch 86 has been turned on, or if the tendency of a temperature drop of the board 194 over an elapsed period of time after the power supply switch 86 has been turned off is known, then the external force controller 240 may include a timer function, and the magnitude (and polarity) of the control voltages can sequentially be changed depending on the elapsed period of time after the power supply switch 86 was turned on or the elapsed period of time after the power supply switch 86 was turned off, and the changed control voltages can be applied to the electrodes 226, 228, 236, 238. In this case, since external forces depending on the temperature change are applied to the peripheral edges 230 and to the flexible boards 208, 212, the radiation conversion panel 92 can be kept flat.

<Modifications of the First Embodiment>

The electronic cassette 20A according to the first embodiment is not limited to the foregoing descriptions, but may be arranged according to alternative embodiments, as shown in FIGS. 11 through 20.

Figure 11:
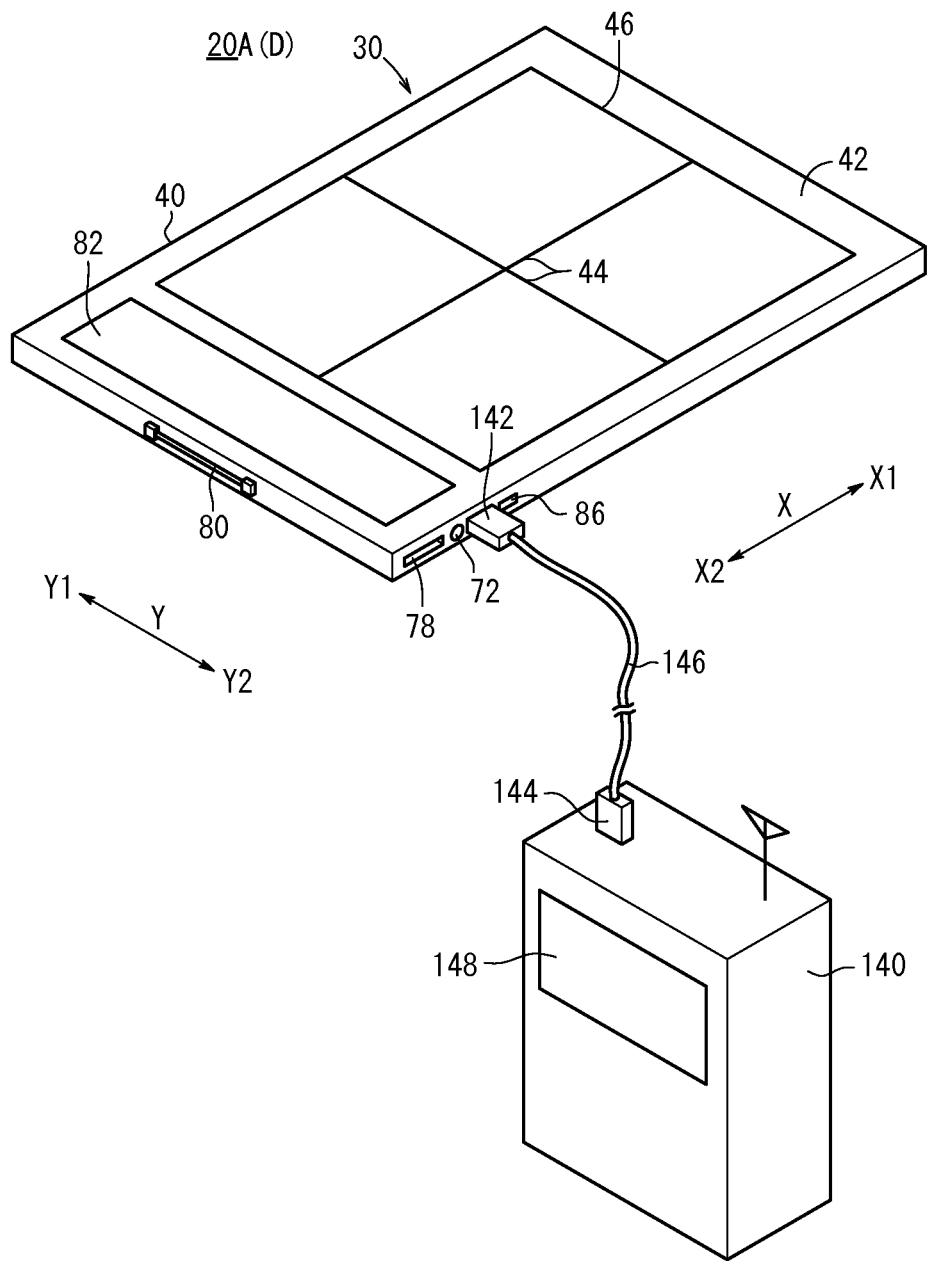
FIG. 11 is a perspective view showing the manner in which the cassette shown in FIG. 1 is charged.

FIG. 11 is a perspective view showing the manner in which the power supply 52 (see FIGS. 5, 6, and 9) is charged by a cradle 140, which is placed at a location in a medical organization.

The electronic cassette 20A and the cradle 140 are electrically connected to each other by a USB cable 146 having connectors 142, 144.

The cradle 140 not only charges the power supply 52, but may also send necessary information to and receive necessary information from the console 22 and the RIS 26 in the medical organization, using a wireless communication function or a wired communication function of the cradle 140. Such information, which is sent and received, may include the radiographic image that is recorded in the image memory 132 (see FIG. 9) of the electronic cassette 20A.

The cradle 140 may have a display unit 148 for displaying necessary information, which represents the charged state of the electronic cassette 20A, and includes the radiographic image acquired from the electronic cassette 20A.

A plurality of cradles 140 may be connected to a network, and charged states of electronic cassettes 20A, which are connected to the cradles 140, may be collected through the network, for thereby confirming locations of electronic cassettes 20A that have been charged and the extent to which the electronic cassettes 20A can be used.

Modifications (hereinafter referred to as first through fourth modifications) of the electronic cassette 20A according to the first embodiment will be described below with reference to FIGS. 12 through 20.

Figure 12:
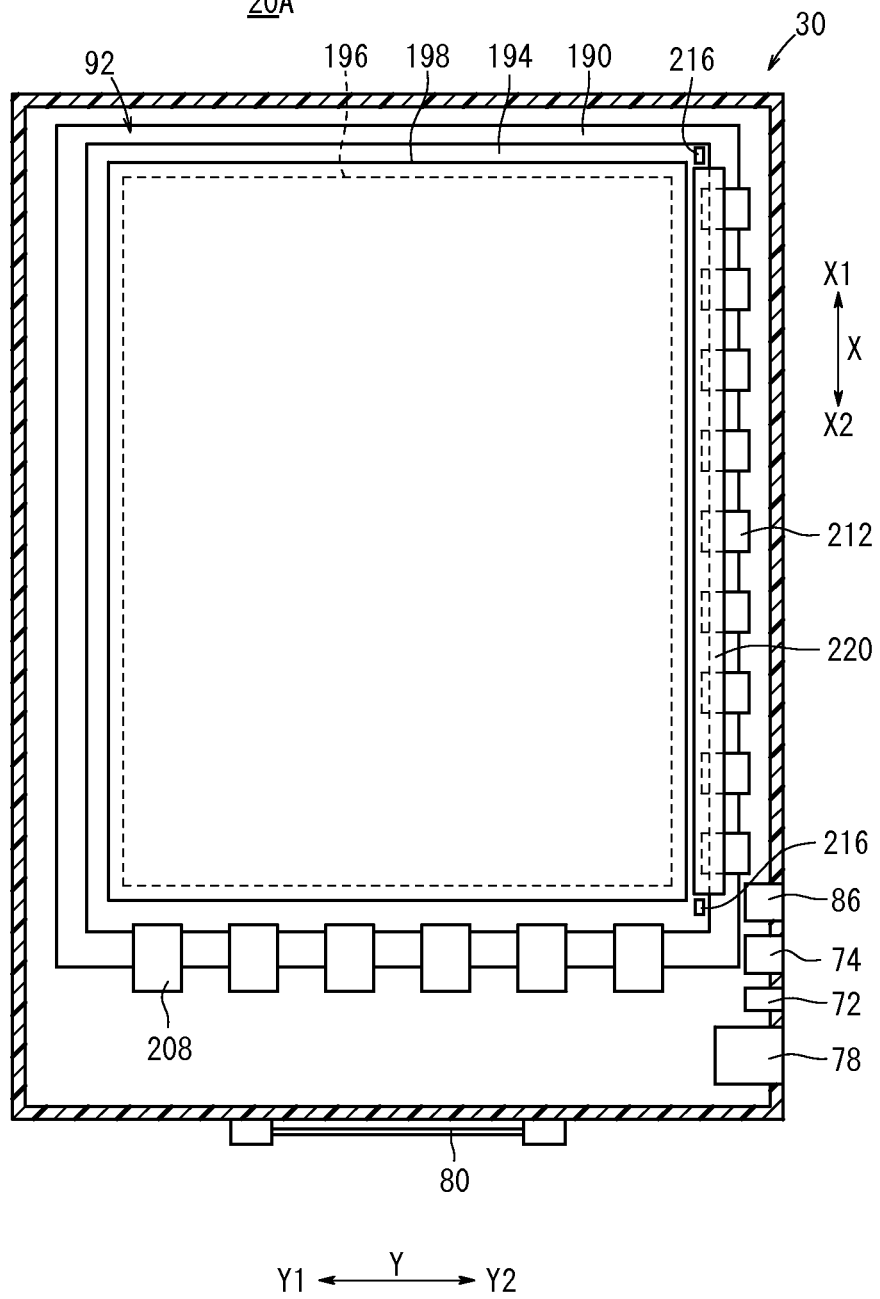
FIG. 12 is a plan view showing an internal arrangement of a cassette according to a first modification.
Figure 13:
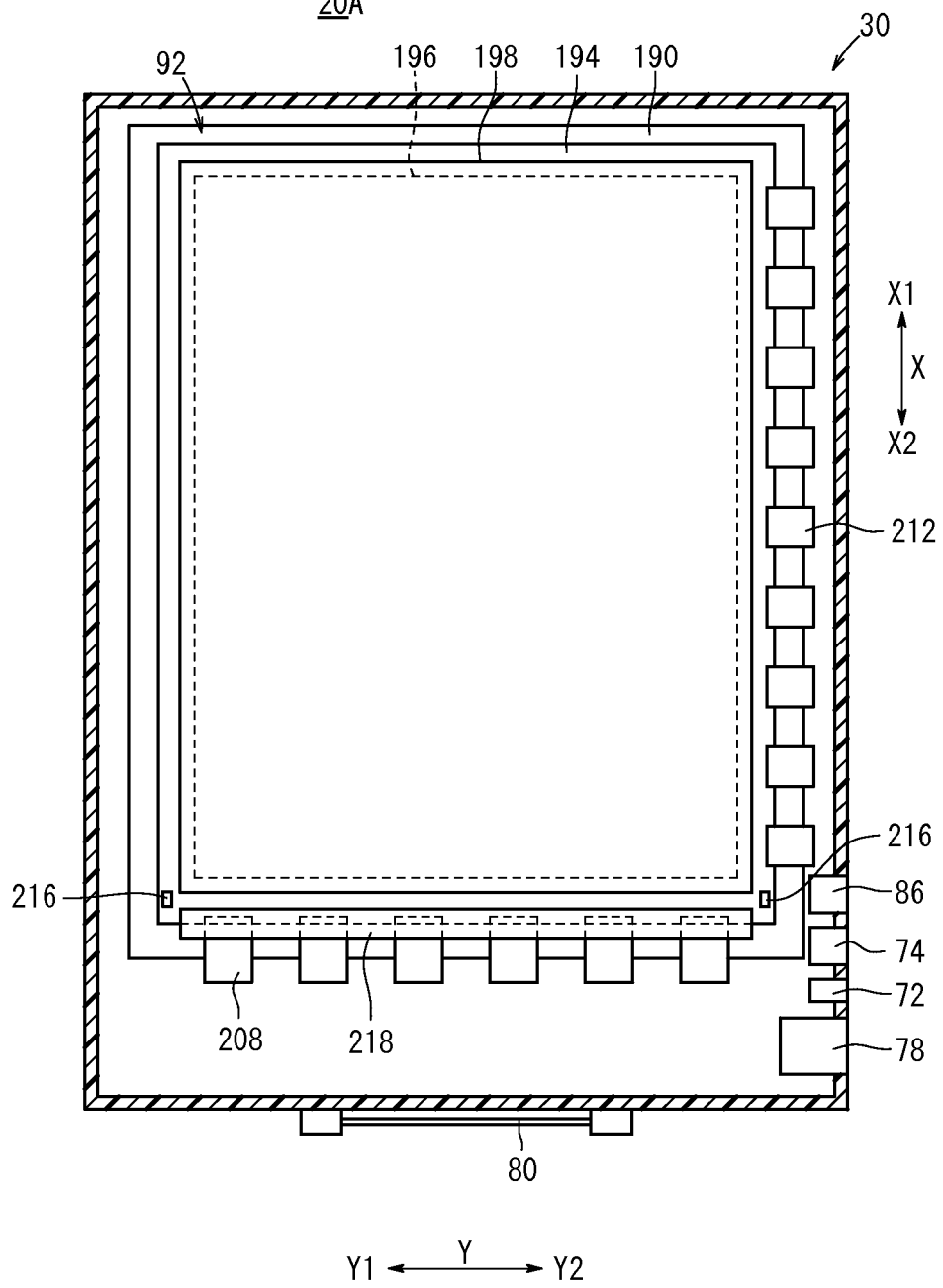
FIG. 13 is a plan view showing another internal arrangement of the cassette according to the first modification.

As shown in FIGS. 12 and 13, the electronic cassette 20A according to the first modification has either one of the external force applying units 218, 220.

In FIG. 12, the electronic cassette 20A includes only the external force applying unit 220, which applies an external force to the peripheral edge 230 facing in the direction indicated by the arrow Y2, and to ends of the flexible boards 212. Two temperature sensors 216 are disposed at two respective corners of the board 194 near the external force applying unit 220.

In FIG. 13, the electronic cassette 20A includes only the external force applying unit 218, which applies an external force to the peripheral edge 230 facing in the direction indicated by the arrow X2, and to ends of the flexible board 208. Two temperature sensors 216 are disposed at two respective corners of the board 194 near the external force applying unit 218.

According to the first modification, the external force is applied to only the peripheral edge 230 on one side of the board 194. The first modification offers the same advantages as those provided by the external force applying units 218 and 220.

Figure 14:
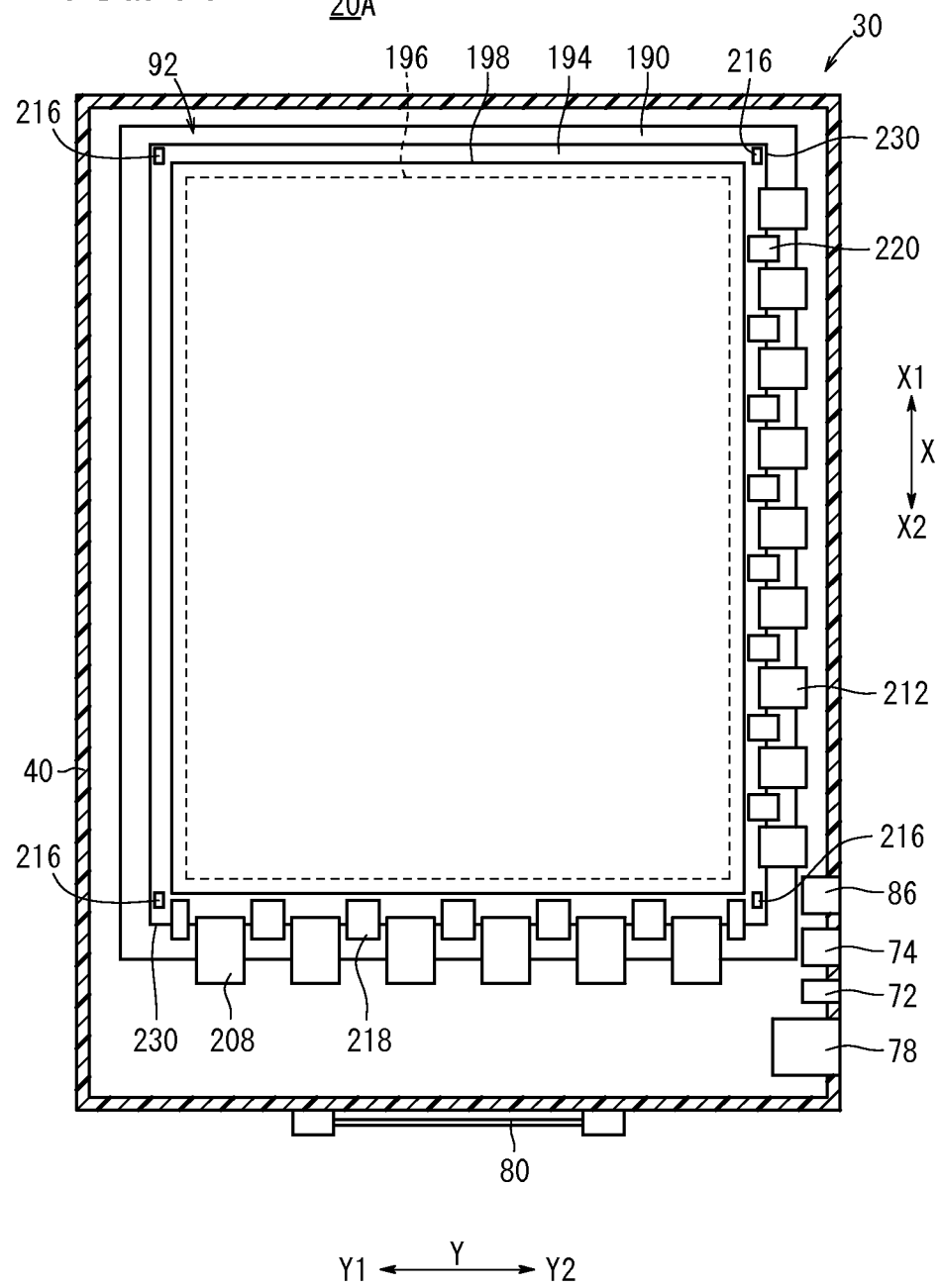
FIG. 14 is a plan view showing an internal arrangement of a cassette according to a second modification.

As shown in FIGS. 14 through 15B, the electronic cassette 20A according to the second modification includes a plurality of short external force applying units 218, 220 disposed between the flexible boards 208, 212 out of interference with the flexible boards 208, 212, on the peripheral edges 230 to which the flexible boards 208, 212 are connected. The external force applying units 218, 220 apply external forces only to the peripheral edges 230.

The external force applying units 218, 220 may apply external forces to the peripheral edges 230 in two ways, as shown in FIGS. 15A and 15B.

In FIG. 15A, the external force applying units 218, 220 directly apply external forces to the peripheral edges 230. In FIG. 15B, bosses 243 project upwardly from the peripheral edges 230, and the external force applying units 218, 220 apply external forces to the peripheral edges 230 through the bosses 243.

In either case, since the external forces are applied to the peripheral edges 230 without going through the flexible boards 208, 212, the flexible boards 208, 212 are prevented from becoming peeled off from peripheral edges 230 by excessive external forces, which otherwise would be applied to the flexible boards 208, 212, which are connected to the peripheral edges 230 by thermocompression bonding or the like.

Figure 17:
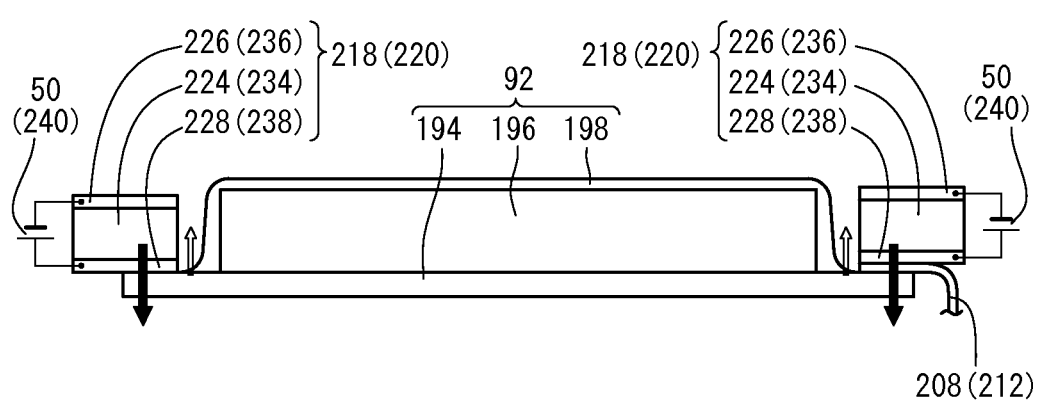
FIG. 17 is a view schematically showing the manner in which the external force applying unit of the cassette shown in FIG. 16 applies an external force to a peripheral portion of a board.

As shown in FIGS. 16 and 17, the electronic cassette 20A according to the third modification has external force applying units 218, 220 disposed on all four sides, i.e., on the peripheral edges 230, of the board 194. Since external forces are applied to all of the peripheral edges 230, the peripheral edges 230 are reliably prevented from becoming warped.

Figure 18:
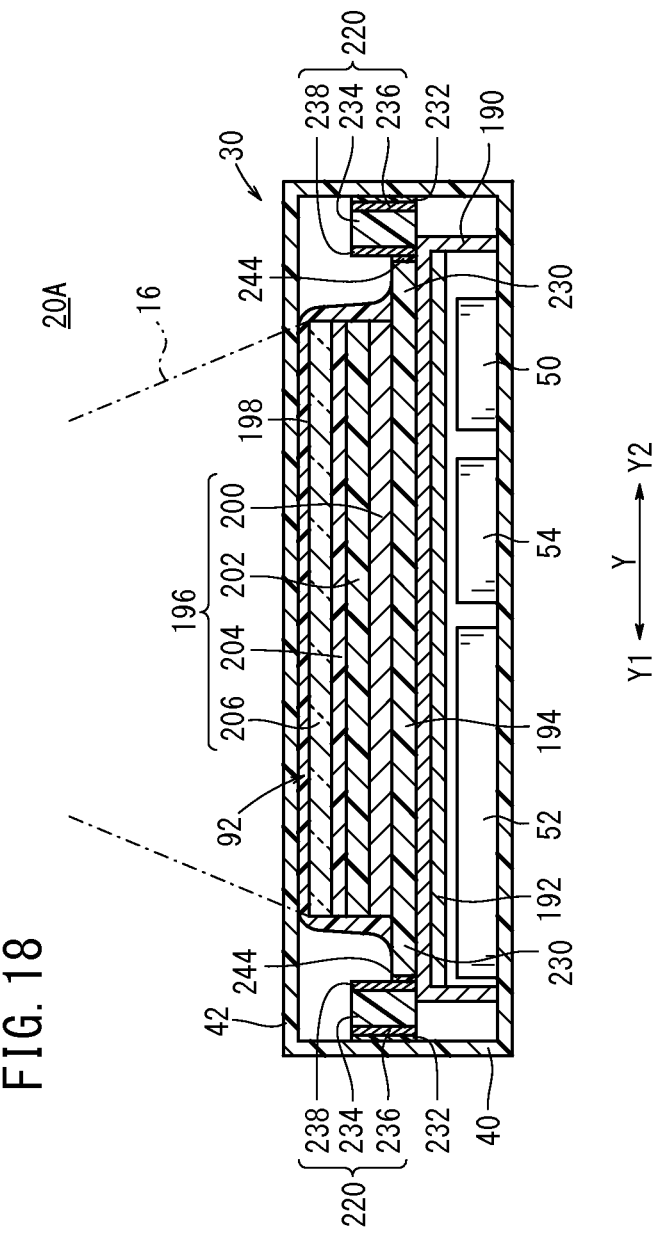
FIG. 18 is a cross-sectional view of a cassette according to a fourth modification.
Figure 19:
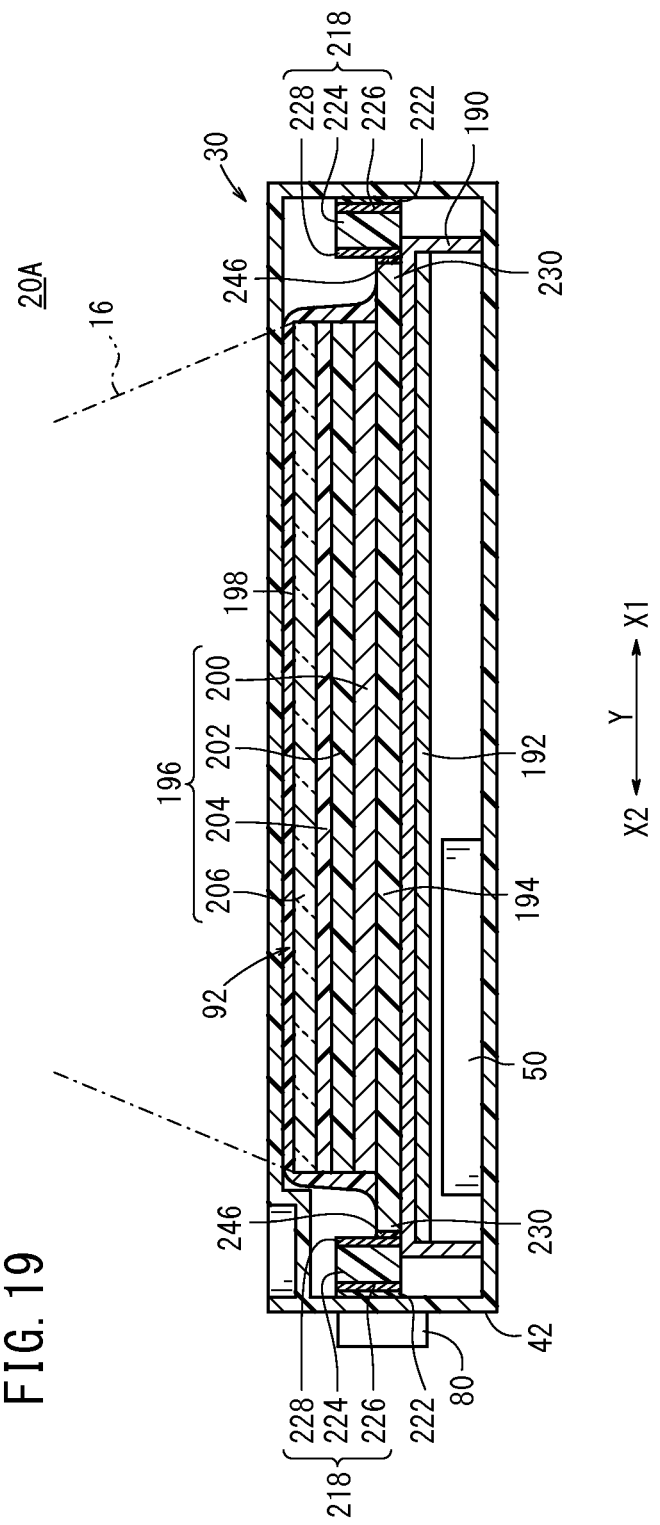
FIG. 19 is a cross-sectional view of the cassette according to the fourth modification.
Figure 20:
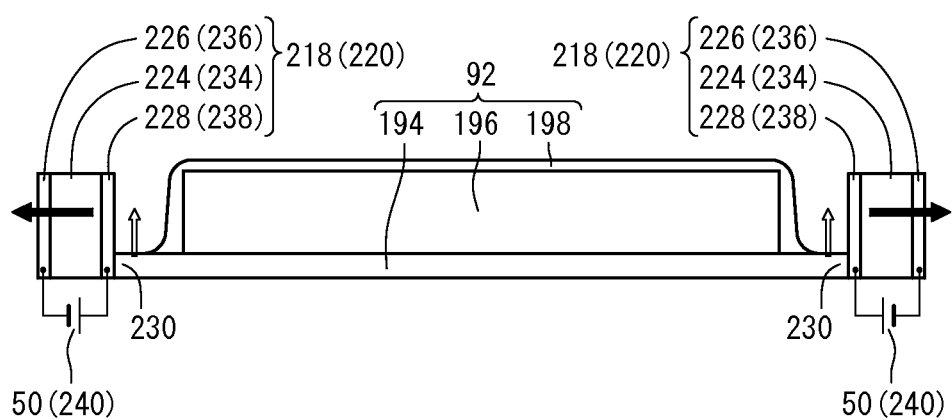
FIG. 20 is a view schematically showing the manner in which the external force applying unit of the cassette shown in FIGS. 18 and 19 applies an external force to a peripheral portion of a board.
Figure 21:
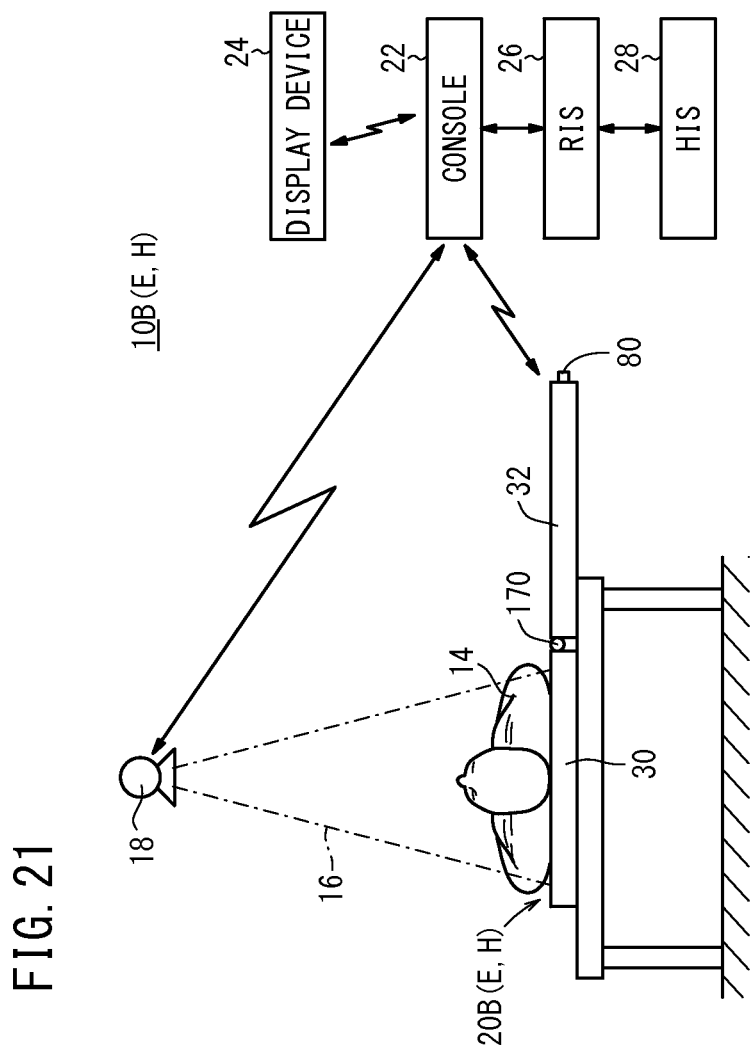
FIG. 21 is a schematic view of a radiographic image capturing system incorporating a cassette according to a second embodiment of the present invention.
Figure 22:
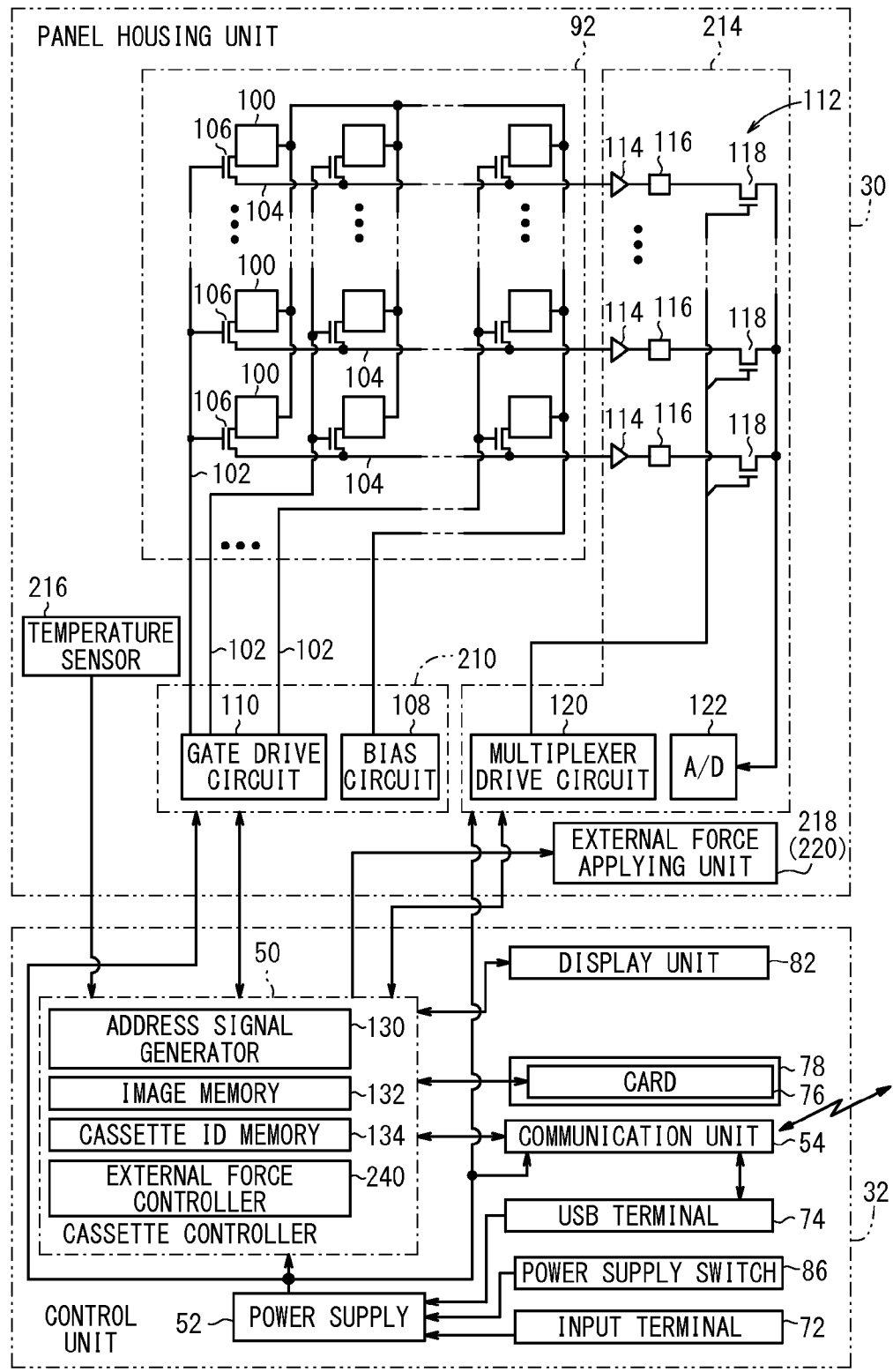
FIG. 22 is a block diagram of the cassette shown in FIG. 21.

As shown in FIGS. 18 through 20, the electronic cassette 20A according to the fourth modification differs from electronic cassettes 20A shown in FIGS. 1 through 17, in that the external force applying units 218, 220 are arranged horizontally rather than vertically.

As shown in FIG. 18, the external force applying units 220 are arranged horizontally between the peripheral edge 230 that faces in the direction of the arrow Y1 and the side of the casing 40 that faces in the direction of the arrow Y1, and between the peripheral edge 230 that faces in the direction of the arrow Y2 and the side of the casing 40 that faces in the direction of the arrow Y2. The external force applying units 220 have respective ends, i.e., electrodes 236, which are bonded to the sides of the casing 40 by respective dismantlable adhesives 232, and respective other ends, i.e., electrodes 238, which are partially bonded to the peripheral edges 230 by respective dismantlable adhesives 244.

As shown in FIG. 19, the external force applying units 218 are arranged horizontally between the peripheral edge 230 that faces in the direction of the arrow X1 and the side of the casing 40 that faces in the direction of the arrow X1, as well as between the peripheral edge 230 that faces in the direction of the arrow X2 and the side of the casing 40 that faces in the direction of the arrow X2. The external force applying units 218 have respective ends, i.e., electrodes 226, which are bonded to sides of the casing 40 by respective dismantlable adhesives 222, and respective other ends, i.e., electrodes 228, which are partially bonded to the peripheral edges 230 by respective dismantlable adhesives 246.

Upon application of control voltages to the external force applying units 218, 220, as shown in FIG. 20, the actuator elements 224, 234 of the external force applying units 218, 220 shrink, thereby applying external forces horizontally to the peripheral edges 230 in order to pull both ends, i.e., two confronting peripheral edges 230, of the board 194 toward the sides of the casing 40. Since the external forces horizontally pull the two confronting peripheral edges 230, the radiation conversion panel 92 including the board 194 is reliably kept flat depending on the temperature change.

Since both ends of the external force applying units 218, 220 are securely bonded by the dismantlable adhesives 222, 232, 244, 246, the external force applying units 218, 220 can easily be replaced at the time that functions thereof become lowered as a result of being irradiated with radiation 16.

The above-described radiation conversion panel 92 according to the first embodiment is of a so-called reverse side reading type, i.e., a PSS (Penetration Side Sampling) type, wherein the scintillator 206 is disposed forwardly and the photoelectric transducer layer 202 is disposed rearwardly with respect to the direction, i.e., the direction of incidence, in which radiation 16 is applied. However, the electronic cassette 20A according to the first embodiment is not limited to a PSS type. Rather, the electronic cassette 20A may also be applied to a face side reading type of radiation conversion panel, i.e., an ISS (Irradiation Side Sampling) type, wherein the photoelectric transducer layer 202 is disposed forwardly and the scintillator 206 is disposed rearwardly with respect to the direction in which radiation 16 is applied. Details of PSS type and ISS type radiation conversion panels will be described later.

The first embodiment also is applicable to acquisition of radiographic images using a light readout type of radiation conversion panel. Such a light readout type of radiation conversion panel operates in the following manner. If radiation is applied to each of the solid-state detectors, an electrostatic latent image depending on the dose of radiation is stored and recorded in the solid-state detector. For reading the electrostatic latent image, reading light is applied to the radiation conversion panel, and the value of a generated electric current is acquired as a radiographic image. The radiation conversion panel can be reused after being irradiated with erasing light, in order to erase any radiographic image that remains therein as an electrostatic latent image (see Japanese Laid-Open Patent Publication No. 2000-105297).

To prevent the electronic cassette 20A from being contaminated with blood and bacteria, the electronic cassette 20A may have a water-resistant and hermetically sealed structure as a whole. The electronic cassette 20A may be sterilized and cleaned as necessary, so that the electronic cassette 20A can be used repeatedly.

The first embodiment is not limited to capturing radiographic images in a medical organization, but may also be applied to capturing radiographic images of subjects during medical checkups carried out in examination cars. Furthermore, the first embodiment is not limited to capturing radiographic images in the art of medicine, but may also be applied to capturing radiographic images in various types of nondestructive tests.

2. Description of Second Embodiment

An electronic cassette 20B and a radiographic image capturing system 10B according to a second embodiment of the present invention will be described below with reference to FIGS. 21 through 28.

Components of the electronic cassette 20B and the radiographic image capturing system 10B, which are identical to those of the electronic cassette 20A and the radiographic image capturing system 10A according to the first embodiment (see FIGS. 1 through 20), are denoted by identical reference characters, and such features will not be described in detail below. This will also apply to the other embodiments.

The electronic cassette 20B and the radiographic image capturing system 10B according to the second embodiment differ from the electronic cassette 20A and the radiographic image capturing system 10A according to the first embodiment (see FIGS. 1 through 20), in that a control unit 32 is joined to the panel housing unit 30 by a hinge 170.

In the electronic cassette 20B, the control unit 32 has a casing 48, which is shaped substantially the same as the casing 40 of the panel housing unit 30. The casing 48 is made of a material impermeable to radiation 16. The casing 48 houses therein the cassette controller 50, the power supply 52, the communication unit 54, etc. The control unit 32 also has components that are not involved in the conversion of radiation 16 into a radiographic image, e.g., the display unit 82, the handle 80, etc. Therefore, the control unit 32 is not required to have the base table 190 and the shield plate 192, and hence the electronic cassette 20B can be made lightweight.

Figure 23A:
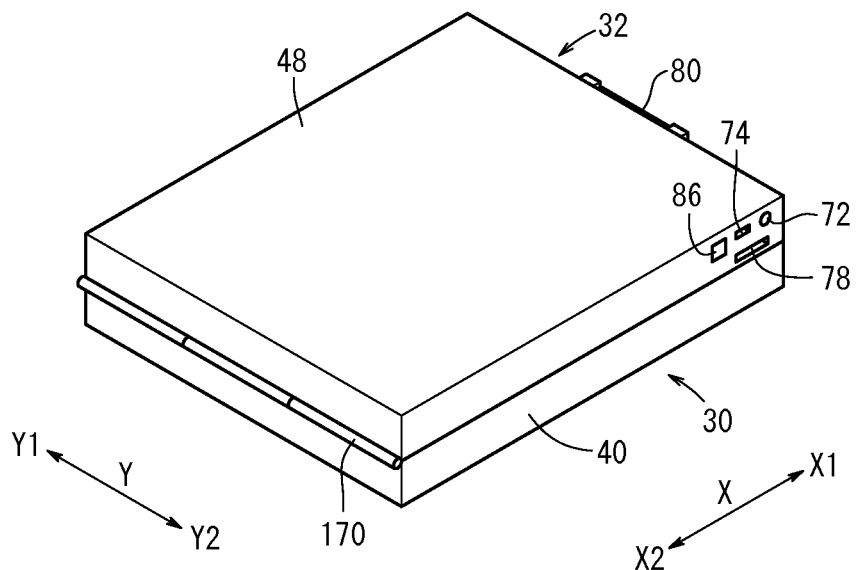
FIG. 23A is a perspective view showing the cassette in a state in which the cassette is carried.
Figure 23B:
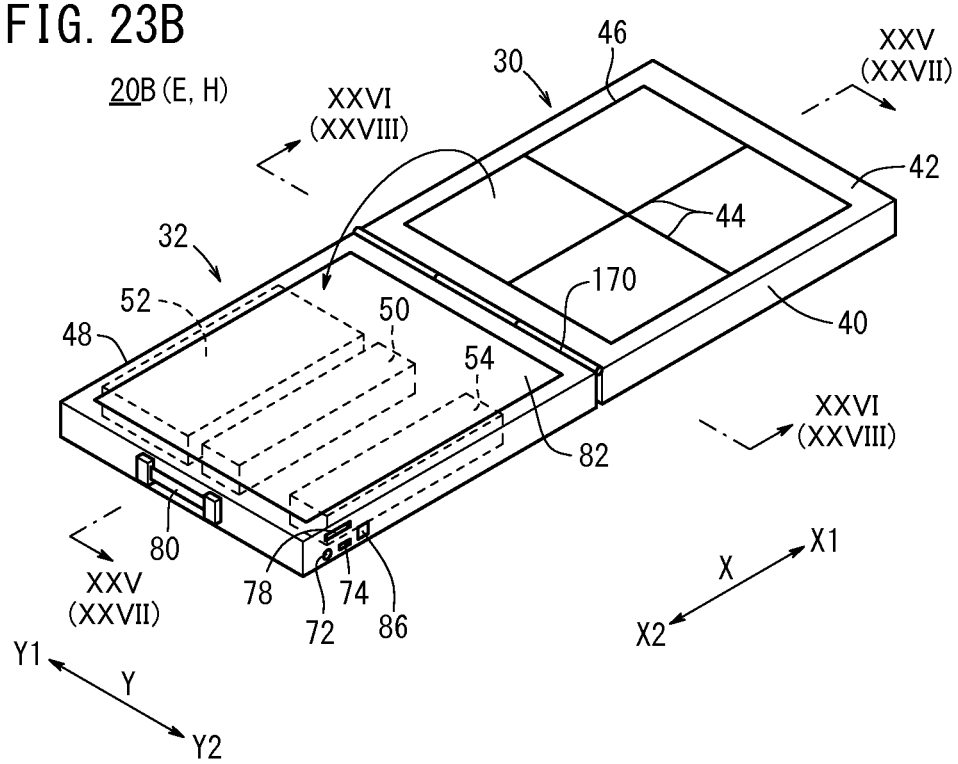
FIG. 23B is a perspective view showing the cassette in a state in which the cassette captures a radiographic image.

FIG. 23A shows the electronic cassette 20B in a state in which the electronic cassette 20B is carried. In a state in which the electronic cassette 20B is carried, the panel housing unit 30 and the control unit 32 are folded upon each other. FIG. 23B shows the electronic cassette 20B during capturing of a radiographic image. If the doctor or radiological technician grips the handle 80 and turns the casing 48 about the hinge 170, the casing 48 is moved angularly from the position shown in FIG. 23A to the position shown in FIG. 23B, in which the electronic cassette 20B is capable of capturing a radiographic image.

Figure 24:
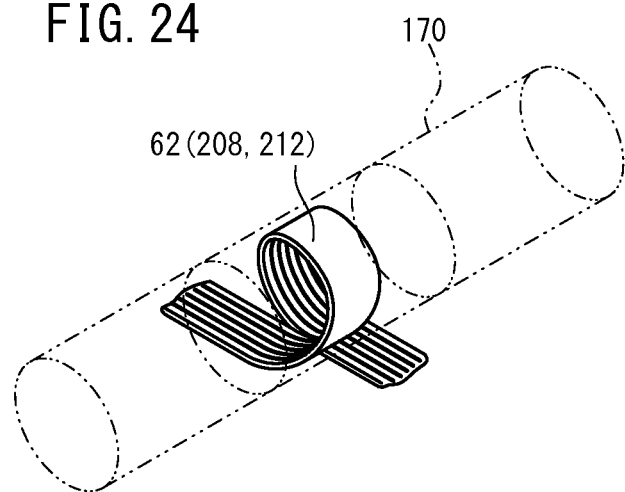
FIG. 24 is a fragmentary perspective view showing the position of a flexible board on a hinge shown in FIGS. 21, 23A, and 23B.

Signals are sent and received, and electric power is supplied, between the panel housing unit 30 and the control unit 32 through a flexible board 62 (see FIGS. 24 through 28). The flexible board 62 is flexible, similar to the case of the flexible boards 208, 212 described above. As shown in FIG. 24, the flexible board 62 is coiled in one turn within the hinge 170. Therefore, if the control unit 32 is angularly moved with respect to the panel housing unit 30, tension and stresses caused by angular movement of the control unit 32 are effectively prevented from being imposed on the flexible board 62.

Figure 25:
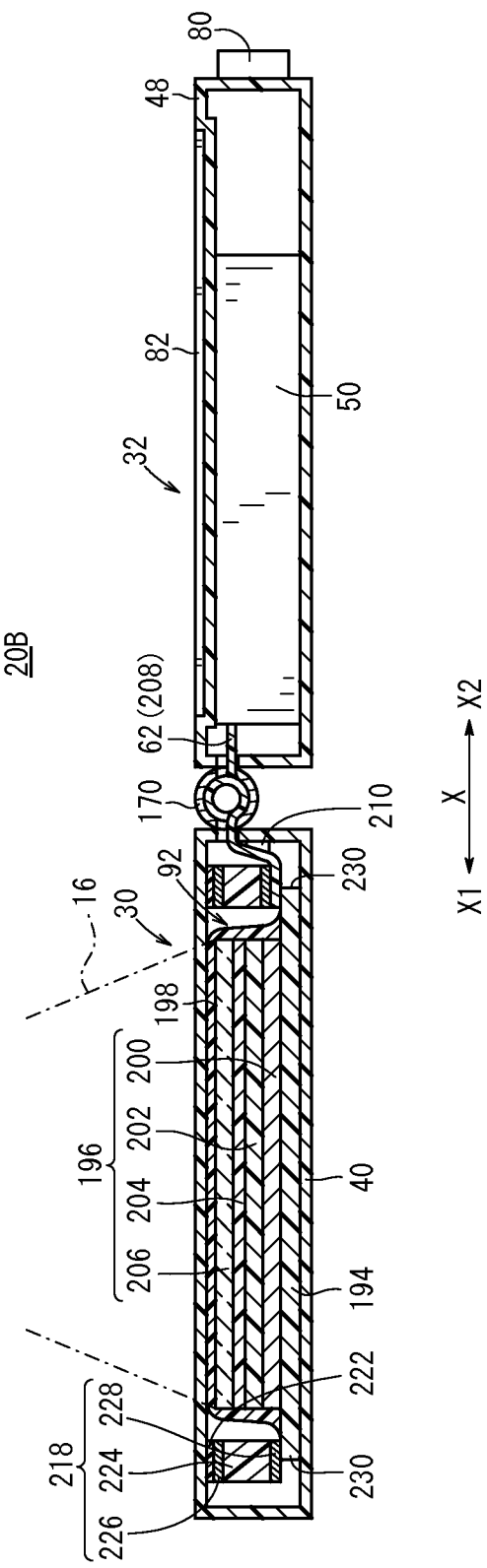
FIG. 25 is a cross-sectional view taken along line XXV-XXV of FIG. 23B.
Figure 26:
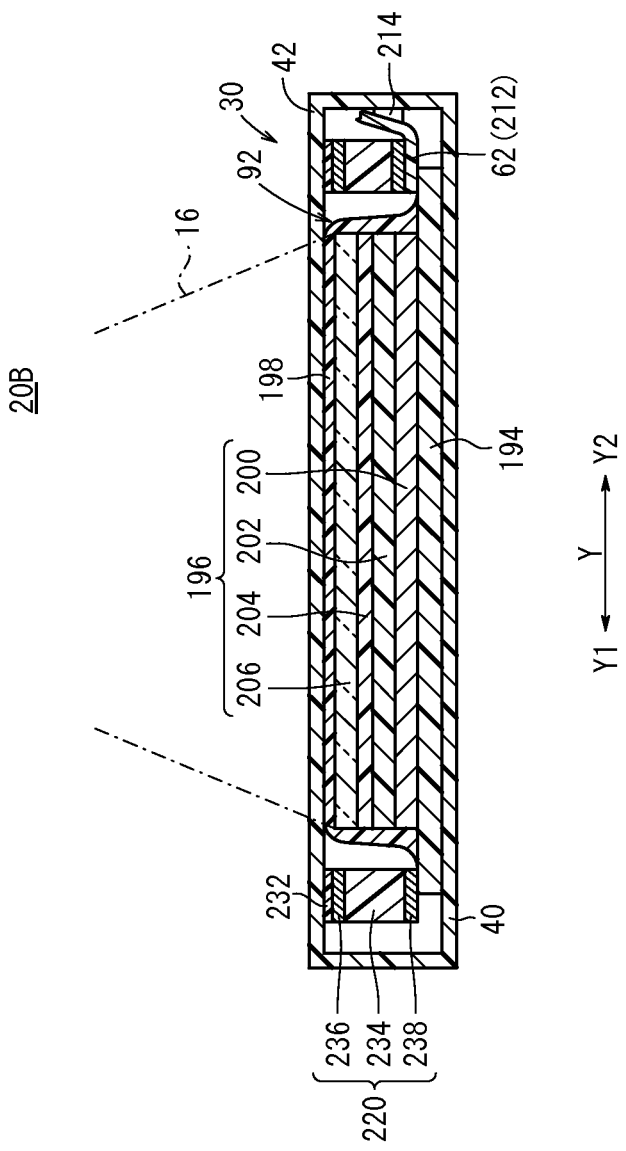
FIG. 26 is a cross-sectional view taken along line XXVI-XXVI of FIG. 23B.
Figure 27:
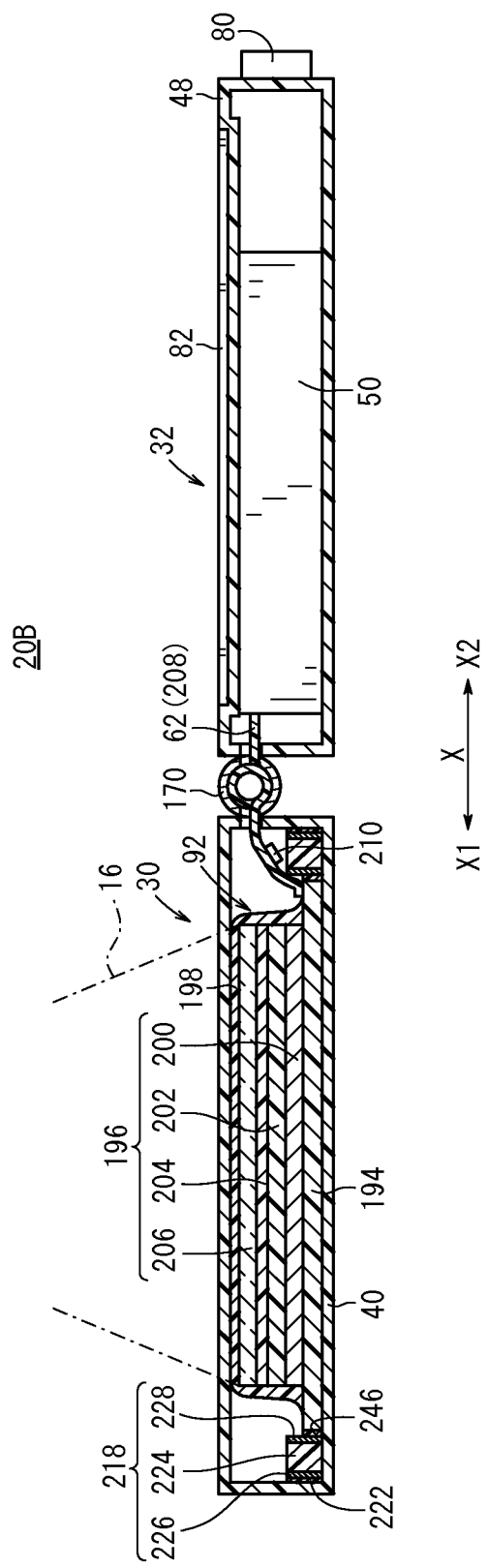
FIG. 27 is a cross-sectional view taken along line XXVII-XXVII of FIG. 23B.
Figure 28:
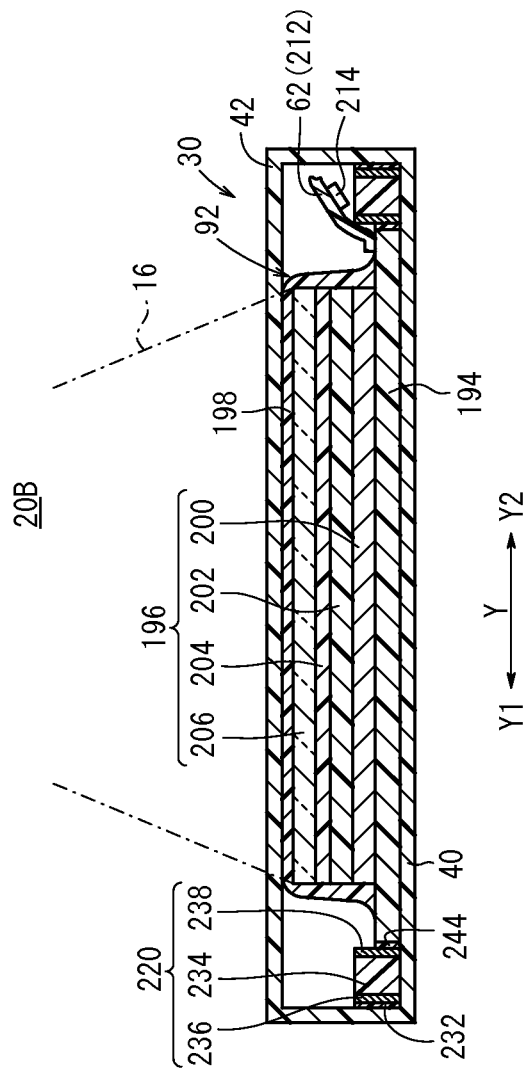
FIG. 28 is a cross-sectional view taken along line XXVIII-XXVIII of FIG. 23B.
Figure 29:
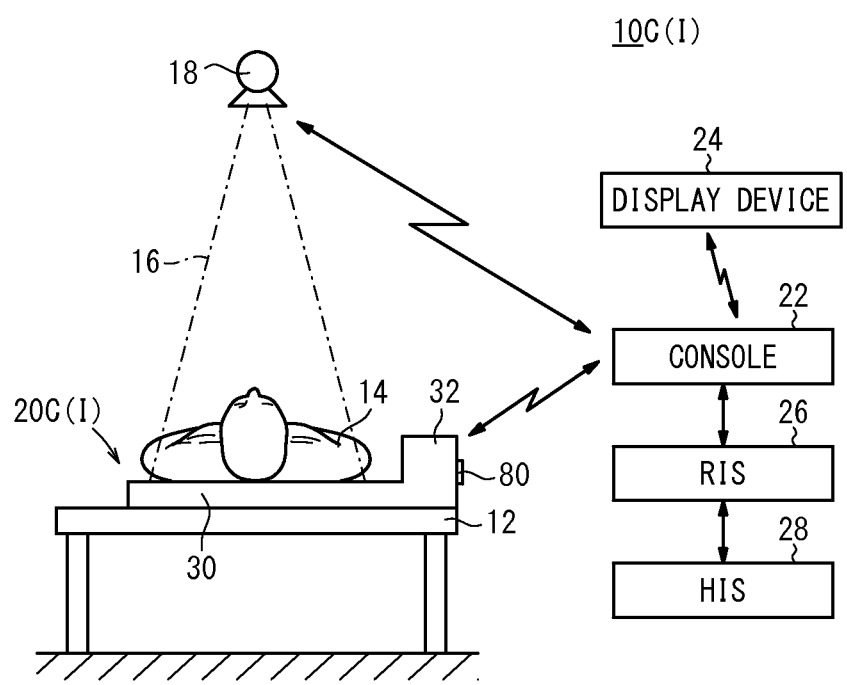
FIG. 29 is a schematic view of a radiographic image capturing system incorporating a cassette according to a third embodiment of the present invention.
Figure 30:
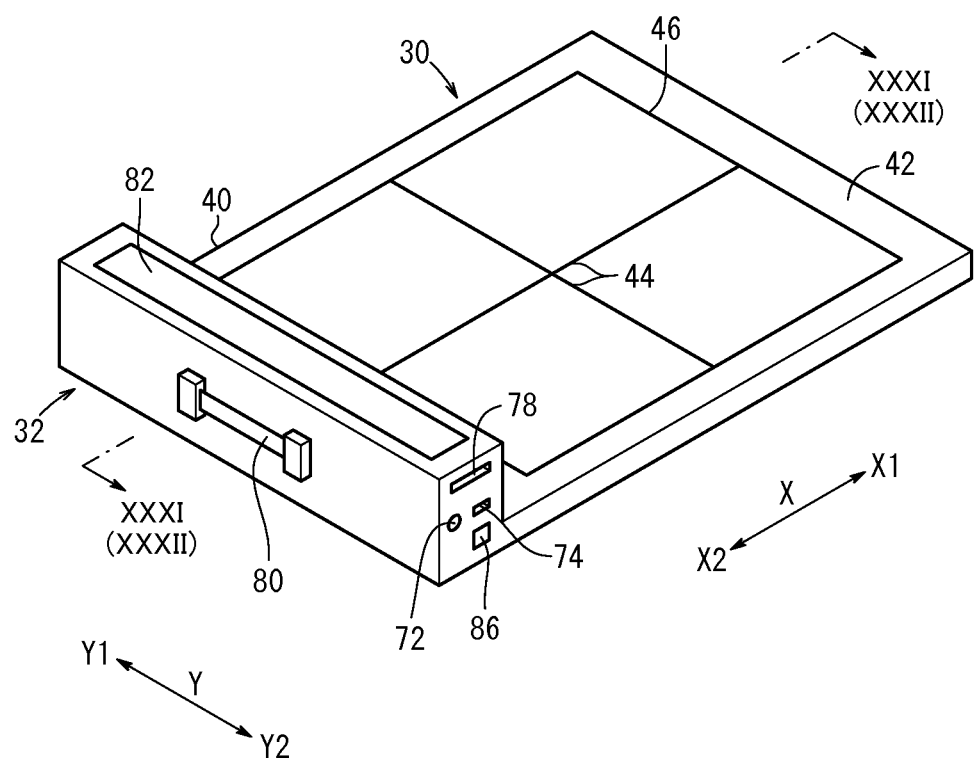
FIG. 30 is a perspective view of the cassette shown in FIG. 29.
Figure 31:
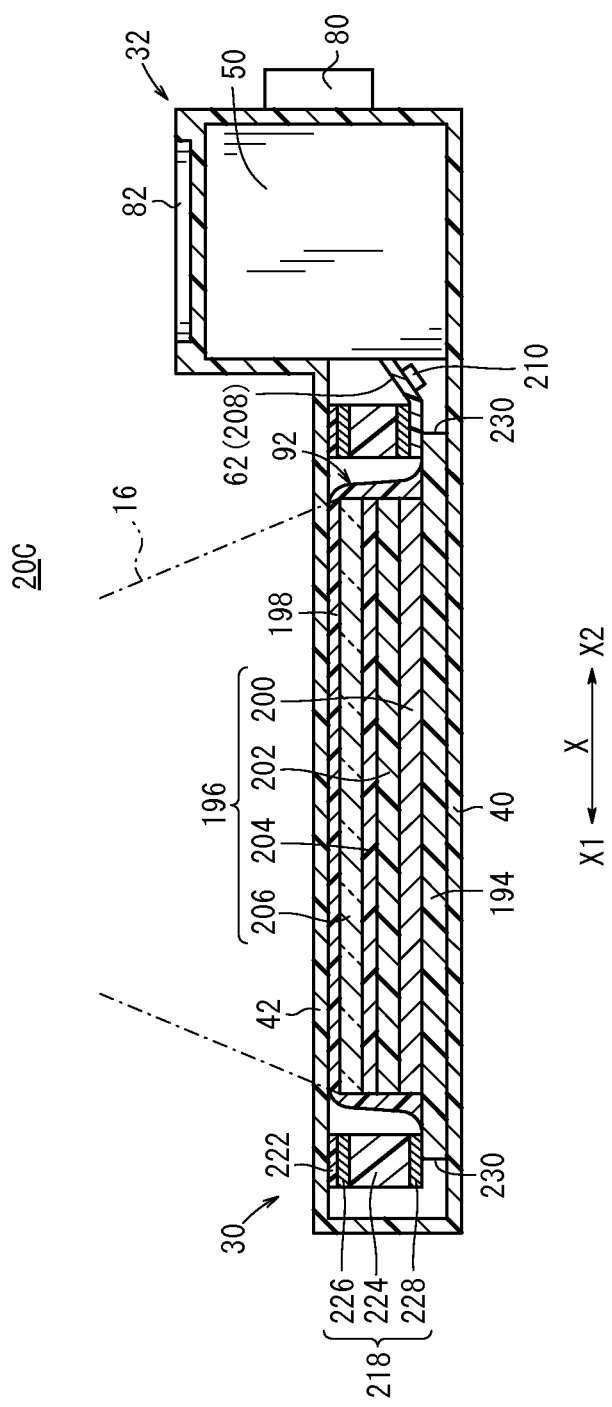
FIG. 31 is a cross-sectional view taken along line XXXI-XXXI of FIG. 30.

In the casing 40 of the panel housing unit 30, the external force applying units 218, 220 may be arranged vertically as shown in FIGS. 25 through 28, as is the case with the first embodiment, or may be arranged horizontally. In either case, the advantages obtained from the vertical arrangement of the external force applying units 218, 220, or the advantages obtained from the horizontal arrangement of the external force applying units 218, 220 can be achieved. FIGS. 25 and 26 show the electronic cassette 20B, which is constructed according to a third modification (see FIGS. 16 and 17), and FIGS. 27 and 28 show the electronic cassette 20B, which is constructed according to a fourth modification (see FIGS. 18 through 20).

3. Description of Third Embodiment

An electronic cassette 20C and a radiographic image capturing system 10C according to a third embodiment of the present invention will be described below with reference to FIGS. 29 through 32.

The electronic cassette 20C and the radiographic image capturing system 10C according to the third embodiment differ from the electronic cassettes 20A, 20B and the radiographic image capturing systems 10A, 10B according to the first and second embodiments (see FIGS. 1 through 28), in that a side portion of the panel housing unit 30 that faces in the direction of the arrow X2 projects upwardly, wherein the projecting portion functions as a control unit 32.

Components that are not involved in the conversion of radiation 16 into a radiographic image, e.g., the cassette controller 50, the power supply 52, the communication unit 54, the display unit 82, the handle 80, etc., are disposed together in the projecting portion. Structures of the radiation conversion panel 92 and the external force applying units 218, 220 in the panel housing unit 30 are the same as those according to the second embodiment, and such features will not be described in detail below.

Figure 32:
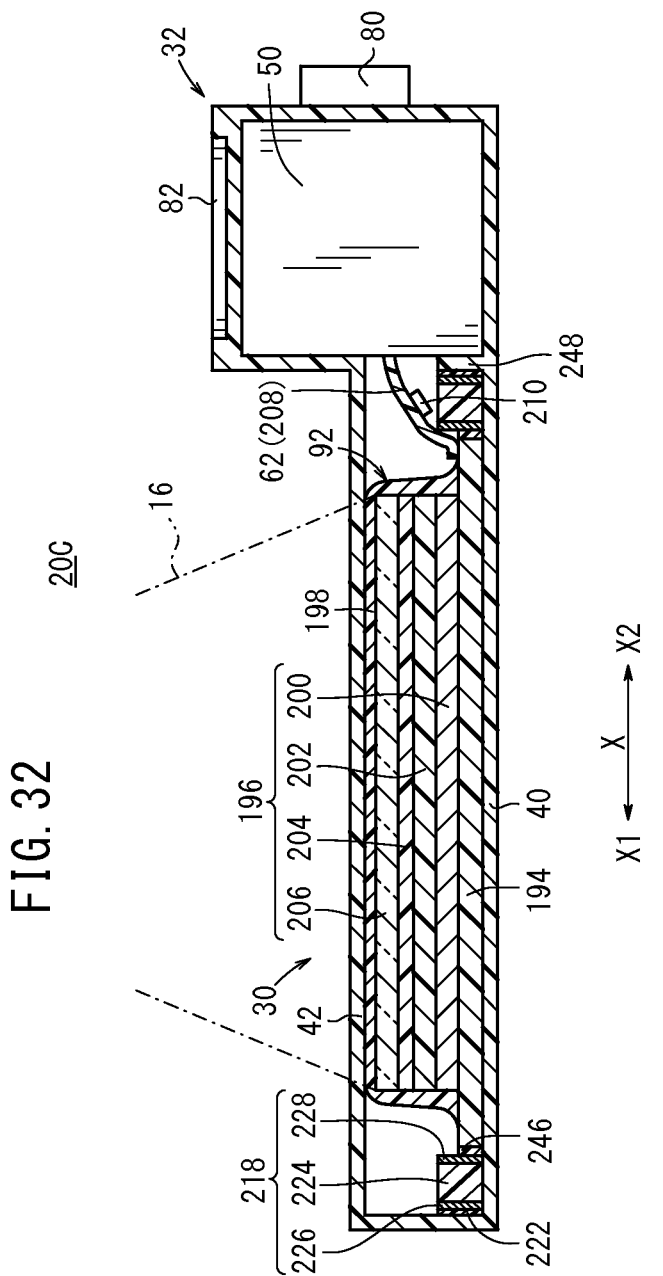
FIG. 32 is a cross-sectional view taken along line XXXII-XXXII of FIG. 30.

In FIG. 32, the bottom of the casing 40 has an upward protrusion 248 at a boundary between the projecting portion, i.e., the control unit 32, and the radiation conversion panel 92 and the external force applying units 218, 220. The electrode 226 of the external force applying unit 218 that faces in the direction of the arrow X2 is bonded to the protrusion 248 by the dismantlable adhesive 222.

The third embodiment with the external force applying units 218, 220 also offers the advantages of the first and second embodiments.

4. Description of Modifications of the First through Third Embodiments

It has been described above that the radiation conversion layer 196 is mounted on the board 194 and includes the signal output layer 200, the photoelectric transducer layer 202, the adhesive layer 204, and the scintillator 206, which are successively deposited upwardly in this order on the board 194, and the radiation conversion layer 196, which is made up of the deposited layers covered with the protective film 198.

Figure 33:
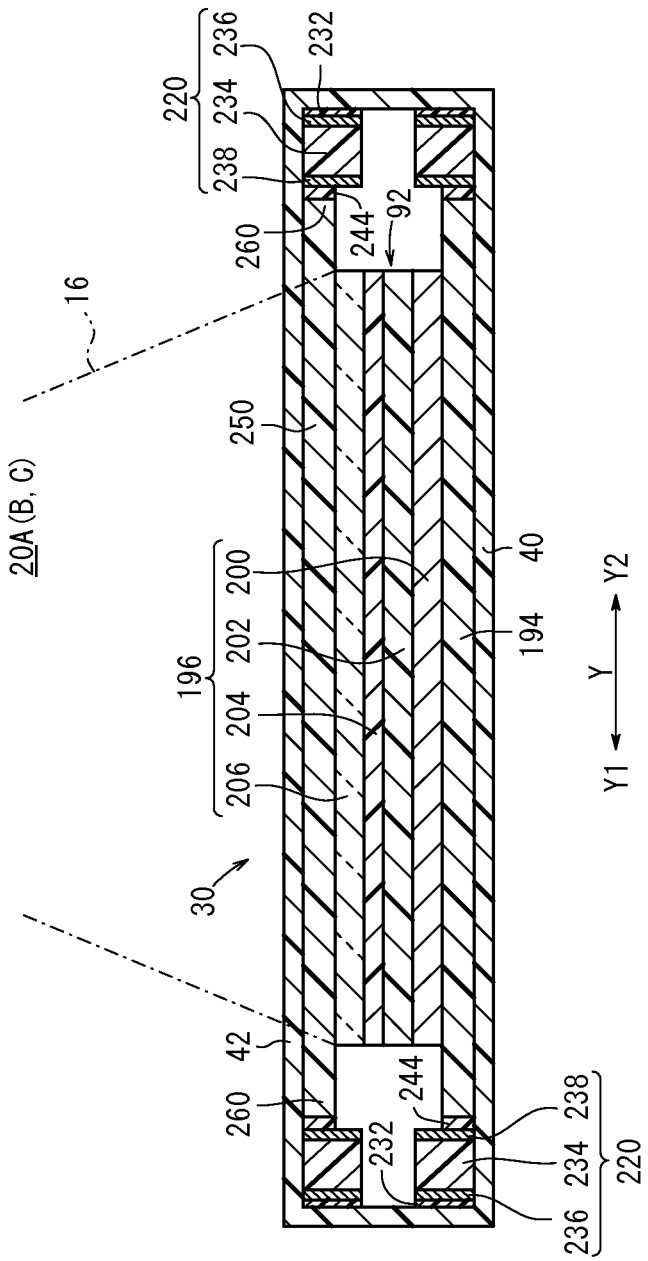
FIG. 33 is a cross-sectional view of a cassette according to a fifth modification.
Figure 34:
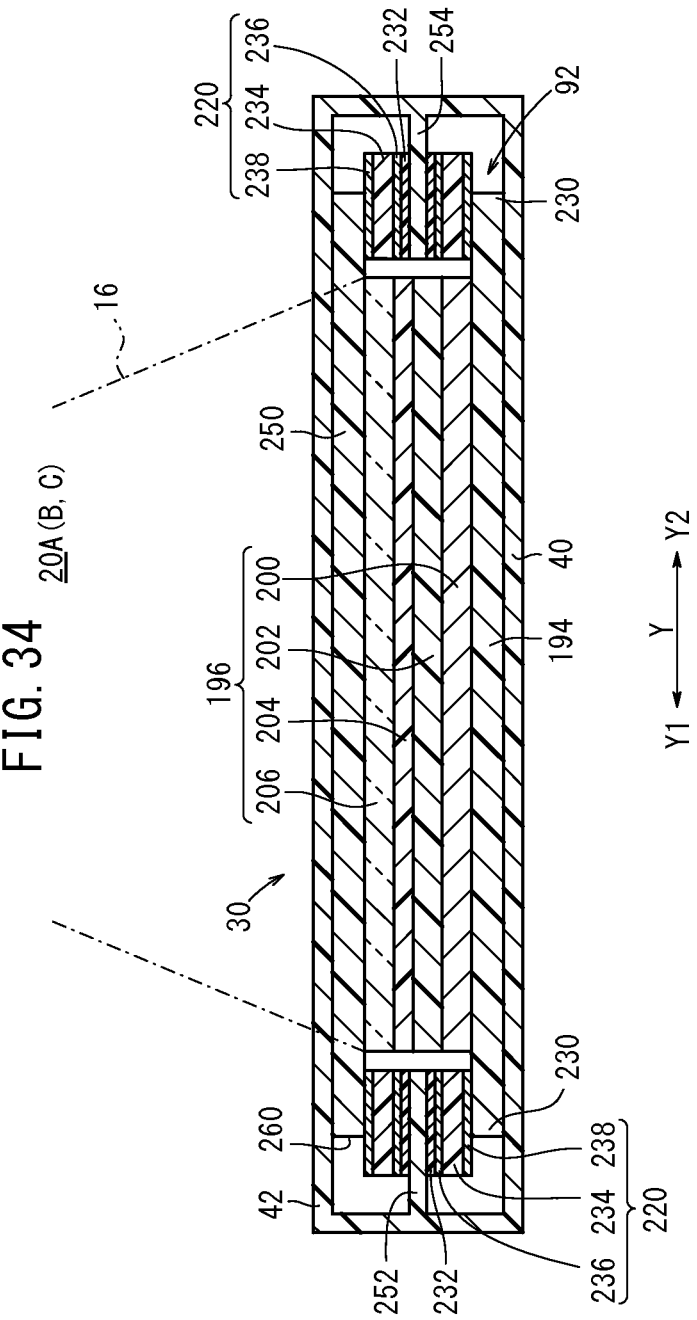
FIG. 34 is a cross-sectional view of the cassette according to the fifth modification.

The electronic cassettes 20A through 20C according to the first through third embodiments may be modified according to another modification (hereinafter referred to as a "fifth modification"), as shown in FIGS. 33 and 34.

According to the fifth modification, as shown in FIGS. 33 and 34, the signal output layer 200 and the photoelectric transducer layer 202 are successively deposited in this order on the board 194, the scintillator 206 is deposited by evaporation or the like on a board 250 made of aluminum, plastic, or the like, and the photoelectric transducer layer 202 and the scintillator 206, which are disposed in confronting relation to each other, are securely bonded to each other by the adhesive layer 204. Therefore, according to the fifth modification, the protective film 198 may be dispensed with. Also, the boards 194, 250 have different coefficients of thermal expansion.

According to the fifth modification, as shown in FIG. 33, external force applying units 220 also are securely bonded horizontally between peripheral edges 260 of the board 250 and sides of the casing 40. Further, as shown in FIG. 34, protrusions 252, 254 extend inwardly from sides of the casing 40, and external force applying units 220 are vertically disposed between the protrusions 252, 254 and the peripheral edges 230, 260 of the boards 194, 250. In FIG. 34, the external force applying units 220 are securely bonded to the protrusions 252, 254 by a dismantlable adhesive 232.

In FIG. 33, although the radiation conversion panel 92 tends to be deformed due to temperature changes, the two external force applying units 220 on the board 194 continuously apply external forces in order to pull the board 194 horizontally, and the two external force applying units 220 on the board 250 continuously apply external forces in order to pull the board 250, thereby keeping the radiation conversion panel 92 flat more reliably and effectively.

In FIG. 34, although the radiation conversion panel 92 tends to be deformed due to temperature changes, the two external force applying units 220 on the board 194 continuously apply external forces vertically to the board 194, whereas the two external force applying units 220 on the board 250 continuously apply external forces vertically to the board 250, thereby keeping the radiation conversion panel 92 flat more reliably and effectively.

In each of the structures shown in FIGS. 33 and 34, since the coefficients of thermal expansion of the boards 194, 250 are different from each other, the peripheral edges 230, 260 are deformed to different degrees if the temperature of the radiation conversion panel 92 changes. Depending on the different degrees of deformation caused by the temperature change, the magnitude (and polarity) of the control voltages applied to the external force applying units 220 on the board 194, and the magnitude (and polarity) of the control voltages applied to the external force applying units 220 on the board 250 are adjusted differently from each other, thereby continuously applying an appropriate amount of external force to the boards 194, 250.

According to the fifth modification, if the scintillator 206 is made of columnar crystals of CsI, then since the radiation conversion panel 92 is kept flat, the columnar crystals are kept perpendicular to the boards 194, 250, allowing the electronic cassette to easily acquire sharp radiographic images regardless of temperature changes. According to the fifth modification, if the actuator elements 224, 234 are made of a rubber-like polymeric film, i.e., an elastomer, then since the actuator elements 224, 234 serve as a shock absorbing member for absorbing shocks from an external source, the actuator elements 224 are effectively capable of protecting the components in the casing 40 from shocks.

The radiation conversion panel 92, which is of a PSS type, is illustrated in FIGS. 33 and 34. However, the radiation conversion panel 92 is not limited to a PSS type, but may be an ISS type in which the scintillator 206 and the board 250 are disposed near the bottom of the casing 40, and the board 194, the signal output layer 200, and the photoelectric transducer layer 202 are disposed near the upper surface of the casing 40, so as to provide the advantages referred to above.

It has also been described above that in order to apply horizontal external forces to the board 194, the external force applying units 218, 220 are securely bonded to the sides, i.e., the peripheral edges 230, of the board 194 by the dismantlable adhesives 244, 246.

Figure 35:
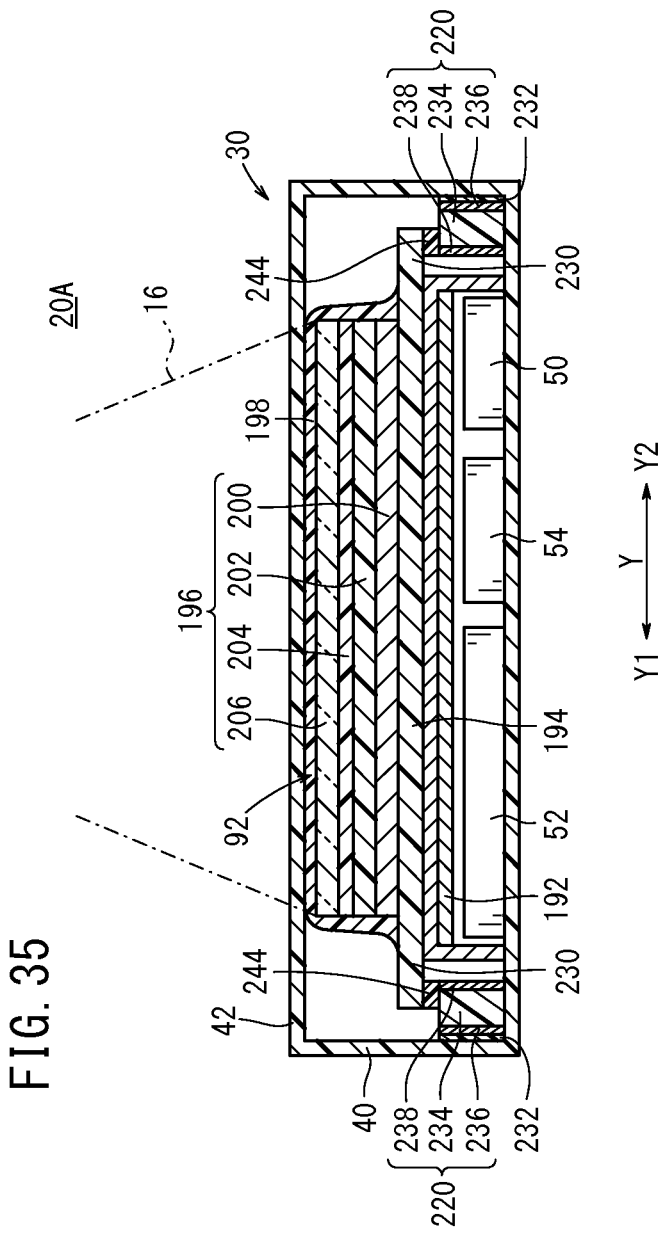
FIG. 35 is a cross-sectional view of a cassette according to a sixth modification.
Figure 36:
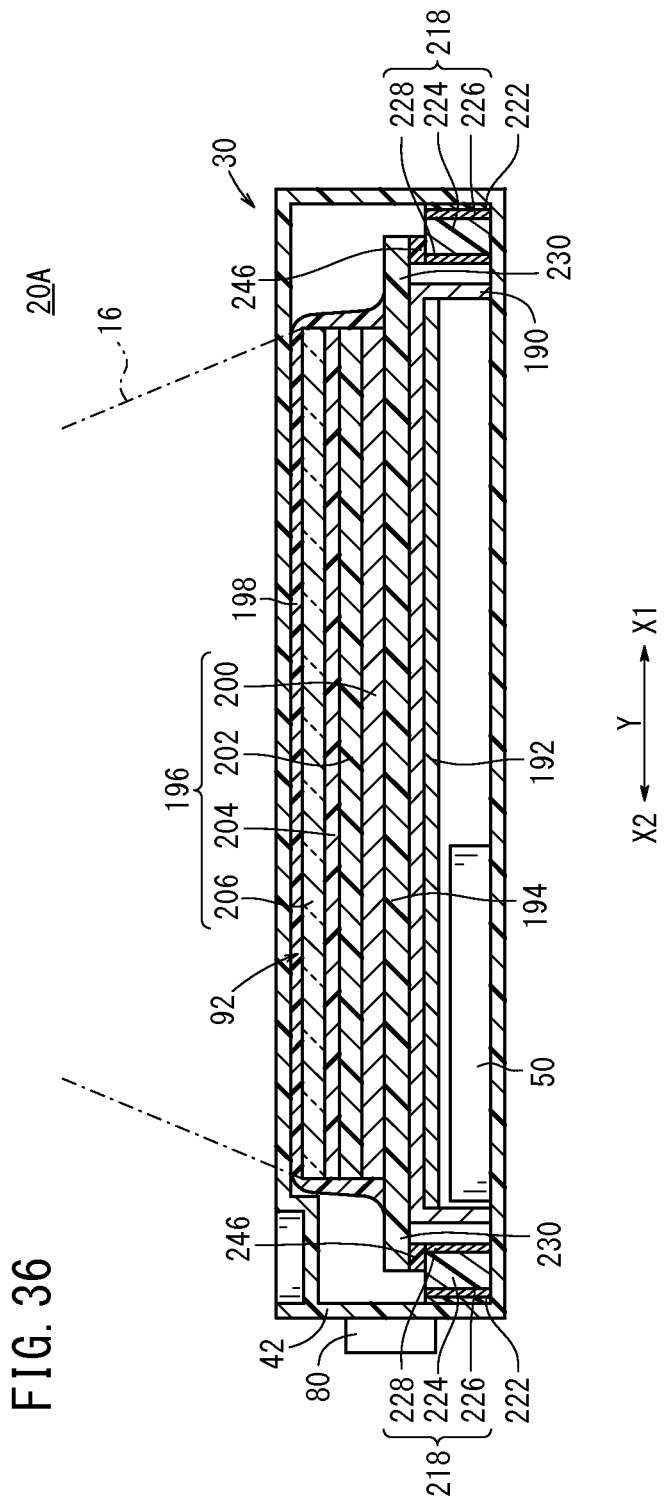
FIG. 36 is a cross-sectional view of the cassette according to the sixth modification.
Figure 37:
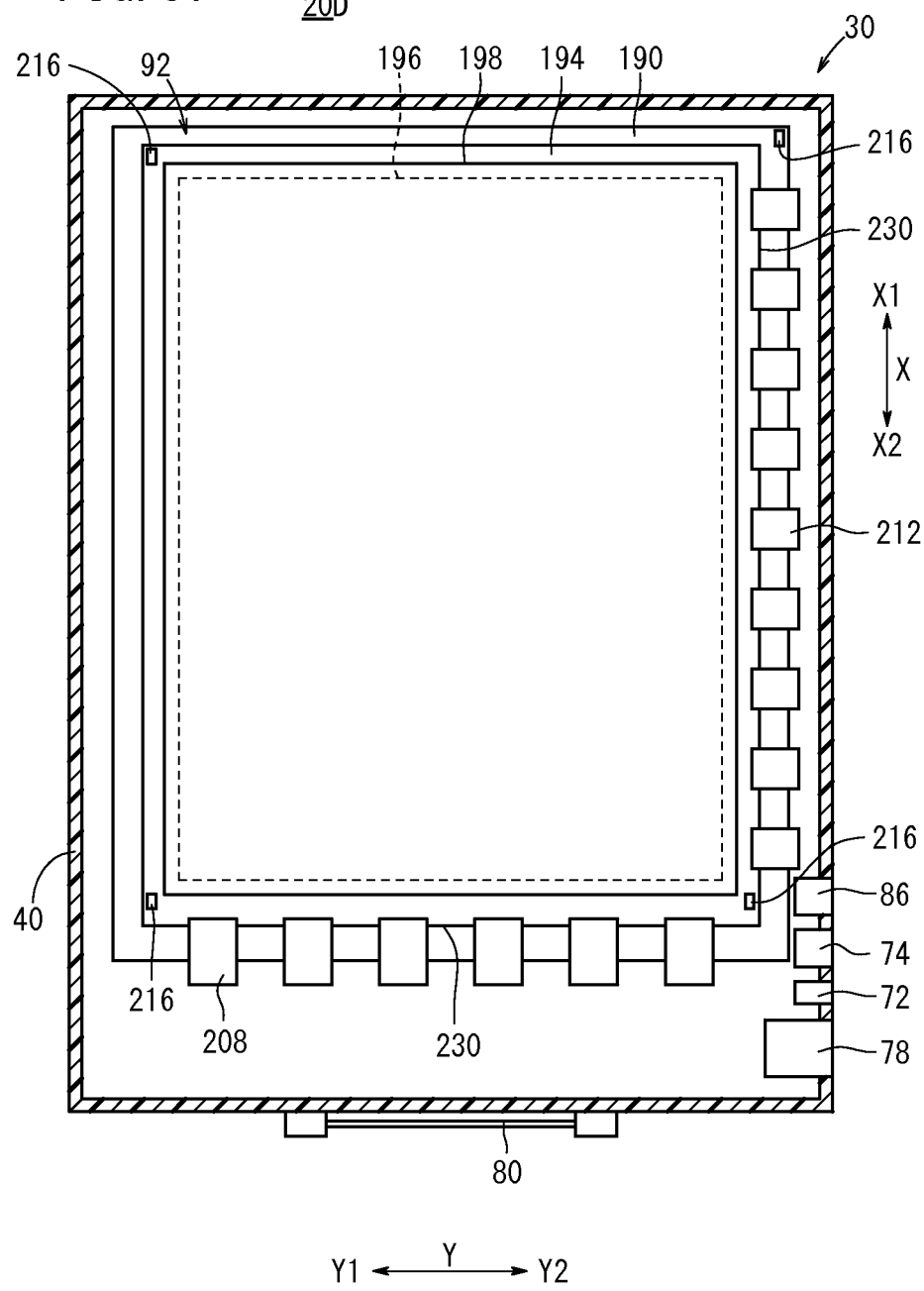
FIG. 37 is a plan view of the cassette according to the fourth embodiment, with an upper wall thereof being cut away.
Figure 38:
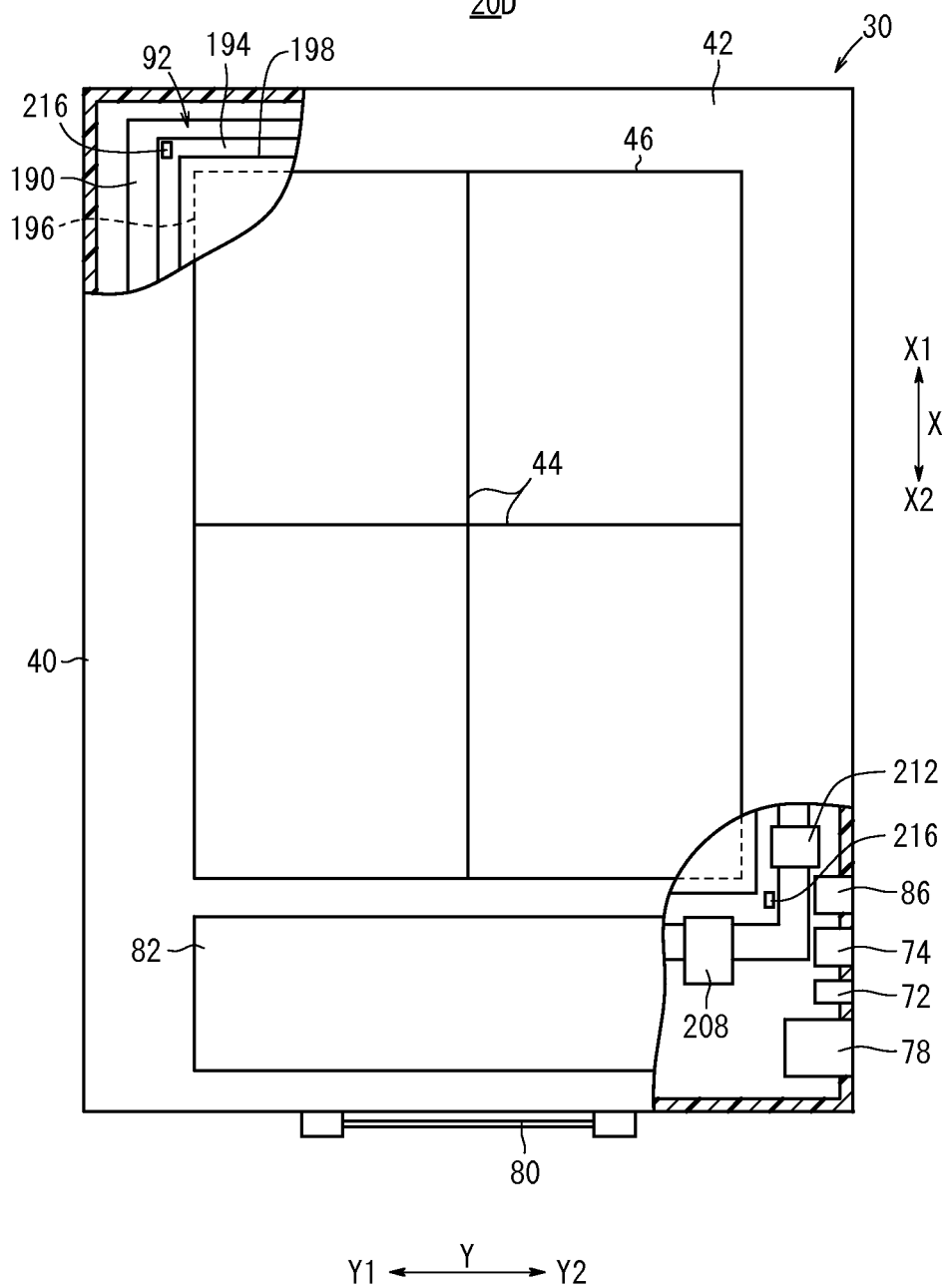
FIG. 38 is a plan view, partially cut away, of the cassette shown in FIG. 37.

The electronic cassette 20A according to the first embodiment may be modified according to another modification (hereinafter referred to as a "sixth modification"), as shown in FIGS. 35 and 36.

The electronic cassette 20A according to the sixth modification shown in FIGS. 35 and 36 differs from the electronic cassette 20A according to the fourth modification (see FIGS. 18 through 20B), in that the external force applying units 218, 220 are bonded to peripheral edges 230 at the bottom surface of the board 194 by the dismantlable adhesives 244, 246. Also, the electronic cassette 20A cooperates with the base table 190 in supporting the board 194.

More specifically, as shown in FIG. 35, the external force applying units 220 are disposed on the bottom of the casing 40 on a side thereof that faces in the direction of the arrow Y1, and on a side thereof facing in the direction of the arrow Y2. Also, the electrodes 236 are securely bonded to the side that faces in the direction of the arrow Y1, and on the side facing in the direction of the arrow Y2 by the dismantlable adhesive 232. The peripheral edges 230 of the board 194 project from the base table 190 in the direction of the arrow Y1 and in the direction of the arrow Y2. The peripheral edge 230 that projects in the direction of the arrow Y1 is securely bonded by the dismantlable adhesive 244 to the electrode 238 of the external force applying unit 220 and to the actuator element 234 in the direction of the arrow Y1, and the peripheral edge 230 that projects in the direction of the arrow Y2 is securely bonded by the dismantlable adhesive 244 to the electrode 238 of the external force applying unit 220 and to the actuator element 234 in the direction of the arrow Y2.

As shown in FIG. 36, the external force applying units 218 are disposed on the bottom of the casing 40 at a side facing in the direction of the arrow X1 and at a side facing in the direction of the arrow X2. The electrodes 226 are securely bonded to the side that faces in the direction of the arrow X1 and to the side that faces in the direction of the arrow X2 by the dismantlable adhesive 222. The peripheral edges 230 of the board 194 project from the base table 190 in the direction of the arrow X1 and in the direction of the arrow X2. The peripheral edge 230 that projects in the direction of the arrow X1 is securely bonded by the dismantlable adhesive 246 to the electrode 228 of the external force applying unit 218 and to the actuator element 224 in the direction of the arrow X1. The peripheral edge 230 that projects in the direction of the arrow X2 is securely bonded by the dismantlable adhesive 246 to the electrode 228 of the external force applying unit 218 and to the actuator element 224 in the direction of the arrow X2.

According to the sixth modification, the control voltages are also applied in the same manner as shown in FIG. 20 to cause the actuator elements 224, 234 of the external force applying units 218, 220 to shrink, which results in the application of horizontal external forces to the peripheral edges 230 on two confronting sides of the bottom surface of the board 194, for thereby pulling the peripheral edges 230 toward the sides of the casing 40. Consequently, the radiation conversion panel 92 including the board 194 is reliably kept flat depending on a temperature change thereof.

According to the sixth modification, since the external force applying units 218, 220 and the base table 190 support the board 194 together, the radiation conversion panel 92 is reliably supported in the casing 40.

Inasmuch as the radiation conversion panel 92 may be positioned so that the radiation conversion layer 196 and the image capturing field 46 overlap with each other (see FIG. 4), the base table 190 may be dispensed with, which makes the electronic cassette 20A lighter, and the board 194 may be supported by the external force applying units 218, 220. In this case, the shield plate 192 may be disposed on the bottom surface of the board 194, for example.

5. Description of Fourth Embodiment

An electronic cassette 20D and a radiographic image capturing system 10D according to a fourth embodiment of the present invention will be described below with reference to FIGS. 37 through 46.

<Arrangement of the Fourth Embodiment>

The electronic cassette 20D and the radiographic image capturing system 10D according to the fourth embodiment differ from the electronic cassettes 20A through 20C and the radiographic image capturing systems 10A through 10C according to the first through third embodiments (see FIGS. 1 through 36), in that a planar external force applying unit 218 for applying external forces to the radiation conversion panel 92 is made integral with, i.e., is stacked on, the radiation conversion panel 92. The overall arrangement of the radiographic image capturing system 10D is essentially the same as the overall arrangement of the radiographic image capturing system 10A shown in FIG. 1.

According to the fourth embodiment, as shown in FIGS. 37 through 40, an insulative sheet 270 is disposed in the casing 40 on the upper surface of the base table 190. The radiation conversion panel 92 and the external force applying unit (external force applying mechanism) 218, which are stacked together, are disposed in the casing 40 between the image capturing surface 42 and the insulative sheet 270.

The insulative sheet 270 is provided to keep the base table 190 and the external force applying unit 218 electrically insulated from each other. The radiation conversion panel 92 is securely bonded to, i.e., is stacked on, the upper surface of the external force applying unit 218, which is placed on the insulative sheet 270 through a dismantlable adhesive 272.

The radiation conversion panel 92 includes a board 194, which is securely bonded to the external force applying unit 218 by the dismantlable adhesive 272, a radiation conversion layer 196 mounted on the board 194, and a protective film 198 that covers the side and upper surfaces of the radiation conversion layer 196 on the board 194.

Figure 39:
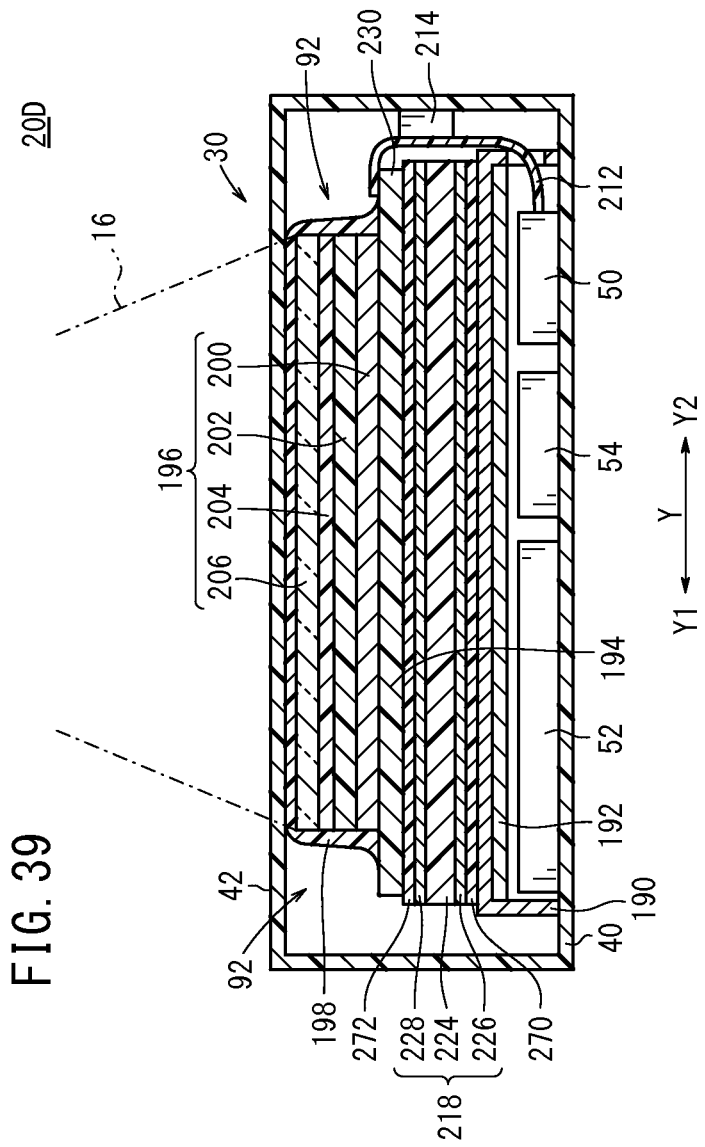
FIG. 39 is a cross-sectional view of the cassette shown in FIGS. 37 and 38.
Figure 40:
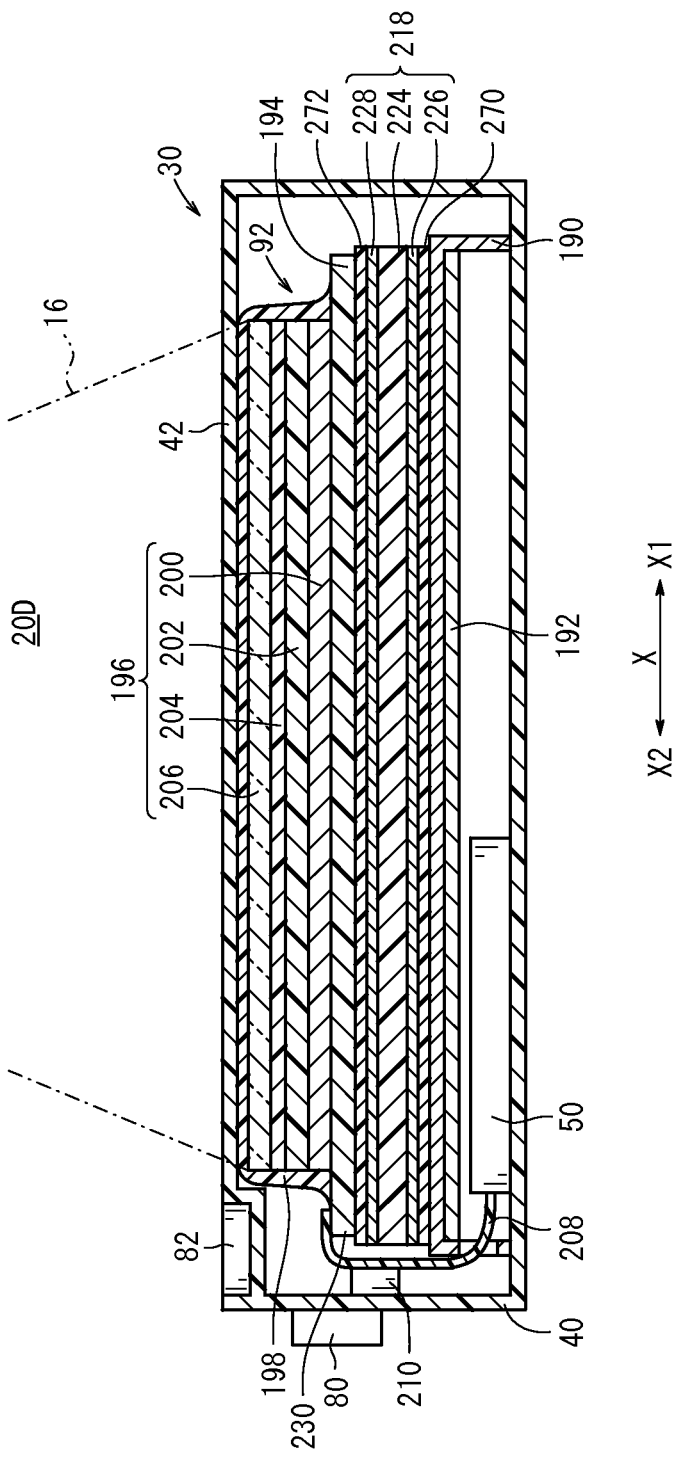
FIG. 40 is a cross-sectional view of the cassette shown in FIGS. 37 and 38.

According to the fourth embodiment, as shown in FIGS. 39 and 40, temperature sensors 216 are disposed on respective four corners of the board 194 for detecting the temperature of the board 194, i.e., the temperature of the radiation conversion panel 92.

As described above, the radiation conversion panel 92 and the external force applying unit 218 are integrally combined as a result of being securely bonded by the dismantlable adhesive 272. If the radiation conversion panel 92, i.e., the board 194, is deformed by the temperature thereof, the external force applying unit 218 also is deformed.

According to the fourth embodiment, more specifically, while the radiation conversion panel 92 is allowed to be deformed, i.e., is caused to expand or shrink thermally, the external force applying unit 218 applies an appropriate external force through the dismantlable adhesive 272 to the board 194. The external force depends on a temperature change of the radiation conversion panel 92 and is based on the temperature detected by the temperature sensors 216. Stated otherwise, the external force depends on the amount of deformation, i.e., the amount of warpage or expansion, of the board 194 caused by the temperature change. Therefore, the radiation conversion panel 92 is kept flat, and planarity of the radiation conversion panel 92 is maintained.

Structural details of the external force applying unit 218 according to the fourth embodiment will be described below.

As shown in FIGS. 39 and 40, the external force applying unit 218 has a surface held in face-to-face contact with the insulative sheet 270, and another surface bonded to the board 194 by the dismantlable adhesive 272. The external force applying unit 218 includes an actuator element 224 sandwiched between two electrodes 226, 228. The external force applying unit 218 serves as an actuator, which applies external forces to the board 194 by applying a control voltage between the electrodes 226, 228 through the cassette controller 50 thereby to deform the actuator element 224, wherein the magnitude and the polarity of the control voltage depend on the temperature change of the radiation conversion panel 92.

Figure 41A:
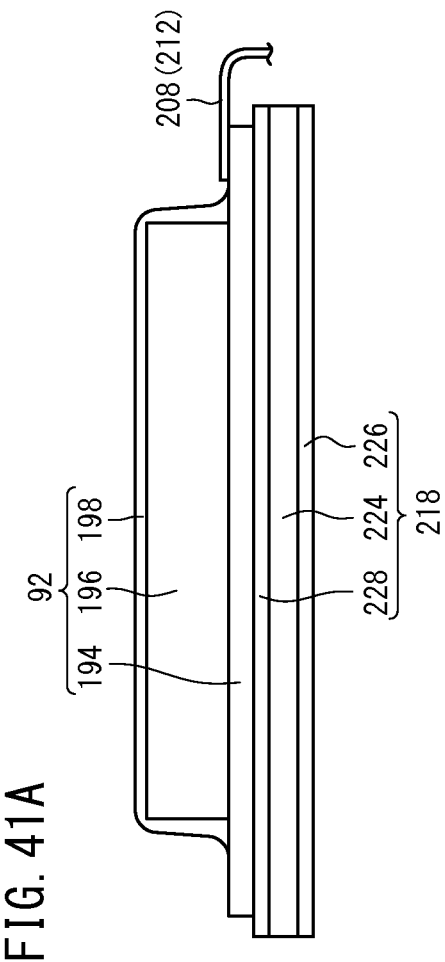
FIG. 41A is a view schematically showing the position of an external force applying unit with respect to the radiation conversion panel.
Figure 41B:
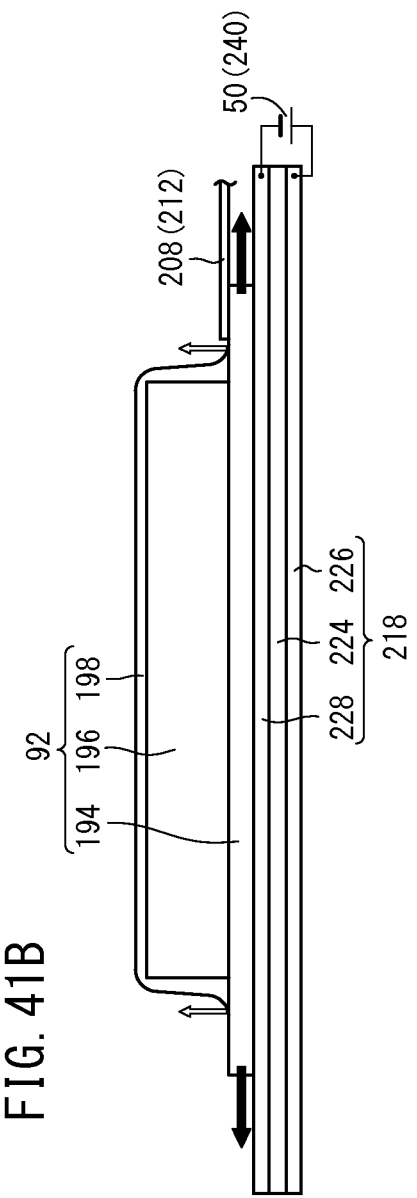
FIG. 41B is a view schematically showing the manner in which the external force applying unit applies external forces to a peripheral portion of a board.

More specifically, the external force applying unit 218 is in the state shown in FIG. 41A before the control voltage is applied thereto. If the control voltage is applied between the electrodes 226, 228, as shown in FIG. 41B, the actuator element 224 shrinks vertically and extends horizontally along the plane thereof. As a result, horizontal external forces indicated by the solid arrows in FIG. 41B are applied to the radiation conversion panel 92, i.e., the board 194 thereof, which is integrally combined with the external force applying unit 218 by the dismantlable adhesive 272 (see FIGS. 39 and 40). Consequently, even in a case where the radiation conversion panel 92 is warped, as indicated by the outline arrows in FIG. 41B due to a temperature change thereof, the radiation conversion panel 92 and the external force applying unit 218 are integrally kept flat.

According to the fourth embodiment, therefore, since the external force applying unit 218, which serves as an actuator, continuously applies external forces indicated by the solid arrows in FIG. 41B to the board 194 depending on a temperature change of the radiation conversion panel 92, the radiation conversion panel 92 can be kept flat in integral combination with the board 194, while also taking into consideration temperature changes of the radiation conversion panel 92.

In FIGS. 41A and 41B, other components apart from the radiation conversion panel 92, the external force applying unit 218, and the flexible boards 208, 212 are omitted from illustration for facilitating understanding of the fourth embodiment. FIG. 41B shows the manner in which external forces are applied to the board 194 at a time that the radiation conversion panel 92 is deformed as shown in FIG. 7A. However, planarity of the radiation conversion panel 92 can be maintained similarly by applying external forces similarly in a case where the radiation conversion panel 92 is deformed as shown in FIG. 7B.

If a control voltage, the polarity of which is opposite to the polarity of the voltage shown in FIG. 41B, is applied between the electrodes 226, 228, then the actuator element 224 expands vertically and shrinks along the plane thereof. Even in this case, the external force applying unit 218 applies external forces to the board 194 through the dismantlable adhesive 272 to thereby keep the radiation conversion panel 92 flat.

In a case where the board 194 is at normal temperature, since the overall radiation conversion panel 92 including the board 194 is highly likely to be kept flat, it is not likely for the board 194 to become deformed. At this time, control voltages are not applied to the electrodes 226, 228.

The dismantlable adhesive 272 may be made of a material, which is the same as the dismantlable adhesives 222, 232. In other words, the dismantlable adhesive 272 is an adhesive that allows the board 194 and the external force applying unit 218, which have been bonded together, to be peeled off from each other by heating, electrically heating, irradiation with ultraviolet radiation, or absorption of water.

The electrodes 226, 228 and the actuator element 224 of the external force applying unit 218 may be made of materials that are the same as the electrodes 226, 228 and the actuator element 224 described in the first through third embodiments. For example, the actuator element 224 may be made of a material that is capable of applying external forces to the board 194 if the board is deformed as shown in FIG. 41B by application of the control voltage between the electrodes 226, 228.

<Operations of the Fourth Embodiment>

Operations of the fourth embodiment are essentially the same as the operations of the first embodiment described above with reference to FIG. 10, except for the following differences.

In step S4, if the external force controller 240 decides that a temperature rise has occurred based on the temperature information sequentially input from the temperature sensors 216, then the external force controller 240 generates a control voltage in the magnitude and direction required for the external force applying unit 218 to apply appropriate external forces depending on the temperature rise to the board 194, and applies the generated control voltage to the electrodes 226, 228.

The actuator element 224 is deformed depending on the polarity and magnitude of the applied control voltage, thereby enabling the external force applying unit 218 to apply external forces to the board 194. Consequently, even if the radiation conversion panel 92 including the board 194 is deformed by a temperature rise, external forces depending on the temperature rise are applied to the board 194, thereby keeping the radiation conversion panel 92 including the board 194 flat.

As described above, since the temperature sensors 216 sequentially monitor and output the temperature of the board 194 to the cassette controller 50, even after step S4, the external force controller 240 sequentially judges whether or not external forces depending on a temperature rise should be applied based on the temperature of the board 194, and sequentially generates and outputs control voltages in magnitudes and directions required to apply the external forces. By sequentially detecting the temperature of the board 194, the electronic cassette 20D can continuously apply external forces to prevent deformation of the radiation conversion panel 92 due to a temperature rise thereof. As a consequence, the electronic cassette 20D can keep the radiation conversion panel 92 flat as a whole.

In step S10, the external force controller 240 judges whether or not the temperature detected by the temperature sensors 216 has dropped to the temperature before the power supply switch 86 was turned on, i.e., to normal temperature. If the temperature detected by the temperature sensors 216 has not dropped to normal temperature, then the external force controller 240 decides that the radiation conversion panel 92 may possibly be deformed depending on the temperature change, i.e., the temperature drop (step S10: NO), and continues to supply the control voltage to the external force applying unit 218. Conversely, if the temperature detected by the temperature sensors 216 has dropped to normal temperature, then the external force controller 240 decides that the radiation conversion panel 92 will not be deformed and will remain flat (step S10: YES). In step S11, the external force controller 240 stops supplying the control voltages to the external force applying unit 218, which stops applying the external forces to the board 194.

<Advantages of the Fourth Embodiment>

With the electronic cassette 20D and the radiographic image capturing system 10D according to the fourth embodiment, as described above, the radiation conversion panel 92 and the external force applying unit 218 are stacked together in integral combination. In a case where the radiation conversion panel 92 becomes deformed, i.e., is caused to expand or shrink thermally, due to a temperature change, the radiation conversion panel 92 and the external force applying unit 218 are deformed integrally together. According to the fourth embodiment, while the radiation conversion panel 92 and the external force applying unit 218 are allowed to deform, the external force applying unit 218 applies external forces depending on the temperature change to the radiation conversion panel 92, thereby keeping the radiation conversion panel 92 flat, i.e., maintaining planarity of the radiation conversion panel 92. As a consequence, the fourth embodiment is more effective at avoiding cracking and peeling of the radiation conversion panel 92 due to a deformation thereof than if other members were simply bonded to the radiation conversion panel 92 according to the technology disclosed in Japanese Patent No. 2706725.

Since the radiation conversion panel 92, i.e., the board 194, is deformed depending on the temperature change, the temperature of the radiation conversion panel 92 is detected by the temperature sensors 216, and appropriate external forces depending on the temperature change, i.e., the amount of deformation of the radiation conversion panel 92, i.e., the board 194, which is caused by the temperature change, are applied to the board 194 to effectively keep the radiation conversion panel 92 flat. In other words, if a deformation, e.g., warpage or an elongation, of the radiation conversion panel 92, which would be caused by the temperature change, is grasped in advance, then external forces depending on such a deformation may be applied continuously to the board 194 to thereby keep the radiation conversion panel 92 including the board 194 flat as a whole.

As the temperature of the radiation conversion panel 92 changes, the board 194, which is made of plastic, becomes warped in the thicknesswise direction of the board 194. Therefore, if the external force applying unit 218 is deformed depending on the temperature change, i.e., is caused to shrink or expand in the thicknesswise direction or is caused to expand or shrink along the plane thereof, the external force applying unit 218 applies external forces to the board 194, thereby keeping the radiation conversion panel 92 flat as a whole. Since the radiation conversion panel 92 is kept flat, the flexible boards 208, 212 are prevented from peeling off from the board 194. As a result, address signals can be supplied and electric signals can be output regardless of the temperature change.

According to the fourth embodiment, since the radiation conversion panel 92 is kept flat by external forces applied thereto depending on a temperature change, the columnar crystals of CsI, which the scintillator 206 is made of, are kept perpendicular to the board 194. As a consequence, crosstalk, which would otherwise be caused between adjacent columnar crystals due to warpage of the radiation conversion panel 92, is minimized, thus enabling the electronic cassette 20D to easily acquire sharp radiographic images free of image blurs.

Since the external force applying unit 218 is bonded to the board 194 by the dismantlable adhesive 272, the external force applying unit 218 can easily be replaced if functions thereof become lowered due to being irradiated with radiation 16.

According to the fourth embodiment, if the actuator element 224 is made of a polymeric material, particularly, a rubber-like polymeric film, i.e., an elastomer, then since the actuator element 224 can serve as a shock absorbing member for absorbing shocks, i.e., loads, vibrations, etc., from an external source, such materials are effectively capable of protecting the components in the casing 40 from shocks.

According to the fourth embodiment, as with the first embodiment, if the tendency of the temperature rise of the board 194 over an elapsed period of time after the power supply switch 86 has been turned on, or if the tendency of a temperature drop of the board 194 over an elapsed period of time after the power supply switch 86 has been turned off is known, then the external force controller 240 may have a timer function, and the magnitude (and polarity) of the control voltage may be changed sequentially depending on the elapsed period of time after the power supply switch 86 is turned on or the elapsed period of time after the power supply switch 86 is turned off, so that the changed control voltage may be applied to the electrodes 226, 228. In this case, since external forces depending on a temperature change are applied to the board 194, the radiation conversion panel 92 can be kept flat.

<Modifications of the Fourth Embodiment>

The electronic cassette 20D according to the fourth embodiment is not limited to the above description, but may be arranged according to the modifications (seventh through ninth modifications) shown in FIGS. 42 through 46.

Figure 42:
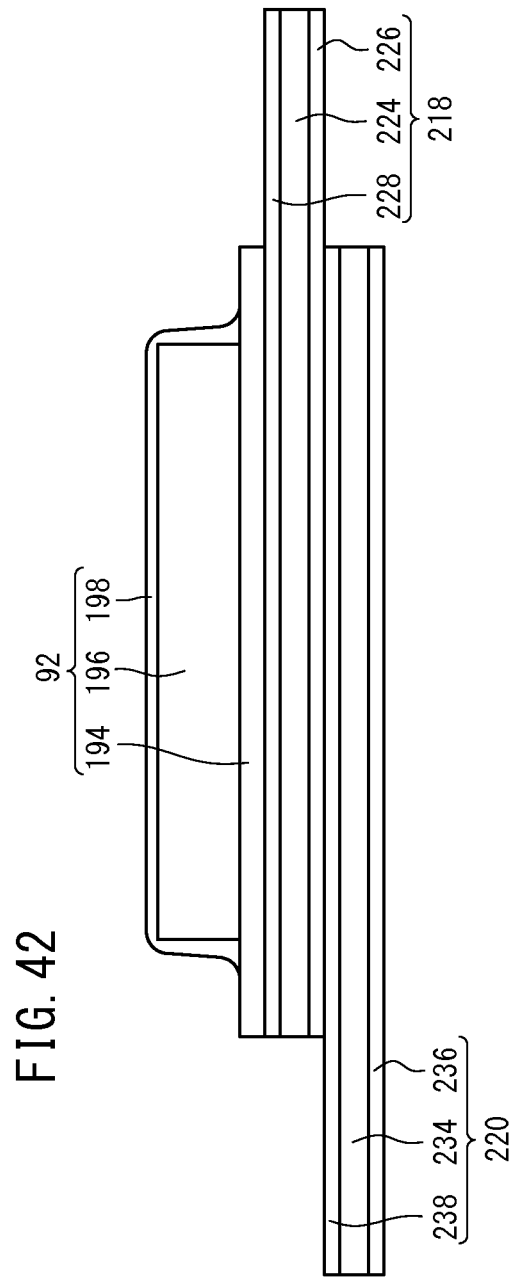
FIG. 42 is a view schematically showing an internal arrangement of a cassette according to a seventh modification.
Figure 43:
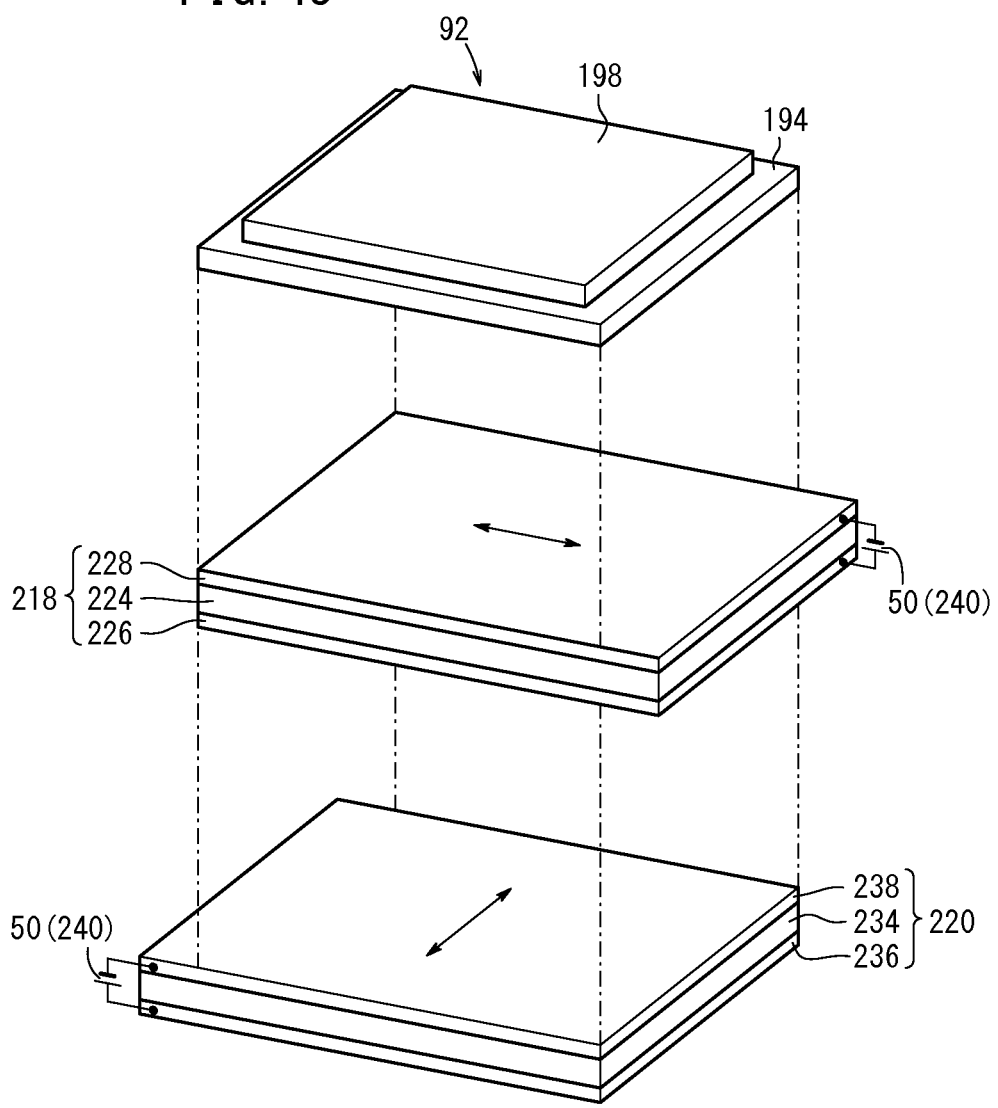
FIG. 43 is a perspective view showing an internal arrangement of the cassette according to the seventh modification.

FIGS. 42 and 43 schematically show an electronic cassette 20D according to a seventh modification, which has the external force applying unit (third external force applying mechanism) 220, the external force applying unit (fourth external force applying mechanism) 218, and the radiation conversion panel 92, which are successively stacked in this order.

The external force applying unit 220 is of the same structure as the external force applying unit 218, and includes the actuator element 234, which has the same function as the actuator element 224, sandwiched between the two electrodes 236, 238. The external force applying unit 220 and the external force applying unit 218 are stacked so that portions directly beneath the board 194 overlap with each other.

According to the seventh modification, in the event that the external force controller 240 applies a control voltage between the electrodes 226, 228 of the external force applying unit 218, and also applies a control voltage between the electrodes 236, 238 of the external force applying unit 220, as shown in FIG. 43, the external force applying unit 220 and the external force applying unit 218 are caused to expand and shrink in different directions, i.e., in the directions indicated by the arrows, with respect to the direction, i.e., the horizontal direction, of the plane of the board 194. According to the seventh embodiment, therefore, the magnitudes and polarities of the control voltages applied to the electrodes 226, 228, 236, 238 may be adjusted depending on the amount and direction of deformation of the board 194, so as to change the amount of expansion or shrinkage along the direction of the plane of the external force applying unit 220 and the external force applying unit 218. As a result, the board 194 can be kept flat efficiently.

Figure 44:
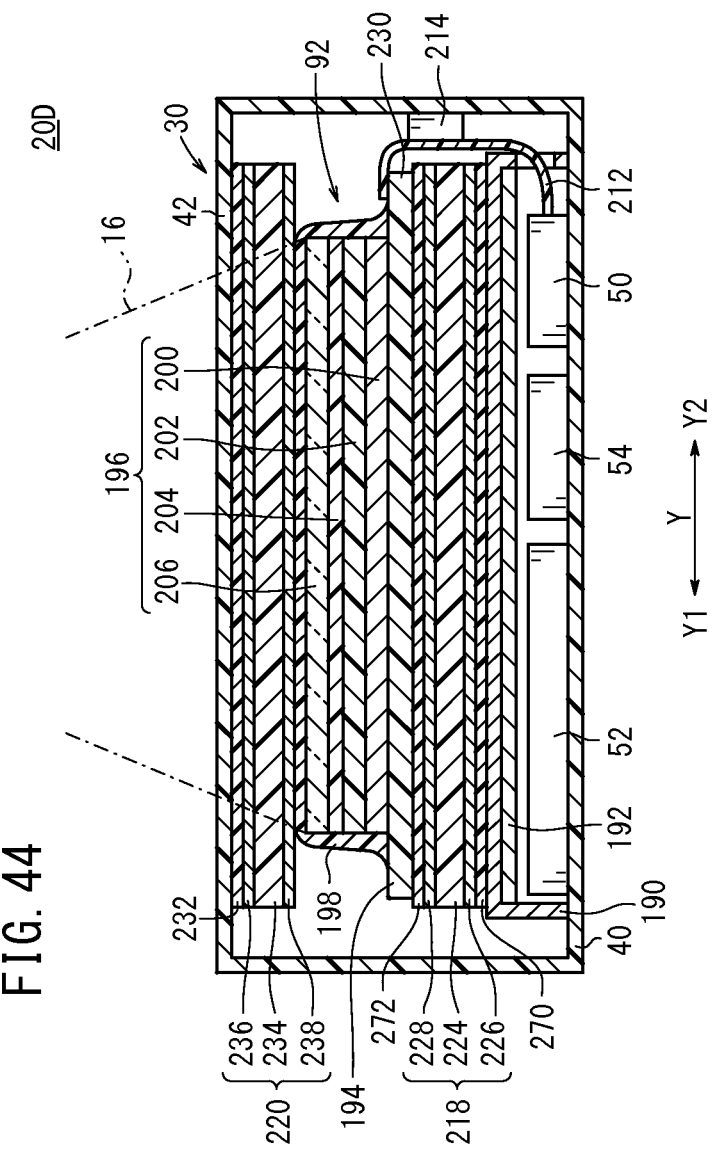
FIG. 44 is a cross-sectional view showing an internal arrangement of a cassette according to an eighth modification.
Figure 45:
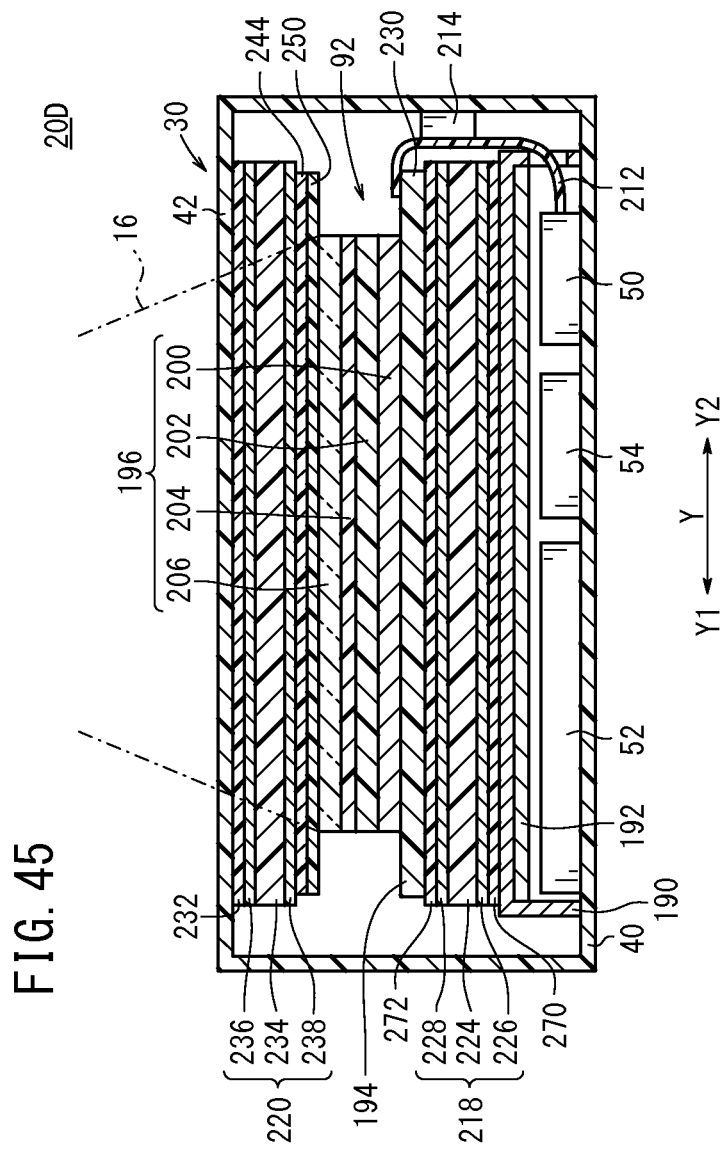
FIG. 45 is a cross-sectional view showing another internal arrangement of the cassette according to the eighth modification.

FIGS. 44 and 45 show an electronic cassette 20D according to an eighth modification, which includes the radiation conversion panel 92 vertically sandwiched by the two external force applying units 218, 220, i.e., the first and second external force applying mechanisms, in integral combination therewith.

According to the electronic cassette 20D shown in FIG. 44, the protective film 198 functions as a dismantlable adhesive, and the electrode 238 of the external force applying unit 220 is bonded to the protective film 198, whereas the electrode 236 thereof is bonded to the upper surface of the casing 40 by the dismantlable adhesive 232.

Even though the radiation conversion panel 92 tends to become deformed due to a temperature change, the external force applying unit 218 on the board 194 continuously applies external forces to the panel 194, and the external force applying unit 220 on the protective film 198 and the scintillator 206 continuously applies external forces to the protective film 198 and the scintillator 206, to thereby keep the radiation conversion panel 92 flat more reliably and effectively.

In FIG. 44, the coefficient of thermal expansion of the board 194 and the coefficient of thermal expansion of the protective film 198 differ from each other, and hence the board 194 and the protective film 198 are deformed to different degrees depending on the temperature change of the radiation conversion panel 92. The magnitudes (and polarities) of the control voltages applied to the external force applying units 218, 220 are adjusted to be different from each other depending on the different degrees of deformation caused by the temperature change, thus making it possible to continuously apply appropriate external forces.

According to the electronic cassette 20D shown in FIG. 45, the signal output layer 200 and the photoelectric transducer layer 202 are successively deposited in this order on the board 194, the scintillator 206 is deposited by evaporation or the like on the other board 250, which is made of aluminum, plastic, or the like, and the photoelectric transducer layer 202 and the scintillator 206, which are disposed in confronting relation to each other, are securely bonded to each other by the adhesive layer 204 to thereby construct the radiation conversion panel 92. In FIG. 45, the protective film 198 is dispensed with. The boards 194, 250 have different coefficients of thermal expansion. The electrode 238 of the external force applying unit 220 is bonded to the board 250 by the dismantlable adhesive 244.

Even though the radiation conversion panel 92 tends to become deformed due to the temperature change, the external force applying unit 218 on the board 194 continuously applies external forces to the board 194, and the external force applying unit 220 on the board 250 and the scintillator 206 continuously applies external forces to the board 250 and the scintillator 206, thereby maintaining the radiation conversion panel 92 flat reliably and efficiently.

In FIG. 45, the coefficients of thermal expansion of the boards 194, 250 also differ from each other, and hence the boards 194, 250 are deformed to different degrees depending on the temperature change of the radiation conversion panel 92. The magnitudes (and polarities) of the control voltages applied to the external force applying units 218, 220 are adjusted to be different from each other depending on the different degrees of deformation caused by the temperature change, thus making it possible to continuously apply appropriate external forces.

According to the eighth modification shown in FIGS. 44 and 45, if the scintillator 206 is made up of columnar crystals of CsI, then since the radiation conversion panel 92 is kept flat, the columnar crystals remain perpendicular to the board 194 or the boards 194, 250, and allow the electronic cassette to easily acquire sharp radiographic images regardless of temperature changes. According to the eighth modification, if the actuator elements 224, 234 are made of a rubber-like polymeric film, i.e., an elastomer, then since the actuator elements 224, 234 serve as shock absorbing members for absorbing shocks from an external source, the actuator elements 224, 234 are effectively capable of protecting components in the casing 40 from shocks.

Since the protective film 198 functions as a dismantlable adhesive, and the external force applying units 218, 220 are securely bonded by the dismantlable adhesives 232, 244, 272 and the protective film 198, the external force applying units 218, 220 can easily be replaced in the event that functions thereof are lowered due to being irradiated with radiation 16.

Figure 46:
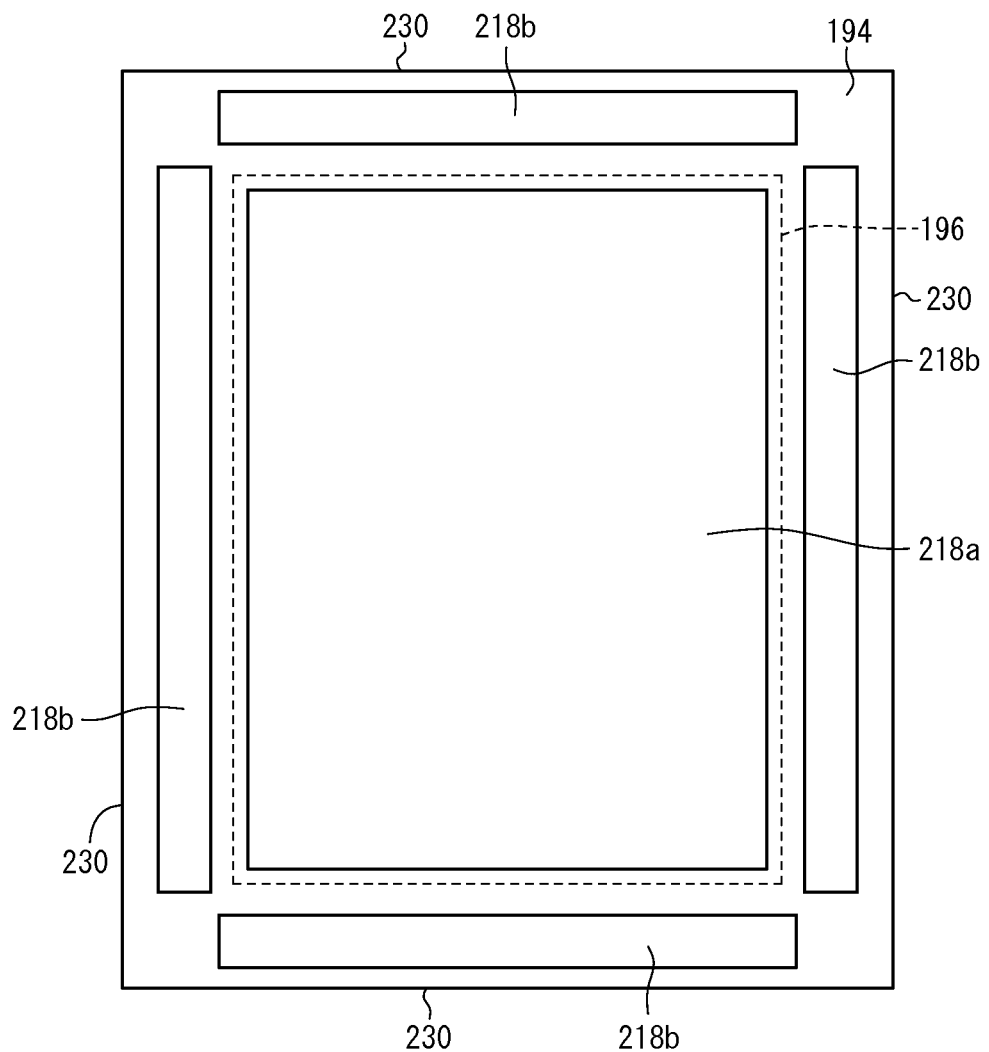
FIG. 46 is a plan view schematically showing an internal arrangement of a cassette according to a ninth modification.

As shown in plan in FIG. 46, an electronic cassette 20D according to a ninth modification includes an external force applying unit (fifth external force applying mechanism) 218a, which is smaller than the projected area of the radiation conversion layer 196, disposed on the bottom surface of the board 194 directly below the radiation conversion layer 196, and a plurality of external force applying units (sixth external force applying mechanisms) 218b around the external force applying unit 218a, i.e., on the peripheral edges 230 of the board 194. The external force applying units 218a, 218b are structurally identical to the external force applying unit 218, and will not be described in detail below.

As described above, since the board 194 is deformed to a greater degree at the peripheral edges 230 than at the radiation conversion layer 196, control voltages, the magnitudes (and directions) of which are different from each other depending on the degree of deformation of the board 194, are applied to the external force applying units 218a, 218b, which then apply external forces of different magnitudes to the board 194, thereby keeping the board 194 flat efficiently.

A plurality of temperature sensors 216 (see FIG. 37) are disposed on the board 194. The external force controller 240 may supply control voltages, the magnitudes and directions of which are based on the temperatures detected by the temperature sensors 216 near the external force applying units 218a, 218b. In this manner, external forces can accurately be applied to the board 194.

6. Description of Fifth Embodiment

An electronic cassette 20E and a radiographic image capturing system 10E according to a fifth embodiment of the present invention will be described below with reference to FIGS. 47 and 48.

The electronic cassette 20E and the radiographic image capturing system 10E according to the fifth embodiment differ from electronic cassette 20D and the radiographic image capturing system 10D according to the fourth embodiment (see FIGS. 37 through 46), in that the control unit 32 is joined to the panel housing unit 30 by the hinge 170. Consequently, the overall arrangement of the radiographic image capturing system 10E is essentially the same as that of the radiographic image capturing system 10B shown in FIG. 21, and the circuit arrangement of the electronic cassette 20E is essentially the same as that of the electronic cassette 20B shown in FIG. 22.

Figure 47:
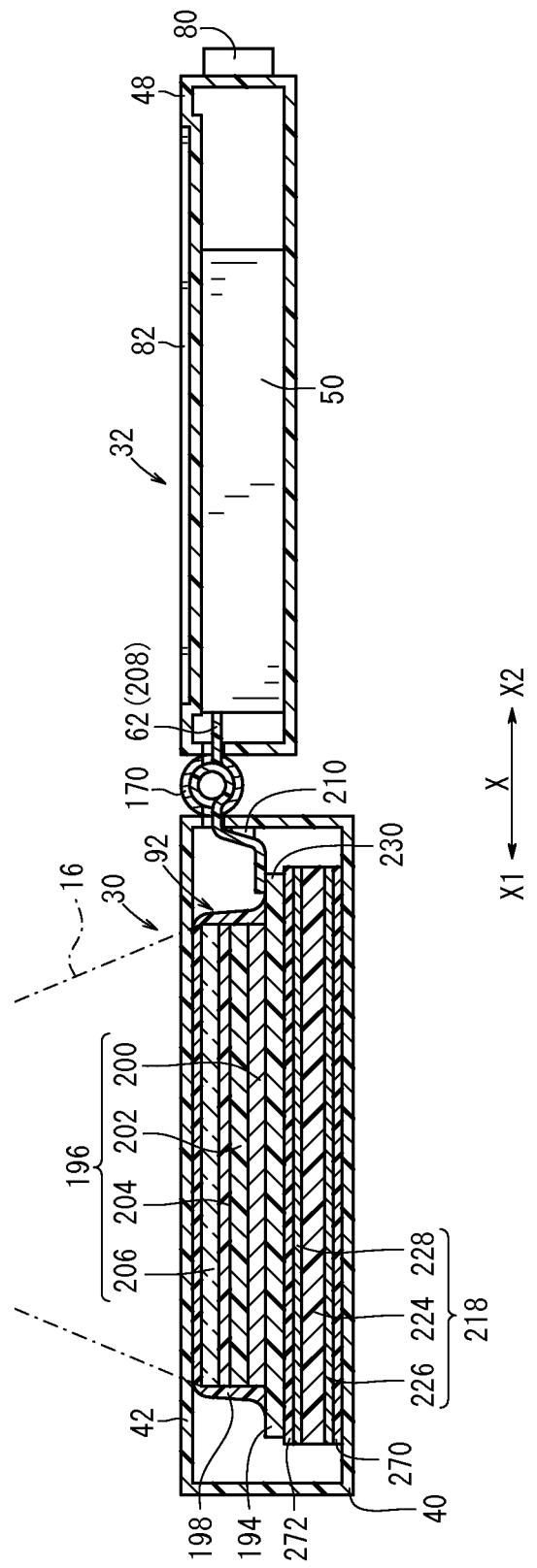
FIG. 47 is a cross-sectional view of a cassette according to a fifth embodiment of the present invention.
Figure 48:
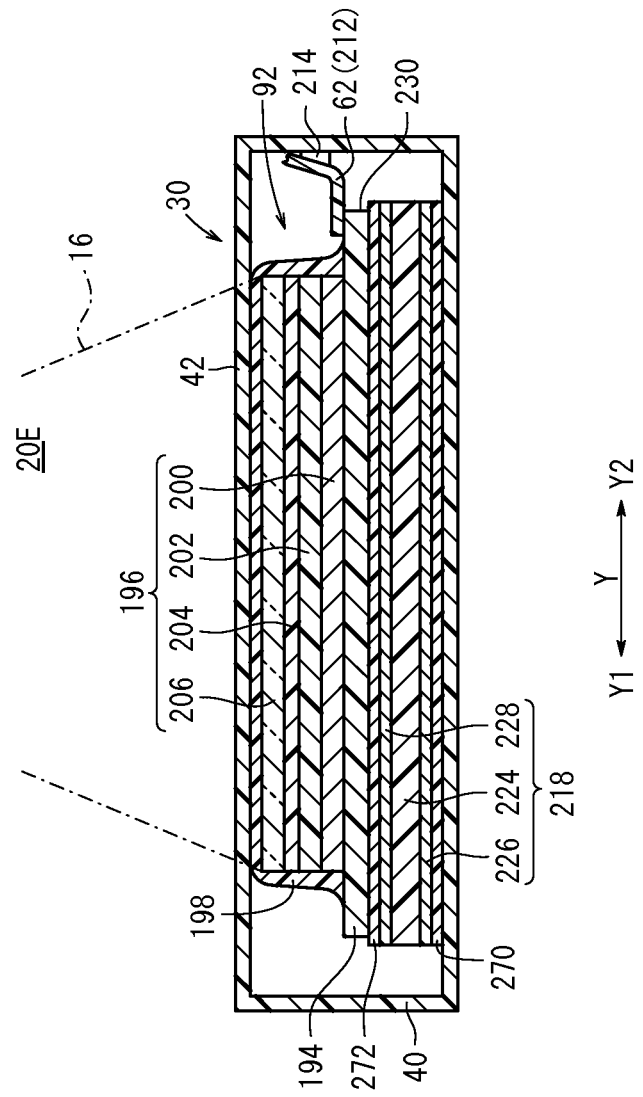
FIG. 48 is a cross-sectional view of the cassette shown in FIG. 47.
Figure 49:
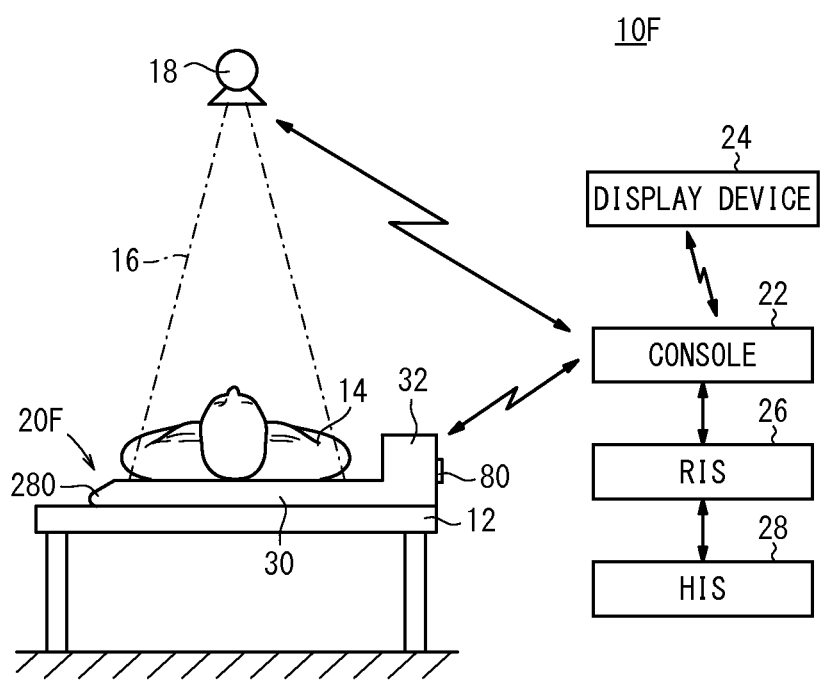
FIG. 49 is a schematic view of a radiographic image capturing system incorporating a cassette according to a sixth embodiment of the present invention.
Figure 50:
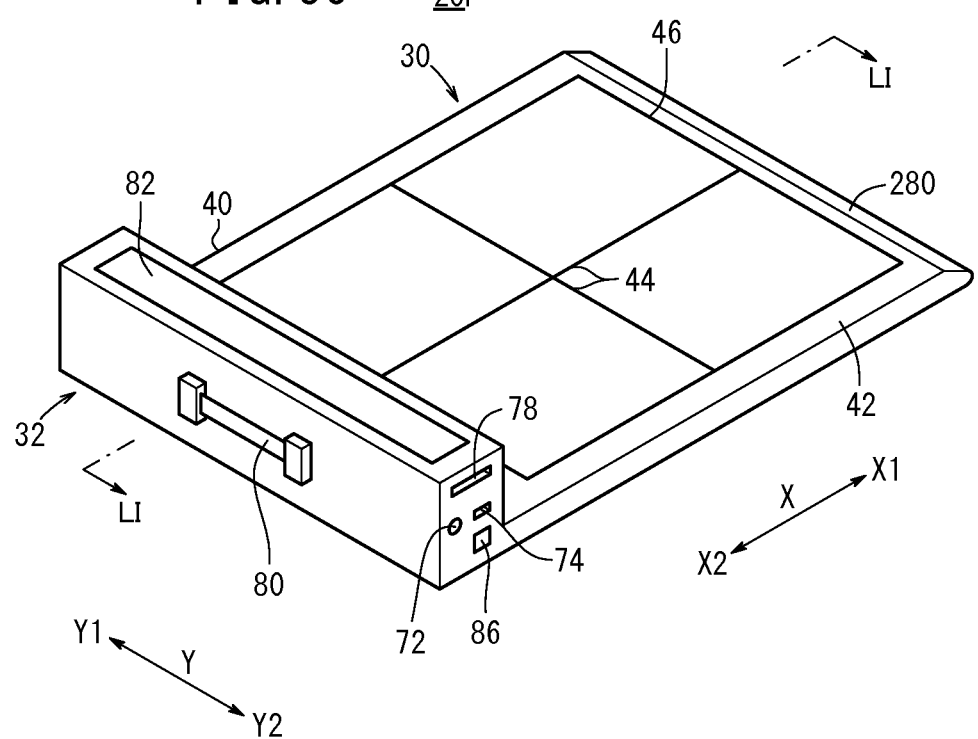
FIG. 50 is a perspective view of the cassette shown in FIG. 49.

As shown in FIGS. 47 and 48, the external force applying unit 218 and the radiation conversion panel 92 are stacked and combined integrally in the casing 40 of the panel housing unit 30, as is the case with the fourth embodiment. Therefore, the fifth embodiment offers the same advantages of the fourth embodiment, in which the external force applying unit 218 and the radiation conversion panel 92 are integrally combined with each other. The fifth embodiment may also be modified according to the seventh through ninth modifications (see FIGS. 42 through 46) described above.

7. Description of Sixth Embodiment

An electronic cassette 20F and a radiographic image capturing system 10F according to a sixth embodiment of the present invention will be described below with reference to FIGS. 49 through 55B.

The electronic cassette 20F and the radiographic image capturing system 10F according to the sixth embodiment differ from the electronic cassettes 20D, 20E and the radiographic image capturing systems 10D, 10E according to the fourth and fifth embodiments (see FIGS. 37 through 48), in that the side portion of the panel housing unit 30, which faces in the direction of the arrow X2, projects upwardly. Further, the projecting portion functions as the control unit 32.

Components that are not involved in conversion of radiation 16 into radiographic images, e.g., the cassette controller 50, the power supply 52, the communication unit 54, the display unit 82, the handle 80, etc., are disposed together in the projecting portion.

The panel housing unit 30 has a sharp side that faces in the direction of the arrow X1, and an apex portion as a curved portion 280, which is curved at a predetermined radius of curvature. Therefore, the doctor or radiological technician can insert the panel housing unit 30 with the curved portion 280 positioned in a forward direction smoothly between the image capturing base 12 and the subject 14 without causing the subject 14 to feel uncomfortable.

The radiation conversion panel 92 and the external force applying unit 218, which are integrally combined with each other in the casing 40, may have either one of the structures shown in FIGS. 51 through 54.

Figure 51:
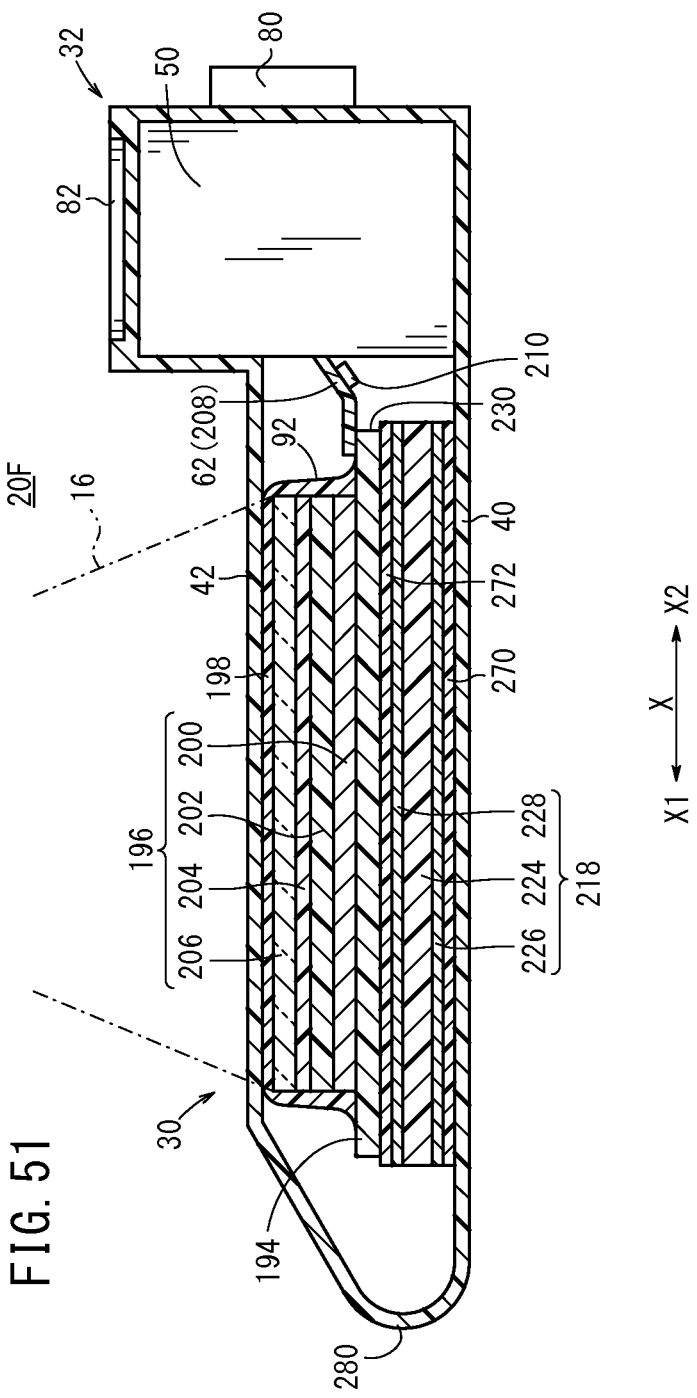
FIG. 51 is a cross-sectional view taken along line LI-LI of FIG. 50.

According to the structure shown in FIG. 51, as with the fifth embodiment (see FIGS. 47 and 48), the external force applying unit 218 and the radiation conversion panel 92 are integrally bonded to each other by the dismantlable adhesive 272. The electronic cassette 20F shown in FIG. 51 thus offers the same advantages as the fifth embodiment.

Figure 52:
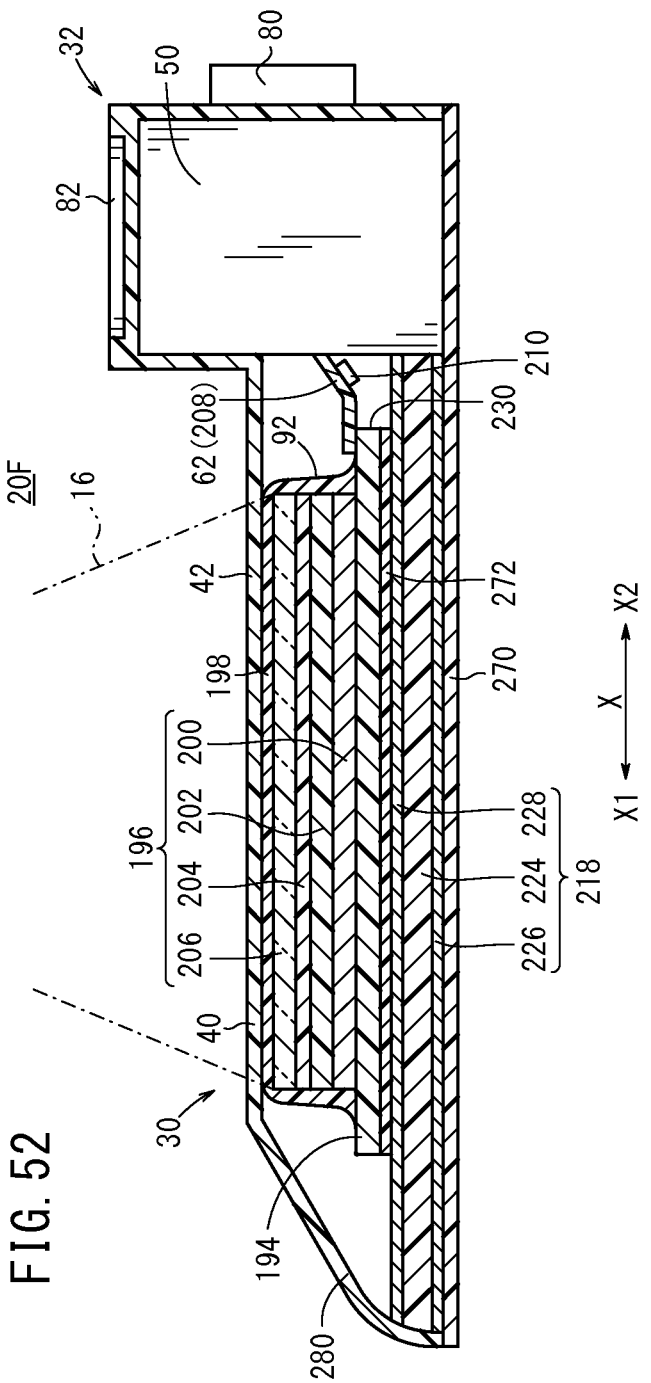
FIG. 52 is a cross-sectional view of a cassette wherein the bottom surface of a panel housing unit serves as an external force applying unit.

According to the structure shown in FIG. 52, the bottom of the electronic cassette 20F is constructed as an insulative sheet 270, and the external force applying unit 218 extends along the direction of the arrow X1 from the curved portion 280 toward the cassette controller 50. The electronic cassette 20F shown in FIG. 52 also offers the same advantages as the fifth embodiment. Since the external force applying unit 218 extends from the curved portion 280 toward the cassette controller 50, the external force applying unit 218 can apply external forces to the entire panel housing unit 30, which includes the radiation conversion panel 92. Therefore, the panel housing unit 30 can be kept flat in its entirety with increased rigidity.

Figure 53:
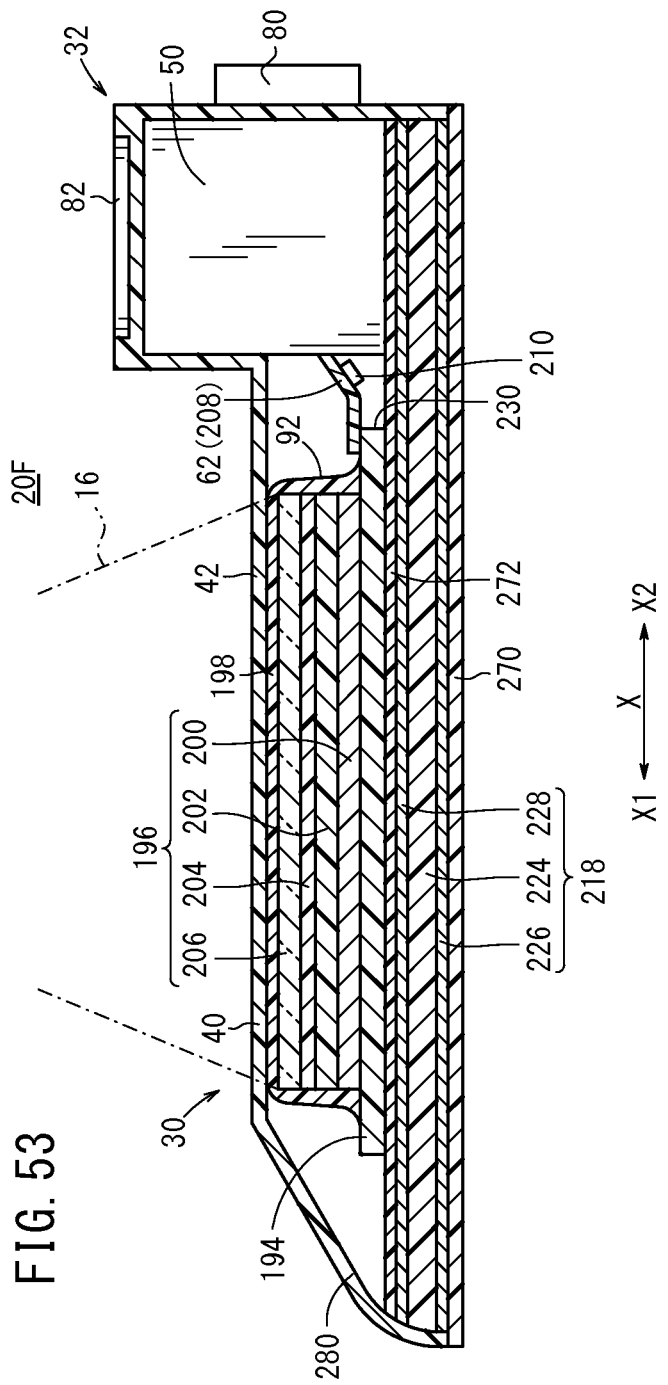
FIG. 53 is a cross-sectional view of a cassette wherein the bottom surfaces of a panel housing unit and a control unit serve as an external force applying unit.

According to the structure shown in FIG. 53, the bottom of the electronic cassette 20F is constructed as the insulative sheet 270 and the external force applying unit 218. The external force applying unit 218 thus extends along the direction of the arrow X from the curved portion 280 toward the cassette controller 50. The electronic cassette 20F shown in FIG. 53 also offers the same advantages as the fifth embodiment. Since the external force applying unit 218 is disposed as the bottom of the panel housing unit 30 and the control unit 32, by application of external forces by the external force applying unit 218 to the entire electronic cassette 20F including the radiation conversion panel 92, the panel housing unit 30 is kept flat in its entirety with increased rigidity, and the panel housing unit 30 and the control unit 32 are firmly connected to each other.

Figure 54:
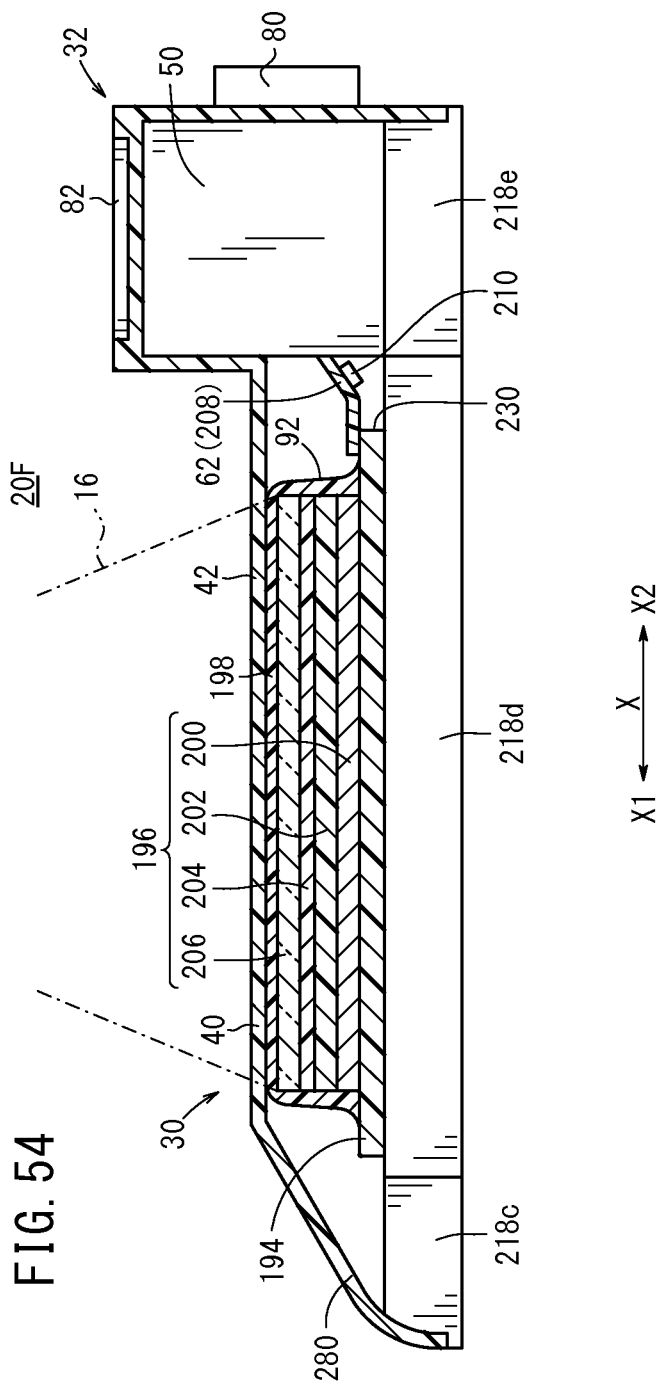
FIG. 54 is a cross-sectional view of a cassette wherein the bottom surfaces of a panel housing unit and a control unit serve as a plurality of external force applying units.

According to the structure shown in FIG. 54, a plurality of external force applying units 218c through 218e are arranged as the bottom of the electronic cassette 20F along the direction of the arrow X. The external force controller 240 (see FIG. 22) may apply control voltages to all of the external force applying units 218c through 218e in order to apply external forces from the external force applying units 218c through 218e. Alternatively, the external force controller 240 may selectively apply control voltages to the external force applying units 218c through 218e in order to apply external forces from certain ones of the external force applying units 218c through 218e. If the external force controller 240 selectively applies control voltages, then the external force applying units that are not supplied with the control voltages stop applying external forces.

Figure 55A:
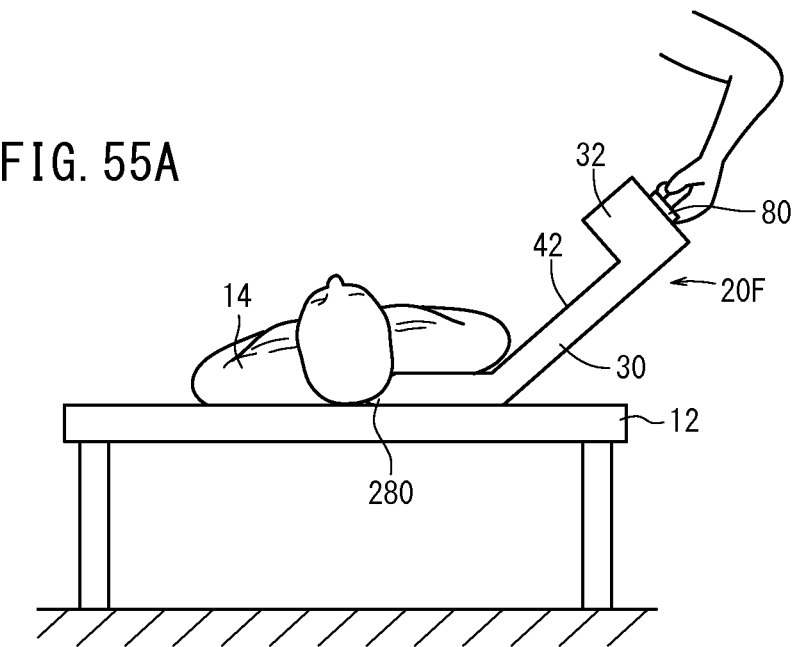
FIG. 55A is a view showing the manner in which a panel housing unit is inserted between a subject and an image capturing base.
Figure 55B:
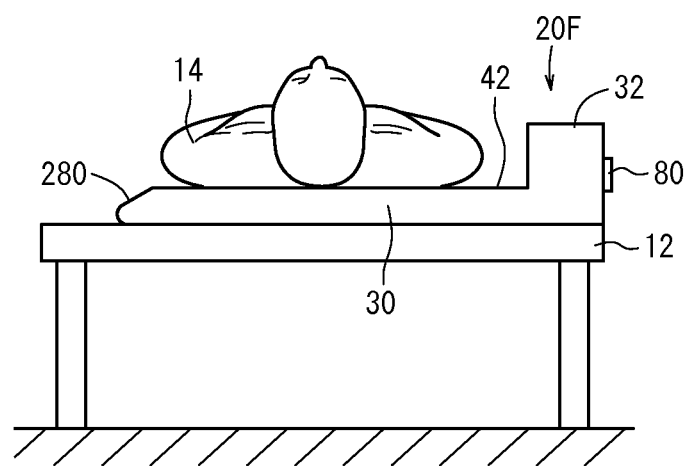
FIG. 55B is a view showing a cassette after the panel housing unit has been inserted.

FIGS. 55A and 55B show the manner in which the electronic cassette 20F shown in FIG. 54 is inserted between the image capturing base 12 and the subject 14.

At the time that the electronic cassette 20F is inserted as shown in FIG. 55A, the external force controller 240 (see FIG. 22) controls the external force applying unit 218c near the curved portion 280 in order to stop applying external forces, and also controls the other external force applying units 218d, 218e to apply external forces. Therefore, the portion of the panel housing unit 30 on the side of the curved portion 280 near the external force applying unit 218c is flexible, whereas the portion of the panel housing unit 30 on the side of the control unit 32 where external forces are applied from the external force applying units 218d, 218e is kept flat and rigid by the applied external forces. Therefore, as shown in FIG. 55A, the panel housing unit 30 bends along a direction from the curved portion 280 toward the control unit 32. As a result, the doctor or radiological technician can smoothly and efficiently insert the panel housing unit 30 with the curved portion 280 positioned in a forward direction and without causing the subject 14 to feel uncomfortable.

After the panel housing unit 30 has been inserted, as shown in FIG. 55B, the external force controller 240 (see FIG. 22) applies control voltages to all of the external force applying units 218c through 218e in order to enable the external force applying units 218c through 218e to apply external forces. The panel housing unit 30 is kept flat with increased rigidity by the external forces applied from the external force applying units 218c through 218e.

At the time that the doctor or radiological technician inserts the panel housing unit 30, the external force controller 240 (see FIG. 22) may apply control voltages to the respective external force applying units 218c through 218e so as to enable the external force applying units 218c through 218e to apply external forces to positively bend the panel housing unit 30, as shown in FIG. 55A. In this case, the doctor or radiological technician can easily and reliably insert the panel housing unit 30 without causing the subject 14 to feel uncomfortable.

8. Description of Seventh Embodiment

An electronic cassette 20G and a radiographic image capturing system 10G according to a seventh embodiment of the present invention will be described below with reference to FIGS. 56 through 66.

<Arrangement of the Seventh Embodiment>

The electronic cassette 20G and the radiographic image capturing system 10G according to the seventh embodiment differ from the electronic cassettes 20A through 20F and the radiographic image capturing systems 10A through 10F according to the first through sixth embodiments (see FIGS. 1 through 55B), in that the radiation conversion panel 92 can be pressed against an inner wall surface 296 of the casing 40 beneath the image capturing surface 42. Otherwise, the overall arrangement of the radiographic image capturing system 10G is essentially the same as that of the radiographic image capturing system 10A shown in FIG. 1.

Figure 57:
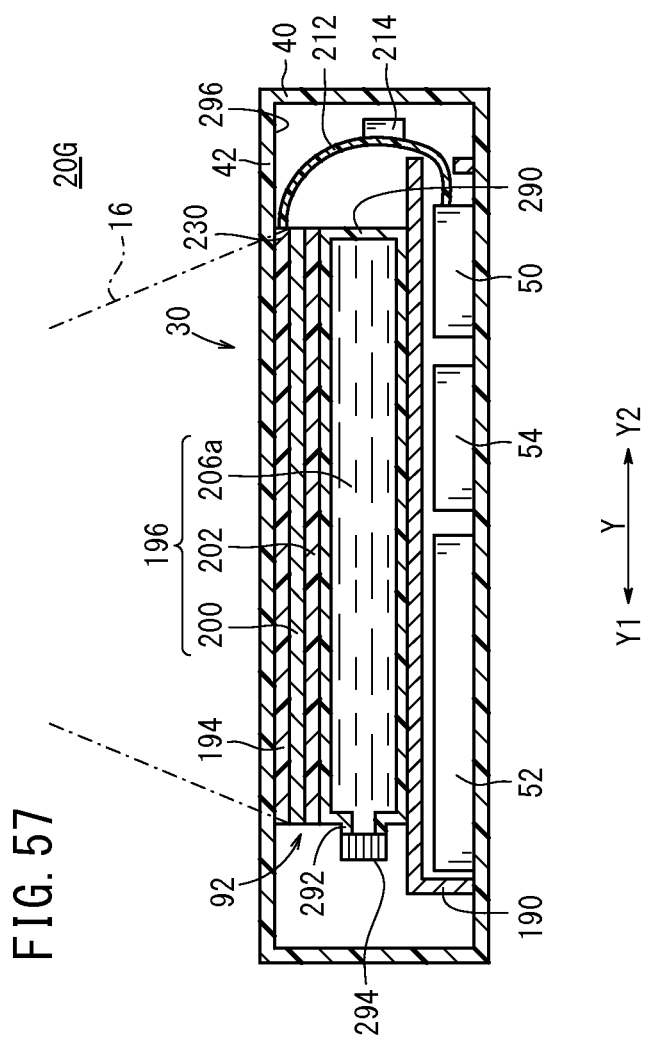
FIG. 57 is a cross-sectional view of the cassette shown in FIG. 56.

According to the seventh embodiment, as shown in FIGS. 56 and 57, the casing 40 houses therein a base table 190 made of a material for blocking radiation 16, i.e., a material containing a heavy metal such as lead or the like, which is arranged in covering relation to the cassette controller 50, the power supply 52, and the communication unit 54, and a scintillator housing bag 290 (pressing mechanism, external force applying mechanism) filled with a scintillator 206a in the form of a liquid (hereinafter also referred to as a "liquid scintillator 206a"), which is placed on the upper surface of the base table 190.

The liquid scintillator 206a converts radiation 16 that has passed through the subject 14 into fluorescence, e.g., visible light. The liquid scintillator 206a may be a product manufactured by Saint-Gobain, e.g., BC-517H or the like (for details, refer to http://www.detectors.saint-gobain.com/Liquid-Scintillator.aspx). For the specific components of the liquid scintillator 206a, refer to http://www.jrias.or.jp/public/hakarou/sintinani.htm.

The scintillator housing bag 290 is a bag made of resin, which is permeable to the fluorescence. The scintillator housing bag 290 expands if the bag is filled with the scintillator 206a through a port 292, and shrinks vertically in FIG. 57 if the scintillator 206a is discharged through the port 292. The scintillator housing bag 290, which is filled with the scintillator 206a, is sealed by a removable cap 294, which is mounted on the port 292.

The board 194, the signal output layer 200 disposed on the board 194, and the photoelectric transducer layer 202 deposited on the signal output layer 200 are disposed between the scintillator housing bag 290, which is filled with the scintillator 206a, and the inner wall surface 296 beneath the image capturing surface 42. The board 194, the signal output layer 200, and the photoelectric transducer layer 202 are securely positioned on the inner wall surface 296 upon being pressed against the inner wall surface 296 by the scintillator housing bag 290, which is expanded by being filled with the scintillator 206a.

As viewed in plan, the area of the board 194, the signal output layer 200, and the photoelectric transducer layer 202, and the area of the scintillator housing bag 290 except for the port 292 thereof are substantially the same as the area of the image capturing field 46 (see FIG. 56). The scintillator housing bag 290 presses the board 194, the signal output layer 200, and the photoelectric transducer layer 202 against the inner wall surface 296, so that the image capturing field 46, the assembly made up of the board 194, the signal output layer 200, and the photoelectric transducer layer 202, and the scintillator housing bag 290 except for the port 292 overlap each other as viewed in plan.

The liquid scintillator 206a, the signal output layer 200, and the photoelectric transducer layer 202 jointly constitute the radiation conversion layer 196. The board 194 and the radiation conversion layer 196 jointly constitute the radiation conversion panel 92.

According to the seventh embodiment, if the temperature of the overall radiation conversion panel 92 rises or drops, the board 194, the signal output layer 200, and the photoelectric transducer layer 202 may become deformed due to the different coefficients of thermal expansion.

According to the seventh embodiment, as shown in FIG. 57, the liquid scintillator 206a is delivered to the scintillator housing bag 290 in order to expand the scintillator housing bag 290 in the casing 40, and the expanded scintillator housing bag 290 is placed on the base table 190, so as to press the board 194, the signal output layer 200, and the photoelectric transducer layer 202 against the inner wall surface 296 beneath the image capturing surface 42. Therefore, the board 194, the signal output layer 200, and the photoelectric transducer layer 202 are held closely together without using an adhesive therebetween, and such components are securely positioned with respect to the inner wall surface 296 and the image capturing field 46.

According to the seventh embodiment, therefore, the components in the radiation conversion panel 92 are held closely together by means of a highly simple structure in which the board 194, the signal output layer 200, and the photoelectric transducer layer 202 are pressed against the inner wall surface 296 by the scintillator housing bag 290, which functions as a pressing mechanism.

Figure 58:
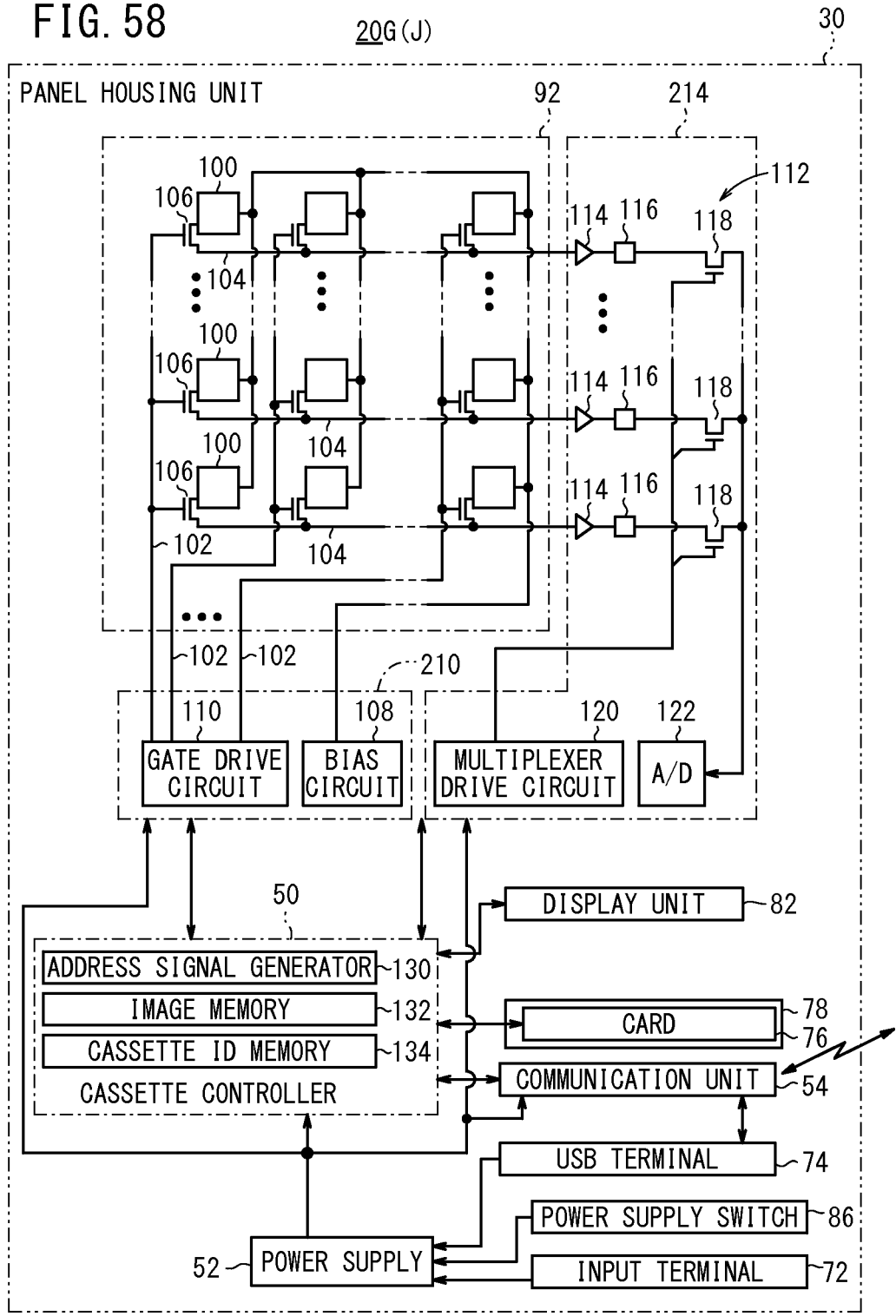
FIG. 58 is a block diagram of the cassette shown in FIGS. 56 and 57.

The circuit arrangement of the electronic cassette 20G according to the seventh embodiment is substantially the same as the circuit arrangement of the electronic cassettes 20A through 20F according to the first through sixth embodiments, except that the temperature sensors 216 and the external force applying units 218, 220 (see FIGS. 9 and 22) are dispensed with, as shown in FIG. 58.

<Operations of the Seventh Embodiment>

The radiographic image capturing system 10G, which incorporates the electronic cassette 20G according to the seventh embodiment, is basically constructed as described above. A process from introducing components into the casing 40 to seal the casing 40, and operations of the electronic cassette 20G and the radiographic image capturing system 10G will be described below with reference to the flowcharts shown in FIGS. 59 and 60, and also to FIGS. 56 through 58, as necessary.

Figure 59:
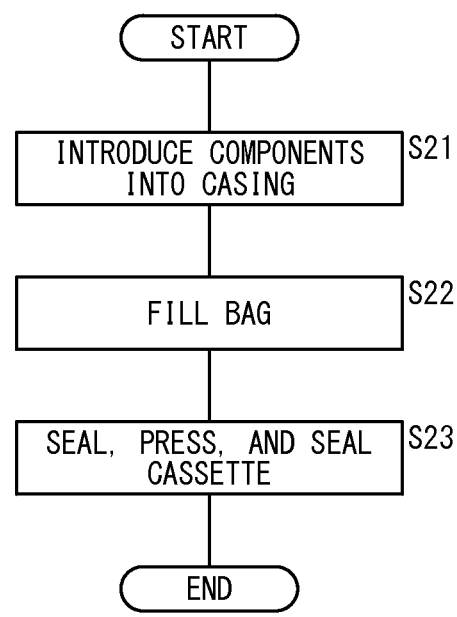
FIG. 59 is a flowchart of a sequence from assembling of various components into a casing to sealing of the cassette.
Figure 60:
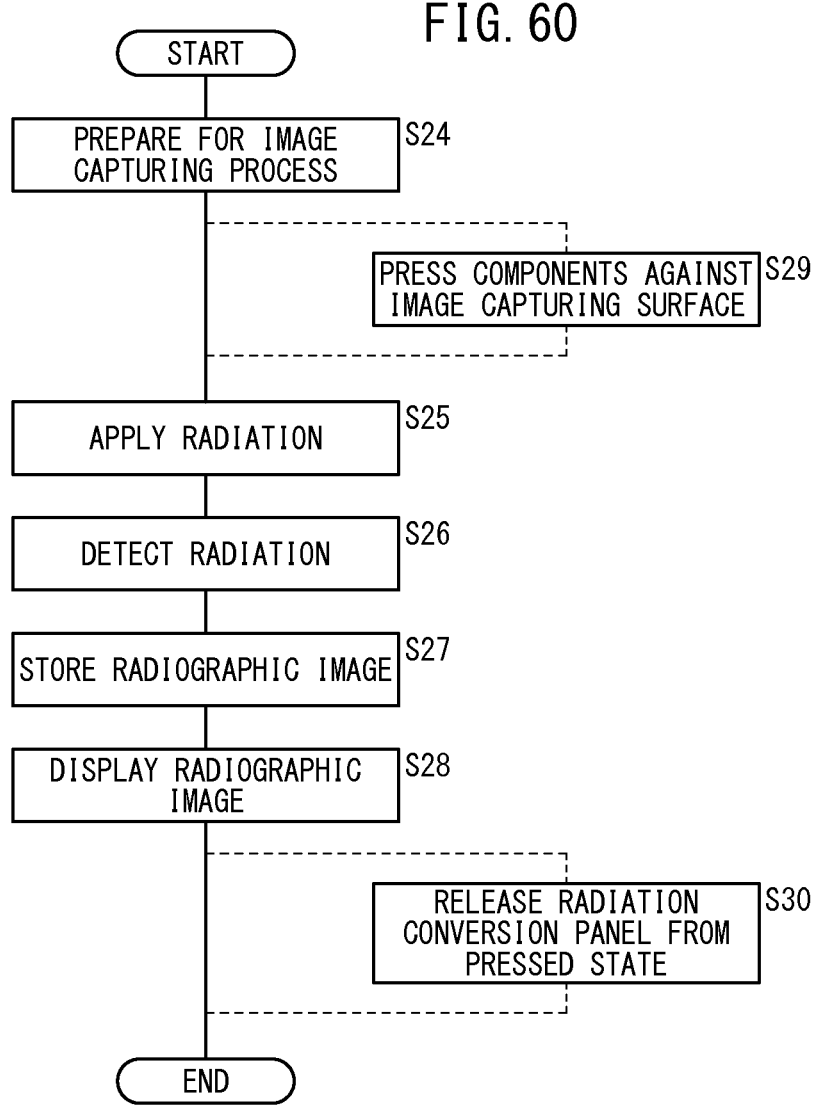
FIG. 60 is a flowchart of a sequence for capturing a radiographic image of a subject with a radiographic image capturing system, which incorporates the cassette shown in FIG. 56.

The procedure of the flowchart shown in FIG. 59 is executed when the electronic cassette 20G is shipped as a product, or when the electronic cassette 20G is serviced for maintenance. The procedure of the flowchart shown in FIG. 60 is executed when a radiographic image of the subject 14 is captured.

If the casing 40 is manufactured using an injection molding machine, then at least one side of the molded casing 40 is kept open. In step S21 of FIG. 59, a worker that works for the manufacturer of the electronic cassette 20G, or a maintenance worker introduces (1) the cassette controller 50, the power supply 52, and the communication unit 54, (2) the base table 190, (3) the scintillator housing bag 290, which is shrunk before being filled with the liquid scintillator 206a, and (4) the board 194, the signal output layer 200, and the photoelectric transducer layer 202 successively in this order into the casing 40 through the open side thereof.

In step S22, the worker fills the scintillator housing bag 290 with the liquid scintillator 206a through the port 292. Upon being filled with the liquid scintillator 206a, the scintillator housing bag 290 expands vertically as shown in FIG. 57. The expanded scintillator housing bag 290 presses the board 194, the signal output layer 200, and the photoelectric transducer layer 202 against the inner wall surface 296 beneath the image capturing surface 42.

In step S23, after confirming that the scintillator housing bag 290 has been filled with the liquid scintillator 206a, the worker seals the scintillator housing bag 290 with the cap 294 mounted on the port 292. Thus, the board 194, the signal output layer 200, and the photoelectric transducer layer 202 are securely positioned and underlie the image capturing field 46 as viewed in plan. Then, the worker seals the casing 40 by a fixing member to the open side of the casing 40, wherein the member has the same size as the open side of the casing 40 and is made of the same material as the casing 40.

The electronic cassette 20G is fabricated, or maintenance of the electronic cassette 20G, e.g., replacement of the liquid scintillator 206a, is carried out according to the process including steps S21 through S23.

A process of capturing a radiographic image of the subject 14 will be described below with reference to the flowchart shown in FIG. 60.

In step S24, the doctor or radiological technician grips the handle 80 and carries the electronic cassette 20G from a prescribed storage location to the image capturing base 12. Thereafter, the doctor or radiological technician adjusts the imaging distance between the radiation source 18 and the radiation conversion panel 92 to a given SID (source-to-image distance), and places the subject 14 on the image capturing surface 42. The doctor or radiological technician positions the subject 14 in order to bring an area to be imaged of the subject 14 into the image capturing field 46, and also to keep the central position of the area to be imaged in substantial alignment with the central position of the image capturing field 46. The doctor or radiological technician also operates the console 22 to register image capturing conditions, e.g., a tube voltage and a tube current for the radiation source 18, and an exposure time for the radiation 16, including subject information concerning the subject 14 as an object to be imaged. If the area to be imaged and an imaging method have been provided in advance, the doctor or radiological technician may also register such image capturing conditions.

The doctor or radiological technician turns on the power supply switch 86. In response to turning on the power supply switch 86, the power supply 52 starts to supply electric power to various components in the casing 40. Thus, the communication unit 54 is made capable of sending signals to and receiving signals from the console 22 through a wireless communication link. The communication unit 54 receives the image capturing conditions registered in the console 22 through the wireless communication link, and outputs the received image capturing conditions to the cassette controller 50. In this manner, the display unit 82 is capable displaying various pieces of information. The drive circuits 210 are activated by electric power supplied from the power supply 52. The bias circuit 108 supplies a bias voltage to the pixels 100, thereby enabling the pixels 100 to store electric charges. The reading circuits 214 also are activated by electric power supplied from the power supply 52 to be placed in a state capable of reading electric charges from the pixels 100. By turning on the power supply switch 86, therefore, the electronic cassette 20A switches from the sleep mode into the active mode.

Upon the electronic cassette 20G entering the active mode, whereupon the signal output layer 200 and the photoelectric transducer layer 202 of the radiation conversion panel 92 become operational, the signal output layer 200 and the photoelectric transducer layer 202 generate heat, thus increasing the temperature of the radiation conversion panel 92 including the board 194. The change in temperature tends to deform the board 194, the signal output layer 200, and the photoelectric transducer layer 202.

According to the seventh embodiment, as described above, the scintillator housing bag 290, which is filled with the liquid scintillator 206a, presses the board 194, the signal output layer 200, and the photoelectric transducer layer 202 against the inner wall surface 296 beneath the image capturing surface 42, thereby holding the board 194, the signal output layer 200, and the photoelectric transducer layer 202 closely together. Therefore, the board 194, the signal output layer 200, and the photoelectric transducer layer 202 are prevented from becoming deformed regardless of temperature changes, i.e., a rise in temperature, of the radiation conversion panel 92, thereby keeping the radiation conversion panel 92 including the board 194 flat as a whole.

In step S25, after step S24, which serves as a preparatory process, the doctor or radiological technician turns on an exposure switch (not shown) provided on the console 22 or the radiation source 18, similar to step S5 (see FIG. 10), thus enabling the radiation source 18 to apply radiation 16 to the subject 14.

In step S26, the scintillator 206a of the radiation conversion panel 92 radiates fluorescence, e.g., visible light, having an intensity depending on the intensity of the radiation 16. The pixels 100 of the photoelectric transducer layer 202 convert the fluorescence into electric signals, which are stored as electric charges. Then, electric charge information, which is representative of a radiographic image of the subject 14 and is held by the pixels 100, is read from the pixels 100 by address signals, which are supplied from the address signal generator 130 of the cassette controller 50 to the gate drive circuit 110 and the multiplexer drive circuit 120. In step S27, the electric charge information is stored as a radiographic image in the image memory 132 of the cassette controller 50. Thereafter, in step S28, similar to step S8, the display device 24 displays the processed radiographic image.

Operations in steps S25 through S28 are essentially the same as those of steps S5 through S8, except for the fact that the liquid scintillator 206a is used, and thus these steps will not be described in detail.

In step S28, the doctor or radiological technician visually checks the radiographic image, which is displayed on the display device 24 or the display unit 82, and confirms that the displayed radiographic image is a proper radiographic image of the subject 14. Thereafter, the doctor or radiological technician releases the subject 14 from the image capturing base 12, thereby completing the image capturing process on the subject 14, and presses the power supply switch 86 in order to de-energize the electronic cassette 20G. The power supply 52 stops supplying electric power to the components of the casing 40. As a result, the electronic cassette 20G switches from an active mode into a sleep mode. Then, the doctor or radiological technician grips the handle 80 and carries the electronic cassette 20G to a prescribed storage location.

In sleep mode, the radiation conversion panel 92 may possibly become deformed within a period of time during which the temperature thereof drops to normal temperature. However, since the scintillator housing bag 290 presses the board 194, the signal output layer 200, and the photoelectric transducer layer 202 against the inner wall surface 296 beneath the image capturing surface 42, irrespective of the operational state of the electronic cassette 20G, the radiation conversion panel 92 is kept flat regardless of the temperature change, i.e., the drop in temperature.

<Advantages of the Seventh Embodiment>

With the electronic cassette 20G and the radiographic image capturing system 10G according to the seventh embodiment, as described above, the scintillator housing bag 290, which serves as a pressing mechanism, is used to press the board 194, the signal output layer 200, and the photoelectric transducer layer 202 against the inner wall surface 296 beneath the image capturing surface 42, thereby holding the components in the radiation conversion panel 92 closely together in a natural configuration, while also easily and securely positioning the radiation conversion panel 92. According to the seventh embodiment, therefore, components in the radiation conversion panel 92 are held closely together by a simple structure. Since the radiation conversion panel 92 is securely positioned by pressing the components thereof, the components do not need to be bonded by an adhesive. Consequently, the radiation conversion panel 92 is prevented from cracking and peeling, and can easily be replaced for facilitating maintainability.

Since planarity of the radiation conversion panel 92 is maintained, the flexible board 212 is prevented from being peeled off from the board 194. As a consequence, address signals can be supplied and electric signals can be output regardless of temperature changes.

Inasmuch as the board 194, the signal output layer 200, and the photoelectric transducer layer 202 are pressed against the inner wall surface 296 beneath the image capturing surface 42, the distance between the subject 14, the liquid scintillator 206a, and the photoelectric transducer layer 202 is reduced.

Since the scintillator housing bag 290, which functions as a pressing mechanism, also serves as a shock dampening member for the casing 40, load resistance and shock resistance of the panel housing unit 30 are increased. Therefore, the radiation conversion panel 92 is effectively prevented from wobbling. In addition, since the base table 190 is fixed to the bottom of the casing 40 and the scintillator housing bag 290 is disposed on the base table 190, the board 194, the signal output layer 200, and the photoelectric transducer layer 202 can be pressed in an efficient manner.

Since the scintillator housing bag 290 comprises a bag made of resin, if the scintillator housing bag 290 is filled with the liquid scintillator 206a, the scintillator housing bag 290 expands in order to securely and reliably position the radiation conversion panel 92.

The port 292 of the scintillator housing bag 290 is sealed by the removable cap 294. Therefore, if the liquid scintillator 206a becomes deteriorated as a result of being irradiated with radiation 16, the liquid scintillator 206a can be removed from the scintillator housing bag 290, and the scintillator housing bag 290 can be refilled with a new liquid scintillator 206a at a time that the electronic cassette 20G is serviced for maintenance or is repaired.

Consequently, the radiation conversion panel 92 including the liquid scintillator 206a, which is expected to deteriorate due to aging and exposure to radiation 16, can easily be replaced for facilitating maintainability.

The cassette controller 50, the power supply 52, and the communication unit 54 are disposed between the base table 190 and the bottom of the casing 40. The base table 190 is made of a material that blocks radiation 16, whereby the cassette controller 50, the power supply 52, and the communication unit 54 are prevented from deteriorating as a result of exposure to radiation 16.

According to the seventh embodiment, the scintillator housing bag 290 is sealed by the cap 294. However, a check valve may be used alone or in combination with the cap 294 in order to prevent the liquid scintillator 206a from leaking out from the port 292. If the liquid pressure in the scintillator housing bag 290 drops, then the bag may be refilled with the liquid scintillator 206a through the check valve and the port 292.

According to the seventh embodiment, after the scintillator housing bag 290 has been filled with the liquid scintillator 206a, the scintillator housing bag 290 remains filled with the liquid scintillator 206a until the electronic cassette 20G is serviced for maintenance, or is replaced or discarded. However, the scintillator housing bag 290 may be filled with the liquid scintillator 206a to enable pressing of the radiation conversion panel 92 only when a radiographic image is captured (step S29 of FIG. 60), and after a radiographic image has been captured, the liquid scintillator 206a may be removed from the scintillator housing bag 290, whereupon the radiation conversion panel 92 is released from the positioned state (step S30 of FIG. 60). Consequently, the radiation conversion panel 92 including the liquid scintillator 206a, which may be expected to deteriorate due to aging and exposure to radiation 16, can easily be replaced for increased maintainability.

<Modifications of the Seventh Embodiment>

The electronic cassette 20G according to the seventh embodiment is not limited to the above descriptions, but may be configured in accordance with the following modifications (tenth through fifteenth modifications) shown in FIGS. 61 through 66.

Figure 61:
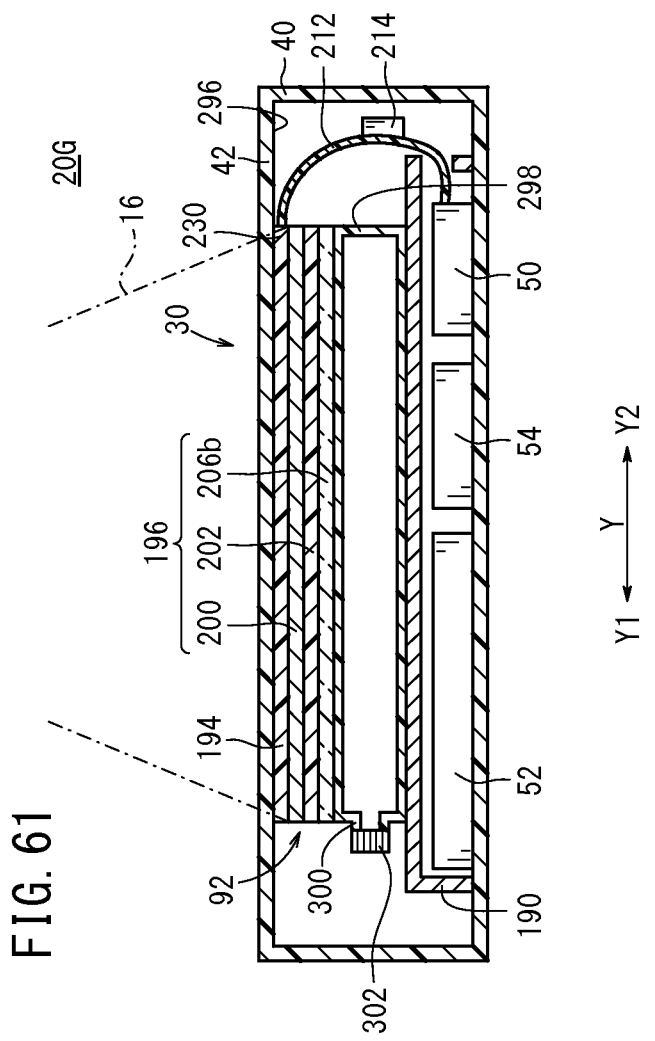
FIG. 61 is a cross-sectional view of a cassette according to a tenth modification.

FIG. 61 shows an electronic cassette 20G according to the tenth modification. The electronic cassette 20G shown in FIG. 61 includes a solid scintillator 206b made of columnar crystals of ScI or the like, instead of the liquid scintillator 206a. The board 194, the signal output layer 200, the photoelectric transducer layer 202, and the scintillator 206b are pressed against the inner wall surface 296 beneath the image capturing surface 42 by a pressing material housing bag 298 made of resin (pressing mechanism, external force applying mechanism). The pressing material housing bag 298 is filled through a port 300 with a flowable material (fluid) such as a liquid or a gas, e.g., air, helium gas, nitrogen gas, or a foamed material such as a tire puncture sealant or the like. After the pressing material housing bag 298 has been filled, a cap 302 is mounted on the port 300 in order to seal the pressing material housing bag 298.

Since the board 194, the signal output layer 200, the photoelectric transducer layer 202, and the scintillator 206b are pressed against the inner wall surface 296 by the pressing material housing bag 298, the components of the radiation conversion panel 92 can be held closely together, and the advantages accruing from the resin bag, i.e., the pressing material housing bag 298, can easily be achieved.

If the scintillator 206b is made of columnar crystals of CsI, then since the radiation conversion panel 92 is maintained in a flat condition, the columnar crystals are kept perpendicular to the board 194, thereby allowing the electronic cassette to easily acquire sharp radiographic images regardless of temperature changes in the radiation conversion panel 92. In FIG. 61, the pressing material housing bag 298 is illustrated as being filled with a gas, for example.

Figure 62:
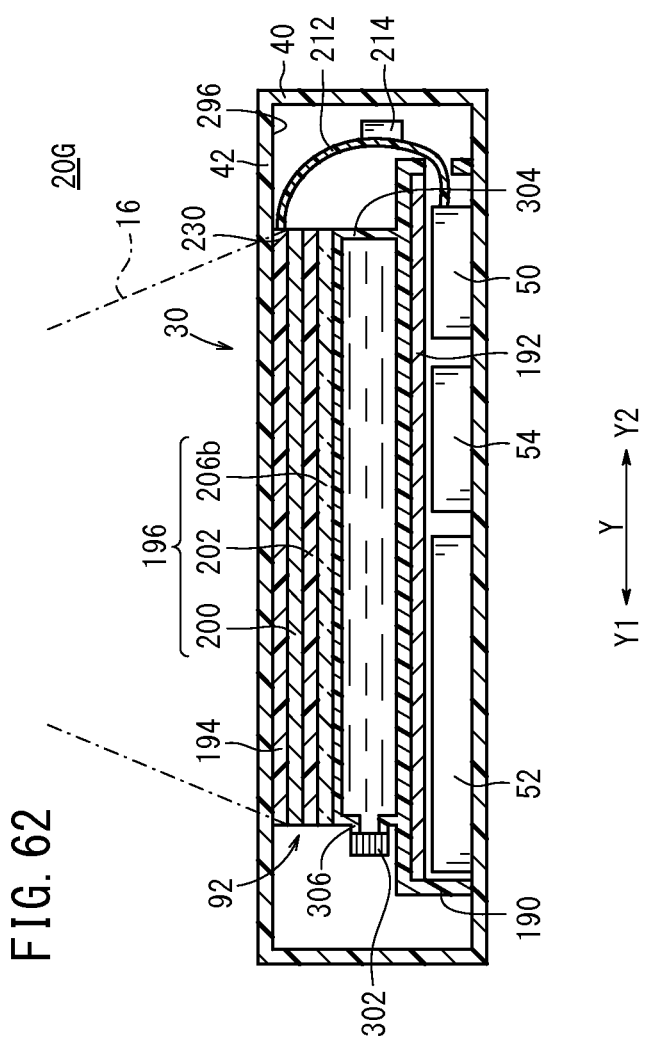
FIG. 62 is a cross-sectional view of a cassette according to an eleventh modification.

With the electronic cassette 20G according to the eleventh modification shown in FIG. 62, the base table 190 is made of resin, and the upper surface of the base table 190, which faces toward the inner wall surface 296, is constructed as a pressing material housing bag 304. The pressing material housing bag 304 is filled with a flowable material or a foamed material through a port 306. After the pressing material housing bag 304 has been filled, a cap 308 is mounted on the port 306 in order to seal the pressing material housing bag 304. Similar to the case of the tenth modification shown in FIG. 61, since the board 194, the signal output layer 200, the photoelectric transducer layer 202, and the scintillator 206b are pressed against the inner wall surface 296 beneath the image capturing surface 42, the components of the radiation conversion panel 92 can be held closely together, and the advantages accruing from the resin bag, i.e., the pressing material housing bag 304, can easily be achieved.

In FIG. 62, the pressing material housing bag 304 is illustrated as being filled with a liquid, for example. The base table 190 includes a shield plate 192 for blocking radiation 16 in a region thereof that faces toward the cassette controller 50, the power supply 52, and the communication unit 54. Therefore, the cassette controller 50, the power supply 52, and the communication unit 54 are protected from deterioration caused by radiation 16.

In FIG. 62, a portion of the base table 190 is constructed as the pressing material housing bag 304. However, the base table 190 may be constructed in its entirety as the pressing material housing bag 304. In this case, the bottom surface of the pressing material housing bag 304, i.e., the base table 190, may be shaped to fit over the cassette controller 50, the power supply 52, and the communication unit 54, and the base table 190 may incorporate a sheet therein for blocking radiation 16.

Figure 63A:
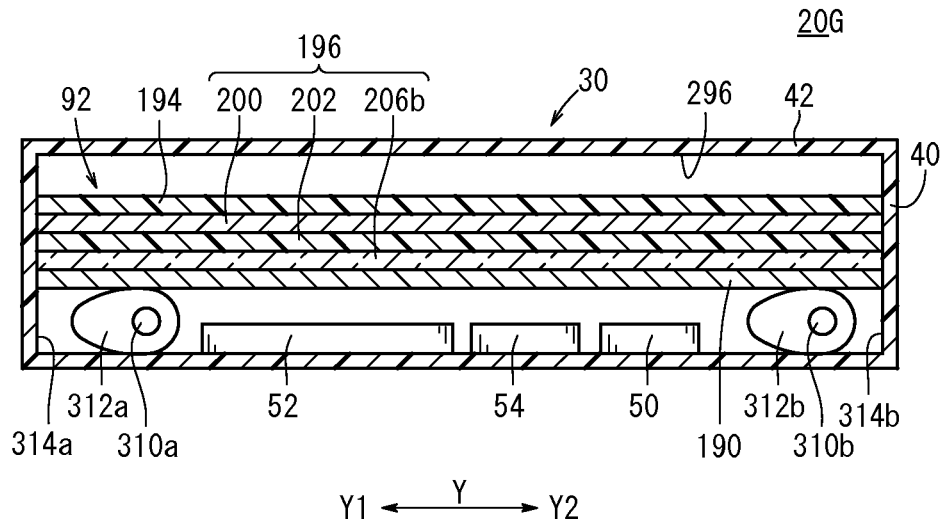
FIG. 63A is a cross-sectional view of a cassette according to a twelfth modification, before components thereof are pressed against an inner wall surface.
Figure 63B:
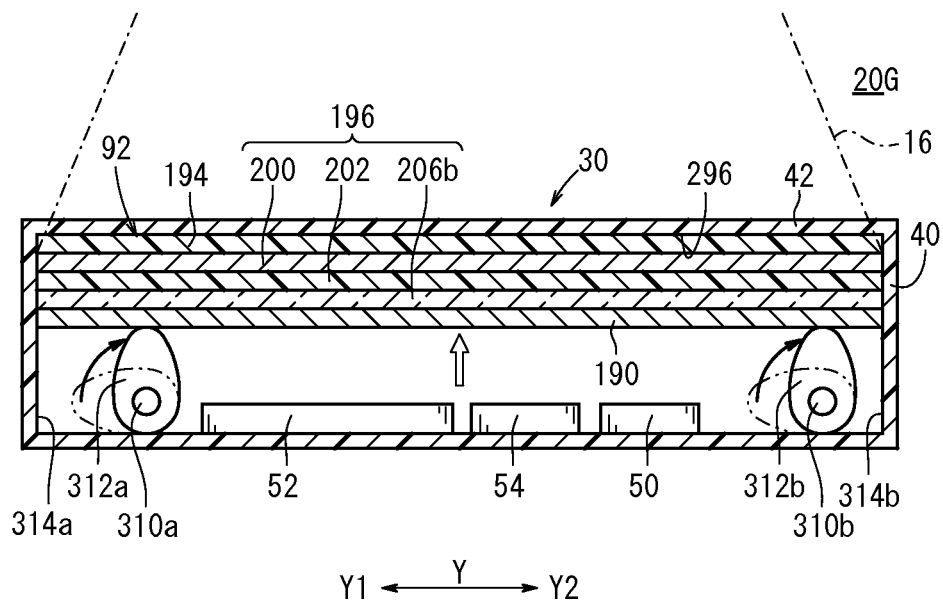
FIG. 63B is a cross-sectional view of the cassette according to the twelfth modification, after the components thereof have been pressed against the inner wall surface.

FIGS. 63A and 63B show an electronic cassette 20G according to a twelfth modification. The electronic cassette 20G shown in FIGS. 63A and 63B includes disc cams 312a, 312b (pressing mechanism, external force applying mechanism) disposed on the bottom of the casing 40, which are coupled to respective rotational shafts 310a, 310b. The disc cams 312a, 312b are turned about the rotational shafts 310a, 310b between the angular position shown in FIG. 63A and the angular position shown in FIG. 63B. More specifically, as shown in FIG. 63A, in a case where a radiographic image is not being captured, the disc cams 312a, 312b are turned to space the board 194, the signal output layer 200, the photoelectric transducer layer 202, the scintillator 206b, and the base table 190, which is of a planar shape, from the inner wall surface 296. In step S29 of FIG. 60, in a case where a radiographic image is captured, as shown in FIG. 63B, the disc cams 312a, 312b are turned to press the board 194, the signal output layer 200, the photoelectric transducer layer 202, the scintillator 206b, and the base table 190 against the inner wall surface 296. Opposite sides of the board 194, the signal output layer 200, the photoelectric transducer layer 202, the scintillator 206b, and the base table 190 are held in contact with side walls 314a, 314b of the casing 40.

The rotational shafts 310a, 310b extend in a direction normal to the sheet of FIGS. 63A and 63B, i.e., the direction of the arrow X. Actually, the disc cams 312a, 312b are spaced along this direction and are coupled to the rotational shafts 310a, 310b, respectively. The disc cams 312a, 312b have a size large enough to keep the cassette controller 50, the power supply 52, and the communication unit 54 out of contact with the base table 190 in a state where the parts are positioned as shown in FIG. 63A.

According to the twelfth modification, as described above, since the board 194, the signal output layer 200, the photoelectric transducer layer 202, the scintillator 206b, and the planar base table 190 are pressed together against the inner wall surface 296 beneath the image capturing surface 42 by the disc cams 312a, 312b, the board 194, the signal output layer 200, the photoelectric transducer layer 202, the scintillator 206b, and the base table 190 are held closely together by a simple structure. Since opposite sides of the board 194, the signal output layer 200, the photoelectric transducer layer 202, the scintillator 206b, and the base table 190 are held in contact with the side walls 314a, 314b, the components of the radiation conversion panel 92 are held very closely together upon being pressed.

Figure 64A:
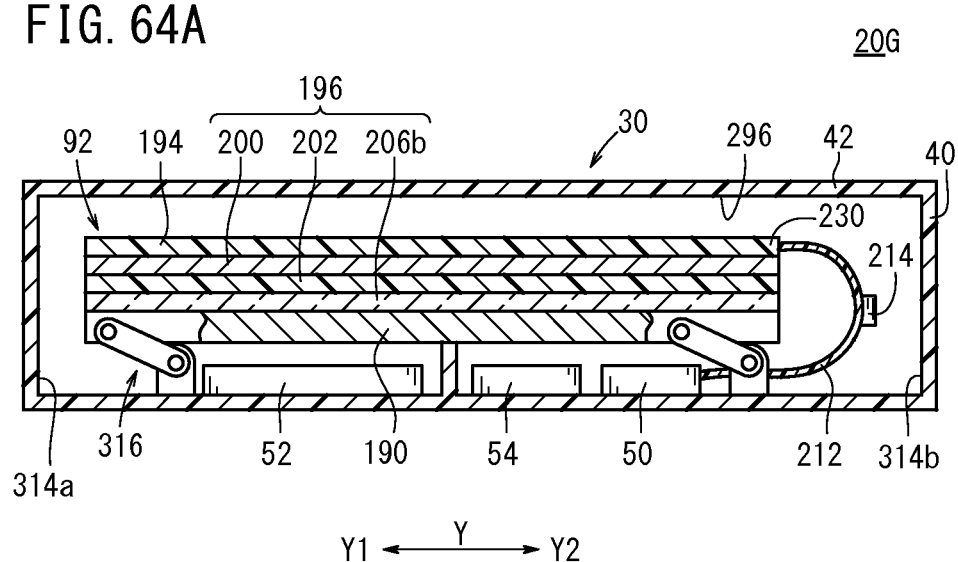
FIG. 64A is a cross-sectional view of a cassette according to a thirteenth modification, before components thereof are pressed against an inner wall surface.
Figure 64B:
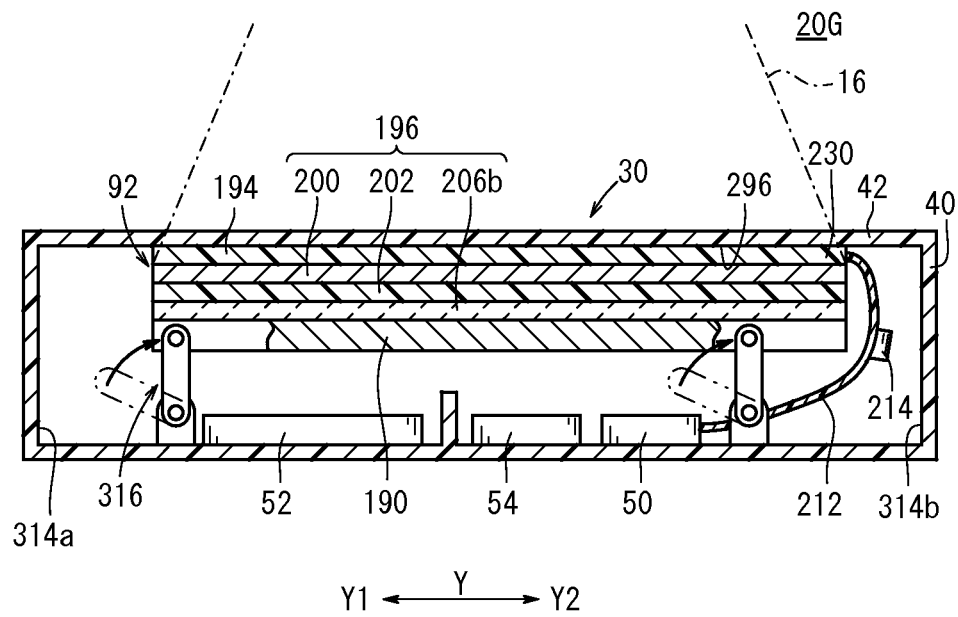
FIG. 64B is a cross-sectional view of the cassette according to the thirteenth modification, after the components thereof have been pressed against the inner wall surface.

FIGS. 64A and 64B show an electronic cassette 20G according to a thirteenth modification. The electronic cassette 20G shown in FIGS. 64A and 64B includes a four-link mechanism 316 including the base table 190, which is disposed on the bottom of the casing 40. If a radiographic image is not being captured, the four-link mechanism 316 is actuated to space the board 194, the signal output layer 200, the photoelectric transducer layer 202, the scintillator 206b, and the base table 190 from the inner wall surface 296, as shown in FIG. 64A. In the case that a radiographic image is captured, in step S29 of FIG. 60, the four-link mechanism 316 is actuated to press the board 194, the signal output layer 200, the photoelectric transducer layer 202, the scintillator 206b, and the base table 190 against the inner wall surface 296, as shown in FIG. 64B. The four-link mechanism 316 has a size large enough to keep the cassette controller 50, the power supply 52, and the communication unit 54 out of contact with the base table 190 in a state where the parts are positioned as shown in FIG. 64A.

According to the thirteenth modification, as described above, since the board 194, the signal output layer 200, the photoelectric transducer layer 202, the scintillator 206b, and the base table 190 are pressed together against the inner wall surface 296 beneath the image capturing surface 42 by the four-link mechanism 316, the board 194, the signal output layer 200, the photoelectric transducer layer 202, the scintillator 206b, and the base table 190 are held closely together by a simple structure, similar to the case of the twelfth modification.

Figure 65:
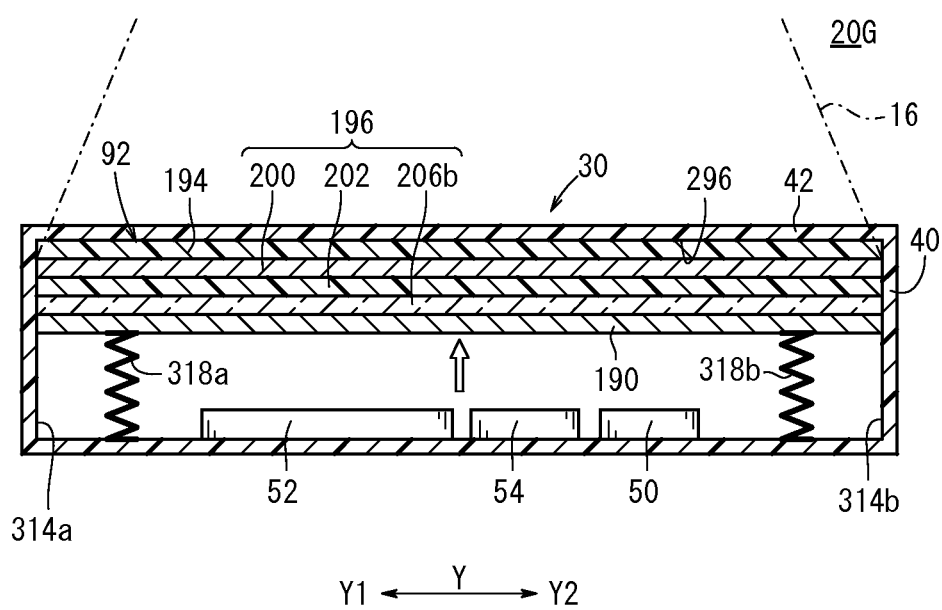
FIG. 65 is a cross-sectional view of a cassette according to a fourteenth modification.

FIG. 65 shows an electronic cassette 20G according to a fourteenth modification. The electronic cassette 20G shown in FIG. 65 differs from the electronic cassette 20G according to the twelfth modification (see FIGS. 63A and 63B), in that springs 318a, 318b are interposed between the bottom of the casing 40 and the base table 190. According to the fourteenth modification, the board 194, the signal output layer 200, the photoelectric transducer layer 202, the scintillator 206b, and the base table 190 are pressed against the inner wall surface 296 at all times by the springs 318a, 318b. Therefore, the board 194, the signal output layer 200, the photoelectric transducer layer 202, the scintillator 206b, and the base table 190 are also held closely together by a simple structure. Since opposite sides of the board 194, the signal output layer 200, the photoelectric transducer layer 202, upon being pressed, the scintillator 206b, and the base table 190 are held in contact with the side walls 314a, 314b, the components of the radiation conversion panel 92 are held very closely together.

Figure 66:
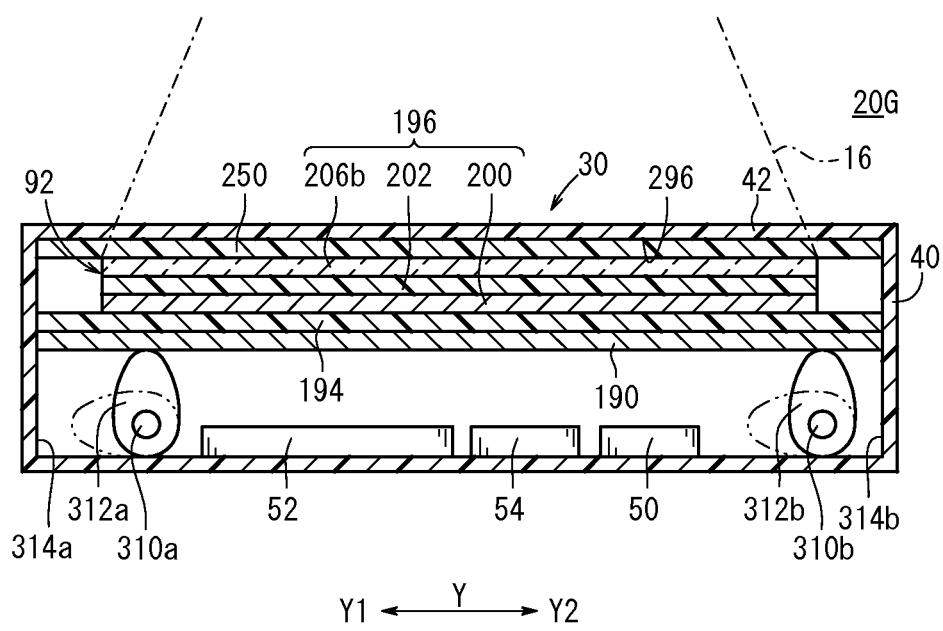
FIG. 66 is a cross-sectional view of a cassette according to a fifteenth modification.

FIG. 66 shows an electronic cassette 20G according to a fifteenth modification. In the electronic cassette 20G shown in FIG. 66, the signal output layer 200 and the photoelectric transducer layer 202 are successively deposited in this order on the board 194. The scintillator 206 is deposited by evaporation or the like on the board 250, which is of aluminum, plastic, or the like, and the photoelectric transducer layer 202 and the scintillator 206b are disposed in confronting relation to each other, thereby making up the radiation conversion panel 92. The boards 194, 250 have different coefficients of thermal expansion.

According to the fifteenth modification, similar to the case with the twelfth modification (see FIGS. 63A and 63B), in the case that a radiographic image is captured, in step S29 shown in FIG. 60, the disc cams 312a, 312b are turned to press the board 194, the signal output layer 200, the photoelectric transducer layer 202, the scintillator 206b, the board 250, and the base table 190 against the inner wall surface 296.

Even though the radiation conversion panel 92 tends to become deformed due to a temperature change, the disc cams 312a, 312b are turned to press the components against the inner wall surface 296, thereby keeping the radiation conversion panel 92 flat reliably and efficiently.

9. Description of Eighth Embodiment

Figure 67:
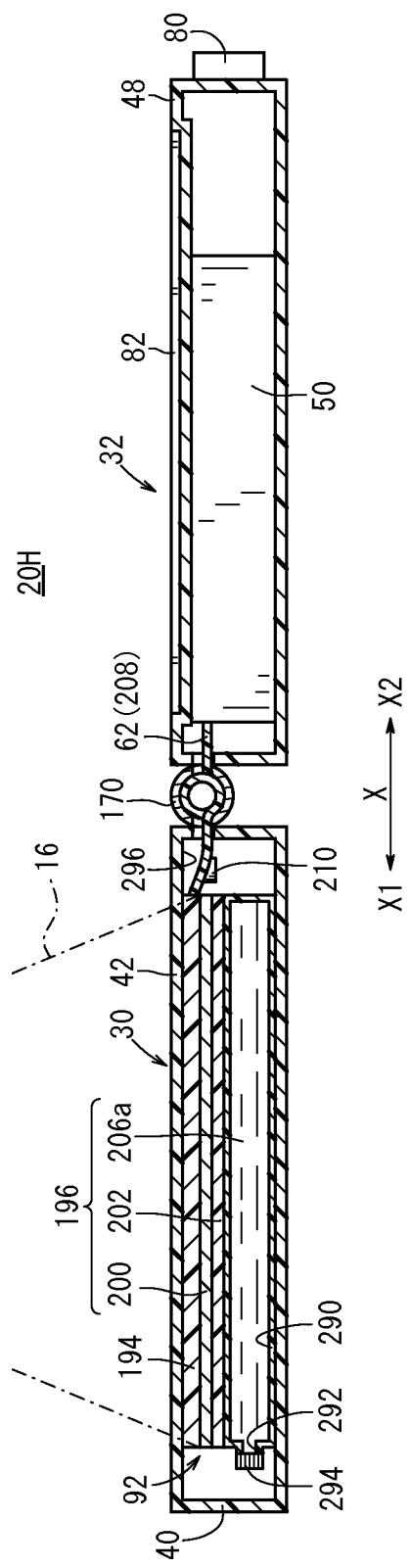
FIG. 67 is a cross-sectional view of a cassette according to an eighth embodiment of the present invention.
Figure 68:
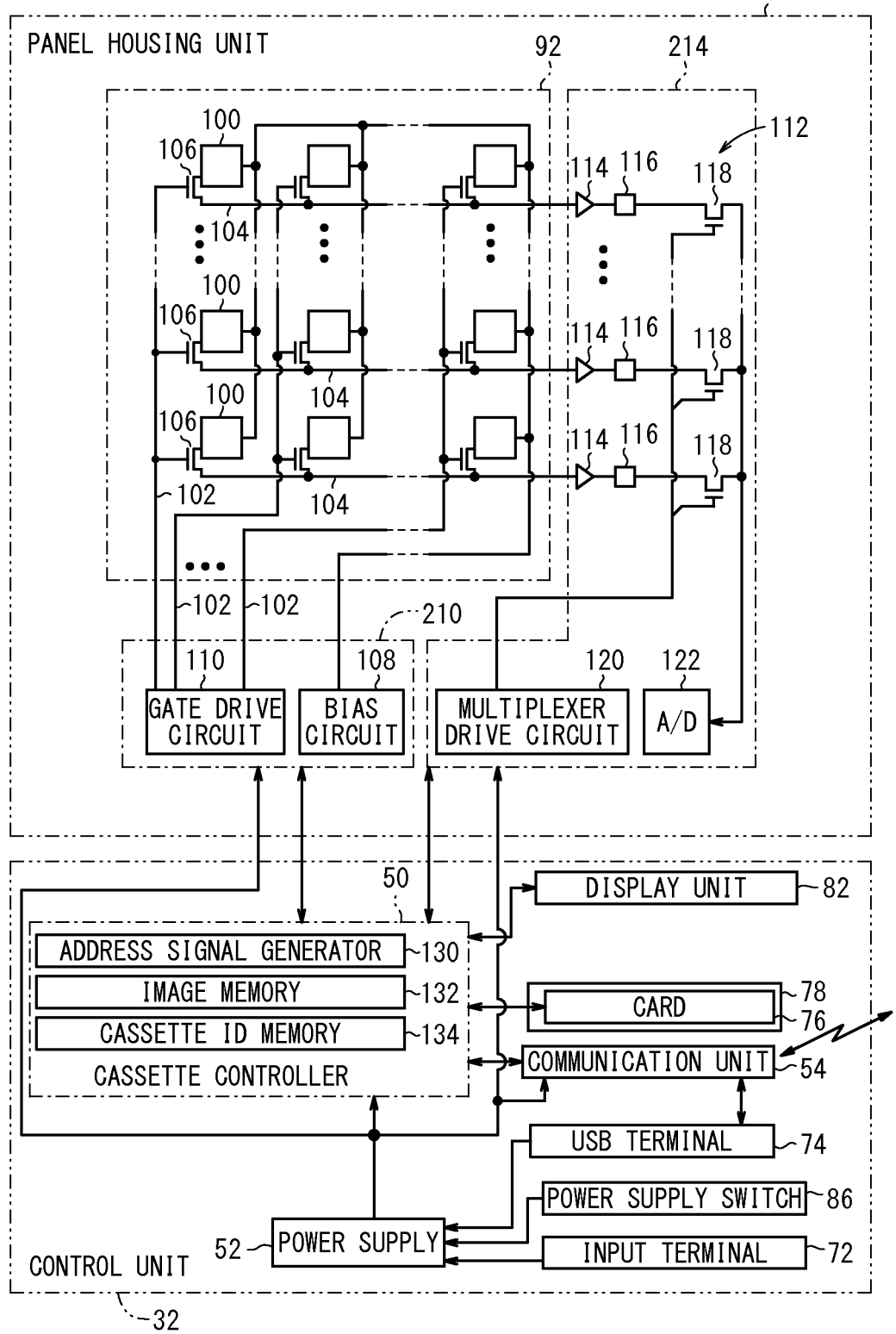
FIG. 68 is a block diagram of the cassette shown in FIG. 67.

An electronic cassette 20H and a radiographic image capturing system 10H according to an eighth embodiment of the present invention will be described below with reference to FIGS. 67 through 68.

The electronic cassette 20H and the radiographic image capturing system 10H according to the eighth embodiment differ from the electronic cassette 20G and the radiographic image capturing system 10G according to the seventh embodiment (see FIGS. 56 through 66), in that the control unit 32 is joined to the panel housing unit 30 through the hinge 170. Consequently, the overall arrangement of the radiographic image capturing system 10H essentially is the same as that of the radiographic image capturing system 10B shown in FIG. 21.

In the electronic cassette 20H, the control unit 32 includes the casing 48, which has substantially the same shape as the casing 40 of the panel housing unit 30, and is made of a material impermeable to radiation 16. The casing 48 houses therein the cassette controller 50, the power supply 52, the communication unit 54, etc. The control unit 32 also includes components that are not involved in conversion of radiation 16 into a radiographic image, e.g., the display unit 82, the handle 80, etc. Therefore, the control unit 32 is not required to have the base table 190, and hence the electronic cassette 20B is lightweight. The components in the casing 40 are the same as those of the seventh embodiment, except that the cassette controller 50, the power supply 52, the communication unit 54, and the base table 190 are not housed in the casing 40. Therefore, the eighth embodiment can easily provide the advantages that accrue from pressing the radiation conversion panel 92 against the inner wall surface 296. The eighth embodiment may also be modified according to the tenth through fifteenth modifications described above (see FIGS. 61 through 66).

10. Description of Ninth Embodiment

Figure 69:
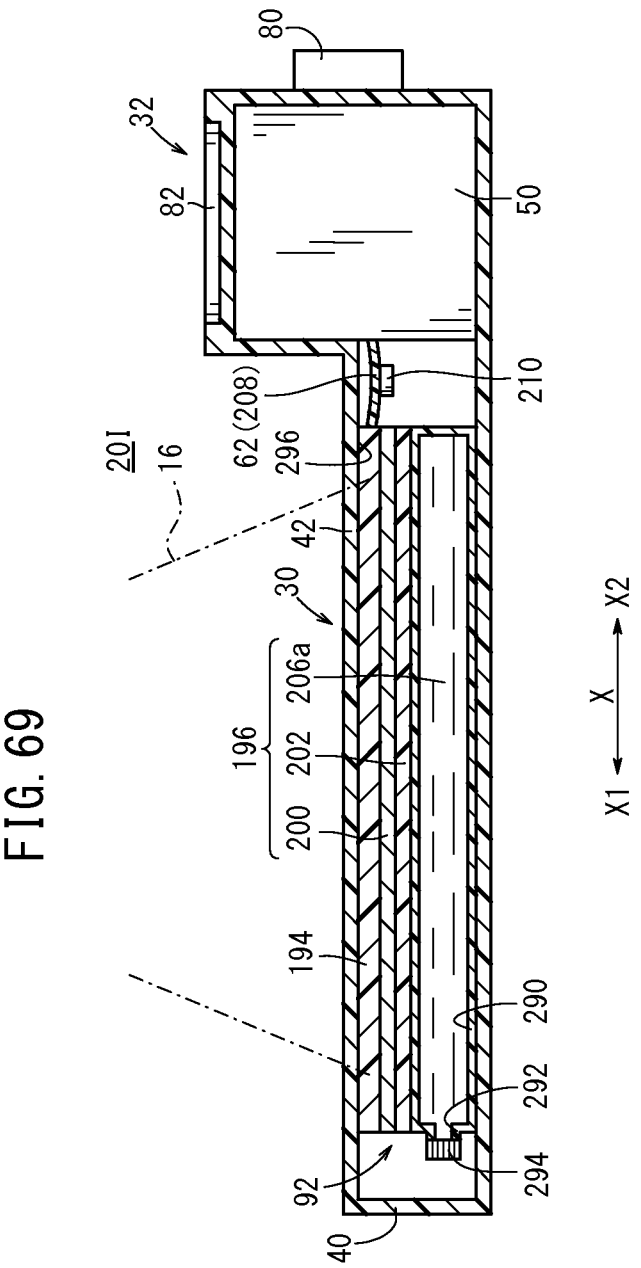
FIG. 69 is a cross-sectional view of a cassette according to a ninth embodiment of the present invention.
Figure 70:
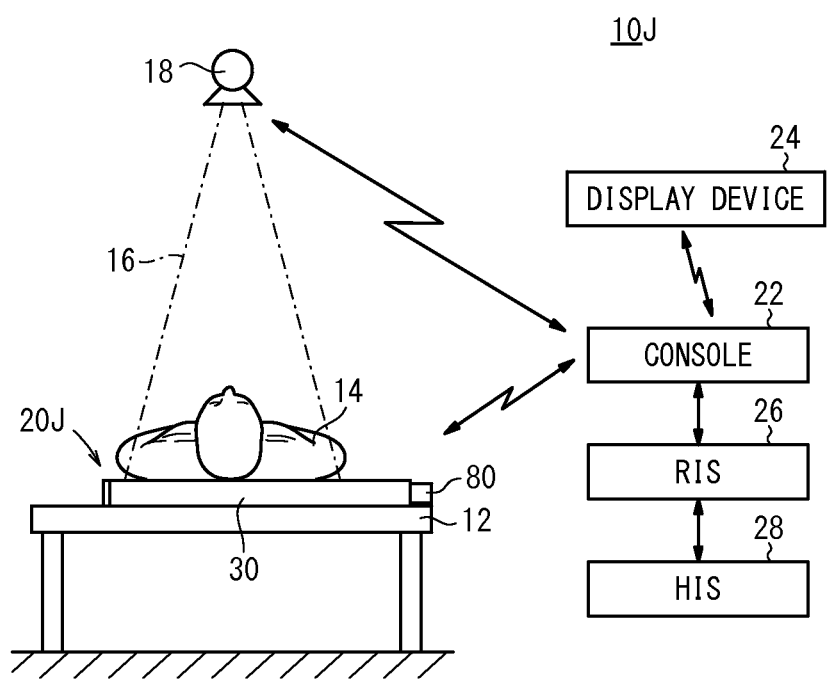
FIG. 70 is a schematic view of a radiographic image capturing system incorporating a cassette according to a tenth embodiment of the present invention.
Figure 71:
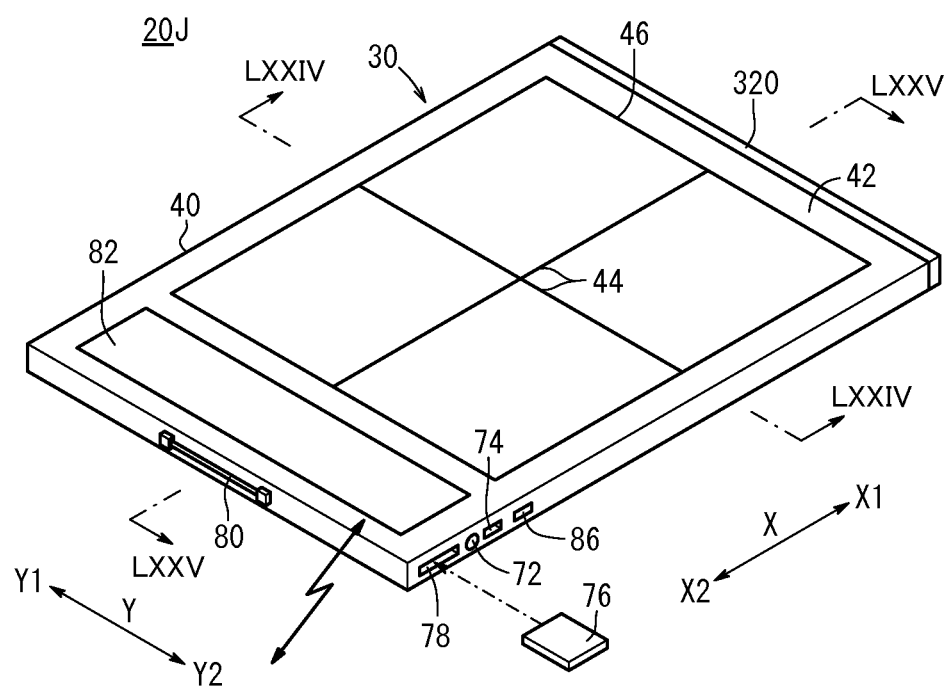
FIG. 71 is a perspective view of the cassette shown in FIG. 70.

An electronic cassette 20I and a radiographic image capturing system 10I according to a ninth embodiment of the present invention will be described below with reference to FIG. 69.

The electronic cassette 20I and the radiographic image capturing system 10I according to the ninth embodiment differ from the electronic cassettes 20G, 20H and the radiographic image capturing systems 10G, 10H according to the seventh and eighth embodiments (see FIGS. 56 through 68), in that a side portion of the panel housing unit 30, which faces in the direction of the arrow X2 projects upwardly, and the projecting portion functions as a control unit 32. The overall arrangement of the radiographic image capturing system 10I essentially is the same as that of the radiographic image capturing system 10C shown in FIG. 29.

In the ninth embodiment also, components not involved in conversion of radiation 16 into radiographic images, e.g., the cassette controller 50, the power supply 52, the communication unit 54, the display unit 82, the handle 80, etc., are disposed together in the projecting portion. The configuration of the radiation conversion panel 92 in the panel housing unit 30 is the same as that according to the eighth embodiment, and this feature will not be described in detail below. The ninth embodiment can easily provide the advantages that accrue from pressing of the radiation conversion panel 92 against the inner wall surface 296.

11. Description of Tenth Embodiment

An electronic cassette 20J and a radiographic image capturing system 10J according to a tenth embodiment of the present invention will be described below with reference to FIGS. 70 through 85B.

<Arrangement of the Tenth Embodiment>

The electronic cassette 20J and the radiographic image capturing system 10J according to the tenth embodiment differs from the electronic cassettes 20G through 20I and the radiographic image capturing systems 10G through 10I according to the seventh through ninth embodiments (see FIGS. 56 through 69), in that the radiation conversion panel 92 can be pressed against the inner wall surface 296 beneath the image capturing surface 42 at least during capturing of a radiographic image in which radiation 16 is applied thereto. The overall arrangement of the radiographic image capturing system 10J essentially is the same as the overall arrangement of the radiographic image capturing system 10G shown in FIG. 58.

Figure 72:
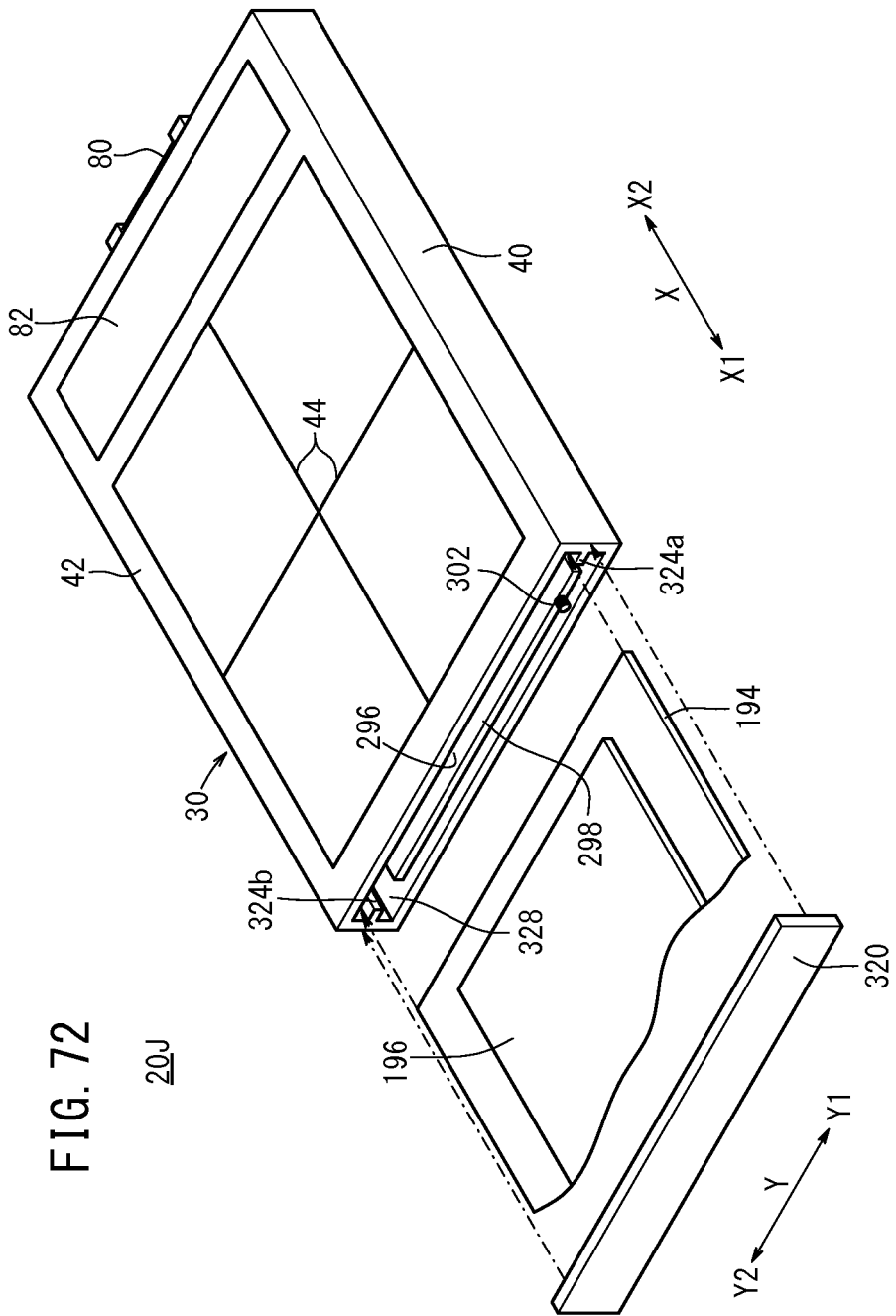
FIG. 72 is a perspective view showing the manner in which a radiation conversion panel is taken into and out of the cassette shown in FIG. 70.

According to the tenth embodiment, as shown in FIGS. 70 through 73, a side plate 320 is fixed to a side of the casing 40, which faces in the direction of the arrow X1. Preferably, the side plate 320 is removable at the time that components in the casing 40 are reworked or serviced for maintenance. For example, the side plate 320 is bonded to the casing 40 by a dismantlable adhesive. As shown in FIG. 72, the casing 40 has an open side facing in the direction of the arrow X1, so as to allow the components to be taken into and out of the casing 40 through the open side. The casing 40 preferably is integrally molded using a material such as CFRP, resin, or the like, so as to make the casing 40 seamless on the other sides and on upper and lower surfaces thereof.

As shown in FIGS. 73 through 75B, the casing 40 houses, in a chamber 326 thereof, the cassette controller 50, the power supply 52, and the communication unit 54, which are located in a region facing in the direction of the arrow X2, i.e., near the display unit 82. The side wall 314a, which faces in the direction of the arrow Y1, and the side wall 314b, which faces in the direction of the arrow Y2, have respective rails 324a, 324b that project into the chamber 326 and extend along the direction of the arrows X. The rails 324a, 324b have the same height, and extend from the side of the casing 40, which faces in the direction of the arrow X1, i.e., the side plate 320, to a position proximate to the cassette controller 50, the power supply 52, and the communication unit 54.

The radiation conversion panel 92 is disposed in a space between the rails 324a, 324b and the inner wall surface 296 beneath the image capturing surface 42. The resin-made pressing material housing bag 298 (pressing mechanism, external force applying mechanism) is disposed on a bottom inner wall surface 328, which confronts the inner wall surface 296.

The radiation conversion panel 92 includes a board 194 held in contact with the side walls 314a, 314b and which is mountable on the rails 324a, 324b, a signal output layer 200 disposed on the board 194, a photoelectric transducer layer 202 deposited on the signal output layer 200, and a solid scintillator 206b made of columnar crystals of CsI or the like, which are deposited on the photoelectric transducer layer 202. The signal output layer 200, the photoelectric transducer layer 202, and the scintillator 206b jointly constitute a radiation conversion layer 196. As viewed in plan, the area of the radiation conversion layer 196 is substantially the same as the area of the image capturing field 46 (see FIG. 73).

Figure 74A:
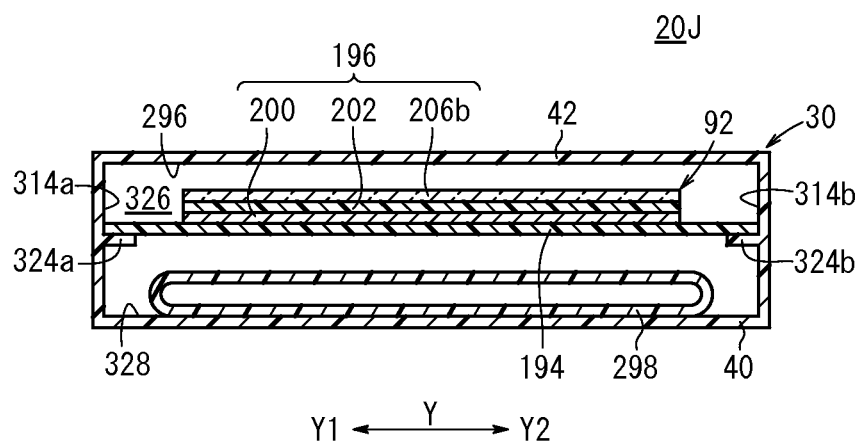
FIGS. 74A and 74B are cross-sectional views taken along line LXXIV-LXXIV of FIG. 71.
Figure 74B:
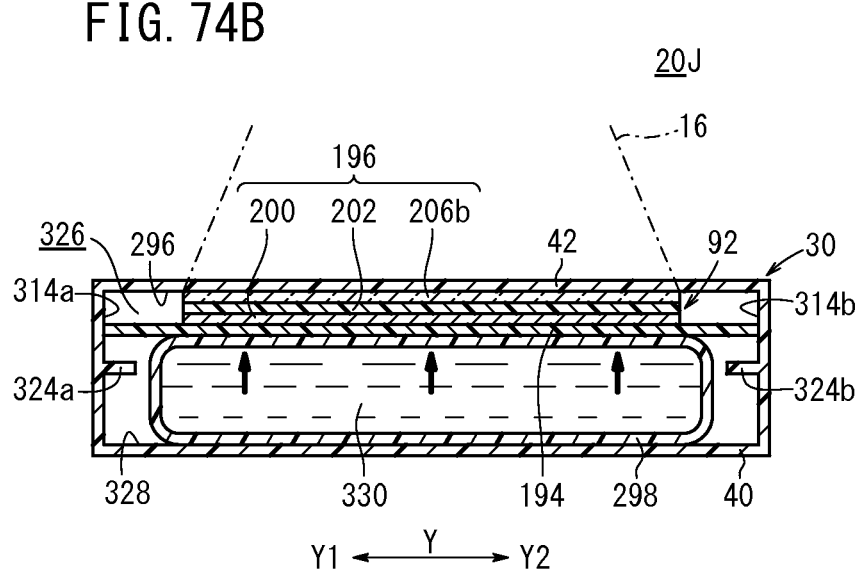

The pressing material housing bag 298 is filled through the port 300 with a filling material 330, which may be a flowable material (fluid) such as a liquid or a gas, e.g., air, helium gas, or nitrogen gas, or a foamed material such as a tire puncture sealant or the like. After the pressing material housing bag 298 has been filled, a cap 302 is mounted on the port 300 in order to seal the pressing material housing bag 298. At least during capturing of radiographic images by applying radiation 16 to the electronic cassette 20J, the pressing material housing bag 298, which has been expanded by being filled with the filling material 330, presses the radiation conversion panel 92 against the inner wall surface 296, thereby positioning the radiation conversion panel 92 with respect to the inner wall surface 296 (see FIGS. 74A and 74B). In FIGS. 74A and 74B, the pressing material housing bag 298 is filled with a liquid, which serves as the filling material 330.

In order to take the components into and out of the chamber 326 if the chamber 326 needs to be reworked or serviced for maintenance, or if a radiographic image is not captured at the time that the electronic cassette 20J is manufactured, the casing 40 and the side plate 320 are separated from each other in order to open the side of the casing 40, which faces in the direction of the arrow X1, whereupon the filling material 330 is removed from the pressing material housing bag 298. Thereafter, the board 194 is moved in the direction of the arrow X along the rails 324a, 324b and the side walls 314a, 314b (see FIGS. 72, 74A, and 75A).

At this time, the radiation conversion panel 92 is released from the pressing material housing bag 298, and the thickness thereof becomes smaller than the distance between the upper surfaces of the rails 324a, 324b and the inner wall surface 296. If the board 194 is moved along the rails 324a, 324b in the direction of the arrow X, the radiation conversion panel 92 can easily be brought into and out of the casing 40 without the radiation conversion layer 196, i.e., the scintillator 206b thereof, and the inner wall surface 296 being held in contact with each other.

<Operation of the Tenth Embodiment>

The radiographic image capturing system 10J, which incorporates the electronic cassette 20J according to the tenth embodiment, is basically constructed as described above. A process from introducing the components into the casing 40 to sealing the casing 40, and operations of the electronic cassette 20J and the radiographic image capturing system 10J will be described below.

Operations of the tenth embodiment are essentially the same as that of the seventh through ninth embodiments (see FIGS. 59 and 60), but differ in the following ways.

In step S21 shown in FIG. 59, (1) the cassette controller 50, the power supply 52, and the communication unit 54, (2) the pressing material housing bag 298 that is shrunk before being filled with the filling material 330, and (3) the radiation conversion panel 92 are introduced successively in this order into the casing 40 through the open side thereof.

At this time, the worker moves the radiation conversion panel 92 through the open side along the direction indicated by the arrow X2, while both sides of the board 194, which face in directions of the arrows Y, are guided along the side walls 314a, 314b and the rails 324a, 324b. Thus, the worker can insert the radiation conversion panel 92 into the casing 40 without bringing the scintillator 206b of the radiation conversion panel 92 into contact with the inner wall surface 296. The worker inserts the radiation conversion panel 92 to a position at which the radiation conversion layer 196 and the image capturing field 46 become substantially aligned with each other.

In step S22, the worker fills the pressing material housing bag 298 with the filling material 330 through the port 300. Upon being filled with the filling material 330, the pressing material housing bag 298 is expanded vertically, as shown in FIGS. 74A through 75B. The expanded pressing material housing bag 298 presses the radiation conversion panel 92 against the inner wall surface 296 beneath the image capturing surface 42 (see FIGS. 75A and 75B).

In step S23, after confirming that the pressing material housing bag 298 has been filled with the filling material 330, the worker seals the pressing material housing bag 298 by mounting the cap 302 on the port 300. Thus, the radiation conversion panel 92 is securely positioned so as to underlie the image capturing field 46 as viewed in plan. Then, the worker seals the casing 40 by fixing the side plate 320 to the open side of the casing 40 with a dismantlable adhesive. The side plate 320 is of the same size as the open side of the casing 40 and is made of the same material as the casing 40.

The electronic cassette 20J is manufactured, or reworking or maintenance is carried out on the electronic cassette 20J, i.e., replacement of the radiation conversion panel 92 is completed, according to the process including steps S21 through S23.

For capturing a radiographic image of the subject 14, in step S6 shown in FIG. 60, the scintillator 206b of the radiation conversion panel 92 radiates fluorescence having an intensity depending on the intensity of the radiation 16. The pixels 100 of the photoelectric transducer layer 202 convert the fluorescence into electric signals and store the signals as electric charges.

If the radiation conversion panel 92 is removed from the casing 40, i.e., if the electronic cassette 20J is reworked or serviced for maintenance, then the casing 40 and the side plate 320 are separated from each other, and thereafter, the filling material 330 is removed from the pressing material housing bag 298 to allow the pressing material housing bag 298 to shrink. Accordingly, the radiation conversion panel 92 is released from the pressed state, and then is moved in the direction of the arrow X1 along the rails 324a, 324b and the side walls 314a, 314b.

The radiation conversion panel 92 is thus removed from the open side of the casing 40.

<Advantages of the Tenth Embodiment>

With the electronic cassette 20J and the radiographic image capturing system 10J according to the tenth embodiment, as described above, at least during times that radiographic images are captured by applying radiation 16 to the electronic cassette 20J, the pressing material housing bag 298, which serves as a pressing mechanism, is capable of pressing the radiation conversion panel 92 against the inner wall surface 296 of the casing 40 of the panel housing unit 30. Thus, in a case where a radiographic image is not being captured and the radiation conversion panel 92 is taken into and out of the casing 40, the radiation conversion panel 92 can be taken into and out of the casing 40 in a state where the radiation conversion panel 92 is being released from being pressed against the inner wall surface 296 by the pressing material housing bag 298. Therefore, the radiation conversion panel 92 can be taken into and out of the casing 40 without contact with the inner wall surface 296. In a case where the casing 40 is made of CFRP, therefore, it is possible to prevent carbon fibers of the CFRP from becoming broken and frayed thereby to degrade the quality of the captured radiographic image due to such frayed portions. In addition, it is possible to prevent the radiation conversion panel 92 from being damaged by coming into contact with the inner wall surface 296 and thereby degrading the quality of the captured radiographic image. Further, the gate lines 102 and the signal lines 104 can be prevented from breaking.

At least upon capturing of radiographic images, the pressing material housing bag 298 holds the inner wall surface 296 and the radiation conversion panel 92 closely together in a natural configuration, and the radiation conversion panel 92 is easily and securely positioned with respect to the inner wall surface 296. As a result, since the inner wall surface 296 and the radiation conversion panel 92 are held very closely together by a simple structure, load resistance and shock resistance of the electronic cassette 20J are increased, and the radiation conversion panel 92 is effectively prevented from wobbling. Inasmuch as the radiation conversion panel 92 is easily brought closely to the inner wall surface 296 beneath the image capturing surface 42, the distance between the subject 14 and the liquid scintillator 206b and the photoelectric transducer layer 202 is reduced, thereby making it possible to minimize blurring of the radiographic image, as well as to reduce the thickness of the electronic cassette 20J.

Since the radiation conversion panel 92 does not need to be bonded to the inner wall surface 296 and can easily be taken into and out of the casing 40, reworkability and maintainability of the radiation conversion panel 92 are increased.

Upon removing the filling material 330 from the pressing material housing bag 298 to enable the radiation conversion panel 92 to be taken into or out of the casing 40, the radiation conversion panel 92 changes from a state of being pressed against the inner wall surface 296 to a state of being released from the inner wall surface 296. Therefore, the radiation conversion panel 92 can easily be taken into or out of the casing 40 while reliably avoiding contact with the inner wall surface 296. If a radiographic image is to be captured, the pressing material housing bag 298 is expanded by being filled with the filling material 330, thereby pressing the radiation conversion panel 92 against the inner wall surface 296. Thus, the scintillator 206b and the photoelectric transducer layer 202 of the radiation conversion panel 92 are easily held in highly close contact with each other, and the scintillator 206b and the inner wall surface 296 are easily held very closely together.

Since the scintillator 206b is made of columnar crystals of CsI, if the pressing material housing bag 298 presses the radiation conversion panel 92 against the inner wall surface 296, planarity of the radiation conversion panel 92 is maintained, thereby keeping the columnar crystals perpendicular to the board 194 and allowing the electronic cassette 20J to easily acquire sharp radiographic images.

Since the pressing material housing bag 298 functions as a shock dampening member for the panel housing unit 30, load resistance and shock resistance of the panel housing unit 30 are increased. In addition, since the pressing material housing bag 298 comprises a bag made of resin, upon being filled with the filling material 330, the pressing material housing bag 298 expands to securely and reliably position the radiation conversion panel 92.

Inasmuch as the port 300 of the pressing material housing bag 298 is sealed by the removable cap 302, the filling material 330 can easily be removed from the pressing material housing bag 298 if the electronic cassette 20J is required to be reworked, serviced for maintenance, or repaired.

Consequently, the radiation conversion panel 92 including the scintillator 206b, which is expected to deteriorate due to aging or by being exposed to radiation 16, can easily be replaced for increased reworkability and maintainability.

According to the tenth embodiment, the pressing material housing bag 298 is sealed by the cap 302. However, a check valve may be used alone or in combination with the cap 302, so as to prevent the filling material 330 from leaking out from the port 300. If the pressure in the pressing material housing bag 298 drops, then the pressing material housing bag 298 may be refilled with the filling material 330 through the check valve and the port 300.

According to the tenth embodiment, after the pressing material housing bag 298 has been filled with the filling material 330, the pressing material housing bag 298 remains filled with the same filling material 330 until the electronic cassette 20J needs to be serviced for maintenance, or is replaced or discarded. However, the pressing material housing bag 298 may be filled with the filling material 330 only during times that a radiographic image is to be captured, in step S29 of FIG. 60, and the filling material 330 may be removed from the pressing material housing bag 298 whereupon the radiation conversion panel 92 is released from the positioned state after the radiographic image has been captured, in step S30 of FIG. 60. Consequently, the radiation conversion panel 92 including the liquid scintillator 206b, which is expected to deteriorate due to aging or by exposure to radiation 16, can easily be replaced to increase reworkability and maintainability.

<Modifications of the Tenth Embodiment>

The electronic cassette 20J according to the tenth embodiment is not limited to the above description, but may be arranged as shown in FIGS. 76 through 85B.

Figure 75A:
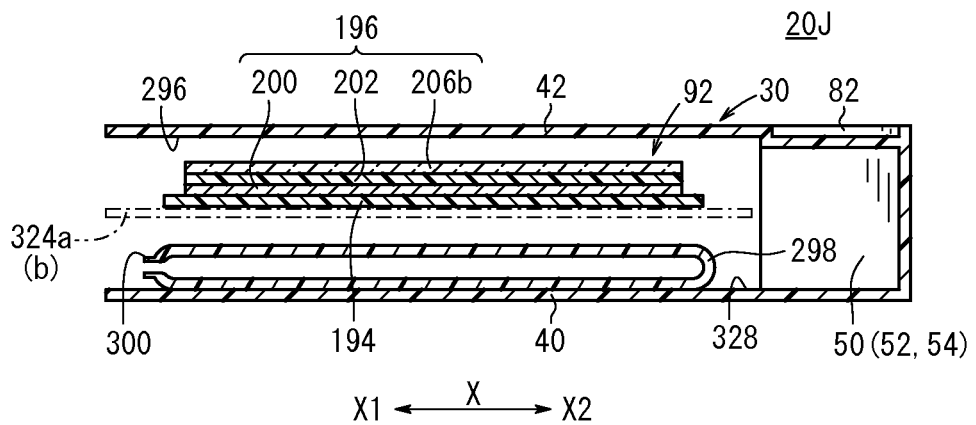
FIGS. 75A and 75B are cross-sectional views taken along line LXXV-LXXV of FIG. 71.
Figure 75B:
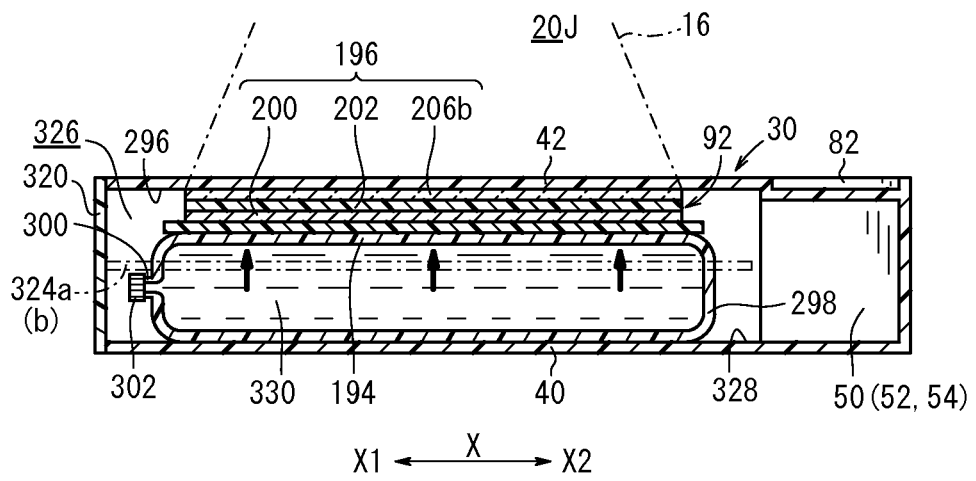
Figure 76:
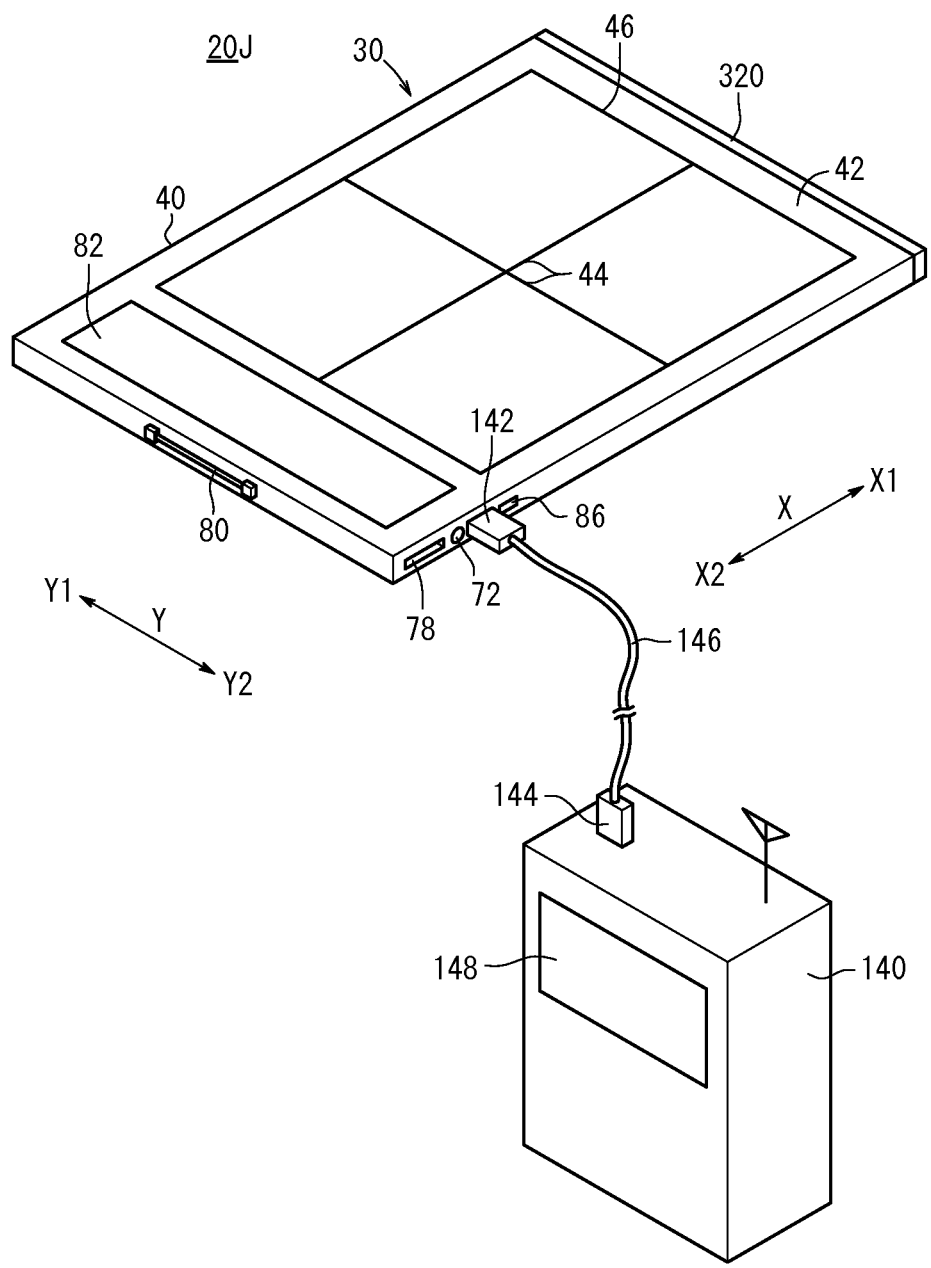
FIG. 76 is a perspective view showing the manner in which the cassette shown in FIG. 70 is charged.
Figure 77A:
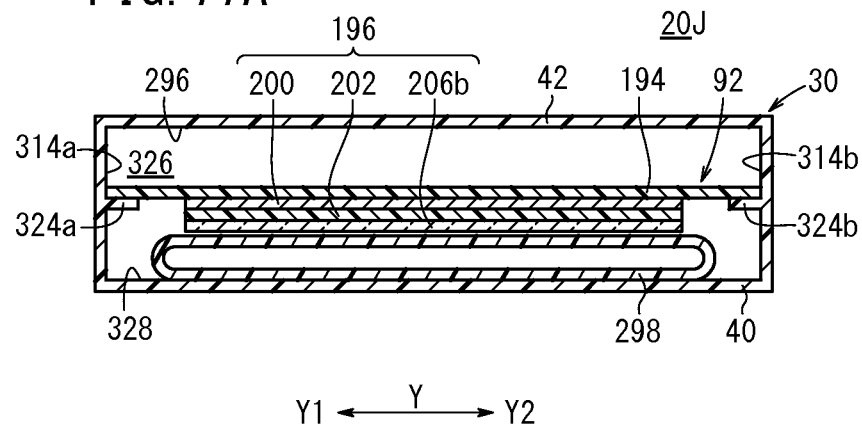
FIGS. 77A and 77B are cross-sectional views of a cassette according to a sixteenth modification.
Figure 77B:
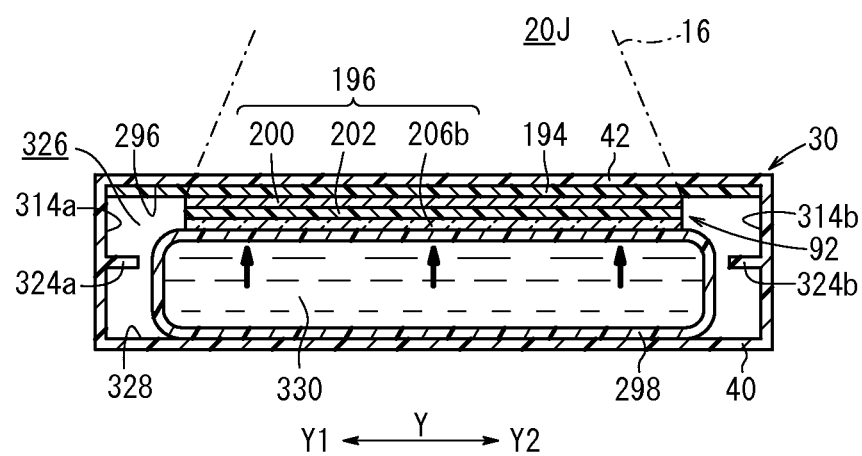
Figure 78A:
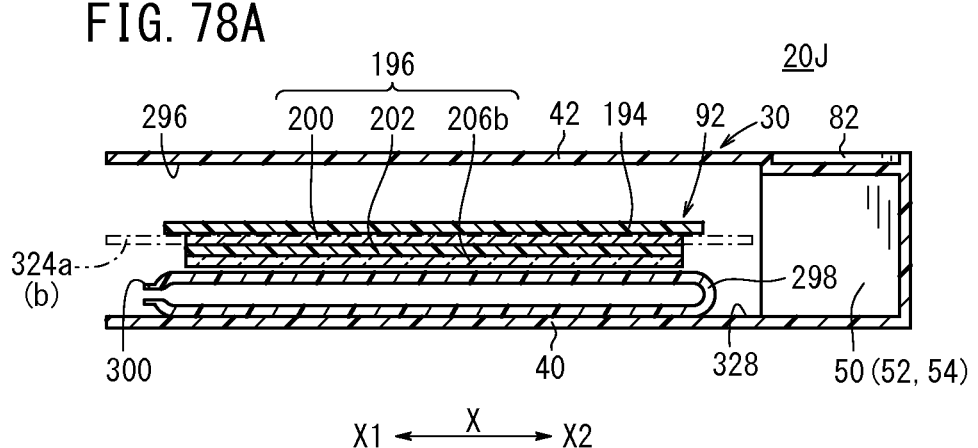
FIGS. 78A and 78B are cross-sectional views of the cassette according to the sixteenth modification.
Figure 78B:
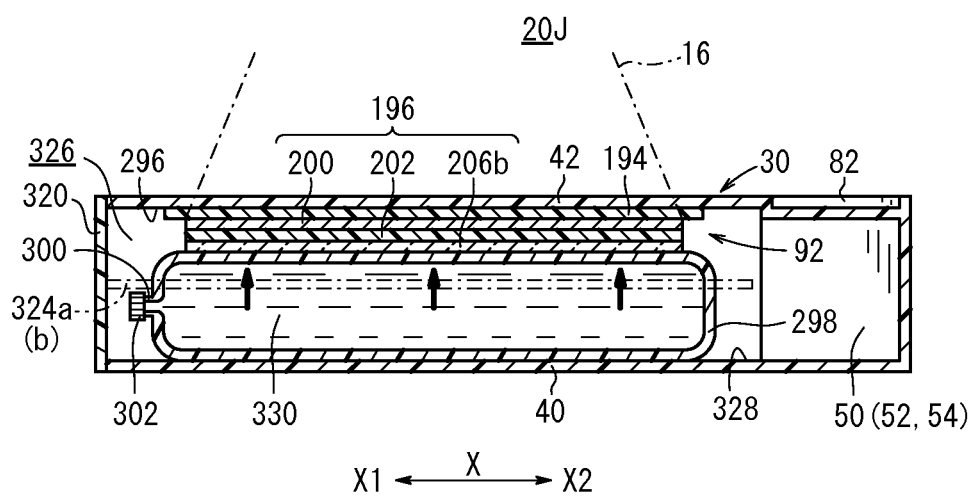
Figure 80A:
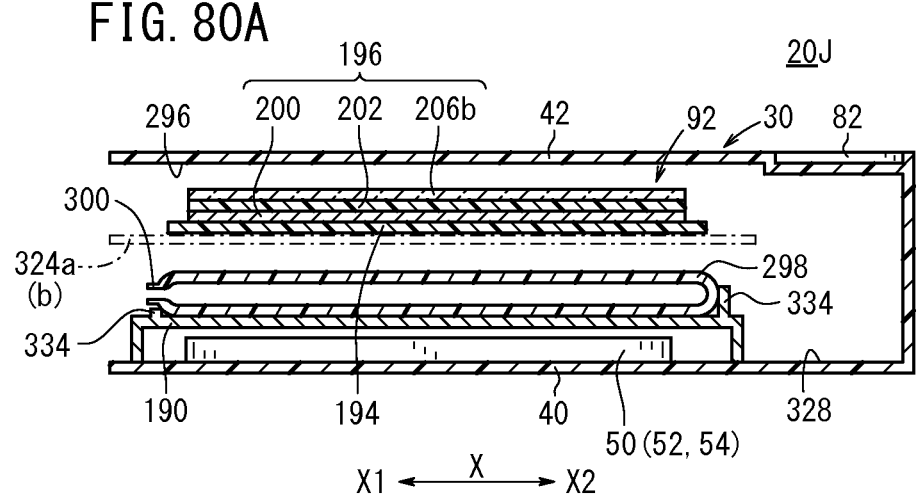
FIGS. 80A and 80B are cross-sectional views of the cassette according to the seventeenth modification.
Figure 80B:
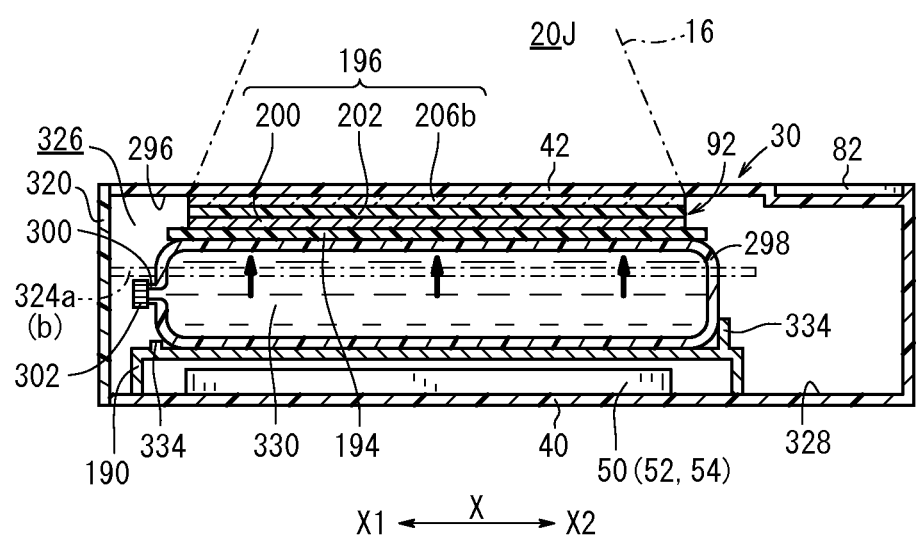

FIG. 76 is a perspective view showing the manner in which the power supply 52 (see FIGS. 73, 75A, and 75B) is charged by the cradle 140, which is placed at a location in a medical organization.

The electronic cassette 20J and the cradle 140 are electrically connected to each other by the USB cable 146 having the connectors 142, 144.

The cradle 140 not only is capable of charging the power supply 52, but also may send necessary information to and receive necessary information from the console 22 and the RIS 26 in the medical organization, using a wireless communication function or a wired communication function of the cradle 140. Information that is sent and received may include the radiographic image that is recorded in the image memory 132 (see FIG. 58) of the electronic cassette 20J.

The cradle 140 may include a display unit 148 for displaying necessary information representative of the charged state of the electronic cassette 20J, and which displays the radiographic image acquired from the electronic cassette 20J.

A plurality of cradles 140 may be connected to a network, and the charged states of electronic cassettes 20J that are connected to the cradles 140 may be collected through the network, for thereby confirming the locations of electronic cassettes 20J that have been charged and the extent to which the electronic cassettes 20J can be used.

Modifications (hereinafter referred to as sixteenth through twenty-first modifications) of the electronic cassette 20J according to the tenth embodiment will be described below with reference to FIGS. 77A through 85B.

FIGS. 77A through 78B show the electronic cassette 20J according to a sixteenth modification. In the electronic cassette 20J according to the sixteenth modification, the radiation conversion panel 92 is vertically inverted so as to position the scintillator 206b, etc., beneath the board 194. More specifically, the electronic cassette 20J shown in FIGS. 75A through 75B is a cassette, which incorporates a PSS type of radiation conversion panel 92, in which the scintillator 206b is disposed in a forward direction and the photoelectric transducer layer 202 is disposed in a rearward direction with respect to the direction in which radiation 16 is applied. However, the electronic cassette 20J according to the sixteenth modification is a cassette, which incorporates an ISS type of radiation conversion panel 92, in which the photoelectric transducer layer 202 is disposed in a forward direction and the scintillator 206 is disposed in a rearward direction with respect to the direction in which radiation 16 is applied.

At times that the pressing material housing bag 298 presses the radiation conversion panel 92 against the inner wall surface 296, the components of the radiation conversion panel 92 can easily be held very closely together, and the radiation conversion panel 92 and the inner wall surface 296 can easily be held very closely together. Therefore, the advantages that accrue from using the pressing material housing bag 298 can easily be achieved.

FIGS. 79A through 80B show an electronic cassette 20J according to a seventeenth modification. In the electronic cassette 20J according to the seventeenth modification, the cassette controller 50, the power supply 52 such as a battery or the like, and the communication unit 54 are disposed on the inner wall surface 328. The base table 190, which is made of a material that blocks radiation 16, i.e., a material containing a heavy metal such as lead or the like, is fixed to the inner wall surface 328 in covering relation to the cassette controller 50, the power supply 52, and the communication unit 54, and the pressing material housing bag 298 is disposed on the upper surface of the base table 190. Two walls 332 are disposed on the upper surface of the base table 190 at opposite ends thereof in the direction of the arrow Y, and two walls 334 are disposed on the upper surface of the base table 190 at opposite ends thereof in the direction of the arrow X. The pressing material housing bag 298 is placed or fixed in position between the two walls 332 and the two walls 334.

According to the seventeenth modification, at times that the pressing material housing bag 298 presses the radiation conversion panel 92 against the inner wall surface 296, the components of the radiation conversion panel 92 can easily be held very closely together, and further, the radiation conversion panel 92 and the inner wall surface 296 can easily be held very closely together. Therefore, the advantages that accrue from using the pressing material housing bag 298 can easily be achieved.

The base table 190, which is made of a material that blocks radiation 16, is disposed between the radiation conversion panel 92 and the cassette controller 50, the power supply 52, and the communication unit 54. Therefore, the cassette controller 50, the power supply 52, and the communication unit 54 are protected from deterioration caused by radiation 16.

Figure 81A:
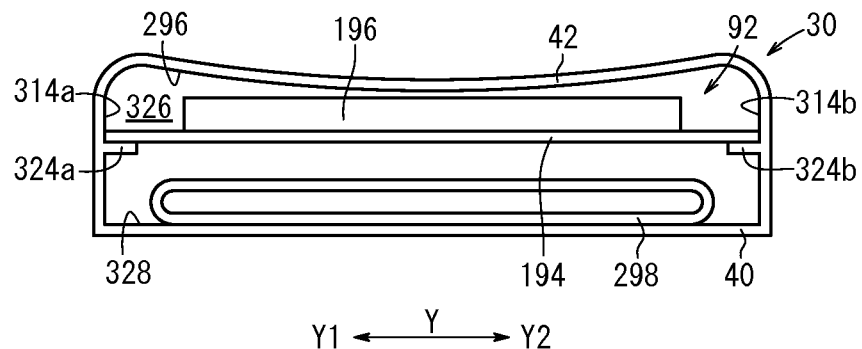
FIGS. 81A and 81B are cross-sectional views of a cassette according to an eighteenth modification.
Figure 81B:
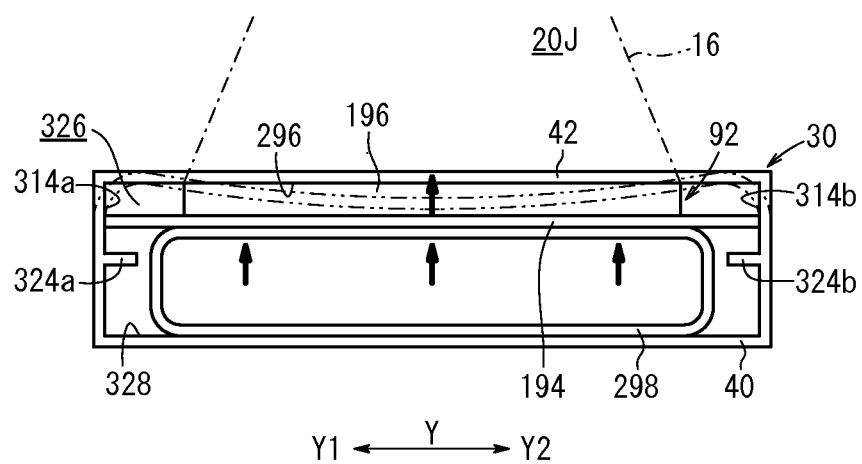
Figure 82A:
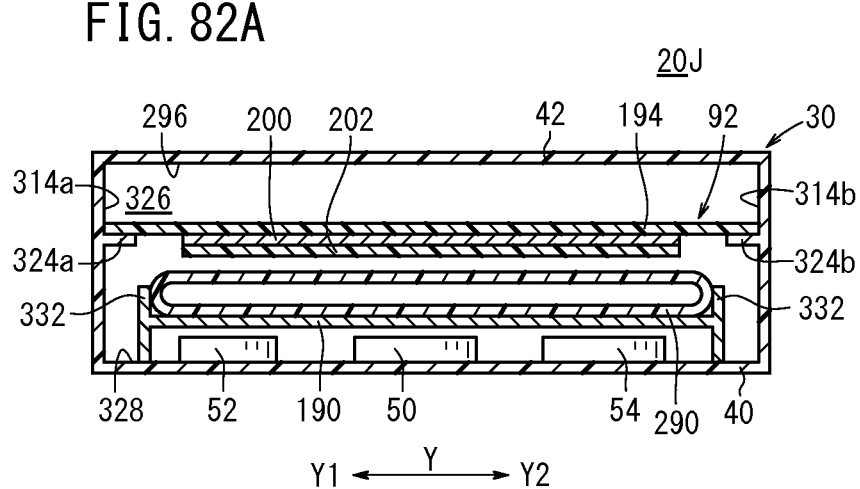
FIGS. 82A and 82B are cross-sectional views of a cassette according to a nineteenth modification.
Figure 82B:
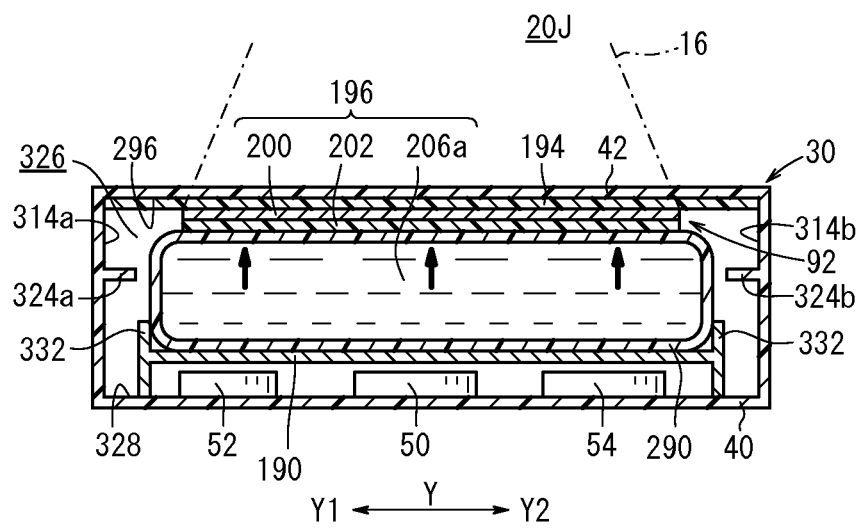
Figure 83A:
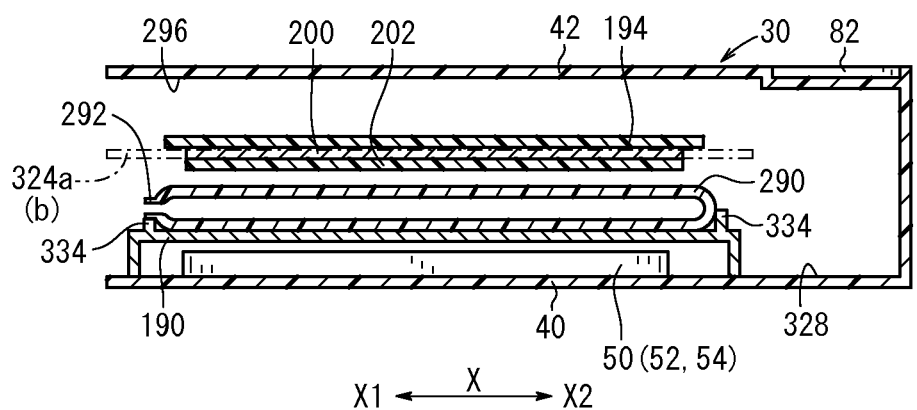
FIGS. 83A and 83B are cross-sectional views of a cassette according to a nineteenth modification.
Figure 83B:
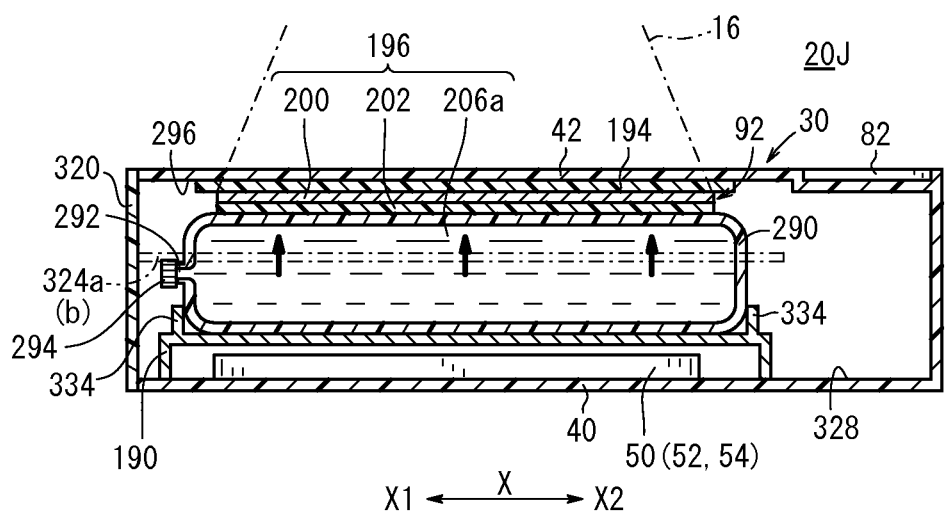

As schematically shown in FIGS. 81A and 81B, in the electronic cassette 20J according to the eighteenth modification, the image capturing surface 42 has a central area curved downwardly concavely or convexly at times that the radiation conversion panel 92 is not pressed by the pressing material housing bag 298, and the image capturing surface 42 is kept flat if the radiation conversion panel 92 is pressed against the inner wall surface 296 by the pressing material housing bag 298. Therefore, even if the casing 40 is manufactured by integral molding in such a manner that the image capturing surface 42 has a concave central area, the image capturing surface 42 can be kept flat by pressing the radiation conversion panel 92 against the inner wall surface 296 with the pressing material housing bag 298. Consequently, the above advantages can easily be achieved.

In the electronic cassette 20J according to the nineteenth modification, as shown in FIGS. 82A through 83B, the scintillator housing bag 290 (pressing mechanism), which is filled with the scintillator 206*a* in the form of a liquid (hereinafter also referred to as a "liquid scintillator 206*a*"), is placed on the upper surface of the base table 190, instead of the pressing material housing bag 298 and the solid scintillator 206*b*.

The scintillator housing bag 290 is a bag made of resin, which is permeable to visible light. The scintillator housing bag 290 expands if the bag is filled with the scintillator 206*a* through the port 292, and shrinks vertically in FIGS. 82A through 83B if the scintillator 206*a* is discharged through the port 292. The scintillator housing bag 290, which is filled with the scintillator 206*a*, is sealed by the removable cap 294, which is mounted on the port 292.

Therefore, the electronic cassette 20J according to the nineteenth modification shown in FIGS. 82A through 83B incorporates an ISS type of radiation conversion panel 92.

According to the nineteenth modification, the board 194, the signal output layer 200, and the photoelectric transducer layer 202 are securely positioned with respect to the inner wall surface 296 upon being pressed against the inner wall surface 296 by the scintillator housing bag 290, which is expanded by being filled with the liquid scintillator 206*a*. The board 194, the signal output layer 200, and the photoelectric transducer layer 202 are released from the pressed state if the liquid scintillator 206*a* is removed from the scintillator housing bag 290.

According to the nineteenth modification, the board 194, the signal output layer 200, and the photoelectric transducer layer 202 are pressed against the inner wall surface 296 upon the scintillator housing bag 290 being filled with the liquid scintillator 206*a*. Therefore, the nineteenth modification can easily provide the advantages that accrue from pressing the radiation conversion panel 92 against the inner wall surface 296, as well as the advantages that accrue from removing the liquid scintillator 206*a* from the scintillator housing bag 290 in order to release the radiation conversion panel 92.

The port 292 of the scintillator housing bag 290 is sealed by the removable cap 294. Therefore, if the liquid scintillator 206*a* becomes deteriorated as a result of being irradiated with radiation 16, the liquid scintillator 206*a* can be removed from the scintillator housing bag 290, and the scintillator housing bag 290 can be filled again with a new liquid scintillator 206*a* at a time that the electronic cassette 20J is reworked, serviced for maintenance, or repaired. Consequently, the radiation conversion panel 92 including the liquid scintillator 206*a*, which is expected to deteriorate due to aging or by way of exposure to radiation 16, can easily be replaced for facilitating reworkability and maintainability.

Figure 84A:
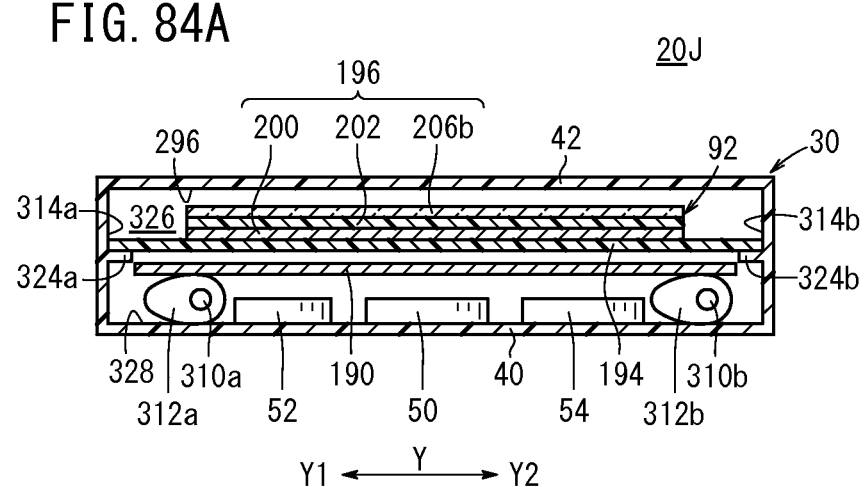
FIGS. 84A and 84B are cross-sectional views of a cassette according to a twentieth modification.
Figure 84B:
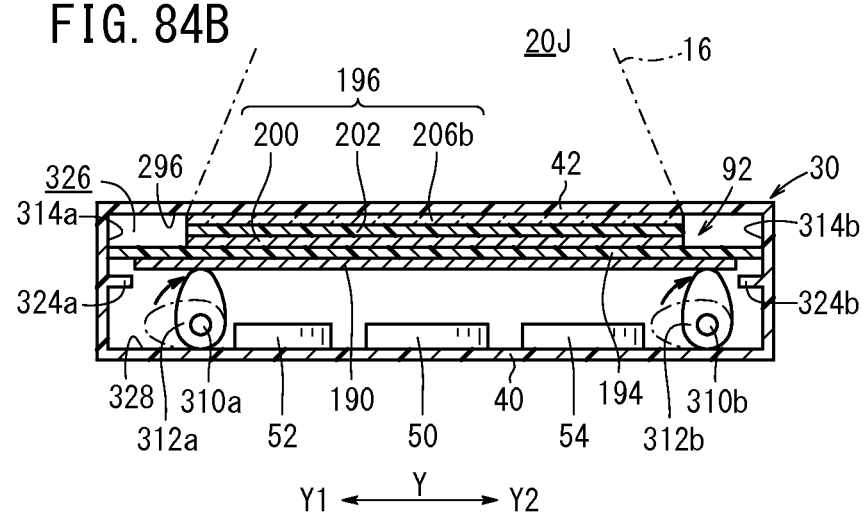

FIGS. 84A and 84B show the electronic cassette 20J according to the twentieth modification. The electronic cassette 20J according to the twentieth modification includes the disc cams 312*a*, 312*b* (pressing mechanism) disposed on the inner wall surface 328 of the casing 40, which are coupled respectively to the rotational shafts 310*a*, 310*b*. The disc cams 312*a*, 312*b* are turned about the rotational shafts 310*a*, 310*b* between the angular position shown in FIG. 84A and the angular position shown in FIG. 84B. More specifically, if a radiographic image is not being captured, the disc cams 312*a*, 312*b* are turned to space the board 194, the signal output layer 200, the photoelectric transducer layer 202, the scintillator 206*b*, and the planar base table 190 from the inner wall surface 296, as shown in FIG. 84A. If a radiographic image is captured, in step S29 of FIG. 60, the disc cams 312*a*, 312*b* are turned to press the board 194, the signal output layer 200, the photoelectric transducer layer 202, the scintillator 206*b*, and the base table 190 against the inner wall surface 296, as shown in FIG. 84B. The board 194 and the base table 190 have opposite sides thereof held in contact with the side walls 314*a*, 314*b* of the casing 40.

The rotational shafts 310*a*, 310*b* extend in directions normal to the sheet of FIGS. 84A and 84B, i.e., in the direction of the arrow X. Actually, the disc cams 312*a*, 312*b* are spaced along such directions and are coupled to the rotational shafts 310*a*, 310*b*, respectively. The disc cams 312*a*, 312*b* have a size large enough to keep the cassette controller 50, the power supply 52, and the communication unit 54 out of contact with the base table 190.

According to the twentieth modification, as described above, since the board 194, the signal output layer 200, the photoelectric transducer layer 202, the scintillator 206*b*, and the planar base table 190 are pressed together against the inner wall surface 296 beneath the image capturing surface 42 by the disc cams 312*a*, 312*b*, the board 194, the signal output layer 200, the photoelectric transducer layer 202, the scintillator 206*b*, and the base table 190 are held closely together, and the radiation conversion panel 92 and the inner wall surface 296 are closely held together by a simple structure.

Figure 85A:
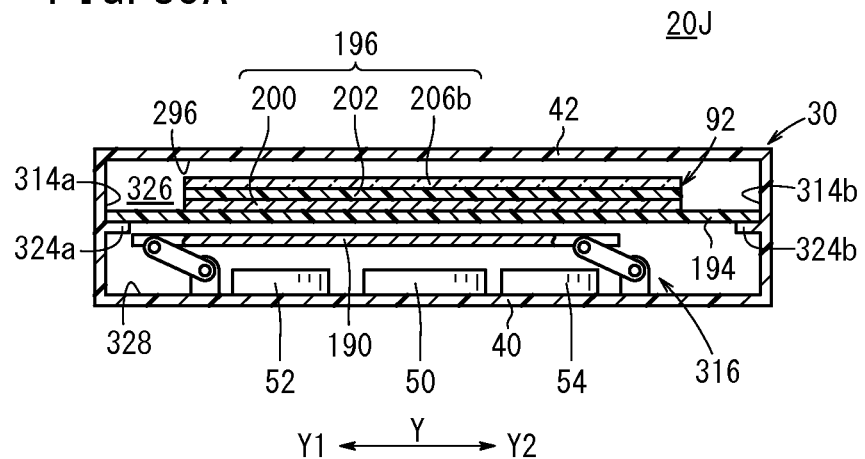
FIGS. 85A and 85B are cross-sectional views of a cassette according to a twenty-first modification.
Figure 85B:
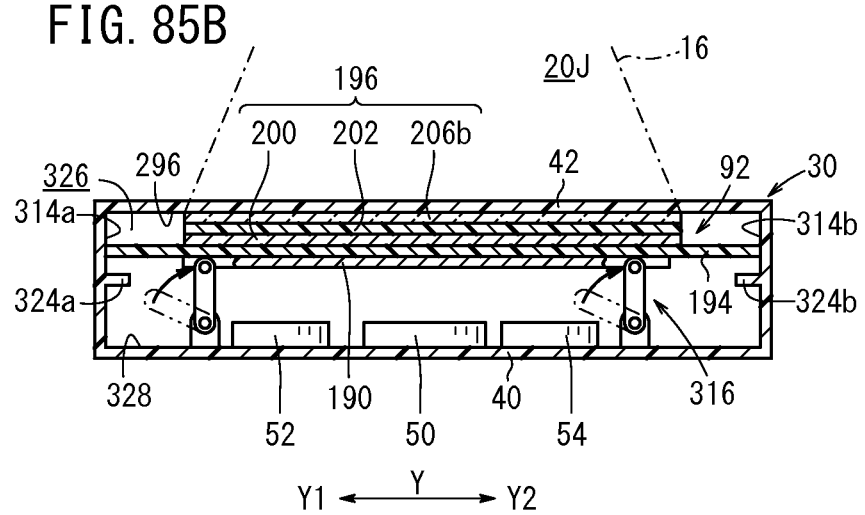
Figure 86:
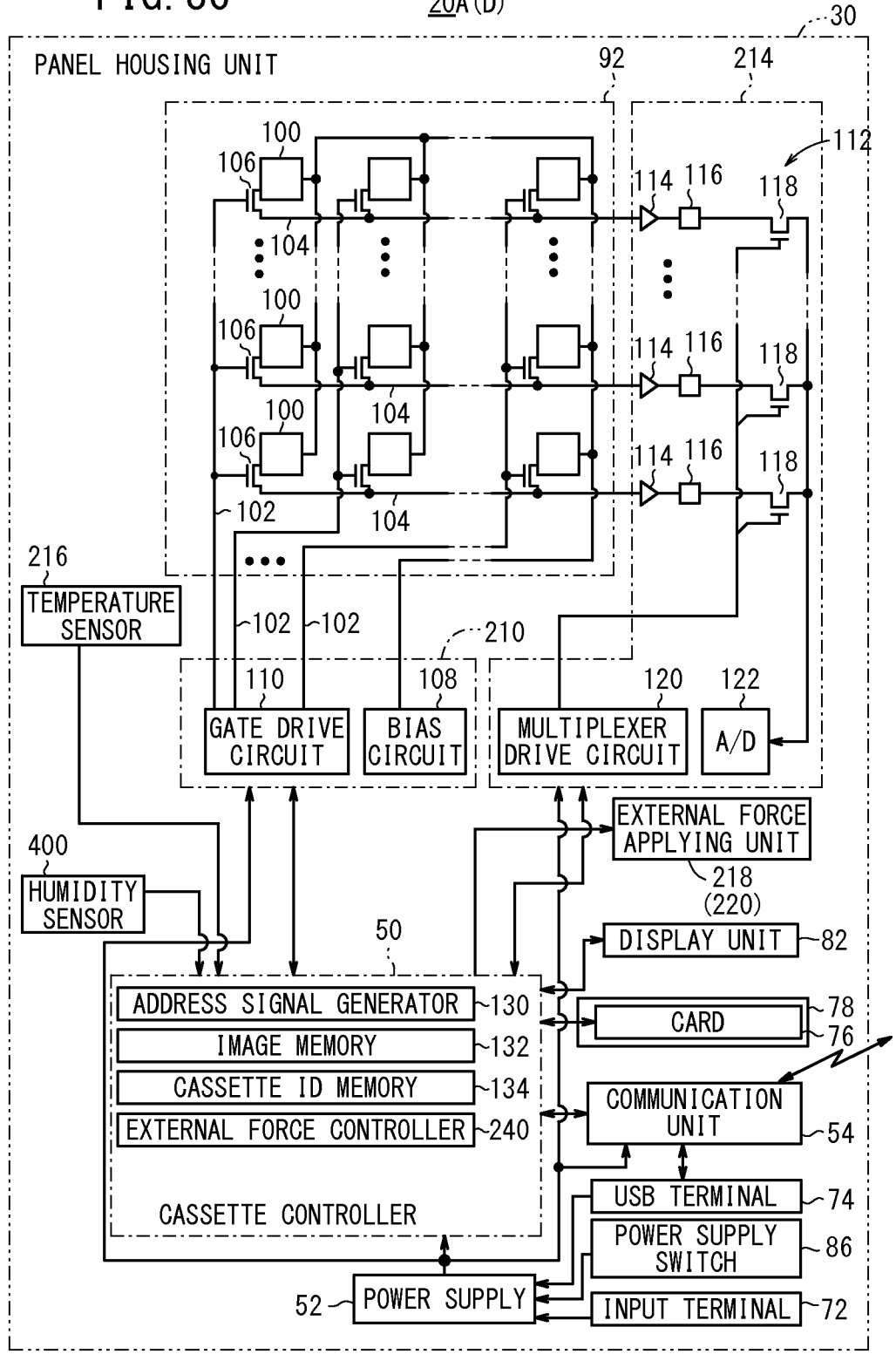
FIG. 86 is a block diagram of a modification (twenty-second modification) of the cassettes according to the first and fourth embodiments.
Figure 87:
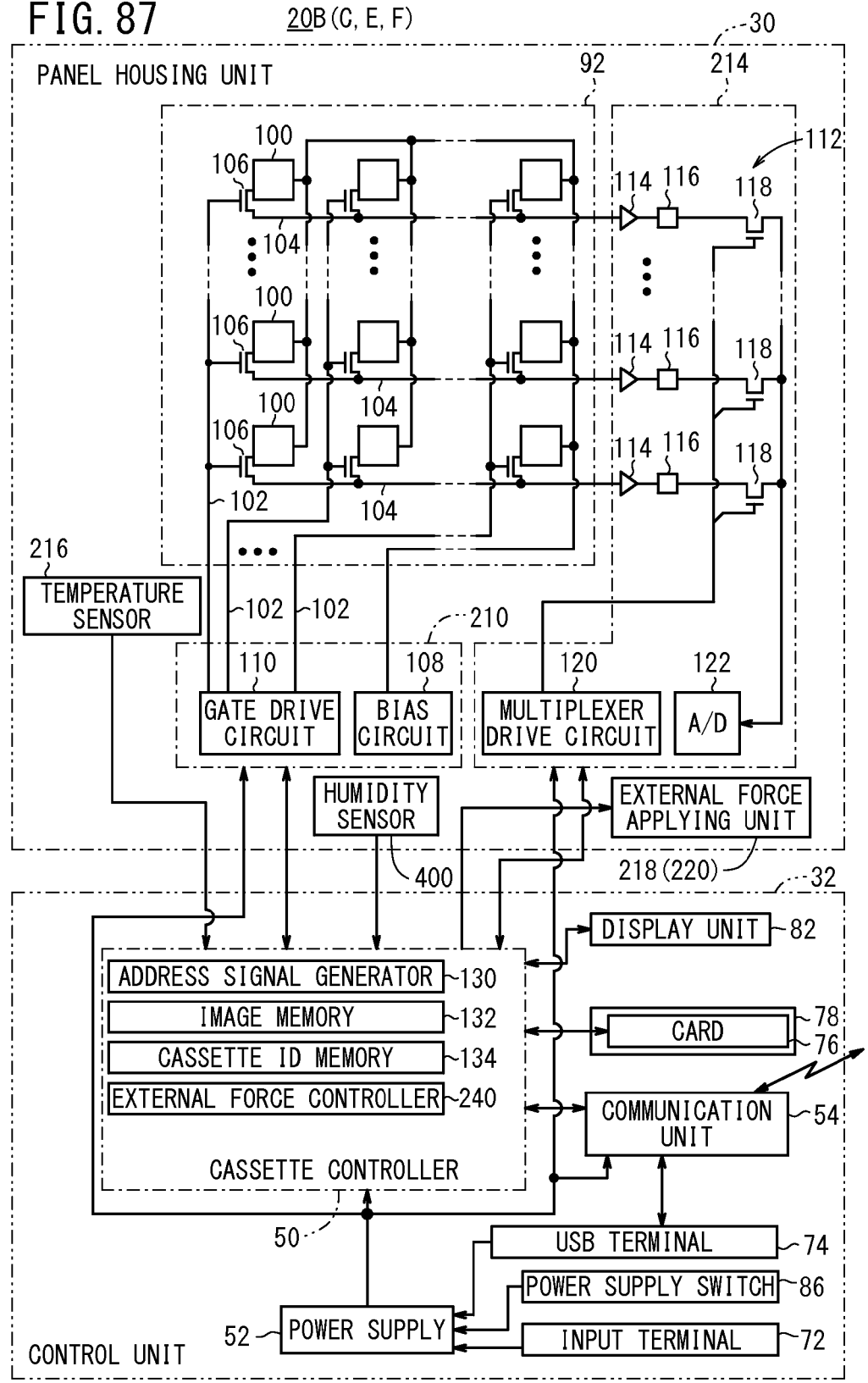
FIG. 87 is a block diagram of a modification (twenty-third modification) of the cassettes according to the second, third, fifth, and sixth embodiments.

FIGS. 85A and 85B show the electronic cassette 20J according to the twenty-first modification. The electronic cassette 20J shown in FIGS. 85A and 85B comprises the four-link mechanism 316, including the base table 190, disposed on the inner wall surface 328 of the casing 40. If a radiographic image is not being captured, the four-link mechanism 316 is actuated to space the board 194, the signal output layer 200, the photoelectric transducer layer 202, the scintillator 206*b*, and the base table 190 from the inner wall surface 296, as shown in FIG. 85A. If a radiographic image is captured, in step S29 of FIG. 60, the four-link mechanism 316 is actuated to press the board 194, the signal output layer 200, the photoelectric transducer layer 202, the scintillator 206*b*, and the base table 190 against the inner wall surface 296, as shown in FIG. 85B. The four-link mechanism 316 has a size large enough to keep the cassette controller 50, the power supply 52, and the communication unit 54 out of contact with the base table 190.

According to the twenty-first modification, as described above, since the board 194, the signal output layer 200, the photoelectric transducer layer 202, the scintillator 206*b*, and the base table 190 are pressed together against the inner wall surface 296 beneath the image capturing surface 42 by the four-link mechanism 316, the board 194, the signal output layer 200, the photoelectric transducer layer 202, the scintillator 206*b*, and the base table 190 are held closely together, and the radiation conversion panel 92 and the inner wall surface 296 are closely held together by a simple structure, similar to the case of the twentieth modification.

According to the tenth embodiment and the sixteenth through twenty-first modifications, a radiographic image capturing apparatus incorporating a radiation conversion panel 92 of an ISS or PSS type has been illustrated. However, the ISS type of radiation conversion panel 92 may be changed to a PSS type of radiation conversion panel 92, or alternatively, the PSS type of radiation conversion panel 92 may be changed to an ISS type of radiation conversion panel 92, while still achieving the advantages described above.

More specifically, the PSS type radiation conversion panel 92 according to the seventeenth, twentieth, and twenty-first modifications shown in FIGS. 79A through 80B and FIGS. 84A through 85B may be changed to an ISS type radiation conversion panel 92. According to the eighteenth modification shown in FIGS. 81A and 81B, either an ISS type or a PSS type of radiation conversion panel 92 may be employed. According to the nineteenth modification shown in FIGS. 82A through 83B, the radiation conversion panel 92 may be inverted vertically to result in a PSS type of radiation conversion panel 92, with the scintillator housing bag 290 disposed on the inner wall surface 296 thereof.

According to the tenth embodiment, the electronic cassette 20J may incorporate a radiation conversion panel 92 that includes both the scintillator housing bag 290, which is filled with the liquid scintillator 206*a*, and the solid scintillator 206*b*. The radiation conversion panel 92 may be any one of the structure (1) which is a double-sided reading type in which one scintillator is disposed on the face side of the radiation conversion panel 92 and the other scintillator is disposed on the reverse side of the radiation conversion panel 92, the structure (2) which is a PSS type in which the scintillator housing bag 290 and the solid scintillator 206*b* are disposed on the face side of the radiation conversion panel 92, and the structure (3) which is an ISS type in which the scintillator housing bag 290 and the solid scintillator 206*b* are disposed on the reverse side of the radiation conversion panel 92. If the solid scintillator 206*b* is made of CsI, then in structure (1), the scintillator 206*b* may be disposed on the face side of the radiation conversion panel 92, and the scintillator housing bag 290 may be disposed on the reverse side of the radiation conversion panel 92.

In the tenth embodiment, the electronic cassette 20J has been illustrated in which the radiation conversion panel 92 is an indirect conversion type. However, the tenth embodiment may be applied to an electronic cassette incorporating a radiation conversion panel of a direct conversion type, which directly converts the dose of radiation 16 into electric signals with a solid-state detector made of amorphous selenium (a-Se) or the like, wherein the components of the radiation conversion panel can be held closely together.

In the tenth embodiment, a negative pressure may be developed in the casing 40, i.e., the chamber 326, in order to prevent dew condensation. In such a case that a negative pressure is developed, a central area of the image capturing surface 42 may possibly become curved downwardly in a concave shape due to the pressure difference between the inside of the casing 40 and the outside of the casing 40, similar to the case of the eighteenth modification (see FIGS. 81A and 81B). However, the image capturing surface 42 is kept flat by pressing the radiation conversion panel 92 against the inner wall surface 296 by means of the pressing material housing bag 298, the scintillator housing bag 290, the disc cams 312*a*, 312*b*, or the four-link mechanism 316. Consequently, the advantages of the tenth embodiment can easily be achieved even if a negative pressure is developed in the casing 40.

12. Description of Other Modifications of the First Through Tenth Embodiments:

The electronic cassettes 20A through 20J and the radiographic image capturing systems 10A through 10J according to the first through tenth embodiments are not limited to the foregoing descriptions, but may be modified as shown in FIGS. 86 through 92B.

<Twenty-Second Through Twenty-Fifth Modifications>

FIGS. 86 through 89 show twenty-second through twenty-fifth modifications, in which the temperature sensors 216 and a humidity sensor (environmental condition detector) 400 for detecting the humidity (environmental condition) in the casing 40 are disposed in the electronic cassettes 20A through 20J. The electronic cassettes 20G through 20J also have an acceleration sensor (acceleration detector) 402 for detecting acceleration of the electronic cassettes 20G through 20J.

Figure 88:
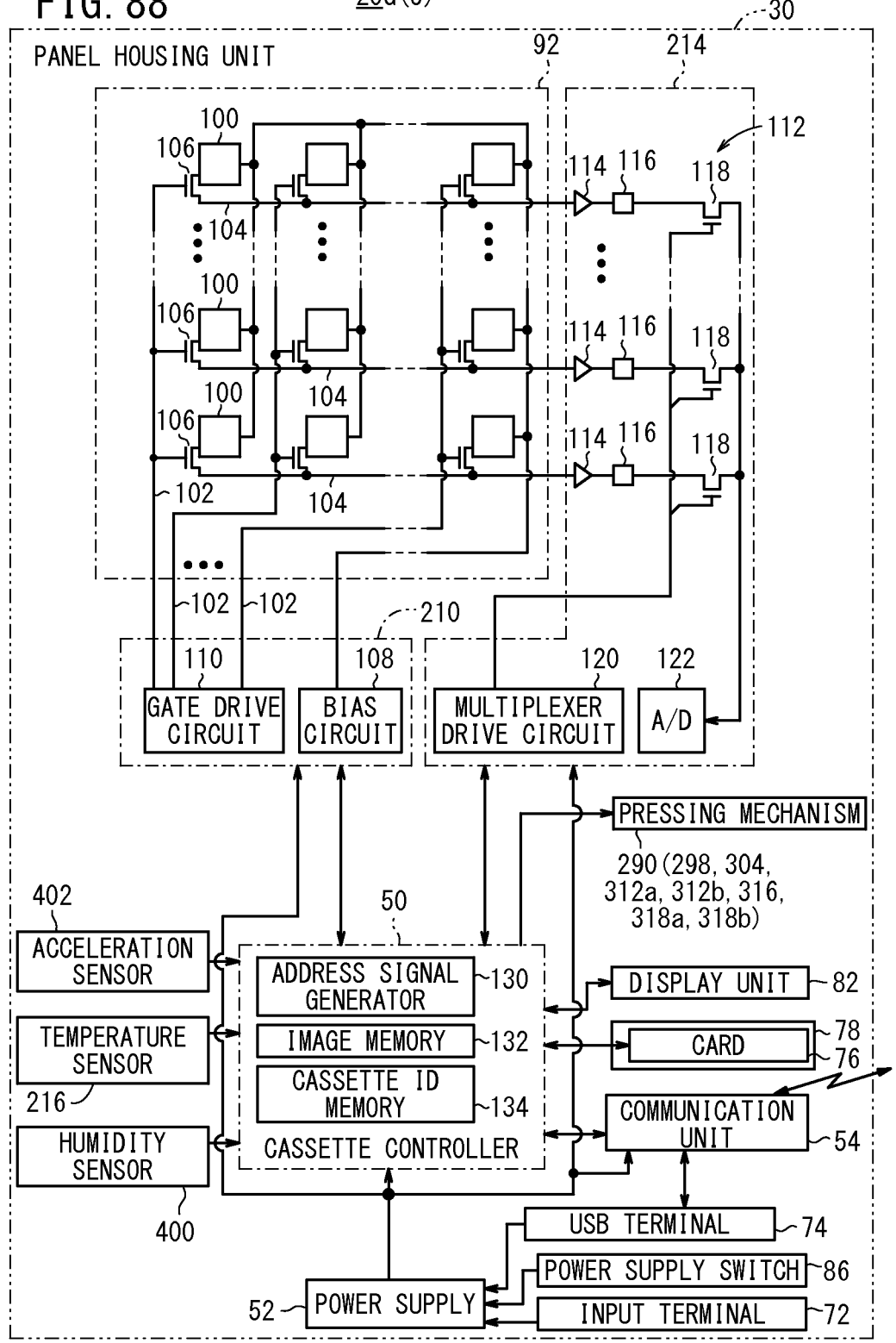
FIG. 88 is a block diagram of a modification (twenty-fourth modification) of the cassettes according to the seventh and tenth embodiments.
Figure 89:
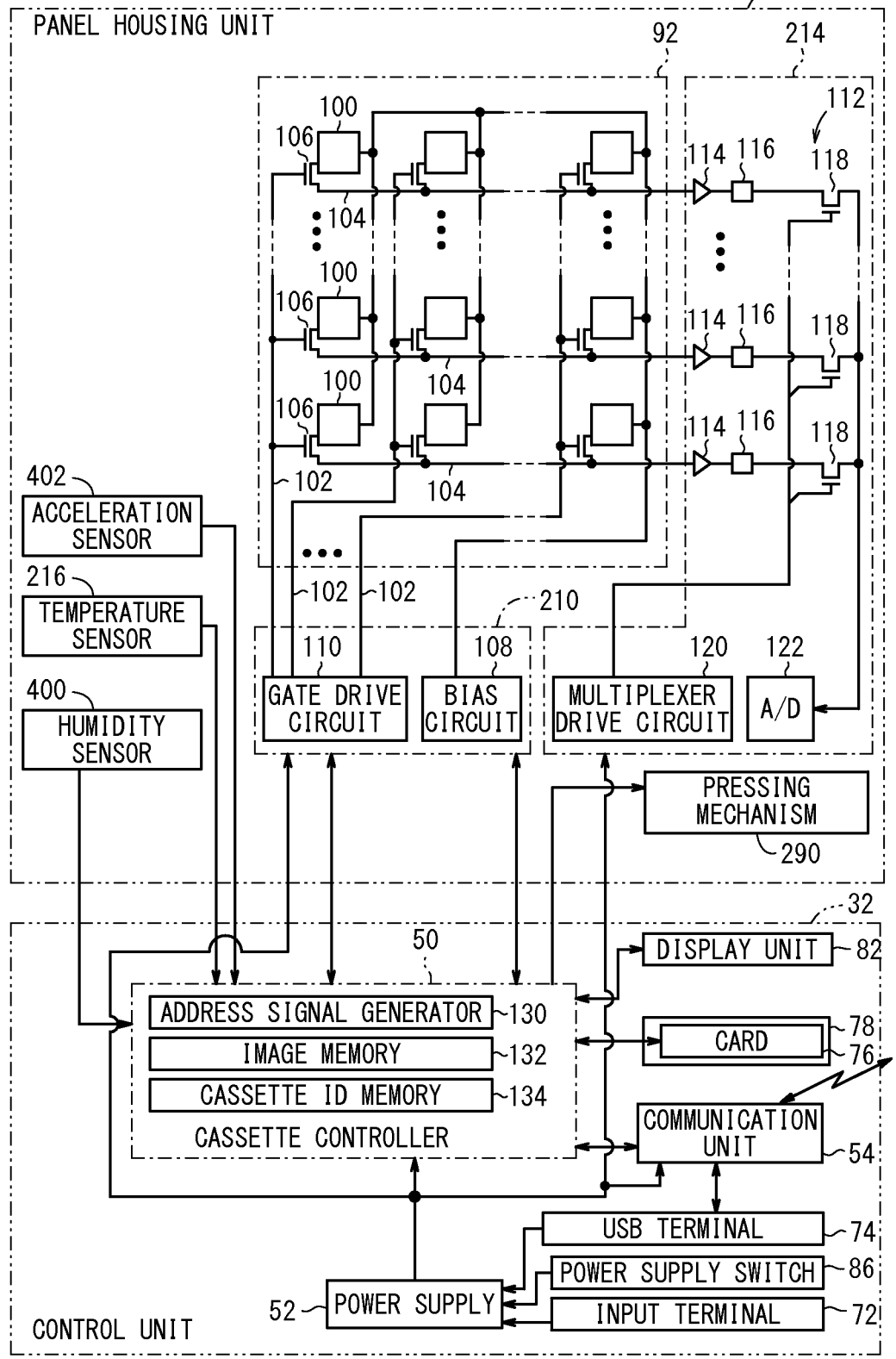
FIG. 89 is a block diagram of a modification (twenty-fifth modification) of the cassettes according to the eighth and ninth embodiments.

In FIG. 88, the pressing mechanism, which is shown in block form, is represented by the scintillator housing bag 290, the pressing material housing bag 298, 304, the disc cams 312*a*, 312*b*, the four-link mechanism 316, and the springs 318*a*, 318*b*. In FIG. 89, the pressing mechanism, which is shown in block form, is represented by the scintillator housing bag 290.

As described above, the radiation conversion panel 92, i.e., the plastic board 194, changes in shape depending on changes in temperature. Similarly, the radiation conversion panel 92, i.e., the board 194, changes in shape if the board 194 absorbs humidity.

According to the twenty-second through twenty-fifth modifications, the cassette controller 50, i.e., the external force controller 240, controls the external force applying units 218, 220, the scintillator housing bag 290 that serves as a pressing mechanism, the pressing material housing bag 298, 304, the disc cams 312*a*, 312*b*, the four-link mechanism 316, and the springs 318*a*, 318*b* based on the humidity detected by the humidity sensor 400, in order to apply appropriate external forces depending on a humidity change, i.e., external forces for minimizing the amount of deformation of the board 194 caused by changes in humidity, to the radiation conversion panel 92, i.e., the board 194 or the peripheral edges 230. The action of applying external forces, or the action of pressing the radiation conversion panel 92, i.e., the board 194 or the peripheral edges 230, has already been described above in connection with the first through tenth embodiments, and thus this feature will not be described in detail below.

By thus detecting the humidity as the environmental condition in the casing 40 and applying appropriate external forces to the radiation conversion panel 92 depending on a humidity change, it is possible to achieve the various advantages including the advantage of keeping the radiation conversion panel 92 flat, in the same manner as the advantage of preventing the radiation conversion panel 92 from changing in shape due to a temperature change thereof, as described in the first through tenth embodiments.

As shown in FIGS. 86 through 89, the temperature sensors 216 are combined, and appropriate external forces are applied to the radiation conversion panel 92 depending on a temperature change and a humidity change based on the temperature detected by the temperature sensors 216 and the humidity detected by the humidity sensor 400. Since the radiation conversion panel 92 is prevented from being changed in shape depending on the temperature change and the humidity change, planarity of the radiation conversion panel 92 is effectively maintained.

According to the twenty-fourth modification shown in FIG. 24 and the twenty-fifth modification shown in FIG. 25, the acceleration sensor 402 detects an acceleration of the electronic cassettes 20G through 20J. If the acceleration detected by the acceleration sensor 402 exceeds a predetermined acceleration (threshold value) due to falling of the electronic cassettes 20G through 20J, or an acceleration (threshold value) caused by shocks to the electronic cassettes 20G through 20J from an external source, then the cassette controller 50 controls the scintillator housing bag 290, the pressing material housing bags 298, 304, the disc cams 312a, 312b, the four-link mechanism 316, or the springs 318a, 318b in order to release the radiation conversion panel 92 from the inner wall surface 296.

FIGS. 90A through 91B schematically show the radiation conversion panel 92, which is pressed against the inner wall surface 296, and the radiation conversion panel 92, which is released from the inner wall surface 296.

Figure 90A:
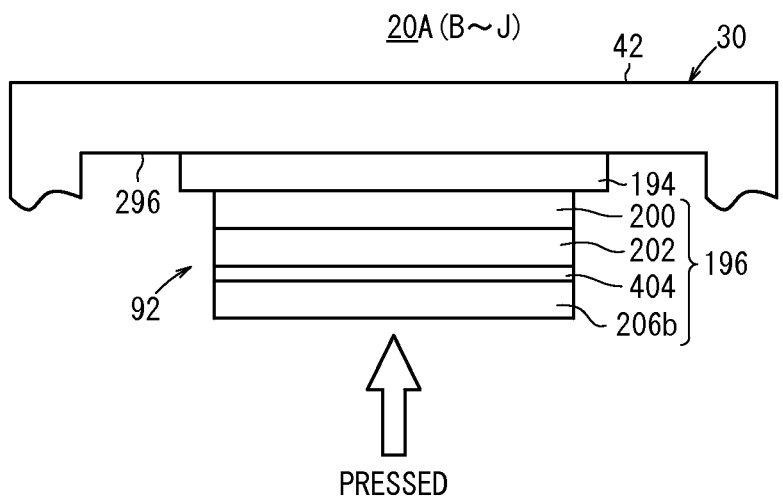
FIG. 90A is a view schematically showing the manner in which a radiation conversion panel, as an integrally stacked assembly made up of a photoelectric transducer layer, a scintillator, etc., is pressed against an inner wall surface near an image capturing surface.
Figure 90B:
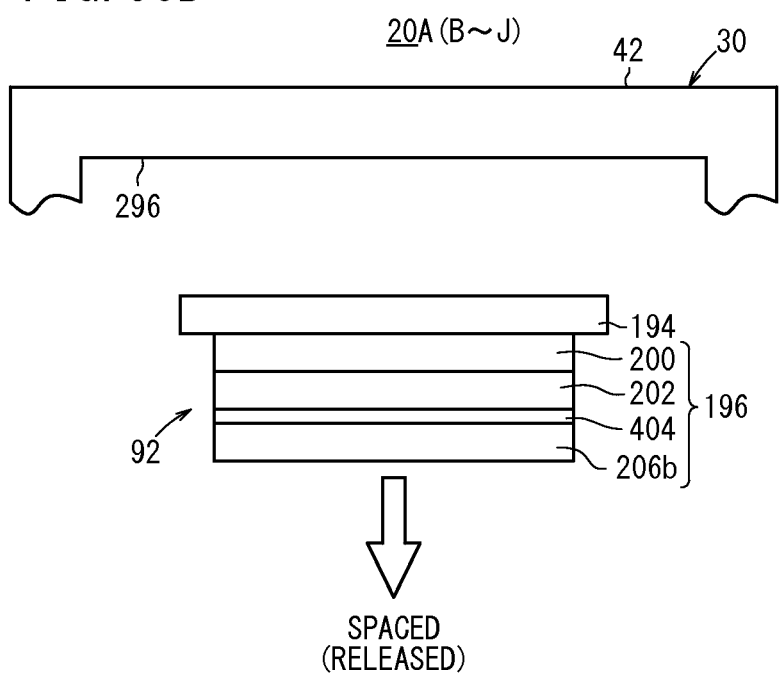
FIG. 90B is a view schematically showing the manner in which the radiation conversion panel is spaced from the inner wall surface.

FIGS. 90A and 90B show an ISS type of radiation conversion panel 92 in which the solid scintillator 206b made of columnar crystals of CsI or the like, and the photoelectric transducer layer 202 are bonded to each other by an adhesive layer 404, which is of the same material as the dismantlable adhesives 222, 232, 244, 246, 272. The signal output layer 200, the photoelectric transducer layer 202 on the board 194, and the scintillator 206b are integrally, i.e., inseparably, stacked together.

Figure 91A:
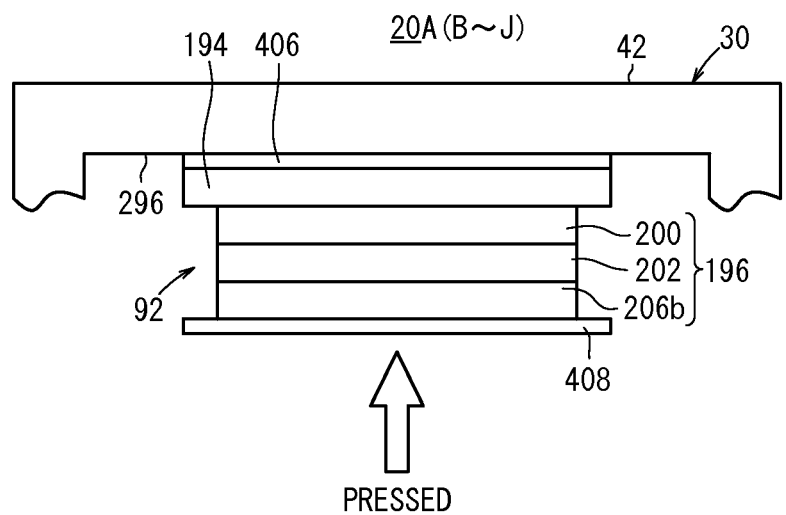
FIG. 91A is a view schematically showing the manner in which a radiation conversion panel, as a separably stacked assembly of a photoelectric transducer layer, a scintillator, etc., is pressed against an inner wall surface near an image capturing surface.
Figure 91B:
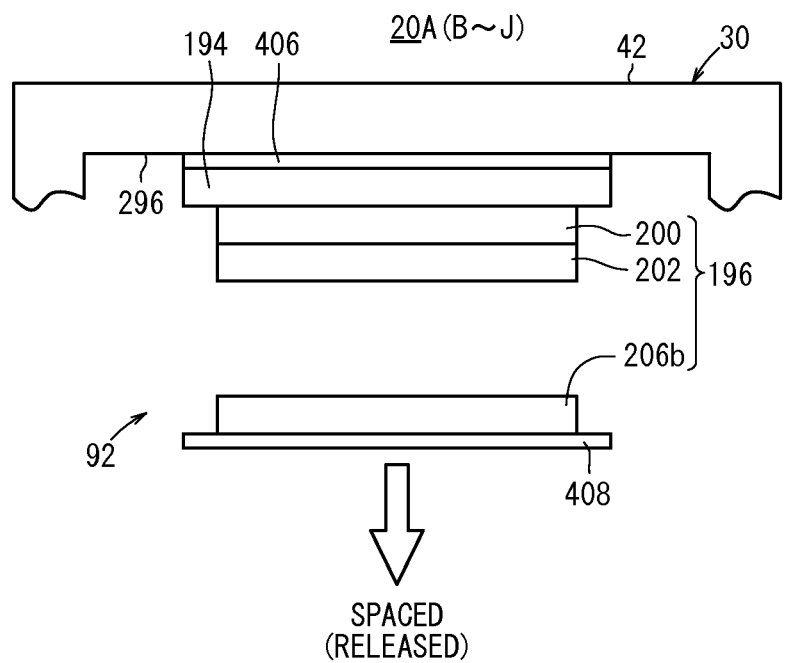
FIG. 91B is a view schematically showing the manner in which only the scintillator and a board are spaced from the inner wall surface.

FIGS. 91A and 91B show an ISS type of radiation conversion panel 92 in which the board 194, with the signal output layer 200 and the photoelectric transducer layer 202 disposed thereon, is fixed to the inner wall surface 296 by an adhesive layer 406, which is of the same material as the adhesive layer 404, so that the scintillator 206b on the support board 408 and the photoelectric transducer layer 202 are separably stacked together.

While the radiation conversion panel 92 is pressed against the inner wall surface 296 (see FIGS. 90A and 91A), if the acceleration detected by the acceleration sensor 402 exceeds the predetermined threshold due to falling of the electronic cassettes 20G through 20J or due to shocks applied thereto from an external source, then the cassette controller 50 controls the scintillator housing bag 290, the pressing material housing bag 298, 304, the disc cams 312a, 312b, the four-link mechanism 316, or the springs 318a, 318b in order to release the radiation conversion panel 92 from the inner wall surface 296.

More specifically, if the pressing material housing bags 298, 304 are used as pressing mechanisms, then the filling material is removed from the pressing material housing bags 298, 304 to allow the pressing material housing bags 298, 304 to shrink in the thickness directions thereof, thereby spacing the radiation conversion panel 92 or the scintillator 206b from the inner wall surface 296 (see FIGS. 90B and 91B).

If the disc cams 312a, 312b are used as the pressing mechanism, then the rotational shafts 310a, 310b are turned to space the radiation conversion panel 92 or the scintillator 206b from the inner wall surface 296.

If the four-link mechanism 316 is used as the pressing mechanism, then the four-link mechanism 316 is actuated to space the radiation conversion panel 92 or the scintillator 206b from the inner wall surface 296.

If the springs 318a, 318b are used as the pressing mechanism, then a moving mechanism, not shown, is actuated to displace the radiation conversion panel 92 or the scintillator 206b away from the inner wall surface 296 in opposition to the resiliency of the springs 318a, 318b.

By releasing the radiation conversion panel 92 from being pressed against the inner wall surface 296 based on the acceleration of the electronic cassettes 20G through 20J, the radiation conversion panel 92, i.e., the scintillator 206b and the photoelectric transducer layer 202, etc., is prevented from being damaged by shocks or by falling of the electronic cassettes 20G through 20J. In a case where the radiation conversion panel 92, the scintillator 206b, the photoelectric transducer layer 202, and the casing 40 need to be replaced, the radiation conversion panel 92 is released from the inner wall surface 296, thereby allowing such components to be replaced with ease.

In FIGS. 90A through 91B, the radiation conversion panel 92 is pressed against the inner wall surface 296, and the radiation conversion panel 92 or the scintillator 206b is released from the inner wall surface 296 based on the acceleration of the electronic cassettes 20G through 20J. However, the radiation conversion panel 92 may be pressed against the inner wall surface 296, and the radiation conversion panel 92 or the scintillator 206b may be released from the inner wall surface 296 based on at least one of the temperature of the radiation conversion panel 92 and the humidity in the casing 40.

In FIGS. 90A through 91B, an ISS type of radiation conversion panel 92 is illustrated. However, a PSS type of radiation conversion panel 92 offers the same advantages by releasing the radiation conversion panel 92 from being pressed against the inner wall surface 296.

A solid scintillator 206b has been described above. However, if the radiation conversion panel 92 incorporates the liquid scintillator 206a, then the liquid scintillator 206a may be removed from the scintillator housing bag 290 in order to allow the scintillator housing bag 290 to shrink in the thicknesswise direction, thereby releasing the radiation conversion panel 92 from being pressed against the inner wall surface 296. Therefore, the radiation conversion panel 92, which incorporates the liquid scintillator 206a, offers the same advantages as the aforementioned other pressing mechanisms.

<Twenty-Sixth Modification>

Figure 92A:
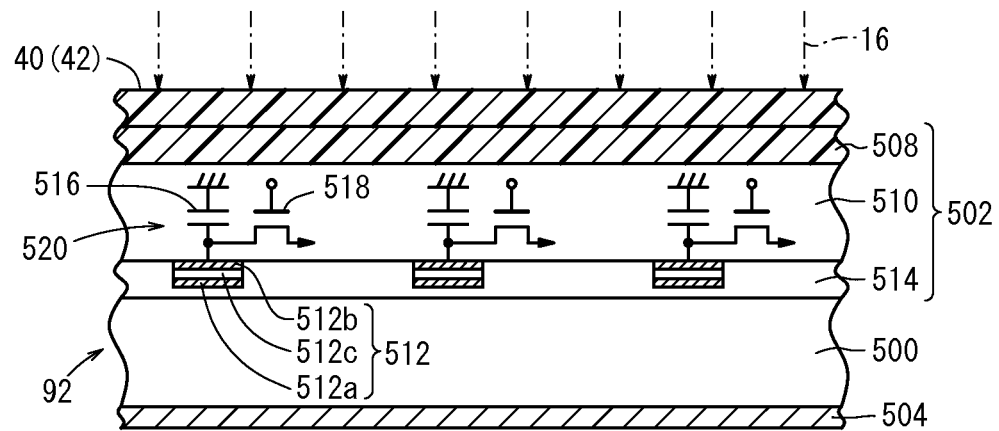
FIG. 92A is a fragmentary cross-sectional view schematically showing an internal arrangement of a cassette according to a twenty-sixth modification.
Figure 92B:
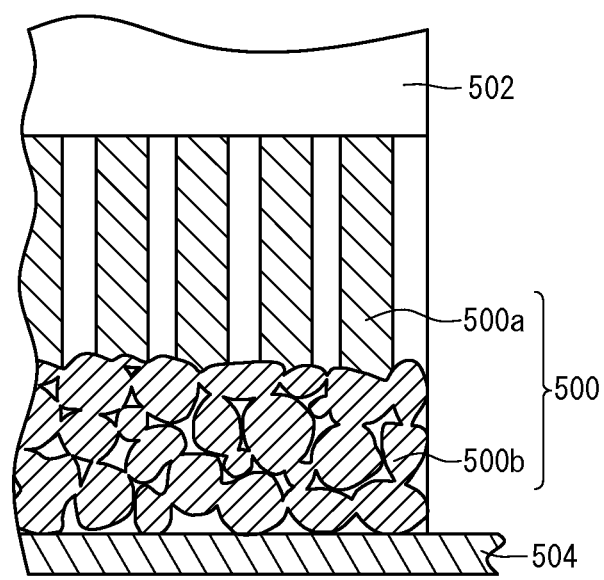
FIG. 92B is a fragmentary cross-sectional view schematically showing an example of a scintillator shown in FIG. 92A.

The radiation conversion panel 92 according to the first through tenth embodiments may be modified according to a twenty-sixth modification, as shown in FIGS. 92A and 92B. Specific structural details according to the twenty-sixth modification of the radiation conversion panel 92, which incorporates the scintillator of CsI according to the first through tenth embodiments, will be described below.

According to the twenty-sixth modification shown in FIGS. 92A and 92B, the radiation conversion panel 92 includes a scintillator 500 for converting radiation 16 that has passed through the subject 14 into visible light, i.e., absorbing radiation 16 and emitting visible light, and a radiation detector 502 for converting the visible light from the scintillator 500 into electric signals, i.e., electric charges, representative of a radiographic image. The scintillator 500 corresponds to the scintillators 206, 206a, 206b described above, and the radiation detector 502 corresponds to the signal output layer 200 and the photoelectric transducer layer 202. In FIGS. 92A and 92B, the protective film 198 is omitted from illustration.

As described above, as shown in FIGS. 92A and 92B, the radiation conversion panel 92 may comprise an ISS type of radiation conversion panel 92, in which the radiation detector 502 and the scintillator 500 are successively arranged in this order from the image capturing surface 42 that is irradiated with radiation 16, and a PSS type of radiation conversion panel 92, in which the scintillator 500 and the radiation detector 502 are successively arranged in this order from the image capturing surface 42. The scintillator 500 emits stronger light from the side thereof closer to the image capturing surface 42 that is irradiated with radiation 16. Since in an ISS type, the scintillator 500 is positioned closer to the image capturing surface 42 than in a PSS type, an ISS type of radiation conversion panel 92 produces a radiographic image of higher resolution, and the radiation detector 502 thereof detects a greater amount of visible light from the scintillator 500. Accordingly, an ISS type of radiation conversion panel 92, i.e., any of the electronic cassettes 20A through 20J, is more sensitive than a PSS type of radiation conversion panel 92.

The scintillator 500 may be made of a material such as CsI:Tl (thallium-added cesium iodide), CsI:Na (sodium-activated cesium iodide), GOS($Gd_2O_2S$:Tb), or the like.

FIG. 92B shows the scintillator 500 including a columnar crystal region, which is produced by evaporating a material containing CsI on an evaporation board 504.

More specifically, the scintillator 500 shown in FIG. 92B includes a columnar crystal region, which is made up of columnar crystals 500a, disposed in close proximity to the image capturing surface 42, i.e., the radiation detector 502 that is irradiated with radiation 16, and a non-columnar crystal region, which is made up of non-columnar crystals 500b remote from the image capturing surface 42. The evaporation board 504 preferably is made of a highly heat-resistant material, e.g., aluminum (Al), which is low in cost. The columnar crystals 500a in the scintillator 500 have a substantially uniform average diameter along the longitudinal direction of the columnar crystals 500a.

As described above, the scintillator 500 includes the columnar crystal region, i.e., the columnar crystals 500a, and the non-columnar crystal region, i.e., the non-columnar crystals 500b. The columnar crystal region of the columnar crystals 500a, which are capable of highly efficient light emission, is disposed in close proximity to the radiation detector 502. Therefore, visible light emitted by the scintillator 500 travels through the columnar crystals 500a to the radiation detector 502. As a result, visible light emitted toward the radiation detector 502 is prevented from spreading, so that the radiographic image detected by the electronic cassettes 20A through 20J can be prevented from blurring. Since visible light that reaches a deep region of the scintillator 500, i.e., the non-columnar crystal region, is reflected toward the radiation detector 502 by the non-columnar crystals 500b, the amount of visible light applied to the radiation detector 502, i.e., the efficiency at which visible light emitted by the scintillator 500 is detected, can be increased.

If it is assumed that the columnar crystal region of the scintillator 500, which is positioned closely to the image capturing surface 42, has a thickness t1, and the non-columnar crystal region of the scintillator 500, which is positioned closely to the evaporation board 504, has a thickness t2, then the thicknesses t1 and t2 preferably satisfies the relationship $0.01 \leq (t2/t1) \leq 0.25$.

If the thickness t1 of the columnar crystal region and the thickness t2 of the non-columnar crystal region satisfy the above relationship, the ratio of the columnar crystal region, which exhibits high light emission efficiency and prevents visible light from spreading, and the non-columnar crystal region, which reflects visible light, along the thicknesswise direction of the scintillator 500 falls within an appropriate range, so as to increase the light emission efficiency of the scintillator 500, the efficiency at which visible light emitted by the scintillator 500 is detected, and the resolution of the detected radiographic image.

If the thickness t2 of the non-columnar crystal region is too large, then a region of low light emission efficiency increases, resulting in a reduction in the sensitivity of the electronic cassettes 20A through 20J. The ratio (t2/t1) preferably is in a range from 0.02 to 0.1.

The scintillator 500 described above includes the columnar crystal region and the non-columnar crystal region, which are arranged successively. The non-columnar crystal region may be replaced with a light reflecting layer made of Al or the like, in which case, only the columnar crystal region is included. Alternatively, the scintillator 500 may be of a different structure.

The radiation detector 502 serves to detect visible light emitted from the light emitting side, i.e., the columnar crystals 500a, of the scintillator 500. In side elevation, as shown in FIG. 92A, the radiation detector 502 includes an insulative substrate 508, a TFT layer 510, and a plurality of photoelectric transducers 512, which are successively deposited on the image capturing surface 42 along the direction in which radiation 16 is applied. A planarization layer 514 is disposed on the bottom surface of the TFT layer 510 in covering relation to the photoelectric transducers 512. The photoelectric transducers 512 correspond to the aforementioned photoelectric transducer layer 202, and the TFT layer 510 corresponds to the aforementioned signal output layer 200.

The radiation detector 502 is constructed as a TFT active matrix board (hereinafter referred to as a "TFT board") comprising a matrix of pixels 520 on the insulative substrate 508. Each of the pixels 520 includes a photoelectric transducer 512 such as a photodiode (PD) or the like, a storage capacitor 516, and a TFT 518.

The TFTs 518 correspond to the aforementioned TFTs 106, and the photoelectric transducers 512 and the storage capacitors 516 correspond to the pixels 100.

The photoelectric transducer 512 comprises a lower electrode 512a in close proximity to the scintillator 500, an upper electrode 512b in close proximity to the TFT layer 510, and a photoelectric conversion film 512c, which is disposed between the lower electrode 512a and the upper electrode 512b. The photoelectric conversion film 512c absorbs visible light emitted from the scintillator 500 and generates electric charges depending on the absorbed visible light.

Since the lower electrode 512a must allow visible light emitted from the scintillator 500 to be applied to the photoelectric conversion film 512c, the lower electrode 512a preferably is made of an electrically conductive material, which is transparent at least to the wavelength of visible light emitted from the scintillator 500. More specifically, the lower electrode 512a preferably is made of a transparent conducting oxide (TCO), the transmittance of which is high with respect to visible light, and the resistance of which is low.

The lower electrode 512a may be in the form of a thin metal film made of Au or the like. However, TCO is preferable because such a thin metal film tends to exhibit increased resistance if the thin metal film is required to have a light transmittance of 90% or higher. For example, the lower electrode 512a preferably is made of ITO (Indium Tin Oxide), IZO (Indium Zinc Oxide), AZO (Aluminum-doped Zinc Oxide), FTO (Fluorine-doped Tin Oxide), $SnO_2$, $TiO_2$, $ZnO_2$, or the like. Among these oxides, ITO is most preferable in view of processing simplicity, low resistance, and transparency. The lower electrode 512a may be in the form of either a single electrode, which is shared by all of the pixels 520, or a plurality of divided electrodes, which are assigned respectively to each of the pixels 520.

The photoelectric conversion film 512c may be made of a material that absorbs visible light and generates electric charges from absorbed visible light. For example, the photoelectric conversion film 512c may be made of amorphous silicon (a-Si), an organic photoconductor (OPC) material, or the like. If the photoelectric conversion film 512c is made of amorphous silicon, then the photoelectric conversion film 512c can absorb visible light emitted from the scintillator 500 in a wide range of wavelengths. However, since an evaporation process needs to be carried out in order to fabricate the photoelectric conversion film 512c from amorphous silicon, heat resistance of the insulative substrate 508 has to be taken into account if the insulative substrate 508 is made of a synthetic resin.

If the photoelectric conversion film 512c is made of a material containing an organic photoconductor material, then since the photoelectric conversion film 512c exhibits an absorption spectrum with high absorption in the visible light range, the photoelectric conversion film 512c absorbs almost no electromagnetic waves apart from visible light emitted from the scintillator 500. As a result, the photoelectric conversion film 512c generates almost no noise upon absorption of radiation 16, which may be X-rays, γ-rays, or the like.

A photoelectric conversion film 512c made of an organic photoconductor material can be fabricated by depositing the organic photoconductor material on a target using a liquid droplet propulsion head such as an ink jet head or the like. Therefore, the target is not required to be resistant to heat. According to the twenty-sixth modification, the photoelectric conversion film 512c is made of an organic photoconductor material.

If the photoelectric conversion film 512c is made of an organic photoconductor material, then since the photoelectric conversion film 512c absorbs almost no radiation 16, attenuation of radiation 16 that passes through the radiation detector 502 is minimized in an ISS type of radiation conversion panel 92, in which the radiation detector 502 is positioned to allow radiation 16 to pass therethrough. Therefore, sensitivity of the radiation conversion panel 92 with respect to radiation 16 is prevented from being reduced. The photoelectric conversion film 512c, which is made of an organic photoconductor material, is particularly preferable in an ISS type of radiation conversion panel 92.

The organic photoconductor material of the photoelectric conversion film 512c preferably has an absorption peak wavelength, which is as close as possible to the peak wavelength of visible light emitted from the scintillator 500, in order to efficiently absorb visible light emitted from the scintillator 500. Although the absorption peak wavelength of the organic photoconductor material and the peak wavelength of visible light emitted from the scintillator 500 should ideally be equal to each other, if the difference between the peak wavelengths is small enough, the organic photoconductor material is sufficiently effective at absorbing visible light emitted from the scintillator 500. More specifically, the difference between the absorption peak wavelength of the organic photoconductor material and the peak wavelength of visible light emitted from the scintillator 500 preferably is 10 nm or smaller, and more preferably, is 5 nm or smaller.

Organic photoconductor materials satisfying the above requirements include quinacridone-based organic compounds and phthalocyanine-based organic compounds, for example. Since quinacridone has an absorption peak wavelength of 560 nm in the visible range, if quinacridone is used as the organic photoconductor material and CsI:T1 is used as the material of the scintillator 500, then the difference between the above peak wavelengths can be reduced to 5 nm or smaller, thereby making it possible to substantially maximize the quantity of electric charges generated in the photoelectric conversion film 512c.

The photoelectric conversion film 512c, which is applicable to the radiation conversion panel 92, will be described in specific detail below.

The radiation conversion panel 92 includes an electromagnetic wave absorption/photoelectric conversion region provided by an organic layer including the upper and lower electrodes 512b, 512a, and the photoelectric conversion film 512c sandwiched between the upper and lower electrodes 512b, 512a. The organic layer may be formed by superposition or mixture of an electromagnetic wave absorption region, a photoelectric conversion region, an electron transport region, a hole transport region, an electron blocking region, a hole blocking region, a crystallization preventing region, an electrode, and an interlayer contact improving region, etc.

The organic layer preferably includes an organic p-type compound or an organic n-type compound. An organic p-type semiconductor (compound) is a donor organic compound, which is mainly typified by a hole transport organic compound, and refers to an organic compound that tends to donate electrons. More specifically, in a case where two organic materials are used in contact with each other, one of the organic materials, which has a lower ionization potential, is referred to as a donor organic compound. Any organic compounds capable of donating electrons can be used as a donor organic compound. An organic n-type semiconductor (compound) is an acceptor organic compound, which is mainly typified by an electron transport organic compound, and refers to an organic compound that tends to accept electrons. More specifically, in a case where two organic materials are used in contact with each other, one of the organic materials, which has a larger electron affinity, is referred to as an acceptor organic compound. Any organic compounds capable of accepting electrons can be used as an acceptor organic compound.

Materials that can be used as the organic p-type semiconductor and the organic n-type semiconductor, and arrangements of the photoelectric conversion film 512c are disclosed in detail in Japanese Laid-Open Patent Publication No. 2009-032854, and such features will not be described in detail below.

Each of the photoelectric transducers 512 may include at least the upper electrode 512b, the lower electrode 512a, and the photoelectric conversion film 512c. In addition, for preventing dark current from increasing, each of the photoelectric transducers 512 preferably includes either an electron blocking film or a hole blocking film, and more preferably, includes both the electron blocking film and the hole blocking film.

The electron blocking film may be disposed between the upper electrode 512b and the photoelectric conversion film 512c. If a bias voltage is applied between the upper electrode 512b and the lower electrode 512a, the electron blocking film can prevent electrons from being injected from the upper electrode 512b into the photoelectric conversion film 512c, thereby preventing dark current from increasing. The electron blocking film may be made of an organic material, which is capable of donating electrons. The electron blocking film actually is made of a material, which is selected depending on the material of the electrode and the material of the photoelectric conversion film 512c, which lie adjacent to the electron blocking film. Preferable materials should have an electron affinity (Ea) that is at least 1.3 eV greater than the work function (Wf) of the material of the adjacent electrode, and an ionization potential (Ip) equal to or smaller than the Ip of the material of the adjacent photoelectric conversion film 512c. Materials that can be used as an organic material capable of donating electrons are disclosed in detail in Japanese Laid-Open Patent Publication No. 2009-032854, and such materials will not be described in detail below.

The thickness of the electron blocking film preferably is in the range from 10 nm to 200 nm, more preferably, is in the range from 30 nm to 150 nm, and particularly preferably, is in the range from 50 nm to 100 nm, in order to reliably achieve a dark current reducing capability and to prevent the photoelectric conversion efficiency of the photoelectric transducer 512 from being lowered.

The hole blocking film may be disposed between the photoelectric conversion film 512c and the lower electrode 512a. If a bias voltage is applied between the upper electrode 512b and the lower electrode 512a, the hole blocking film can prevent holes from being injected from the lower electrode 512a into the photoelectric conversion film 512c, thereby preventing dark current from increasing. The hole blocking film may be made of an organic material, which is capable of accepting electrons. The hole blocking film actually is made of a material that is selected depending on the material of the electrode and the material of the photoelectric conversion film 512c, which are disposed adjacent to the hole blocking film. Preferably, the hole blocking film material has an ionization potential (Ip) that is at least 1.3 eV greater than the work function (Wf) of the material of the adjacent electrode, and an electron affinity (Ea) equal to or greater than the Ea of the material of the adjacent photoelectric conversion film 512c. Materials capable of being used as an organic material and which can accept electrons are disclosed in detail in Japanese Laid-Open Patent Publication No. 2009-032854, and such materials will not be described in detail below.

The thickness of the hole blocking film preferably is in the range from 10 nm to 200 nm, more preferably, is in the range from 30 nm to 150 nm, and particularly preferably, is in the range from 50 nm to 100 nm, in order to reliably achieve a dark current reducing capability and to prevent the photoelectric conversion efficiency of the photoelectric transducer 512 from being lowered.

The electron blocking film and the hole blocking layer may be switched in position in order to set a bias voltage to move the holes, from among the electric charges generated in the photoelectric conversion film 512c, toward the lower electrode 512a, and to move the electrons, from among the electric charges generated in the photoelectric conversion film 512c, toward the upper electrode 512b. Both the electron blocking film and the hole blocking layer may not be required, in which case, either one may be included in order to ensure a certain dark current reducing capability.

Each of the TFTs 518 in the TFT layer 510 includes a stacked assembly made up of a gate electrode, a gate insulating film, and an active layer (channel layer). A source electrode and a drain electrode are disposed on the active layer and are spaced from each other by a gap. The active layer may be made of any one of amorphous oxide, an organic semiconductor material, carbon nanotubes, etc., although the active layer is not limited to such materials.

The amorphous oxide, which the active layer may be made of, preferably is an oxide (e.g., In—O oxide) including at least one of In, Ga, and Zn, more preferably, is an oxide (e.g., In—Zn—O oxide, In—Ga—O oxide, or Ga—Zn—O oxide) including at least two of In, Ga, and Zn, and particularly preferably, is an oxide including In, Ga, and Zn. An In—Ga—Zn—O amorphous oxide preferably is an amorphous oxide, the crystalline composition of which is represented by $InGaO_3(ZnO)_m$, where m represents a natural number smaller than 6. Particularly preferably, the In—Ga—Zn—O amorphous oxide is $InGaZnO_4$. However, the amorphous oxide, which the active layer may be made of, is not limited to such oxides.

The organic semiconductor material, which the active layer may be made of, preferably is a phthalocyanine compound, pentacene, vanadyl phthalocyanine, or the like, although the organic semiconductor material is not limited to these compositions. A composition made of a phthalocyanine compound is disclosed in detail in Japanese Laid-Open Patent Publication No. 2009-212389, and will not be described in detail below.

If the active layer of the TFTs 518 is made of any one of an amorphous oxide, an organic semiconductor material, and carbon nanotubes, then since the active layer does not absorb radiation 16 such as X-rays or the like, or only absorbs an extremely small amount of such radiation 16, the active layer is effective at reducing noise generated in the radiation detector 502.

If the active layer is made of carbon nanotubes, then the TFTs 518 can have a high switching speed and exhibit a low absorption rate for light in the visible range. If the active layer is made of carbon nanotubes, then since the performance of the TFTs 518 could be degraded significantly by trace metal impurities mixed therewith, it is necessary to separate and extract highly pure carbon nanotubes by a centrifugal separator or the like, and to use such separated and extracted highly pure carbon nanotubes to make the active layer.

Since a film made of an organic photoconductor material and a film made of an organic semiconductor material are sufficiently flexible, the combination of the photoelectric conversion film 512c, which is made of an organic photoconductor material, and the TFTs 518, the active layer of which is made of an organic semiconductor material, does not require the radiation detector 502 to be highly rigid, even though the weight of the subject 14 is applied as a load to the radiation detector 502.

The insulative substrate 508 may be made of a material that is permeable to light and which absorbs a small amount of radiation 16. The amorphous oxide in the active layer of the TFTs 518, and the organic photoconductor material of the photoelectric conversion film 512c of the photoelectric transducers 512 can be deposited as films at low temperatures. Therefore, the insulative substrate 508 is not limited to being a highly heat-resistant substrate, such as a semiconductor substrate, a quartz substrate, a glass substrate, or the like, but may be a flexible substrate of plastic, a substrate of aramid fibers, or a substrate of bionanofibers. More specifically, the insulative substrate 508 may be a flexible substrate of polyester such as polyethylene terephthalate, polybutylene phthalate, polyethylene naphthalate, or the like, or polystyrene, polycarbonate, polyethersulfone, polyarylate, polyimide, polycycloolefine, norbornene resin, poly(chlorotrifluoro-ethylene), or the like. A flexible substrate made of plastic makes the radiation detector 502 lightweight and hence easy to carry around. The insulative substrate 508 may include an insulating layer for making the insulative substrate 508 electrically insulative, a gas barrier layer for making the insulative substrate 508 impermeable to water and oxygen, and an undercoat layer for making the insulative substrate 508 flat for achieving better intimate contact with the electrode.

Aramid fibers, which are used as the insulative substrate 508, are advantageous in that, since a high-temperature process at 200 degrees Celsius or higher is applicable thereto, aramid fibers allow a transparent electrode material to be set at a high temperature to decrease resistance, and also allow driver ICs to be automatically mounted thereon by a process including a solder reflow process. Furthermore, inasmuch as aramid fibers have a coefficient of thermal expansion close to that of ITO and glass, an insulative substrate made of aramid fibers is less liable to warp and crack after fabrication thereof. In addition, an insulative substrate made of aramid fibers may be made thinner than a glass substrate or the like. The insulative substrate 508 may be in the form of a stacked assembly made up of an ultrathin glass substrate together with aramid fibers.

Bionanofibers are made by compounding a bundle of cellulose microfibrils (bacteria cellulose) produced by bacteria (acetic acid bacteria, Acetobacter Xylinum) and a transparent resin. The bundle of cellulose microfibrils has a width of 50 nm, which is 1/10 of the wavelength of visible light, is highly strong and highly resilient, and is subject to low thermal expansion. Bionanofibers, which contain 60% to 70% fibers and exhibit a light transmittance of about 90% at a wavelength of 500 nm, can be produced by impregnating bacteria cellulose with a transparent resin such as an acrylic resin, an epoxy resin, or the like, and setting the transparent resin. Bionanofibers have a low coefficient of thermal expansion ranging from 3 ppm to 7 ppm, which is comparable to silicon crystals, a high strength of 460 MPa that matches the strength of steel, and a high resiliency of 30 GPa. Bionanofibers also are flexible. Therefore, an insulative substrate 508 made of bionanofibers can be made thinner than glass substrates or the like.

If the insulative substrate 508 comprises a glass substrate, then the radiation detector 502, i.e., a TFT board, has an overall thickness of about 0.7 mm, for example. According to the twenty-sixth modification, the insulative substrate 508 comprises a thin light permeable substrate of synthetic resin in order to make the electronic cassettes 20A through 20J thin. Accordingly, the overall thickness of the radiation detector 502 is reduced to about 0.1 mm, for example, making the radiation detector 502 flexible. Consequently, the electronic cassettes 20A through 20J are more resistant to shocks and hence less susceptible to damage if exposed to shocks. Plastic, aramid fibers, and bionanofibers absorb a small amount of radiation 16. If the insulative substrate 508 is made of any of these materials, then since the amount of radiation 16 absorbed by the insulative substrate 508 is small, the sensitivity of the radiation detector 502 to radiation 16 is prevented from becoming reduced, even though radiation 16 passes through the ISS type radiation detector 502.

The insulative substrate 508 of the electronic cassettes 20A through 20J may not necessarily be made of synthetic resin, but may be made of other materials, such as glass or the like, although such other materials may tend to make the electronic cassettes 20A through 20J thicker.

The planarization layer 514 for planarizing the radiation detector 502 is disposed on the side of the radiation detector 502, i.e., the TFT board, which is in close proximity to the scintillator 500, i.e., remote from the side of the radiation detector 502 to which radiation 16 is applied.

According to the twenty-sixth modification, the radiation conversion panel 92 may be arranged in the following ways.

(1) The photoelectric transducers 512, which comprise PDs, may be made of an organic photoconductor material, and the TFT layer 510 may be constructed to incorporate CMOS sensors therein. Since only the PDs are made of an organic photoconductor material, the TFT layer 510 including the CMOS sensors is not flexible. Photoelectric transducers 512 made of an organic photoconductor material and CMOS sensors are disclosed in detail in Japanese Laid-Open Patent Publication No. 2009-212377, and such features will not be described in detail below.

(2) The photoelectric transducers 512, which comprise photodiodes, may be made of an organic photoconductor material, and the TFT layer 510 may be made flexible by incorporating CMOS circuits having TFTs made of an organic material. The CMOS circuits employ a p-type organic semiconductor material made of pentacene, and an n-type organic semiconductor material made of fluorinated copper phthalocyanine ($F_{16}CuPc$). If made in this manner, the TFT layer 510 is flexible and can be bent to a smaller radius of curvature, and thus, the TFT layer 510 is effective to significantly reduce the gate insulating film to result in a lower drive voltage. Furthermore, the gate insulating film, the semiconductor, and the electrodes can be fabricated at room temperature or temperatures that are equal to or lower than 100° C. The CMOS circuits may be fabricated directly on the flexible insulative substrate 508. The TFTs, which are made of an organic material, may be microfabricated using a fabrication process according to a scaling law. The insulative substrate 508 may be produced as a flat substrate, which is free of surface irregularities, by coating a thin polyimide substrate with a polyimide precursor, and then heating the applied polyimide precursor to convert the same into polyimide.

(3) PDs and TFTs, which are made of crystalline Si, may be fabricated as a resin substrate on the insulative substrate 508 by a fluidic self-assembly process. The fluidic self-assembly process allows a plurality of device blocks on the order of microns to be placed at designated positions on a substrate. More specifically, the PDs and the TFTs, which are constituted as device blocks on the order of microns, are prefabricated on another substrate and then the PDs and the TFTs are separated from the substrate. Then, the PDs and the TFTs are dipped into a liquid and the PDs and the TFTs are spread onto the insulative substrate 508 as a target substrate, so as to be statistically placed in respective positions. The insulative substrate 508 is processed in advance to adapt itself to the device blocks, so that the device blocks can be placed selectively on the insulative substrate 508. Accordingly, the device blocks, i.e., the PDs and the TFTs, which are made of an optimum material, can be integrated into the insulative substrate 508 as an optimum substrate. Therefore, it is possible to integrate the PDs and the TFTs into the insulative substrate 508 as a non-crystalline resin substrate.

The present invention is not limited to the above-described embodiments, but may adopt various additional or alternative arrangements without departing from the scope of the invention.

What is claimed is:

1. A radiographic image capturing apparatus comprising:
    a radiation conversion panel for converting radiation into a radiographic image; and
    an external force applying mechanism for applying an external force to the radiation conversion panel,
    wherein the external force applying mechanism applies an external force to a peripheral edge of the radiation conversion panel, applies an external force to the radiation conversion panel while being stacked on the radiation conversion panel, or presses the radiation conversion panel against an inner wall surface of a panel housing unit that houses the radiation conversion panel at least during capturing of a radiographic image by applying the radiation to the radiation conversion panel,
    further comprising:
    an environmental condition detector for detecting an environmental condition in the panel housing unit; and
    an external force controller configured to control the external force applying mechanism to apply the external force to the peripheral edge or to the radiation conversion panel based on the environmental condition detected by the environmental condition detector.

2. The radiographic image capturing apparatus according to claim 1, wherein the environmental condition detector comprises at least one of a temperature detector for detecting the temperature of the radiation conversion panel and a humidity detector for detecting the humidity in the panel housing unit; and wherein the external force controller controls the external force applying mechanism to apply the external force, which depends on at least one of a temperature change of the radiation conversion panel and a humidity change in the panel housing unit, to the peripheral edge or to the radiation conversion panel based on at least one of the temperature detected by the temperature detector and the humidity detected by the humidity detector.

3. The radiographic image capturing apparatus according to claim 2, wherein the radiation conversion panel has a board and a radiation conversion layer mounted on the board for converting the radiation into an electric signal representative of the radiographic image; and wherein the external force applying mechanism is disposed on the peripheral edge of the board, or on at least one of a bottom surface of the board and an upper surface of the radiation conversion layer.

4. The radiographic image capturing apparatus according to claim 3, wherein the board comprises a substantially rectangular flexible board, which is deformable depending on at least one of the temperature change and the humidity change;

wherein the board has four sides, at least one of which has an external connector for inputting a signal to or outputting a signal from the radiation conversion layer; and wherein the external force applying mechanism applies the external force to at least the side of the board that includes the external connector.

5. The radiographic image capturing apparatus according to claim 3, wherein the board is flexible and deformable depending on at least one of the temperature change and the humidity change; and wherein the external force applying mechanism has a planar shape along the board or the radiation conversion layer, and is shrinkable along thicknesswise directions of the board or the radiation conversion layer and expandable along planar directions of the board or the radiation conversion layer, or is expandable along the thicknesswise directions and shrinkable along the planar directions, depending on at least one of the temperature change and the humidity change.

6. The radiographic image capturing apparatus according to claim 1, wherein the external force applying mechanism comprises an actuator made of a polymeric material, an actuator made of a shape memory alloy, or an actuator made of a piezoelectric material.

7. A radiographic image capturing system comprising:

a radiographic image capturing apparatus having a radiation conversion panel for converting radiation into a radiographic image, and an external force applying mechanism for applying an external force to the radiation conversion panel; and a control device for controlling the radiographic image capturing apparatus, wherein the external force applying mechanism applies an external force to a peripheral edge of the radiation conversion panel, applies an external force to the radiation conversion panel while being stacked on the radiation conversion panel, or presses the radiation conversion panel against an inner wall surface of a panel housing unit that houses the radiation conversion panel at least during capturing of a radiographic image by applying the radiation to the radiation conversion panel, the radiographic image capturing apparatus further comprising:

an environmental condition detector for detecting an environmental condition in the panel housing unit; and an external force controller configured to control the external force applying mechanism to apply the external force to the peripheral edge or to the radiation conversion panel based on the environmental condition detected by the environmental condition detector.

* * * * *